(12) United States Patent
Messier

(10) Patent No.: US 7,247,425 B2
(45) Date of Patent: Jul. 24, 2007

(54) METHODS TO IDENTIFY POLYNUCLEOTIDE AND POLYPEPTIDE SEQUENCES WHICH MAY BE ASSOCIATED WITH PHYSIOLOGICAL AND MEDICAL CONDITIONS

(75) Inventor: Walter Messier, Longmont, CO (US)

(73) Assignee: Evolutionary Genomics, LLC, Aurora, CO (US)

( * ) Notice: Subject to any disclaimer, the term of this patent is extended or adjusted under 35 U.S.C. 154(b) by 483 days.

(21) Appl. No.: 10/883,576

(22) Filed: Jun. 30, 2004

(65) Prior Publication Data

US 2005/0037400 A1     Feb. 17, 2005

Related U.S. Application Data

(63) Continuation-in-part of application No. 10/098,600, filed on Mar. 14, 2002, now Pat. No. 6,866,996, which is a continuation-in-part of application No. 09/942,252, filed on Aug. 28, 2001, now abandoned, which is a continuation-in-part of application No. 09/591,435, filed on Jun. 9, 2000, now Pat. No. 6,280,953, which is a continuation-in-part of application No. 09/240,915, filed on Jan. 29, 1999, now Pat. No. 6,228,586.

(60) Provisional application No. 60/545,604, filed on Feb. 17, 2004, provisional application No. 60/484,030, filed on Jun. 30, 2003, provisional application No. 60/098,987, filed on Sep. 2, 1998, provisional application No. 60/073,263, filed on Jan. 30, 1998.

(51) Int. Cl.
*C12Q 1/68* (2006.01)
*C12Q 1/70* (2006.01)

(52) U.S. Cl. ............................... 435/5; 435/6
(58) Field of Classification Search ............ 435/6
See application file for complete search history.

(56) References Cited

U.S. PATENT DOCUMENTS

| | | | |
|---|---|---|---|
| 5,602,005 A | 2/1997 | Herr et al. | |
| 5,965,352 A | 10/1999 | Stoughton et al. | |
| 6,228,586 B1 | 5/2001 | Messier et al. | |
| 6,274,319 B1* | 8/2001 | Messier et al. | 435/6 |
| 6,280,953 B1 | 8/2001 | Messier et al. | |
| 6,743,580 B2* | 6/2004 | Messier et al. | 435/6 |
| 2003/0068630 A1 | 4/2003 | Cimbora et al. | |

FOREIGN PATENT DOCUMENTS

| | | |
|---|---|---|
| EP | 120658 | 10/1984 |
| WO | WO 00/12764 | 3/2000 |
| WO | WO99/39006 | 7/2000 |

OTHER PUBLICATIONS

Alter et al. (1984) Science 226:549-552.
Burger et al. (1994) J. Mol. Evol. 39:255-267.
Edwards et al. (1995) Molecular Ecology 4:719-729.
Endo et al. (1996) Mol. Biol. Evol. 13:685-690.
Fournier et al. (1988) J. Gen. Virol. 79:2367.
Fultz et al. (1986) Journal of Virology 58:116-124.
Gibbons (Sep. 1998) Science 281: 1432-1434.
Goodman et al. (1990) J. Mol. Evol. 30:260-266.
Goodwin et al. (1996) Mol. Biol. Evol. 13:346-358.
Herbet et al. (1996) Mol. Biol. Evol. 13:1054-1057.
Hughes (1997) Mol. Biol. Evol. 14:1-5.
Hughes and Nei (1988) Nature 335:167-170.
Huttley et al. (2000) Nature Genetics 25:410-13.
Jaeger et al. (1994) Immunogenetics 40:184-191.
Jenkins et al. (1995) Proc. R. Soc. Lond. 261:203-207.
Kitamura et al. (1994) Eur. J. Biochem. 224:877-83.
Kreitman and Akashi (1995) Annu. Rev. Ecol. Syst. 26:403-422.
Lee and Vacquier (1992) Biol. Bull. 182:97-104.
Lee et al. (1998) Aids Research and Human Retroviruses 14:1323-1328.
Li (1993) J. Mol. Evol. 36:96-99.
Li (1997) in Molecular Evolution, Sinauer Associates, Inc. Pub., Sunderland, MA, Table of Contents.
Li et al. (1985) Mol. Biol. Evol. 2:150-174.
Lienert and Parham (1996) Immunol. Cell Biol. 74:349-356.
Lyn et al. (1995) Gene 155:241-245.
Malcolm et al. (1990) Nature 345:86-89.
McDonald and Kreitman (1991) Nature 351:652-654.
Messier and Stewart (1994) Current Biology 4:911-913.
Messier and Stewart (1997) Nature 385:151-154.
Metz and Palumbi (1996) Mol. Biol. Evol. 13:397-406.
Nakashima et al. (1995) Proc. Natl. Acad. Sci. USA 92:5605-5609.
Nei (1987) in Molecular Evolutionary Genetics, Columbia University Press Pub., New York, NY, Table of Contents.
Nei and Hughes in Evolution at the Molecular Level, Sinauer Associates, Sunderland, MA, pp. 222-247 (1991).
Niewiesk and Bangham (1996) J. Mol. Evol. 42:452-458.
Novembre et al. (1997) Journal of Virology 71:4086-4091.
Parham and Ohta (1996) Science 272:67-74.
Patzwahl et al. (2000) J. Virology 75(3):1332-38.
Rumin et al. (199) J. Gen. Virology 80:3007.
Sharp (1997) Nature 385:111-112.
Swanson & Vacquier (1995) Proc. Natl. Acad. Sci. USA 92:4957-4961.

(Continued)

*Primary Examiner*—Kenneth R. Horlick
(74) *Attorney, Agent, or Firm*—Swanson & Bratschun, LLC

(57) ABSTRACT

The present invention provides methods for identifying evolutionarily significant polynucleotide and polypeptide sequences in human and/or non-human primates which may be associated with a physiological condition, such as enhanced resistance to AIDS infection. The invention also provides methods for identifying evolutionarily significant polynucleotides with mutations that are correlated with susceptibility to diseases, such as ICAM 1. The methods employ comparison of human and non-human primate sequences using statistical methods. Sequences thus identified may be useful as host therapeutic targets and/or in screening assays.

22 Claims, 31 Drawing Sheets

OTHER PUBLICATIONS

Swanson and Vacquier (1998) Science 281:710-712.
Wettstein et al. (1996) Mol. Biol. Evol. 13:56-66.
Whitfield et al. (1993) Nature 364:713-715.
Wolinsky et al. (1996) Science 272:537-542.
Wu et al. (1997) J. Mol. Evol. 44:477-491.
Xu et al. (1997) Human Mol. Genetics 6(7):1057-62.
Yang (1998) Mol. Biol. Evol. 15:568-573.
Zhou and Li (1996) Mol. Biol. Evol. 13:780-783.
Dennis (1999) Nat. Gen. 22:10.
Favre et al. (2001) CR Acad, Sci. 324:1141-1148.
Galun et al. (1995) J. Infectious Diseases 172:25-30.
Hacia et al. (Feb. 1998) Nat. Gen. 18:155-158.
Labonte et al. (2002) J. Med. Virol. 66:312-319.
Lanford et al. (1991) J. Med. Virology 34:148-153.
Mercer et al. (Aug. 2001) Nat. Med. 7(8):927-933.
Shent et al. (1998) Oncogene 17:3115-3124.
Shimizu et al. (Apr. 1985) Med. Sci. 82:2138-2142.
Takahashi et al. (1990) J. General Virology 71:2005-2011.
Thompson et al. (Apr. 1995) Nat. Gen. 9:444-450.
Walker (1997) Springer Semin Immunopathology 19(1):85-98.
Xu et al. (Mar. 1999) Mol. Cell 3:389-395.
Xu et al. (May 1999) Nat. Gen. 22:37-43.

\* cited by examiner

| HUMAN: | 961 | CAGCCACTGGGCCCCGAGGGCCCAGCTCCTGCTGAAGGCCACCCCAGAGGACAACGGGCGC |
| CHIMPANZEE: | | ‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐ |
| | | Q P L G P R V Q L L L K A T P E D N G R |

| | | AGCTTCTCCTGCTCTGTGTCCCTGTATGGCCCCCGACTGGAGGTGGCAACCCTGGAGGTG |
| | | ‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐ |
| | | S F S C S A T L E V A G Q L I H K N Q T |

| HUMAN: | 1081 | CGGGAGCTTCGTGTCCCTGTATGGCCCCCGACTGGACGAGAGGGATTGTCCGGAAACTGG |
| CHIMPANZEE: | | ‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐ |
| | | R E L R V L Y G P R L D E R D C P G N W |

| | | ACGTGGCCAGAAAAATTCCCAGCAGACTCCAATGTGCCAGGCTTGGGGGAACCCATTGCCC |
| | | ‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐ |
| | | T W P E N S Q Q T P M C Q A S G N P L P |

| HUMAN: | 1201 | GAGCTCAAGTGTCTAAAGGATGGCACTTTCCCACTGCCCCATCCGGGAATCAGTGACTGTC |
| CHIMPANZEE: | | ‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐ |
| | | E L K C L K D G T F P L P P V G E S V T V |

| | | ACTCGAGATCTTGAGGGCACCTACCTCTGTGTCCAGGAGCACTCAAGGGAGGTCACC |
| | | ‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐ |
| | | T R D L E G T Y L C R A R S T Q G E V T |

| HUMAN: | 1321 | CGGCGAGGTGACCGTGAATGTGCTCTCCCCCGTATGAGATTGTCATCATCACTGTGTA |
| CHIMPANZEE: | | ‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐ |
| | | R K V T V N V L S P R Y E I V I I T V V |

| | | GCAGCCGCAGTCATAATGGCAGGCCTCAGCAGCTGCACCACCCTACCCTGTACCTGTAAA |
| | | ‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐ |
| | | A A V I M G T A G L S T Y L Y N R Q R |

FIG. 2 (CONT.)

```
HUMAN:      1441  AAGATCAAGAAATACAGAGACTACAACAGGCCCAAAAAGGGACCCCCATGAAACCGAACACA
                  |||||||||||||||||||||||||||||||||||||||||||||||||||||||||||||
CHIMPANZEE:       AAGATCAGGAAATACAGACTACAACAGGCTCAAACAGGGACCCCCATGAAACCGAACACA
                  K  I  R  K  Y  R  L  Q  Q  A  Q  K  G  T  P  M  K  P  N  T

CAAGCCACGCCTCCCTGA
            ||||||||||||||||||
            CAAGCCACGCCTCCCTGA
            Q  A  T  P  P  *
```

1515 ICAM    GORILLA

```
CAG ACA TCT GTG TCC CCC CCA AAA GTC ATC CTG CCC CGG GGA GGC TCC GTG CTG CTG ACA
TGC AGC ACC TCC TGT GAC CAG CCC AAC ACC TTG TTG GGC TAT CGG ATA GAG ACC CGG TTG CCT CAA GAA AAG
GAG TTG CTC CTG GGG AAC AAC TCA GAA GTG AAG GTG TGG GCA TAT GGG AGC AAT GCT GTG AAA ACC GTG CAA GAA GAT
AGC CAA CCA ATG TGT TCA GAA CGG TGC CTT GAA CTG GAA CTG CCC GCA CCC CCC CCC TCT TGG CAG CCA GTG CTC CTC
ACC GTG TAC TGG ACT CCA CTA GAG GTG CAG GAG GTG GGT CAG GCA CCC TCC CGG GCC AAC CTC ATC
GGC AAG GAC CTT ACC CGC TGC CGT GGG CTG GAG GAG CTG AAA CGG CCA GCT GTG GGG GAG CCC GCC
GTG GTG CTG GGG CGT ACG CCG CCC CAA GGG GTG CGG CAA CAT CAC CTG AAG CTG TTT GAG ACC AAT TTC TGC CGC
ACT GAA CTG GAC ACC TTT GTC GAC ACC TGT CCC ACT GCG GTC CCA CCA AAA CCT CGG GCC CCC TAC
CAG CTC CAA GTG CAG GGG CAG GGG ACT TGT GTC CTT GGG TCC TCC GAC CTG GGG CTG GGG CTC TCG GTC GAG
GAG GTG GAC ACG CAC CTG GCA CAG CTG GAC GTC TGT CAG GAC CCT GAC TTG AAC ACA GTC ACC AAC AAC
GCC CAG GTC CTC TCA GCC AAG GAC GCA GTG CTG ACC AGT GTG ACC GCA GAG GAC TGG ACA GAG GGC CAG TGG
CTG ACG TGT GCA GTA ATA CTG GGG ATT CTG AGA GCC CAG AAG AAG ACG CTG AAC CAG ATC
TAC AGC TTT CCG GCA CCC AAC GTG CAC CAG CCC TTC GAG GCC ACG CTG CAG CTG TCA GAA GGG GAC GAG
GTG ACA GTG AAG TGT GAG GCC ACC GGC CAG CCT CTG CCC CAG AAG AAG AAC ATT ATC ATC GCC CAG CTG GGG CCA GAC GTC CTG GCC CAG
CAG CCA CCG GGC CCG TCT GCA CAA AGG CAG CCC ACC AGT GTT CCT GAG ATA ATC ATC TGT GGG ACG GAC
CGG GAG CTT CGT TAT GTC CTG CGA CTG CCA ACT ATG CCA TGC AGG AGG CTC TAT CAC ATG TGT GGA AAC CAG TGG
ACG CTG CTC CGC TGG AAT TCC AAG AAT CCA CTG CCC AAG CAG GCT TGG GGG AAC TCA GTG ACT TTG CCC
ACT CGA GAT CTT AAG GGC ACC TTT CGG TGT CGG GCC ACT AGC AGC AGC CGA GAA GAG GTG ACC GTC
CGC GTG GAG GTG GCA AAT ATG ATG GGC AAT GCT CTC TCC AGC AGG AGG CTC ACG CGC TAT AAC CGC AGG CAG GTA
GCA ATC AGG GCA GTC ATA ATG TAC CTC AGC TAC CTC TAT AAC CCC ATG AAA ACA ACA
CAA GCC ACG CCT CCC           CAG GCT CAA CTA AGA AAA GGG AAG GGG AGG AAC ACA
```

(SEQ ID NO: 4)

```
1515 ICAM          ORANG
CAC ACA TCT GTG TCC TCC GCC AAC GTC TTC CTG CCC CGG GGA GGC TCC GTG CTA GTG AAT
TGC AGC ACC TCC TGT GAC CAG AAC AAC CCC AAC TGG TTG AAG ATG TTG GGC ATA GAG CCT AAA AAG
GAG TTG CTC CCG GGT GGG AAC AAC TCA GAA ATG TGC CCT GAA CTG GAA CTG TTT AAA CCA GAA GAT
AGC AAC CCA ATG TGG TAT TGC ACT TGC GAA GTG ATG GGA CTG GGA GCA CCC CAG AAC CTC ACC GTG
ACC GTG AAG AAC CTT ACC ACC CTA CGC GTG CAG CGG GCA CCC CCC GGG GCC AAC CTC ACC GTG
GGC GTA TTG CTC GGG GCG GAG CTG GGG AGG GAG AGC CGG CAC CCC GTG AAT TTC TCG GCC CCC CAC
GAG GTC ACG GCC GTG CGG GAC CTG CCC GCG CAA GGG CTG GAG CTG TTT GAG AAC ACC TCG GTC CTA
ACT GAA CTG CAA ACC ACG CTT GTC CTG CCA GCG ACT CCC CAA CTT GTC CTT AGC CCC GTC TCG GAG
CAG CTC CGG GAC AAG AAC GTG ACC CGG GGA CCC CAC TGC GGG CTG ACA GTC TAT GGC GTC
GAG GTG GAC GTG CAG CAG GGG GCA CTG CCC AAG ACA GCA GAG GAG ACA CGG GAG ACC TGG
GCC CAG TCC GTC CAC TTG GCA AAG GTG ACT CCT TCC AGG GAG CCC GAG CAG CCA GTC ACC AGT
GAC TCC CTC TCG TCG CTT TGT GGC GGG ATA CTG AAC GTG ACT CCT TTG ATC
CTG TGG TGT GCA GTG CTG AGG ATA CTG AAC GTG CCA GAG AAG CTG AGG GTC ACC GAG ATC
TAC AGC TTT CCT GCA CCC GCA GCC TTC CTC TGT CTG GCC ACG GTC CAA GGG GTT CCA GCC GAG
GTG ATA GTG AAG TGT GAG GCC TAC TCC GAG CCC AAG CTC CTG ATT GTC ACT GTC AGT GCA ACC TGG CCC
CAG CCG CCG GGC AGG CCG GCC GCT CTC TCC CGG AGG CCA TAT GTC ACC AGC CAG GGG ATT CAA CAC GAG ACC
AGC TTC CTG TGC TCT GCA ACC GTG AGC CTG GAC AAG CAC CTT ATA CAC CAG AAG ACT CAC CAA ACC
CGG GAG CTT CGA GTC TAT CAG ATG CCC GAG CTG GAC GCC AGG GAT TGC CAG CGG CAG ACC
ACG TGG TCA GAA AAC ACC CAG TGC CCA ATG TGC CTG CCC GCG AGC TGC TGG TGG CCC AAC TTG CCC
ACT CTC GAT GAT CTT AAG GGC GAG AAC GAT ACC TTC CTC TCC GCC AGC AGG GTC ACA GTC GAG ACT GTC
CGC GAG GTG GCC GTG ACC TGT CGG CGG CCC ACT GAG GGG ATC ATC CGC ACC GTG TAC GTA
GCA GCC AGA TAC AGA GGA GGC ACT CTG GCA GCC TAT GAT CTC CGG CTC CAG GAG ATG CCC CGG CAG ACA
AAG ATC AGG GCA ATA CTA AGA CAG CAG AAA GGG ACC CCC ATG ACC AAC ACA
CAA ACC ACG CCT CCC
```

(SEQ ID NO:5)

Fig. 4

```
                QTSVSPSKVI  LPRGGSVLVT  CSTSCDQPKL  LGIETPLPKK  ELLLPGNNRK
Human J03132    ..........  ..........  ..........  ..........  ..........
Human X06990    ..........  ..........  ..........  ..........  ..........
Human X59286-8  ..........  ..........  ..........  ..........  ..........
Human #4        .........P  ....Q.....  .........M  ..........  ..........
Human #7        .........P  ....Q.....  .........D  ..........  .......G.W
Human #8        .........P  ..........  .........D  ..........  .......G.W
Human M24283    .........P  ..........  .........T  ..........  .......L.Q
Human U86814    ..........  ..........  ..........  ..........  ..........
Chimp M86848    ..........  ..........  .........T  ..........  .......L.Q
Chimp #1        ..........  ..........  ..........  ..........  ..........
Gorilla #1      ..........  ..........  .........T  ..........  .....PG..W
Gorilla #2      ..........  ..........  ..........  ..........  ..........
Orang           H....SAN.F  ........N.  ..........  ..........  ..........

VYELSNVQED  SQPMCYSNCP  DGQSTAKTFL  TVVYWTPERVE  LAPLPSWQPV
Human J03132    ..........  ..........  ..........  ..........  ..........
Human X06990    ..........  ..........  ..........  ..........  ..........
Human X59286-8  ..........  ..........  ..........  ..........  ..........
Human #4        ..........  ..........  ..........  ..........  ..........
Human #7        ..........  ..........  ..........  ..........  ..........
Human #8        ..........  ..........  ..........  ..........  ..........
Human M24283    ..........  ..........  ..........  ..........  ..........
Human U86814    ..........  ..........  ..........  .....?????  ??????????
Chimp M86848    ..........  ..........  ..........  ..........  ..........
Chimp #1        ..........  ..........  ..........  ..........  ..........
Gorilla #1      ..........  ..........  ..........  ..........  ..........
Gorilla #2      ..........  ..........  .........A  ..........  ..........
Orang           M.........  ..........  ..........  ..........  ..........

GKNLTLRCQV  EGGAPRANLT  VVLLRGEKEL  KREPAVGEPA  EVTTTVLVRR
Human J03132    ..........  ..........  ..........  ..........  ..........
Human X06990    ..........  ..........  ..........  ..........  ..........
Human X59286-8  ..........  ..........  ..........  ..........  ..........
Human #4        ..........  ..........  ..........  ..........  ..........
Human #7        ..........  ..........  ..........  ..........  ..........
Human #8        ..........  ..........  ..........  ..........  ..........
```

(SEQ ID NO:6)
Fig. 5A

Fig. 5B

| | | | | | | |
|---|---|---|---|---|---|---|
| Gorilla #2 | . . . . . . . . . . | . . . . . . . . . . | . . . . . . . . . . | . . . . . . . . . . | . . V . . . . . . . | . . . . . . . . . . |
| Orang | . . . . . . . . . . | . . . . . . . . . . | . . . . . . . . . . | . . . . . . . . . . | . . . . . . . . . . | . . L . . . . . . . |

| | | | | | | |
|---|---|---|---|---|---|---|
| Human J03132 | VTAEDEGTQR | LTCAVILGNQ | SQETLQTVTI | YSFPAPNVIL | TKPEVSEGTE |
| Human X06990 | . . . . . . . . . . | . . . . . . . . . . | . . . . . . . . . . | . . . . . . . . . . | . . . . . . . . . . |
| Human X59286-8 | . . . . . . . . . . | . . . . . . . . . . | . . . . . . . . . . | . . . . . . . . . . | . . . . . . . . . . |
| Human #4 | ?????????? | ?????????? | ?????????? | ?????????? | ?????????? |
| Human #7 | . . . . . . . . . . | . . . . . . . . . . | . . . . . . . . . . | . . . . . . . . . . | . . . . . . . . . . |
| Human #8 | . . . . . . . . . . | . . . . . . . . . . | . . . . . . . . . . | . . . . . . . . . . | . . . . . . . . . . |
| Human M24283 | . . . . . . . . . . | . . . . . . . . . . | . R . . . . . . . . | . . . . . . . . . . | . . . . . . . . . . |
| Human U86814 | . . . . . . . . . . | . . . . . . . . . . | . R . . . . . . . . | . . . . . . . . . . | . . . . . . . . . . |
| Chimp M86848 | . . . . . . . . W . | . T . . . . . . . . | . . . . . . . . . . | . . . . . . . . . . | . . . . . . . . . . |
| Chimp #1 | . . . . . . . . W . | . T . . . . . . . . | . . . . . . . . . . | . . . . . . . . . . | . . . . . . . . . . |
| Gorilla #1 | . . . . . . . . . . | . R . . . . . . . . | . . . . . . . . . . | . . . . . . . . . . | . . . . . . . . . . |
| Gorilla #2 | . E . . . . . . . W | . . . . . . . . . . | . . . . . . . . . . | . . . . . . . . . . | . . . . . . . . . . |
| Orang | . . . . . . . . . . | . . . . . . . . . . | . . . . . . . . . . | . T . . . . . . . . | . M . . . . . . . . |

| | | | | | | |
|---|---|---|---|---|---|---|
| Human J03132 | VTVKCEAHPR | AKVTLNGVPA | QPLGPRAQLL | LKATPEDNGR | SFSCSATLEV |
| Human X06990 | . . . . . . . . . . | . . . . . . . . . . | . . . . . . . . . . | . . . . . . . . . . | . . . . . . . . . . |
| Human X59286-8 | . . . . . . . . . . | . . . . . . . . . . | . . . . . . . . . . | . . . . . . . . . . | . . . . . . . . . . |
| Human #4 | ?????????? | ?????????? | ?????????? | ?????????? | ?????????? |
| Human #7 | . . . . . . . . . . | . . . . . . . . . . | . . . . . . . . . . | . . . . . . . . . . | . . . . . . . . . . |
| Human #8 | . . . . . . . . . . | . . . . . . . . . . | . . . . . . . . . . | . . . . . . . . . . | . . . . . . . . . . |
| Human M24283 | ?????????? | ?????????? | ?????????? | ?????????? | ?????????? |
| Human U86814 | . . . . . . . . . . | . . . . . . . . . . | . V . . V . . . . . | . . . . . . . . . . | . . . . . . . . . . |
| Chimp M86848 | . . . . . . . . . . | . . . . . . . . . . | . V . . V . . . . . | . . . . . . . . . . | . . . . . . . . . . |
| Chimp #1 | . . . . . . . . . . | . . . . . . . . . . | . P . . T . F . . . | . . . . . . . . . . | . . . . . . . . . . |
| Gorilla #1 | . . . . . . . . . . | . . . . . . . . . . | . P . . T . F . . . | . . . . . . . . . . | . . . . . . . . . . |
| Gorilla #2 | . . . . . . . . . . | . . . . . . . . . . | . P . . . . F . . . | . . . . . . . . . . | . . . . . . . . . . |
| Orang | . I . . . . . . . . | . N . . . . . . . . | . . . . . . . . . . | . . . . . . . . . . | . . . . . . . . . . |

| | | | | | |
|---|---|---|---|---|---|
| Human J03132 | AGQLIHKNQT | RELRVLYGPR | LDERDCPGNW | TWPENSQQTP | MCQAWGNPLP |
| Human X06990 | . . . . . . . . . . | . . . . . . . . . . | . . . . . . . . . . | . . . . . . . . . . | . . . . . . . . . . |

Fig. 5C

| | | | | | | | |
|---|---|---|---|---|---|---|---|
| Human X59286-8 | .......... | .......... | .......... | .......... | .......... | .......... | .......... |
| Human #4 | .......... | .......... | .......... | .......... | .......... | .......... | .......... |
| Human #7 | .......... | .......... | .......... | .......... | .......... | .......... | .......... |
| Human #8 | .......... | .......... | .......... | .......... | .......... | .......... | .......... |
| Human M24283 | .......... | .......... | .......... | .......... | .......... | .......... | .......... |
| Human U86814 | ????????? | ????????? | ????????? | ????????? | ????????? | ????????? | ????????? |
| Chimp M86848 | .......... | .......... | .......... | .......... | .......... | .....S.... | .......... |
| Chimp #1 | .......... | .......... | .......... | .......... | .......... | .....S.... | .......... |
| Gorilla #1 | .......... | .......... | .......... | .......... | .......... | .......... | .......... |
| Gorilla #2 | .......... | .......... | .......... | .......... | .......... | .......... | .......... |
| Orang | .......... | .......... | .......... | .......... | .......... | .......... | .......... |

| | | | | | | | |
|---|---|---|---|---|---|---|---|
| Human J03132 | ELKCLKDGTF | PLPIGESVTV | TRDLEGTYLC | RARSTQGEVT | REVTVNVLSP | | |
| Human X06990 | .......... | .......... | .......... | .......... | .......... | | |
| Human X59286-8 | ????????? | ????????? | ????????? | ????????? | ????????? | | |
| Human #4 | .......... | .......... | .......... | .......... | .......... | | |
| Human #7 | .......... | .......... | .......... | .......... | .......... | | |
| Human #8 | .......... | .......... | .......... | .......... | .......... | | |
| Human M24283 | .......... | .......... | .......... | .......... | ....K..... | | |
| Human U86814 | ????????? | ????????? | ????????? | ????????? | ????????? | | |
| Chimp M86848 | .......... | ...V...... | .......... | .......... | ....K..... | | |
| Chimp #1 | .......... | ...V...... | .......... | .......... | ....K..... | | |
| Gorilla #1 | .......... | ...V...... | .......... | .......... | .......... | | |
| Gorilla #2 | .......... | .......... | .......... | .......... | .......... | | |
| Orang | .......... | .......... | .......... | .......... | .......... | | |

| | | | | | |
|---|---|---|---|---|---|
| Human J03132 | RYEIVIITVV | AAAVIMGTAG | LSTYLYNRQR | KIKKYRLQQA | QKGTPMKPNT |
| Human X06990 | .......... | .......... | .......... | .......... | .......... |
| Human X59286-8 | .......... | .......... | .......... | .......... | .......... |
| Human #4 | .......... | .......... | .......... | .......... | .......... |
| Human #7 | .......... | .......... | .......... | .......... | .......... |
| Human #8 | .......... | .......... | .......... | .......... | .......... |
| Human M24283 | .......... | .......... | .......... | .......... | .......... |
| Human U86814 | ????????? | ????????? | ????????? | ????????? | ????????? |
| Chimp M86848 | .......... | .......... | .......... | .....R.... | .......... |
| Chimp #1 | .......... | .......... | .......... | .....R.... | .......... |

Fig. 5D

```
Gorilla #1        ..F...A..  .........  .........  ..R......  .........
Gorilla #2        ..F...A..  .........  .........  ..R......  .........
Orang             .........  ...A.L...  .........  ..RI.....  .........

Human J03132      QATPP
Human X06990      .....
Human X59286-8    .....
Human #4          .....
Human #7          .....
Human #8          ?????
Human M24283      .....
Human U86814      .....
Chimp M86848      .....
Chimp #1          .....
Gorilla #1        .....
Gorilla #2        .....
Orang             ..T..
```

Fig. 5E

| | | | | | |
|---|---|---|---|---|---|
| Human M32331 | SDEKVFEVHV | RPKKLAVEPK | GSLEVNCSTT | CNQPEVGGLE | TSLDKILLDE |
| Human #4     | .......... | .......... | .......... | .......... | .......... |
| Human #8     | .......... | .......... | .......... | .......... | .......... |
| Human X15606 | .......... | .......... | .......... | .......... | ...N...... |
| Chimp #1     | .......... | .......... | ...K...... | .......... | .......... |
| Chimp #2     | .......... | .......... | ...K...... | .......... | .......... |
| Gorilla #2   | .......... | .......... | A......... | .......... | .......... |

| | | | | | |
|---|---|---|---|---|---|
| Human M32331 | QAQWKHYLVS | NISHDTVLQC | HFTCSGKQES | MNSNVSVYQP | PRQVILTLQP |
| Human #4     | .......... | .......... | .......... | .......... | .......... |
| Human #8     | .......... | .......... | .......... | .......... | .......... |
| Human X15606 | .......... | .......... | .......... | .......... | .......... |
| Chimp #1     | .......... | .......... | .......... | .......... | .......... |
| Chimp #2     | .......... | .......... | .......... | .......... | .......... |
| Gorilla #2   | .......... | .......... | .......... | .......... | .......... |

| | | | | | |
|---|---|---|---|---|---|
| Human M32331 | TLVAVGKSFT | IECRVPTVEP | LDSLTLFLFR | GNETLHYETF | GKAAPAPQEA |
| Human #4     | .......... | .......... | .......... | .......... | .......... |
| Human #8     | .......... | .......... | .......... | .......... | .......... |
| Human X15606 | .......... | .......... | .......... | .......... | .......... |
| Chimp #1     | .......... | .......... | .......... | .......... | .......... |
| Chimp #2     | .......... | .......... | .......... | .......... | .......... |
| Gorilla #2   | .......... | .......... | .......... | ......NQ.. | ......L... |

| | | | | | |
|---|---|---|---|---|---|
| Human M32331 | TATFNSTADR | EDGHRNFSCL | AVLDLMSRGG | NIFHKHSAPK | MLEIYEPVSD |
| Human #4     | .......... | .......... | .......... | .......... | .......... |
| Human #8     | .......... | .......... | .......... | .......... | .......... |
| Human X15606 | .......... | .......... | .......... | .......... | .......... |
| Chimp #1     | .V........ | D......... | .......... | .......... | .......... |
| Chimp #2     | .V........ | D......... | .......... | .......... | .......... |
| Gorilla #2   | .......... | .......... | .....I.... | ...QE..... | .......... |

(SEQ ID NO:7)

Fig. 6A

```
Human M32331      SQMVIIVTVV   SVLLSLFVTS   VLLCFIFGQH   LRQQRMGTYG   VRAAWRRLPQ
Human #4          ..........   ..........   ..........   ..........   ..........
Human #8          ..........   ..........   ..........   ..........   ..........
Human X15606      ..........   ..........   ..........   ..........   ..........
Chimp #1          ..........   ..........   ..........   ..........   ..........
Chimp #2          ..........   ..........   ..........   ..........   ..........
Gorilla #2        ..........   ..........   ..........   ..........   ..........

Human M32331      AFRP
Human #4          ....
Human #8          ....
Human X15606      ....
Chimp #1          ....
Chimp #2          ....
Gorilla #2        ....
```

Fig. 6B

| | | | | | |
|---|---|---|---|---|---|
| Human X69819 | QEFLLRVEPQ | NPVLSAGGSL | FVNCSTDCPS | SEKIALETSL | SKELVASGMG |
| Human #4 | .......... | .......... | .......... | .......... | .......... |
| Human #5 | .......... | .......... | .......... | .......... | .......... |
| Human #7 | .......... | .......... | .......... | .......... | .......... |
| Human S50015 | .......... | .......... | .......... | F......... | .......... |
| Chimp #3 | .......... | .......... | .......... | .......... | .......... |
| Chimp #4 | .......... | .......... | .......... | .......... | .......... |
| Chimp #5 | .......... | .......... | .......... | .......... | .......... |
| Gorilla #1 | .......... | .......... | .......... | .......... | .......... |
| Gorilla #2 | .......... | .......... | .......... | .......... | .......... |
| Orang | .......... | ....P..... | L......... | .K........ | .....DN... |

| | | | | | |
|---|---|---|---|---|---|
| Human X69819 | WAAFNLSNVT | GNSRILCSVY | CNGSQITGSS | NITVYGLPER | VELAPLPPWQ |
| Human #4 | .......... | .......... | .......... | .......... | .......... |
| Human #5 | .......... | .......... | .......... | .......... | .......... |
| Human #7 | .......... | .......... | .......... | .......... | .......... |
| Human S50015 | .......... | .......... | .......... | .......... | .......... |
| Chimp #3 | .......... | .......... | .......... | .....R.... | .......... |
| Chimp #4 | .......... | .......... | .......... | .....R.... | .......... |
| Chimp #5 | .......... | .......... | .......... | .....R.... | .......... |
| Gorilla #1 | .......... | .......... | .......... | .....R.... | .......... |
| Gorilla #2 | .......... | .......... | .......... | .....R.... | .......... |
| Orang | ....Y..... | .......... | ......I... | .....R.... | .......L.. |

| | | | | | |
|---|---|---|---|---|---|
| Human X69819 | PVGQNFTLRC | QVEGGSPRTS | LTVVLLRWEE | ELSRQPAVEE | PAEVTATVLA |
| Human #4 | .......... | .......... | .......... | .......... | .......... |
| Human #5 | .......... | .......... | .......... | .......... | .......... |
| Human #7 | .......... | .......... | .......... | .......... | .......... |
| Human S50015 | .......... | .......... | .......... | .......... | .......... |
| Chimp #3 | Q......... | .......... | .......... | .......... | .......... |
| Chimp #4 | Q......... | .......... | .......... | .......... | .......... |
| Chimp #5 | R......... | .......... | .......... | .......... | .......... |
| Gorilla #1 | .......... | .......... | .......... | .......... | ......P... |
| Gorilla #2 | .......... | .......... | .......... | .......... | ......P... |

(SEQ ID NO:8)

Fig. 7A

| | | | | | |
|---|---|---|---|---|---|
| Human X69819 | SRDDHGAPFS | CRTELDMQPQ | GLGLFVNTSA | PRQLRTFVLP | VTPPRLVAPR |
| Human #4     | .......... | .......... | .......... | .......... | .......... |
| Human #5     | .......... | .......... | .......... | .......... | .......... |
| Human #7     | .......... | .......... | .......... | .......... | .......... |
| Human S50015 | .......... | .......... | .......... | .......... | .......... |
| Chimp #3     | .......... | .......... | .......... | .......... | .......... |
| Chimp #4     | .......... | .......... | .......... | .......... | .......... |
| Chimp #5     | .......... | .......... | .......... | .......... | .......... |
| Gorilla #1   | ..G....... | .......... | .......... | .......... | M......... |
| Gorilla #2   | ..G....... | .......... | .......... | .......... | M...S..... |
| Orang        | ..GH...H.. | .......... | .......... | .......... | .......... |

| | | | | | |
|---|---|---|---|---|---|
| Human X69819 | FLEVETSWPV | DCTLDGLFPA | SEAQVYLALG | DQMLNATVMN | HGDTLTATAT |
| Human #4     | .......... | .......... | .......... | .......... | .......... |
| Human #5     | .......... | .......... | .......... | .......... | .......... |
| Human #7     | .......... | .......... | .......... | .......... | .......... |
| Human S50015 | .......... | .......... | .......... | .......... | .......... |
| Chimp #3     | .......... | .......... | .......... | .......... | .......... |
| Chimp #4     | .......... | .......... | .......... | .......... | .......... |
| Chimp #5     | .......... | .......... | .......... | .......... | .......... |
| Gorilla #1   | .......... | .......... | .......... | .......... | .......... |
| Gorilla #2   | .......... | .......... | .......... | .......... | .......... |
| Orang        | ...A...... | .......... | .......... | .......V. | .......... |

| | | | | | |
|---|---|---|---|---|---|
| Human X69819 | ATARADQEGA | REIVCNVTLG | GERREARENL | TVFSFLGPIV | NLSEPTAHEG |
| Human #4     | .......... | .......... | .......... | .......... | .......... |
| Human #5     | .......... | .......... | .......... | .......... | .......... |
| Human #7     | .......... | .......... | .......... | .......... | .......... |
| Human S50015 | .......... | .......... | .......... | .......... | .......... |
| Chimp #3     | .......... | .......... | .......... | ........T. | .......P.. |

Fig. 7B

| | | | | | |
|---|---|---|---|---|---|
| Chimp #4 | .......... | .......... | .......... | .......T. | .......P.. |
| Chimp #5 | .......... | .......... | .......... | .......T. | .......P.. |
| Gorilla #1 | ...L...... | .......... | .......... | .I........ | .......P.. |
| Gorilla #2 | ...L...... | .......... | .......... | .I........ | .......P.. |
| Orang | .M........ | Q......... | .......... | .........L | .....S.P.. |
| | | | | | |
| Human X69819 | STVTVSCMAG | ARVQVTLDGV | PAAAPGQPAQ | LQLNATESDD | GRSFFCSATL |
| Human #4 | .......... | .......... | .......... | .......... | .......... |
| Human #5 | .......... | .......... | .......... | .......... | .......... |
| Human #7 | .......... | .......... | .......... | .......... | .......... |
| Human S50015 | .......... | .......... | .......... | .......... | .......... |
| Chimp #3 | .......... | .......... | .......... | .......... | R......... |
| Chimp #4 | .......... | .......... | .......... | .......... | R......... |
| Chimp #5 | .......... | .......... | .......... | .......... | R......... |
| Gorilla #1 | .......... | .......... | .......... | .......... | .......... |
| Gorilla #2 | .......... | .......... | .......... | .......... | .......... |
| Orang | .......... | .......... | .......... | .......... | .......... |
| | | | | | |
| Human X69819 | EVDGEFLHRN | SSVQLRVLYG | PKIDRATCPQ | HLKWKDKTRH | VLQCQARGNP |
| Human #4 | .......... | .......... | .......... | .......... | .......... |
| Human #5 | .......... | .......... | .......... | .......... | .......... |
| Human #7 | .......... | .......... | .......... | .......... | .......... |
| Human S50015 | .......... | .......... | .......... | .......... | .......... |
| Chimp #3 | .......... | .......... | .......... | ........T. | .......... |
| Chimp #4 | .......... | .......... | .......... | ........T. | .......... |
| Chimp #5 | .......... | .......... | .......... | ........T. | .......... |
| Gorilla #1 | .......... | .......... | .......... | ........T. | .......... |
| Gorilla #2 | .......... | .......... | .......... | ........T. | .......... |
| Orang | ......F... | .......... | .......... | .......... | .......... |
| | | | | | |
| Human X69819 | YPELRCLKEG | SSREVPVGIP | FFVNVTHNGT | YQCQASSSRG | KYTLVVVMDI |
| Human #4 | .......... | .......... | .......... | .......... | .......... |
| Human #5 | .......... | .......... | .......... | .......... | .......... |
| Human #7 | .......... | .......... | .......... | .......... | .......... |

Fig. 7C

| | | | | | |
|---|---|---|---|---|---|
| Human S50015 | .......... | .......... | .......... | .......... | .......... |
| Chimp #3 | .......... | .......... | .......... | .......... | .......... |
| Chimp #4 | .......... | .......... | .......... | .......... | .......... |
| Chimp #5 | .......... | .......... | .......... | .......... | .......... |
| Gorilla #1 | .......... | .......... | .......... | .......... | .......... |
| Gorilla #2 | .......... | .......... | .......... | .......... | .......... |
| Orang | H......... | .......... | .......... | .......... | R......... |
| | | | | | |
| Human X69819 | EAGSSHFVPV | FVAVLLTLGV | VTIVLALMYV | FREHQRSGSY | HVREESTYLP |
| Human #4 | .......... | .......... | .......... | .......... | .......... |
| Human #5 | .......... | .......... | .......... | .......... | .....T.... |
| Human #7 | .......... | .......... | .......... | .......... | .......... |
| Human S50015 | .......... | .......... | .......... | .......... | .......... |
| Chimp #3 | .......... | .......... | .......... | ....K..... | .......... |
| Chimp #4 | .......... | .......... | .......... | ....K..... | .......... |
| Chimp #5 | .......... | .......... | .......... | ....K..... | .......... |
| Gorilla #1 | .......... | .......... | .......... | ....K..... | .......... |
| Gorilla #2 | .......... | .......... | .......... | ....K..... | .......... |
| Orang | ...N....L. | .L...V.... | ..V.V..... | ....K...R. | ...Q...S.. |
| | | | | | |
| Human X69819 | LTSMQPTEAM | GEEPSRAE | | | |
| Human #4 | .......... | ........ | | | |
| Human #5 | .......... | ........ | | | |
| Human #7 | .......... | ........ | | | |
| Human S50015 | .......... | ........ | | | |
| Chimp #3 | .......Q.. | ........ | | | |
| Chimp #4 | .......Q.. | ........ | | | |
| Chimp #5 | .......... | ........ | | | |
| Gorilla #1 | .......... | ........ | | | |
| Gorilla #2 | .......... | ........ | | | |
| Orang | .......... | .....T.. | | | |

Fig. 7D

Human

ATGAGTGACTCCAAGGAACCAAGACTGCAGCAGCTGGGCCTCCTGGAGGAGGAACA
GCTGAGAGGCCTTGGATTCCGACAGACTCGAGGATACAAGAGCTTAGCAGGGTGTC
TTGGCCATGGCCCTGGTGCTGCAACTCCTCCTTCACGCTCTTGGCTGGCTCCT
TGTCCAAGTGTCCAAGGTCCCCAGCTCCAGCTTCAGGAACAATCCAGGCAAGACG
CGATCTACCAGAACCTGACCCAGCTTAAAGCTGACGTGGGTGAGCTCTCAGAGAAA
TCCAAGCTGCAGGAGATCTACCAGGAGCTGACCCAGCTGAAGGCTGCAGTGGGTGA
GCTTCCAGAGAAATCTAAGCTGCAGGAGATCTACCAGGAGCTGACCCGGCTGAAGG
CTGCAGTGGGTGAGCTTCCAGAGAAATCTAAGCTGCAGGAGATCTACCAGGAGCTG
ACCTGGCTGAAGGCTGCAGTCGGCTGACTCGGCTGAAGGCTGAGCTTCCAGAGAAATCTA
AGCAGGAGGAGATCTACCAGGAGCAGGAGAAATCTAAGCAGGAGCTGACCCGGCTGAAGGCTGC
CCAGAGAAATCTAAGCAGCAGGAGATCTACCAGGAGCTGACCCGGCTGAAGGCTGC
AGTGGGTGAGCTTCCAGAGAAATCTAAGCAGGAGATCTACCAGGAGCTGACC
CAGCTGAAGGCTGCAGTGGCAGACTGTTACTTCATGTCTAACTGTCCAGCGAATGGACATT
CTTCCAAGGAAACTGTTACTTCATGTCTAACTGTCCCAGCGAACTGGCACGACTCCAT
CACCGCCTGCAAAGAAGAAGTGGGCCAGCTCGTCGTAATCAAAGTGCTGAGGAGC
AGAACTTCTACAGCAGCTGCAGTCTTCCAGAAGCTTCACCTGGATGGGACTTT
CAGATCTAAATCAGGAAGGCACGTGGGTGCAATGGGTGGACGCTCACCCTCTGTTGCCC
AGCTTCAAGCAGTATTGGGCAATGGCTGGAACGACCAACGTTGGGAGGAAGACTG
CGGGAATTTAGTGGCAATGGCTGGAACGACGACAAATGTAATCTGCCAAATTCTG
GATCTGCAAAAGTCCGCAGCCTCTGCTCCAGGGATGAAGAACAGTTTCTTCTCC
AGCCCCTGCCACCCCAAACCCCCCTCCTGCG (SEQ. ID. NO. 9)

Fig. 11

Chimpanzee

ATGAGTGACTCCAAGGAACCAAGACTGCAGCAGCTGGGCCTGGAGGAGGAACA
GCTGAGAGGCCTTGGATTCCGACAGACTCGAGGCTACAAGAGCTTAGCAGGGTGTC
TTGGCCATGGTCCCCTGGTGCTGCTCAACTCCTCCTTCACGGCTTGGCTGGGCTCCT
TGTCCAAGTGTCCAAGGTCCCCAGCTCCAGTCTCAGGAAGAATCAGGCAAGACG
TGATCTACCAGAACCTGACCCAGCCAGCTTAAAGCTGCAGTGGGTGAGCTCTCAGAGAAA
TCCAAGCTGCAGGAGATCTACCAGGAGCTGACCCAGCTGAAGGCTGCAGTGGGTGA
GCTCCAGAGAAATCTAAGCAGCAGGAGATCTACCAGGAGCTGACCCGGCTGAAGG
CTGCAGTGGGTGAGCTTCCAGAGAAATCTAAGATGCAGGAGATCTACCAGGAGCTG
ACTGGGCTGAAGGCTGCAGTGGGTGAGCTTCCAGAGAAATCTAAGATGCAGGAGAT
CTACCAGGAGCTGACTGGGCTGAAGGCTGCAGTGGGTGAGCTTCCAGAGAAATCTA
AGCAGCAGGAGATCTACCAGGAGCTGACCCAGCTGAAGGCTGCAGTGGGTGAGCTT
CCAGAGAAATCTAAGCAGCAGGAGATCTACCAGGAGCTGACCCAGCTGAAGGCTGC
AGTGGGTGAGCTTCCAGAGAAATCTAAGCAGCAGGAGATCTACCAGGAGCTGACC
CGGCTGAAGGCTGCAGTGGAACGCCTGTGCCGCCGGCTGCCCCTGAACTGCACGACTCCAT
CTTCCAAGGAAACTGTTACTTCATGTCTAACTCCGGCAACTGCACGACTCCAT
CACTGCCTGCAAAGAAGTGCTGCAGTCTTCCAGAAGTGCCAGTCGTAATCAAAAGTGCTGAGGAGC
AGAACTTCCTACAGTGTGGAAGGCATGTGGCAACAGAGGAGCCAACAACGTTGGGAGGACTG
CAGATCTAAATGAGGAAGGCATGTGGCAACAGAGGAGCCAACAACGTTGGGAGGAAGACTG
AGCTTCAACCAGTAYTGGCAACAGAGGAGCCAACAACGTGTAATCTTGCCAAATTCTG
CGGGAATTTAGTGGCAATGGCTGAATGACGACAAATGTAATCTTGCCAAATTCTG
GATCTGCAAAAGGTCCGCAGCCTGCCAGGATGAAGAACAGTTTCTTCTCC
AGCCCTGCCACCCAAACCCCCCCTGCG (SEQ. ID. NO. 10)

Fig. 12

Gorilla

ATGAGTGACTCCAAGGAACCAAGGAACTGCAGCAGCTGGGCCTCCTGGAGGAACA
GCTGAGAGGCCTTGAGATTCCGAGACTCGAGGCTACAAGAGCTTAGCAGGGTGTC
TTGGCCATGTCCCCTGGTGCTGCAACTCCTCCTTCACGCTCTTGGCTGCGCTCCT
TGTCCAAGTGCAAGGTCCCCAGCTCCCATAAGTCAGGAACAATCCAGGCAAGACG
CGATCTACCAGAACCTGACCCAGTTTAAAGCTGCAGTGGGTGAGCTCTCAGAGAAA
TCCAAGCTGCAGGAGATCTATCAGGAGCTGACCCAGCTGAAGGCTGCAGTGGGTGA
GCTTCCAGAGAAATCTAAGCAGGAGATCTACCAGGAGCTGAGCCAGCTGAAGG
CTGCAGTGGGTGAGCTTCCAGAGCTTCCAGAGAAATCTAAGCAGGAGATCTACCAGGAGCTG
ACCCGGCTGAAGGCTGCAGTGGGTGAGCTTCCAGAGCTTCCAGAGCAGTGGGTGAGCTT
CTACCAGGAGCTGACCCGGCTGAAGGCTGAGCCAGCTGAAGGCTGCAGTGGGTGAGCTT
AGCAGCAGGAGATCTACCAGGAGCTGAGCCAGCTGAAGGCTGCAGCCAGCTGAAGGCTGC
CCAGAGAAATCTAAGCAGGAGATCTACCAGGAGCTGAGCCAGCTGAAGGCTGCC
AGTGGGTGAGCTTCCAGAGCTTCCAGAGAAATCTAAGCAGCAGGAGATCTACCAGGAGCTGACC
CAGCTGAAGGCTGCAGTGGGTTACTTCATGTCTAACTCCCAGCGACTGGGAATGGACATT
CTTCCAAGGAAACTGTTACTTCATGTCTAACTCCCAGCGAACTGGCACGACTCCAT
CACCCGCTGCCAAGAAGTGGGGCCCAGCTCGTGTAATCAAAAGTGCTGAGGAGC
AGAACTTCCTACAGCTGCAGTCTTCCAGAGTAACCGCTTCACCTGGATGGACTTT
CAGATCTAAATCATGAAGGCACGTGGCAATGGGTGACGCGTCACCTCTGTTGCCC
AGCTTCGAGCAGTATTGGTGGCAATGGGAGAGCCAACAACGTTGGGGAGAAGACTG
CGGGAATTTAGTGGCAATGGGAACGATGACAAATGTAATCTTGCCAAATTCTG
GATCTGCAAAAGTCTGCAGCCTCCTGCTCCAGGGATGAAGAACAGTTTCTTCTCC
AGCCCTCTGCCACCCCCAAACCCCCCTGCG (SEQ. ID. NO. 11)

Fig. 13

```
   1 ctccagacct acccagaaag atgcccggat ggatcctgca gctccgtggc ttttctggga
  61 agcagcggcc cctgctctca agagaccctg gctcctgatg gtggcccaa ggttgccagc
 121 tggtgctagg gactcaggac agtttcccag aaaaggccaa gcggcagcc cctccagggg
 181 ccgggtgagg aagctggggg gtgcggaggc cacactggt ccctgaaccc cctgcttggt
 241 tacagtgcag ctcctcaagt ccacagacgt gggccggcac agcctcctgt acctgaagga
 301 aatcggccgt ggctggttcg ggaaggtgtt cctgggggag gtgaactctg catcagcag
 361 tgcccaggtg gtggtgaagg agctgcaggc tagtgccagc gtgcaggagc agatgcagtt
 421 cctggaggag gtgcagccct acagggccct gaagcacagc aacctgctcc agtgcctggc
 481 ccagtgcgcc gaggtgacgc cctacctgct ggtgatggag ttctgcccac tgggggacct
 541 caaggctac ctgcggagct gccgggtggc ggagtccatg gctcccgacc cccggaccct
 601 gcagcgcatg gcctgtgagg tggcctgtgg cgtcctgcac cttcatcgca acaatttcgt
 661 gcacagcgac ctggccctgc ggaactgcct gctcacggct gacctgacgg tgaagattgg
 721 tgactatggc ctggctcact gcaagtacag agaggactac ttcgtgactg ccgaccagct
 781 gtgggtgcct ctgcgctgga tcgcgccaga gctggtggac gaggtgcata gcaacctgct
 841 cgtcgtggac cagaccaaga gcgggaatgt gtggtccctg ggcgtgacca tctgggagct
 901 ctttgagctg ggcacgcagc cctatcccca gcactcggac cagcaggtgc tggcgtacac
 961 ggtccgggag cagcagctca agctgcccaa gccccagctg cagctgaccc tgtcggaccg
1021 ctggtacgag gtgatgcagt tctgctggct gcagcccgag cagcggccca gccgagga
1081 ggtgcacctg ctgctgtcct acctgtgtgc caaggcgcc accgaagcag aggaggagtt
1141 tgaacggcgc tggcgctctc tgcggcccgg cggggcggc gtggggcccg ggcccggtgc
1201 ggcggggccc atgctgggcg cgtggtgga gctcgccgct gcctcgtcct tcccgctgct
1261 ggagcagttc gcgggcgacg gcttccacgc ggacggcgac gacgtgctga cggtgaccga
1321 gaccagccga ggcctcaatt ttgagtacaa gtgggaggcg gccgcggcg cggaggcctt
1381 cccggccacg ctgagccctg ccgcaccgc acgcctgcag gagctgtgcg ccccgacgg
1441 cgcgccccg gcgtggttc cggtgctcag cgcgcacagc ccgtcgctgg gcagcgagta
1501 cttcatccgc ctagaggagg ccgcacccgc cgccggccac gaccctgact gcgccggctg
1561 cgcccccagt ccacctgcca ccgcggacca ggacgacgac tctgacggca gcaccgccgc
1621 ctcgctggcc atggagccgc tgctgggcca cgggccaccc gtcgacgtcc cctggggccg
1681 cggcgaccac taccctcgca gaagcttggc gcgggacccg ctctgcccct cacgctctcc
1741 ctcgccctcg gcggggcccc tgagtctggc ggagggagga gcggaggatg cagactgggg
1801 cgtggccgcc ttctgtcctg ccttcttcga ggacccactg ggcacgtccc ctttggggag
1861 ctcaggggcg ccccgctgc cgctgactgg cgaggatgag ctagaggagg tgggagcgcg
1921 gagggccgcc cagcgcgggc actggcgctc aacgtgtca gccaacaaca acagcggcag
1981 ccgctgtcca gagtcctggg accccgtctc tgcgggctgc cacgctgagg gctgccccag
2041 tccaaagcag acccacgggg cctcccccga gccggggtac cctggagagc ctctgcttgg
2101 gctccaggca gcctctgccc aggagccagg ctgctgcccc ggcctccctc atctatgctc
2161 tgcccagggc ctggcacctg ctccctgcct ggttacaccc tcctggacag agacagccag
2221 tagtgggggt gaccacccgc aggcagagcc aagcttgcc acggaggctg agggcactac
2281 cggaccccgc ctgccccttc cttccgtccc ctccccatcc caggagggag ccccacttcc
2341 ctcggaggag gccagtgccc ccgacgcccc tgatgccctg cctgactctc ccacgcctgc
2401 tactggtggc gaggtgtctg ccatcaagct ggcttctgcc ctgaatggca gcagcagctc
2461 tcccgaggtg gaggcaccca gcagtgagga tgaggacacg gctgaggcca cctcaggcat
2521 cttcaccgac acgtccagcg acggcctgca ggccaggagg ccggatgtgg tgccagcctt
2581 ccgctctctg cagaagcagg tggggacccc cgactccctg gactcctgg acatcccgtc
2641 ctcagccagt gatggtggct atgaggtctt cagcccgtcg ccactggcc cctctggagg
2701 gcagccgcga cgcgctggaca gtggctatga caccgagaac tatgagtccc ctgagtttgt
2761 gctcaaggag cgcgcaggaag ggtgtgagcc ccaggccttt gcggagctgg cctcagaggg
2821 tgagggcccc gggcccgaga cacggctctc cacctccctc agtggcctca acgagaagaa
2881 tccctaccga gactctgcct acttctcaga cctcgaggct gaggccgagg ccacctcagg
2941 cccagagaag aagtgcggcg ggaccgagc ccccgggcca gagctgggcc tgccgagcac
3001 tgggcagccg tctgagcagg tctgtctcag gcctggggtt ccggggagg cacaaggctc
```

Figure 14A

```
3061 tggccccggg gaggtgctgc ccccactgct gcagcttgaa gggtcctccc cagagcccag
3121 cacctgcccc tcgggcctgg tcccagagcc tccggagccc caaggcccag ccaaggtgcg
3181 gcctgggccc agccccagct gctcccagtt tttcctgctg accccggttc cgctgagatc
3241 agaaggcaac agctctgagt tccaggggcc cccaggactg ttgtcagggc cggccccaca
3301 aaagcggatg gggggcccag gcaccccag agccccactc cgcctggctc tgcccggcct
3361 ccctgcggcc ttggagggcc ggccggagga ggaggaggag gacagtgagg acagcgacga
3421 gtctgacgag gagctccgct gctacagcgt ccaggagcct agcgaggaca gcgaagagga
3481 ggcgccggcg gtgcccgtgg tggtggctga gagccagagc gcgcgcaacc tgcgcagcct
3541 gctcaagatg cccagcctgc tgtccgagac cttctgcgag gacctggaac gcaagaagaa
3601 ggccgtgtcc ttcttcgacg acgtcaccgt ctacctcttt gaccaggaaa gccccacccg
3661 ggagctcggg gagcccttcc cgggcgccaa ggaatcgccc cctacgttcc ttaggggag
3721 ccccggctct cccagcgccc caaccggcc gcagcaggct gatggctccc caaatggctc
3781 cacagcggaa gagggtggtg ggttcgcgtg ggacgacgac ttcccgctga tgacggccaa
3841 ggcagccttc gccatggccc tagacccggc cgcacccgcc ccggctgcgc cacgcccac
3901 gcccgctccc ttctcgcgct tcacggtgtc gcccgcgccc acgtcccgct tctccatcac
3961 gcacgtgtct gactcggacg ccgagtccaa gagaggacct gaagctggtg ccggggggtga
4021 gagtaaagag gct<ins>tga</ins>gacc tgggcagctc ctgcccctca aggctggcgt caccggagcc
4081 cctgccaggc agcagcgagg atggtgaccg agaaggtggg gaccacgtcc tggtggctgt
4141 tggcagcaga ttcaggtgcc tctgccccac gcggtgtcct ggagaagccc gtgggatgag
4201 aggccctgga tggtagatcg gccatgctcc gccccagagg cagaattcgt ctgggctttt
4261 aggcttgctg ctagcccctg ggggcgcctg gagccacagt gggtgtctgt acacacatac
4321 acactcaaaa ggggccagtg cccctgggca cggcggcccc caccctctgc cctgcctgcc
4381 tggcctcgga ggacccgcat gccccatccg gcagctcctc cggtgtgctc acaggacact
4441 taaaccagga cgaggcatgg ccccgagaca ctggcaggtt tgtgagcctc ttcccacccc
4501 ctgtgccccc acccttgcct ggttcctggt ggctcagggc aaggagtggc cctgggcgcc
4561 cgtgtcggtc ctgtttccgc tgcccttatc tcaaagtccg tggctgtttc cccttcactg
4621 actcagctag accgtaagc ccaccccttcc cacaggaac aggctgctcc cacctgggtc
4681 ccgctgtggc cacggtgggc agcccaaaag atcaggggtg gagggcttc caggctgtac
4741 tcctgccccg tgggccccgt tctagaggtg cccttggcag gaccgtgcag gcagctcccc
4801 tctgtgggc agtatctggt cctgtgcccc agctgccaaa ggagagtggg ggccatgccc
4861 cgcagtcagt gttgggggc tcctgcctac agggagaggg atggtgggga aggggtggag
4921 ctgggggcag ggcagcacag ggaatatttt tgtaactaac taactgctgt ggttggagcg
4981 aatggaagtt gggtgatttt aagttattgt tgccaaagag atgtaaagtt tattgttgct
5041 tcgcagggg atttgttttg tgtttgttt gaggcttaga acgctggtgc aatgttttct
5101 tgttccttgt tttttaagag aaatgaagct aagaaaaaag (SEQ ID NO: 14 and 15)
```

Figure 14A (continued)

MQFLEEVQPYRALKHSNLLQCLAQCAEVTPYLLVMEFCPLGDLKGYLRSCRVAESMAP
DPRTLQRMACEVACGVLHLHRNNFVHSDLALRNCLLTADLTVKIGDYGLAHCKYRED
YFVTADQLWVPLRWIAPELVDEVHSNLLVVDQTKSGNVWSLGVTIWELFELGTQPYPQ
HSDQQVLAYTVREQQLKLPKPQLQLTLSDRWYEVMQFCWLQPEQRPTAEEVHLLLSYL
CAKGATEAEEEFERRWRSLRPGGGGVGPGPGAAGPMLGGVVELAAASSFPLLEQFAGD
GFHADGDDVLTVTETSRGLNFEYKWEAGRGAEAFPATLSPGRTARLQELCAPDGAPPG
VVPVLSAHSPSLGSEYFIRLEEAAPAAGHDPDCAGCAPSPPATADQDDDSDGSTAASLA
MEPLLGHGPPVDVPWGRGDHYPRRSLARDPLCPSRSPSPSAGPLSLAEGGAEDADWGV
AAFCPAFFEDPLGTSPLGSSGAPPLPLTGEDELEEVGARRAAQRGHWRSNVSANNNSGS
RCPESWDPVSAGCHAEGCPSPKQTPRASPEPGYPGEPLLGLQAASAQEPGCCPGLPHLCS
AQGLAPAPCLVTPSWTETASSGGDHPQAEPKLATEAEGTTGPRLPLPSVPSPSQEGAPLP
SEEASAPDAPDALPDSPTPATGGEVSAIKLASALNGSSSSPEVEAPSSEDEDTAEATSGIFT
DTSSDGLQARRPDVVPAFRSLQKQVGTPDSLDSLDIPSSASDGGYEVFSPSATGPSGGQP
RALDSGYDTENYESPEFVLKEAQEGCEPQAFAELASEGEGPGPETRLSTSLSGLNEKNPY
RDSAYFSDLEAEAEATSGPEKKCGGDRAPGPELGLPSTGQPSEQVCLRPGVSGEAQGSG
PGEVLPPLLQLEGSSPEPSTCPSGLVPEPPEPQGPAKVRPGPSPSCSQFFLLTPVPLRSEGN
SSEFQGPPGLLSGPAPQKRMGGPGTPRAPLRLALPGLPAALEGRPEEEEEDSEDSDESDE
ELRCYSVQEPSEDSEEEAPAVPVVVAESQSARNLRSLLKMPSLLSETFCEDLERKKKAVS
FFDDVTVYLFDQESPTRELGEPFPGAKESPPTFLRGSPGSPSAPNRPQQADGSPNGSTAEE
GGGFAWDDDFPLMTAKAAFAMALDPAAPAPAAPTPTPAPFSRFTVSPAPTSRFSITHVS
DSDAESKRGPEAGAGGESKEA (SEQ ID NO:16)

Figure 14B

```
GCTCCCTGCCTGGTTACACCCTCCTGGACAGAGACAGCCGGTAGTGGGGGTGACCACCCGCAGGCAGAGCC
CAAGCTTGCCACGGAGGCTGAGGGCACTGCCGGACCCTGTCTGCCCCTTCCTTCCGTCCCCTCCCCATCCC
AGGAGGGAGCCCCACTTCCCTCGGAGGAGGCCAGTGCCCCTGACGCCCTGATGCCCTGCCTGACTCTCCC
ATGCCTGCTACTGGTGGCGAGGTGTCTGCCATCAAGCTGGCTTCTGTCCTGAATGGCAGCAGCAGCTCTCC
CGAGGTGGAGGCACCCAGCAGCGAGGATGAGGACACGGCTGAGGCCACCTCAGGCATCTTCACCGACACGT
CCAGCGACGGCCTGCAGGCCGAGAGGCTGGATGTGGTGCCAGCCTTCCGCTCTCTGCAGAAGCAGGTGGGG
ACCCCCGACTCCCTGGACTCCCTGGACATCCCATCCTCAGCCAGTGATGGTGGCTATGAGGTCTTCAGCCC
GTCGGCCACTGGCCCCTCTGGAGGGCAGCCCCGAGCGCTGGACAGTGGCTATGACACCGAGAACTATGAGT
CCCCTGAGTTTGTGCTCAAGGAGGCGCAGGAAGGGTGTGAGCCCCAGGCCTTTGAGGAGCTGGCCTCAGAG
GGTGAGGGCCCCGGCCCCGGGCCCGAGACGCGGCTCTCCACCTCCCTCAGTGGCCTCAACGAGAAGAATCC
CTACCGAGACTCTGCCTACTTCTCAGACCTGGAGGCTGAGGCCGAGGCCGAGGCCACCTCAGGCCCAGAGA
AGAAGTGCGGCGGGGACCAAGCCCCGGGCCAGAGCTGGACCTGCCGAGCACTGGGCAGCCGTCTGAGCAG
GTCTCCCTCAGGCCTGGGGTTTCCGGGGAGGCACAAGGCTCTGGCCCCGGGGAGGTGCTGCCCCACTGCT
GCGGCTTGAAGGATCCTCCCCAGAGCCCAGCACCTGCCCCTCGGGCCTGGTCCCAGAGCCTCCGGAGCCCC
AAGGCCCAGCCGAGGTGCGGCCTGGGCCCAGCCCCAGCTGCTCCCAGTTTTCCTGCTGACCCCGGTTCCG
CTGAGATCAGAAGGCAACAGCTCTGAGTTCCAGGGGCCCCAGGACTGTTGTCAGGGCCGGCCCCACAAAA
GCGGATGGGGGGCCTAGGCACCCCAGAGCCCCACTCCGCCTGGCTCTGCCCGGCCTCCCTGCGGCCTTGG
AGGGCCGGCCGGAGGAGGAGGAGGAGGACAGTGAGGACAGCGGCGAGTCTGACGAGGAGCTCCGCTGCTAC
AGCGTCCAGGAGCCTAGCGAGGACAGCGAAGAGGAGGCGCCGGCGGTGCCCGTGGTGGTGGCTGAGAGCCA
GAGCGCGCGCAACCTGCGCAGCCTGCTCAAGATGCCCAGCCTGCTGTCCGAGGCCTTCTGCGAGGACCTGG
AACGCAAGAAGAAGGCCGTGTCCTTCTTCGACGACGTCACCGTCTACCTCTTTGACCAGGAAAGCCCCACC
TGGGAGCTCGGGGAGCCCTTCCCGGGCGCCAAGGAATCGCCCCCCACGTTCCTTAGGGGGAGCCCCGGCTC
TCCCAGCGCCCCCAACCGGCCGCAGCAGGCTGATGGCTCCCCAAATGGCTCCACAGCGGAAGAGGGTGGTG
GGTTCGCGTGGGACGACGACTTCCCGCTGATGCCGGCCAAGGCAGCCTTCGCCATGGCCCTAGACCCGGCC
GCACCCGCCCCGGCTGCGCCCACGCCC******GCTCCCTTCTCGCGCTTCACGGTGTCGCCCGCGCCCAC
GTCCACGTCCCGCTTCTCCATCACGCACGTGTCT    (SEQ ID NO:17)
```

Figure 15A

```
GCTCCCTGCCTGGTTACACCCTCCTGGACAGAGACAGACGGTAGTGGGGGTGACCACCCGCAGGCAGAGCC
CAAGCTTGCCACGGAGGCTGAGGGCACTGCCGGACCCCGCCTGCCCCTTCCTTCCGTCCCCTCCCCATCCC
AGGAGGGAGCCCCACTTCCCTCGGAGGAGGCCAGTGCCCCGACGCCCTGATGCCCTGCCTGACTCGCCC
ACGCCTGCTACTGGTGGCGAGGTGTCTGCCACCAAGCTGGCTTCCGCCCTGAATGGCAGCAGCAGCTCTCC
CGAGGTGGAGGCACCCAGCAGTGAGGATGAGGACACGGCTGAGGCAACCTCAGGCATCTTCACCGACACGT
CCAGCGACGGCCTGCAGGCCGAGAGGCAGGATGTGGTGCCAGCCTTCCACTCTCTGCAGAAGCAGGTGGGG
ACCCCCGACTCCCTGGACTCCCTGGACATCCCGTCCTCAGCCAGTGATGGTGGCTATGAGGTCTTCAGCCC
GTCGGCCACGGGCCCCTCTGGAGGGCAGCCCCGAGCGCTGGACAGTGGCTATGACACCGAGAACTATGAGT
CCCCTGAGTTTGTGCTCAAGGAGGCGCAGGAAGGGTGTGAGCCCCAGGCCTTTGCGGAGCTGGCCTCAGAG
GGCGAGGGC******CCCGGGCCCGAGACGCGGCTCTCCACCTCCCTCAGTGGCCTCAACGAGAAGAATCC
CTACCGAGATTCTGCCTACTTCTCAGACCTGGAGGCT******GAGGCCGAGGCTACCTCAGGCCCAGAGA
AGAAGTGCGGTGGGGACCAAGCCCCGGGCCAGAGCTGGGCCTGCCGAGCACTGGGCAGCCGTCTGAGCAG
GTCTCCCTCAGTCCTGGGGTTTCCGTGGAGGCACAAGGCTCTGGCCCCGGGGAGGTGCTGCCCCACTGCT
GCGGCTTGAAGGGTCCTCCCCAGAGCCCAGCACCTGCCCCTCGGGCCTGGTCCCAGAGCCTCCGGAGCCCC
AAGGCCCAGCCGAGGTGCGGCCTGGGCCCAGCCCCAGCTGCTCCCAGTTTTCCTGCTGACCCCGGTTCCG
CTGAGATCAGAAGGCAACAGCTCTGAGTTCCAGGGGCCCCAGGACTGTTGTCAGGGCCGGCCCCACAAAA
GCGGATGGGGGGCCCAGGCACCCCAGAGCCCCACACCGCCTGGCTCTGCCCGGCCTCCCTGCGGCCTTGG
AGGGCCGGCCGGAGGAGGAGGAGGAGGACAGTGAGGACAGCGACGAGTCTGACGAGGAGCTCCGCTGCTAC
AGCGTCCAGGAGCCTAGCGAGGACAGCGAAGAGGAGGCGCCGGCGGTGCCCGTGGTGGTGGCTGAGAGCCA
GAGCGCGCGCAACCTGCGCAGCCTGCTCAAGATGCCCAGCCTGCTGTCCGAGGCCTTCTGCGAGGACCTGG
AACGCAAGAAGAAGGCCGTGTCCTTCTTCGACGACGTCACCGTCTACCTCTTTGACCAGGAAAGCCCCACC
CGGGAGCTCGGGGAGCCCTTCCCGGGCGCCAAGGAATCGCCCCCACGTTCCTTAGGGGGAGCCCCGGCTC
TTCCAGCGCCCCCAACCGGCCGCAGCAGGCTGATGGCTCCCCAAATGGCTCCACAGCGGAAGAGGGTGGTG
GGTTCGCGTGGGACGACGACTTCCCGCTGATGCCGGCCAAGGCAGCCTTCGCCATGGCCCTAGACCCGGCC
GCACCCGCCCCGGCTGCGCCCACGCCC******GCTCCCTTCTCGCGCTTCACGGTGTCGCCCGCGCCCAC
GTCC::::::CGCTTCTCCATCACGCACGTGTCT    (SEQ ID NO:18)
```

Figure 15B

| | | | | | | | | | | |
|---|---|---|---|---|---|---|---|---|---|---|
| Hs | ATG | GCA | GTG | ACA | ACT | CGT | TTG | ACA | TGG | TTG | CAC | GAA | AAG | ATC | CTG | 45 |
| Pt | ATG | GCA | GTG | ACA | ACT | CGT | TTG | ACA | TGG | TTG | CAT | GAA | AAG | ATC | CTG | |
| Hs | CAA | AAT | CAT | TTT | GGA | GGG | AAG | CGG | CTT | CTC | TAT | AAG | GGT | | | 90 |
| Pt | CAA | AAT | CAT | TTT | GGA | GGG | AAG | CGG | CTT | CTC | TAT | AAG | GGT | | | |
| Hs | AGT | GTC | CAT | GGA | TTC | CGT | AAT | GGA | GTT | TTG | CTT | GAC | AGA | TGT | TGT | 135 |
| Pt | AGT | GTC | CAT | GGA | TTC | CAT | AAT | GGA | GTT | TTG | CTT | GAC | AGA | TGT | TGT | |
| Hs | AAT | CAA | GGG | CCT | ACT | CTA | ACA | GTG | ATT | TAT | AGT | GAA | GAT | CAT | ATT | 180 |
| Pt | AAT | CAA | GGG | CCT | ACT | CTA | ACA | GTG | ATT | TAT | AGT | GAA | GAT | CAT | ATT | |
| Hs | ATT | GGA | GCA | TAT | GCA | GAA | GAG | AGT | TAC | CAG | GAA | GGA | AAG | TAT | GCT | 225 |
| Pt | ATT | GGA | GCA | TAT | GCA | GAA | GAG | GGT | TAC | CAG | GMA | AGA | AAG | TAT | GCT | |
| Hs | TCC | ATC | ATC | CTT | TTT | GCA | CTT | CAA | GAT | ACT | AAA | ATT | TCA | GAA | TGG | 270 |
| Pt | TCC | ATC | ATC | CTT | TTT | GCA | CTT | CAA | GAG | ACT | AAA | ATT | TCA | GAA | TGG | |
| Hs | AAA | CTA | GGA | CTA | TGT | ACA | CCA | GAA | ACA | CTG | TTT | TGT | TGT | GAT | GTT | 315 |
| Pt | AAA | CTA | GGA | TAT | ACA | CCA | GAA | ACA | CTG | TTT | TGT | TGT | GAC | GTT | | |
| Hs | ACA | AAA | TAT | AAC | TCC | CCA | ACT | AAT | TTC | CAG | ATA | GAT | GGA | AGA | AAT | 360 |
| Pt | GCA | AAA | TAT | AAC | TCC | CCA | ACT | AAT | TTC | CAG | ATA | GAT | GGA | AGA | AAT | |
| Hs | AGA | AAA | GTG | ATT | ATG | GAC | TTA | AAG | ACA | ATG | GAA | AAT | CTT | GGA | CTT | 405 |
| Pt | AGA | AAA | GTG | ATT | ATG | GAC | TTA | AAG | ACA | ATG | GAA | AAT | CTT | GGA | CTT | |
| Hs | GCT | CAA | AAT | TGT | ACT | ATC | TCT | ATT | CAG | GAT | TAT | GAA | GTT | TTT | CGA | 450 |
| Pt | GCT | CAA | AAT | TGT | ACT | ATC | TCT | ATT | CAG | GAT | TAT | GAA | GTT | TTT | CGA | |

FIGURE 16

| | | | | | | | | | | |
|---|---|---|---|---|---|---|---|---|---|---|
| Hs | TGC | GAA | GAT | TCA | CTG | GAT | GAA | AGA | ATA | AAA | GGG | GTC | ATT | GAG | 495 |
| Pt | TGC | GAA | GAT | TCA | CTG | GAC | GAA | AGA | ATA | AAA | GGG | GTC | ATT | GAG | |
| Hs | CTC | AGG | AAG | AGC | TTA | CTG | TCT | GCC | TTG | AGA | ACT | TAT | GAA | CCA | TAT | 540 |
| Pt | CTC | AGG | AAG | AGC | TTA | CTG | TCT | GCC | TTG | AGA | ACT | TAT | GAA | CCA | TAT | |
| Hs | GGA | TCC | CTG | GTT | CAA | CAA | ATA | CGA | ATT | CTC | CTG | GGT | CCA | ATT | 585 |
| Pt | GGA | TCC | CTG | GTT | CAA | CAA | ATA | CGA | ATT | CTG | CTG | GGT | CCA | ATT | |
| Hs | GGA | GCT | CCC | AAG | TCC | AGC | TTT | TTC | AAC | TCA | GTG | AGG | TCT | GTT | TTC | 630 |
| Pt | GGA | GCT | GGG | AAG | TCT | AGC | TTT | TTC | AAC | TCA | GTG | AGG | TCT | GTT | TTC | |
| Hs | CAA | GGG | CAT | GTA | ACG | CAT | CAG | GCT | TTG | GTG | GGC | ACT | AAT | ACA | ACT | 675 |
| Pt | CAA | GGG | CAT | GTA | ACG | CAT | CAG | GCT | TTG | GTG | GGC | ACT | AAT | ACA | ACT | |
| Hs | GGG | ATA | TCT | GAG | AAG | TAT | AGG | ACA | TAC | TCT | ATT | AGA | GAC | GGG | AAA | 720 |
| Pt | GGG | ATA | TCT | GAG | AAG | TAT | AGG | ACA | TAC | TCT | ATT | AGA | GAC | GGG | AAA | |
| Hs | GAT | GGC | AAA | TAC | CTG | CCG | TTT | ATT | CTG | TGT | GAC | TCA | CTG | GGG | CTG | 765 |
| Pt | GAT | GGC | AAA | TAC | CTG | CCA | TTT | ATT | CTG | TGT | GAC | TCA | CTG | GGG | CTG | |
| Hs | AGT | GAG | AAA | GAA | TAC | CTG | GGC | AGG | GAT | GAC | ATA | TTC | TAT | ATC | 810 |
| Pt | AGT | GAG | AAA | GAA | TAC | CTG | GGC | ATG | GAT | GAC | ATA | TCC | TAC | ATC | |
| Hs | TTG | AAC | GGT | AAC | ATT | CGT | GAT | AGA | TTT | AAT | CCC | ATG | GAA | 855 |
| Pt | TTG | AAC | GGT | AAC | ATT | CGT | GAT | AGA | TTT | AAT | CCC | ATG | GAA | |
| Hs | TCA | ATC | AAA | TTA | AAT | CAT | CAT | GAC | TAC | ATT | GAT | TCC | CCA | TCG | CTG | 900 |
| Pt | TCA | ATC | AAA | TTA | AAT | CAT | CAT | GAC | TAC | ATT | GAT | TCC | CCA | TCG | CTG | |

FIGURE 16 (CONT.)

| | | | | | | | | | | |
|---|---|---|---|---|---|---|---|---|---|---|
| Hs | AAG | GAC | AGA | ATT | CAT | TGT | GTG | GCA | TTT | GAT | GCC | AGC | TCT | 945 |
| Pt | AAG | GAC | AGA | ATT | CAT | TGT | GTG | GCA | TTT | GAT | GCC | AGC | TCT | |
| Hs | ATT | CAA | TAC | TTC | TCC | TCT | CAG | ATG | ATA | AAG | ATC | AAA | AGA | ATT | 990 |
| Pt | ATT | GAA | TAC | TTC | TCC | TCT | CAG | ATG | ATA | AAG | ATC | AAA | AGA | ATT | |
| Hs | CAA | AGG | GAG | TTG | GTA | AAC | GCT | GGT | GTG | CAT | GTG | GCT | TTG | CTC | 1035 |
| Pt | CGA | AGG | GAG | TTG | GTA | AAC | GCT | GGT | GTG | CAT | GTG | GCT | TTG | CTC | |
| Hs | ACT | CAT | GTG | GAT | AGC | ATG | GAT | TTG | ATT | ACA | AAA | GGT | GAC | CTT | ATA | 1080 |
| Pt | ACT | CAT | GTG | GAT | AGC | ATG | GAT | CTG | ATT | ACA | AAA | GGT | GAC | CTT | ATA | |
| Hs | GAA | ATA | GAG | AGA | TGT | GAG | CCT | GTG | AGG | TCC | AAG | CTA | GAG | GAA | GTC | 1125 |
| Pt | GAA | ATA | GAG | AGA | TGT | GTG | CCT | GTG | AGG | TCC | AAG | CTA | GAG | GAA | GTC | |
| Hs | CAA | AGA | AAA | CTT | GGA | TTT | GCT | CTT | TCT | GAC | ATC | CCT | GTA | AAG | CTA | 1170 |
| Pt | CAA | AGA | AAA | CTT | GGA | TTT | GCT | CTT | TCT | GAC | ATC | CCT | GTA | AAG | CTA | |
| Hs | AAT | TAT | TCC | TCT | TCT | GCT | CTG | TGG | GAC | ATG | CTA | TGG | GCT | GCA | GAT | GTT | CTA | 1215 |
| Pt | AAT | TAT | TCC | TCT | TCT | GCT | CTG | TGG | GAC | ATG | CTA | TGG | GCT | GCA | GAT | GTT | CTA | |
| Hs | ATT | CTT | TCT | GCT | CTG | AGA | CGA | ATG | CTA | CAA | ATA | TGG | GCT | GCA | GAT | GAC | TTC | 1260 |
| Pt | ATT | CTT | TCT | GCT | CTG | AGA | CGA | ATG | CTA | CAA | ATA | TGG | GCT | GCA | GAT | GAC | TTC | |
| Hs | TTA | GAG | GAT | TTG | CCT | TTT | GAG | CAA | ATA | GGG | AAT | CTA | AGG | GAG | GAA | 1305 |
| Pt | TTA | GAG | GAT | TTG | CCT | TTT | GAG | CAA | ATA | GGG | AAT | CTA | AGG | GAG | GAA | |
| Hs | ATT | ATC | AAC | TGT | GCA | CAA | GGA | AAA | AAA | TAG | | | | | (SEQ. ID. NO. 34) | 1335 |
| Pt | ATT | ATC | AAC | TGT | GCA | CAA | GGA | AAA | AAA | TAG | | | | | (SEQ. ID. NO. 31) | |

FIGURE 16 (CONT.)

SEQUENCE LISTING

```
<160> NUMBER OF SEQ ID NOS: 84

<210> SEQ ID NO 1
<211> LENGTH: 1518
<212> TYPE: DNA
<213> ORGANISM: Homo sapiens

<400> SEQUENCE: 1
cagacatctg tgtcccctc  aaaagtcatc ctgcccggg  gaggctccgt gctggtgaca        60
tgcagcacct cctgtgacca gcccaagttg ttgggcatag agaccccgtt gcctaaaaag       120
gagttgctcc tgcctgggaa caaccggaag gtgtatgaac tgagcaatgt gcaagaagat       180
agccaaccaa tgtgctattc aaactgccct gatgggcagt caacagctaa aaccttcctc       240
```

-continued

```
accgtgtact ggactccaga acgggtggaa ctggcacccc tccctcttg gcagccagtg      300 ggcaagaacc ttaccctacg ctgccaggtg gagggtgggg caccccgggc aacctcacc      360 gtggtgctgc tccgtgggga aaggagctg aaacgggagc cagctgtggg ggagcccgct      420
gaggtcacga ccacggtgct ggtgaggaga gatcaccatg gagccaattt ctcgtgccgc      480
actgaactgg acctgcggcc ccaagggctg agctgtttg agaacacctc ggcccctac       540 cagctccaga cctttgtcct gccagcgact cccccacaac ttgtcagccc ccgggtccta     600
gaggtggaca cgcaggggac cgtggtctgt tccctggacg ggctgttccc agtctcggag     660
gcccaggtcc acctggcact gggggaccag aggttgaacc ccacagtcac ctatggcaac    720
gactccttct cggccaaggc ctcagtcagt gtgaccgcag aggacgaggg cacccagcgg    780
ctgacgtgtg cagtaatact ggggaaccag agccaggaga cactgcagac agtgaccatc    840
tacagctttc cggcgcccaa cgtgattctg acgaagccag aggtctcaga agggaccgag    900
gtgacagtga agtgtgaggc ccaccctaga gccaaggtga cgctgaatgg ggttccagcc    960
cagccactgg gcccgaggc ccagctcctg ctgaaggcca ccccagagga caacgggcgc    1020
agcttctcct gctctgcaac cctggaggtg gccggccagc ttatacacaa gaaccagacc    1080
cgggagcttc gtgtcctgta tggccccga ctggacgaga gggattgtcc gggaaactgg    1140
acgtggccag aaaattccca gcagactcca atgtgccagg cttggggaa cccattgccc     1200 gagctcaagt gtctaaagga tggcactttc ccactgccca tcggggaatc agtgactgtc   1260
actcgagatc ttgagggcac ctacctctgt cggccaggca cactcaagg ggaggtcacc    1320 cgcgaggtga ccgtgaatgt gctctccccc cggtatgaga ttgtcatcat cactgtggta   1380
gcagccgcag tcataatggg cactgcaggc ctcagcacgt acctctataa ccgccagcgg   1440
aagatcaaga aatacagact acaacaggcc caaaaggga ccccatgaa accgaacaca    1500 caagccacgc ctccctga                                                    1518
```

<210> SEQ ID NO 2
<211> LENGTH: 1518
<212> TYPE: DNA
<213> ORGANISM: Pan troglodytes
<220> FEATURE:
<221> NAME/KEY: CDS
<222> LOCATION: (1)..(1518)

<400> SEQUENCE: 2

```
cag aca tct gtg tcc ccc tca aaa gtc atc ctg ccc cgg gga ggc tcc       48
Gln Thr Ser Val Ser Pro Ser Lys Val Ile Leu Pro Arg Gly Gly Ser
1               5                   10                  15 gtg ctg gtg aca tgc agc acc tcc tgt gac cag ccc aag ttg ttg ggc       96
Val Leu Val Thr Cys Ser Thr Ser Cys Asp Gln Pro Lys Leu Leu Gly
            20                  25                  30 ata gag acc ccg ttg cct aaa aag gag ttg ctc ctg cct ggg aac aac     144
Ile Glu Thr Pro Leu Pro Lys Lys Glu Leu Leu Leu Pro Gly Asn Asn
        35                  40                  45 cgg aag gtg tat gaa ctg agc aat gtg caa gaa gat agc caa cca atg     192
Arg Lys Val Tyr Glu Leu Ser Asn Val Gln Glu Asp Ser Gln Pro Met
    50                  55                  60 tgc tat tca aac tgc cct gat ggg cag tca aca gct aaa acc ttc ctc     240
Cys Tyr Ser Asn Cys Pro Asp Gly Gln Ser Thr Ala Lys Thr Phe Leu
65                  70                  75                  80 acc gtg tac tgg act cca gaa cgg gtg gaa ctg gca ccc ctc ccc tct     288
Thr Val Tyr Trp Thr Pro Glu Arg Val Glu Leu Ala Pro Leu Pro Ser
                85                  90                  95
```

```
tgg cag cca gtg ggc aag aac ctt acc cta cgc tgc cag gtg gag ggt     336
Trp Gln Pro Val Gly Lys Asn Leu Thr Leu Arg Cys Gln Val Glu Gly
            100                 105                 110 ggg gca ccc cgg gcc aac ctc acc gtg gtg ctc ctc cgt ggg gag aag     384
Gly Ala Pro Arg Ala Asn Leu Thr Val Val Leu Leu Arg Gly Glu Lys
        115                 120                 125 gag ctg aaa cgg gag cca gct gtg ggg gag ccc gct gag gtc acg acc     432
Glu Leu Lys Arg Glu Pro Ala Val Gly Glu Pro Ala Glu Val Thr Thr
130                 135                 140 acg gtg ctg gtg agg aga gat cac cat gga gcc aat ttc tcg tgc cgc     480
Thr Val Leu Val Arg Arg Asp His His Gly Ala Asn Phe Ser Cys Arg
145                 150                 155                 160 act gaa ctg gac ctg cgg ccc caa ggg ctg gag ctg ttt gag aac acc     528
Thr Glu Leu Asp Leu Arg Pro Gln Gly Leu Glu Leu Phe Glu Asn Thr
                165                 170                 175 tcg gcc ccc tac cag ctc cag acc ttt gtc ctg cca gcg act ccc cca     576
Ser Ala Pro Tyr Gln Leu Gln Thr Phe Val Leu Pro Ala Thr Pro Pro
            180                 185                 190 caa ctt gtc agc ccc cgg gtc cta gag gtg gac acg cag ggg acc gtg     624
Gln Leu Val Ser Pro Arg Val Leu Glu Val Asp Thr Gln Gly Thr Val
        195                 200                 205 gtc tgt tcc ctg gac ggg ctg ttc cca gtc tcg gag gcc cag gtc cac     672
Val Cys Ser Leu Asp Gly Leu Phe Pro Val Ser Glu Ala Gln Val His
210                 215                 220 ctg gca ctg ggg gac cag agg ttg aac ccc aca gtc acc tat ggc aac     720
Leu Ala Leu Gly Asp Gln Arg Leu Asn Pro Thr Val Thr Tyr Gly Asn
225                 230                 235                 240 gac tcc ttc tcg gcc aag gcc tca gtc agt gtg acc gca gag gac gag     768
Asp Ser Phe Ser Ala Lys Ala Ser Val Ser Val Thr Ala Glu Asp Glu
                245                 250                 255 ggc acc cag cgg ctg acg tgt gca gta ata ctg ggg aac cag agc cag     816
Gly Thr Gln Arg Leu Thr Cys Ala Val Ile Leu Gly Asn Gln Ser Gln
            260                 265                 270 gag aca ctg cag aca gtg acc atc tac agc ttt ccg gcg ccc aac gtg     864
Glu Thr Leu Gln Thr Val Thr Ile Tyr Ser Phe Pro Ala Pro Asn Val
        275                 280                 285 att ctg acg aag cca gag gtc tca gaa ggg acc gag gtg aca gtg aag     912
Ile Leu Thr Lys Pro Glu Val Ser Glu Gly Thr Glu Val Thr Val Lys
290                 295                 300 tgt gag gcc cac cct aga gcc aag gtg acg ctg aat ggg gtt cca gcc     960
Cys Glu Ala His Pro Arg Ala Lys Val Thr Leu Asn Gly Val Pro Ala
305                 310                 315                 320 cag cca ctg ggc ccg agg gcc cag ctc ctg ctg aag gcc acc cca gag    1008
Gln Pro Leu Gly Pro Arg Ala Gln Leu Leu Leu Lys Ala Thr Pro Glu
                325                 330                 335 gac aac ggg cgc agc ttc tcc tgc tct gca acc ctg gag gtg gcc ggc    1056
Asp Asn Gly Arg Ser Phe Ser Cys Ser Ala Thr Leu Glu Val Ala Gly
            340                 345                 350 cag ctt ata cac aag aac cag acc cgg gag ctt cgt gtc ctg tat ggc    1104
Gln Leu Ile His Lys Asn Gln Thr Arg Glu Leu Arg Val Leu Tyr Gly
        355                 360                 365 ccc cga ctg gac gag agg gat tgt ccg gga aac tgg acg tgg cca gaa    1152
Pro Arg Leu Asp Glu Arg Asp Cys Pro Gly Asn Trp Thr Trp Pro Glu
370                 375                 380 aat tcc cag cag act cca atg tgc cag gct tgg ggg aac cca ttg ccc    1200
Asn Ser Gln Gln Thr Pro Met Cys Gln Ala Trp Gly Asn Pro Leu Pro
385                 390                 395                 400 gag ctc aag tgt cta aag gat ggc act ttc cca ctg ccc atc ggg gaa    1248
Glu Leu Lys Cys Leu Lys Asp Gly Thr Phe Pro Leu Pro Ile Gly Glu
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 405 |     |     |     |     | 410 |     |     |     |     | 415 |     |     |     |      |
| tca | gtg | act | gtc | act | cga | gat | ctt | gag | ggc | acc | tac | ctc | tgt | cgg | gcc | 1296 |
| Ser | Val | Thr | Val | Thr | Arg | Asp | Leu | Glu | Gly | Thr | Tyr | Leu | Cys | Arg | Ala |      |
|     |     | 420 |     |     |     |     | 425 |     |     |     |     | 430 |     |     |     |      |
| agg | agc | act | caa | ggg | gag | gtc | acc | cgc | gag | gtg | acc | gtg | aat | gtg | ctc | 1344 |
| Arg | Ser | Thr | Gln | Gly | Glu | Val | Thr | Arg | Glu | Val | Thr | Val | Asn | Val | Leu |      |
|     |     | 435 |     |     |     |     | 440 |     |     |     |     | 445 |     |     |     |      |
| tcc | ccc | cgg | tat | gag | att | gtc | atc | atc | act | gtg | gta | gca | gcc | gca | gtc | 1392 |
| Ser | Pro | Arg | Tyr | Glu | Ile | Val | Ile | Ile | Thr | Val | Val | Ala | Ala | Ala | Val |      |
|     | 450 |     |     |     |     | 455 |     |     |     |     | 460 |     |     |     |     |      |
| ata | atg | ggc | act | gca | ggc | ctc | agc | acg | tac | ctc | tat | aac | cgc | cag | cgg | 1440 |
| Ile | Met | Gly | Thr | Ala | Gly | Leu | Ser | Thr | Tyr | Leu | Tyr | Asn | Arg | Gln | Arg |      |
| 465 |     |     |     |     | 470 |     |     |     |     | 475 |     |     |     |     | 480 |      |
| aag | atc | aag | aaa | tac | aga | cta | caa | cag | gcc | caa | aaa | ggg | acc | ccc | atg | 1488 |
| Lys | Ile | Lys | Lys | Tyr | Arg | Leu | Gln | Gln | Ala | Gln | Lys | Gly | Thr | Pro | Met |      |
|     |     |     |     | 485 |     |     |     |     | 490 |     |     |     |     | 495 |     |      |
| aaa | ccg | aac | aca | caa | gcc | acg | cct | ccc | tga |     |     |     |     |     |     | 1518 |
| Lys | Pro | Asn | Thr | Gln | Ala | Thr | Pro | Pro |     |     |     |     |     |     |     |      |
|     |     | 500 |     |     |     |     | 505 |     |     |     |     |     |     |     |     |      |

<210> SEQ ID NO 3
<211> LENGTH: 505
<212> TYPE: PRT
<213> ORGANISM: Pan troglodytes

<400> SEQUENCE: 3

```
Gln Thr Ser Val Ser Pro Ser Lys Val Ile Leu Pro Arg Gly Gly Ser
1               5                   10                  15

Val Leu Val Thr Cys Ser Thr Ser Cys Asp Gln Pro Lys Leu Leu Gly
            20                  25                  30

Ile Glu Thr Pro Leu Pro Lys Lys Glu Leu Leu Leu Pro Gly Asn Asn
        35                  40                  45

Arg Lys Val Tyr Glu Leu Ser Asn Val Gln Glu Asp Ser Gln Pro Met
    50                  55                  60

Cys Tyr Ser Asn Cys Pro Asp Gly Gln Ser Thr Ala Lys Thr Phe Leu
65                  70                  75                  80

Thr Val Tyr Trp Thr Pro Glu Arg Val Glu Leu Ala Pro Leu Pro Ser
                85                  90                  95

Trp Gln Pro Val Gly Lys Asn Leu Thr Leu Arg Cys Gln Val Glu Gly
            100                 105                 110

Gly Ala Pro Arg Ala Asn Leu Thr Val Val Leu Leu Arg Gly Glu Lys
        115                 120                 125

Glu Leu Lys Arg Glu Pro Ala Val Gly Glu Pro Ala Glu Val Thr Thr
    130                 135                 140

Thr Val Leu Val Arg Arg Asp His His Gly Ala Asn Phe Ser Cys Arg
145                 150                 155                 160

Thr Glu Leu Asp Leu Arg Pro Gln Gly Leu Glu Leu Phe Glu Asn Thr
                165                 170                 175

Ser Ala Pro Tyr Gln Leu Gln Thr Phe Val Leu Pro Ala Thr Pro Pro
            180                 185                 190

Gln Leu Val Ser Pro Arg Val Leu Glu Val Asp Thr Gln Gly Thr Val
        195                 200                 205

Val Cys Ser Leu Asp Gly Leu Phe Pro Val Ser Glu Ala Gln Val His
    210                 215                 220

Leu Ala Leu Gly Asp Gln Arg Leu Asn Pro Thr Val Thr Tyr Gly Asn
225                 230                 235                 240
```

Asp Ser Phe Ser Ala Lys Ala Ser Val Ser Val Thr Ala Glu Asp Glu
            245                 250                 255

Gly Thr Gln Arg Leu Thr Cys Ala Val Ile Leu Gly Asn Gln Ser Gln
        260                 265                 270

Glu Thr Leu Gln Thr Val Thr Ile Tyr Ser Phe Pro Ala Pro Asn Val
    275                 280                 285

Ile Leu Thr Lys Pro Glu Val Ser Glu Gly Thr Glu Val Thr Val Lys
290                 295                 300

Cys Glu Ala His Pro Arg Ala Lys Val Thr Leu Asn Gly Val Pro Ala
305                 310                 315                 320

Gln Pro Leu Gly Pro Arg Ala Gln Leu Leu Leu Lys Ala Thr Pro Glu
            325                 330                 335

Asp Asn Gly Arg Ser Phe Ser Cys Ser Ala Thr Leu Glu Val Ala Gly
        340                 345                 350

Gln Leu Ile His Lys Asn Gln Thr Arg Glu Leu Arg Val Leu Tyr Gly
    355                 360                 365

Pro Arg Leu Asp Glu Arg Asp Cys Pro Gly Asn Trp Thr Trp Pro Glu
370                 375                 380

Asn Ser Gln Gln Thr Pro Met Cys Gln Ala Trp Gly Asn Pro Leu Pro
385                 390                 395                 400

Glu Leu Lys Cys Leu Lys Asp Gly Thr Phe Pro Leu Pro Ile Gly Glu
            405                 410                 415

Ser Val Thr Val Thr Arg Asp Leu Glu Gly Thr Tyr Leu Cys Arg Ala
        420                 425                 430

Arg Ser Thr Gln Gly Glu Val Thr Arg Glu Val Thr Val Asn Val Leu
    435                 440                 445

Ser Pro Arg Tyr Glu Ile Val Ile Thr Val Ala Ala Ala Val
450                 455                 460

Ile Met Gly Thr Ala Gly Leu Ser Thr Tyr Leu Tyr Asn Arg Gln Arg
465                 470                 475                 480

Lys Ile Lys Lys Tyr Arg Leu Gln Gln Ala Gln Lys Gly Thr Pro Met
            485                 490                 495

Lys Pro Asn Thr Gln Ala Thr Pro Pro
        500                 505

<210> SEQ ID NO 4
<211> LENGTH: 1515
<212> TYPE: DNA
<213> ORGANISM: Gorilla gorilla

<400> SEQUENCE: 4
cagacatctg tgtccccccc aaaagtcatc ctgccccggg gaggctccgt gctggtgaca      60
tgcagcacct cctgtgacca gcccaccttg ttgggcatag agacccggtt gcctaaaaag     120
gagttgctcc tgcttgggaa caaccagaag gtgtatgaac tgagcaatgt gcaagaagat     180
agccaaccaa tgtgttattc aaactgccct gatgggcagt caacagctaa accttcctc     240 accgtgtact ggactccaga acgggtggaa ctggcacccc tccctcttg gcagccagtg     300 ggcaaggacc ttaccctacg ctgccaggtg gagggtgggg caccccgggc caacctcatc     360
gtggtgctgc tccgtgggga ggaggagctg aaacggagc cagctgtggg ggagcccgcc     420
gaggtcacga ccacggtgcc ggtggagaaa gatcaccatg gagccaattt cttgtgccgc     480
actgaactgg acctgcggcc ccaagggctg aagctgtttg agaacacctc ggccccctac     540
cagctccaaa cctttgtcct gccagcgact ccccacaac ttgtcagccc tcgggtccta     600

| | |
|---|---:|
| gaggtggaca cgcaggggac tgtggtctgt tccctggacg ggctgttccc agtctcggag | 660 |
| gcccaggtcc acctggcact gggggaccag aggttgaacc ccacagtcac ctatggcaac | 720 |
| gactccttct cagccaaggc ctcagtcagt gtgaccgcag aggacgaggg cacccagtgg | 780 |
| ctgacgtgtg cagtaatact ggggacccag agccaggaga cactgcagac agtgaccatc | 840 |
| tacagctttc cggcacccaa cgtgattctg acgaagccag aggtctcaga agggaccgag | 900 |
| gtgacagtga agtgtgaggc ccaccctaga gccaaggtga cactgaatgg ggttccagcc | 960 |
| cagccaccgg gcccgaggac ccagttcctg ctgaaggcca ccccagagga caacgggcgc | 1020 |
| agcttctcct gctctgcaac cctggaggtg gccggccagc ttatacacaa gaaccagacc | 1080 |
| cgggagcttc gtgtcctgta tggcccccga ctggatgaga gggattgtcc gggaaactgg | 1140 |
| acgtggccag aaaattccca gcagactcca atgtgccagg cttgggggaa cccattgccc | 1200 |
| gagctcaagt gtctaaagga tggcactttc ccactgcccg tcgggaatc agtgactgtc | 1260 |
| actcgagatc ttgagggcac ctacctctgt cgggccagga gcactcaagg ggaggtcacc | 1320 |
| cgcgaggtga ccgtgaatgt gctctccccc cggtatgagt ttgtcatcat cgctgtggta | 1380 |
| gcagccgcag tcataatggg cactgcaggc ctcagcacgt acctctataa ccgccagcgg | 1440 |
| aagatcagga aatacagact acaacaggct caaaaaggga cccccatgaa accgaacaca | 1500 |
| caagccacgc ctccc | 1515 |

<210> SEQ ID NO 5
<211> LENGTH: 1515
<212> TYPE: DNA
<213> ORGANISM: Pongo pygmaeus

<400> SEQUENCE: 5

| | |
|---|---:|
| cacacatctg tgtcctccgc caacgtcttc ctgccccggg gaggctccgt gctagtgaat | 60 |
| tgcagcacct cctgtgacca gcccaccttg ttgggcatag agaccccgtt gcctaaaaag | 120 |
| gagttgctcc cgggtgggaa caactggaag atgtatgaac tgagcaatgt gcaagaagat | 180 |
| agccaaccaa tgtgctattc aaactgccct gatgggcagt cagcagctaa aaccttcctc | 240 |
| accgtgtact ggactccaga acgggtggaa ctggcacccc tcccctcttg gcagccagtg | 300 |
| ggcaagaacc ttaccctacg ctgccaggtg gagggtgggg caccccgggc caacctcacc | 360 |
| gtggtattgc tccgtgggga ggaggagctg agccggcagc cagcggtggg ggagcccgcc | 420 |
| gaggtcacgg ccacggtgct ggcgaggaaa gatgaccacg gagccaattt ctcgtgccgc | 480 |
| actgaactgg acctgcggcc ccaagggctg gagctgtttg agaacacctc ggcccccac | 540 |
| cagctccaaa cctttgtcct gccagcgact ccccacaac ttgtcagccc ccgggtccta | 600 |
| gaggtggaca cgcaggggac cgtggtctgt tccctggacg ggctgttccc agtctcggag | 660 |
| gcccaggtcc acttggcact gggggaccag aggttgaacc ccacagtcac ctatggcgtc | 720 |
| gactccctct cggccaaggc ctcagtcagt gtgaccgcag aggaggaggg cacccagtgg | 780 |
| ctgtggtgtg cagtgatact gaggaaccag agccaggaga cacggcagac agtgaccatc | 840 |
| tacagctttc tgcacccaa cgtgactctg atgaagccag aggtctcaga agggaccgag | 900 |
| gtgatagtga agtgtgaggc ccaccctgca gccaacgtga cgctgaatgg ggttccagcc | 960 |
| cagccgccgg gcccgagggc ccagttcctg ctgaaggcca ccccagagga caacgggcgc | 1020 |
| agcttctcct gctctgcaac cctggaggtg gccggccagc ttatacacaa gaaccagacc | 1080 |
| cgggagcttc gagtcctgta tggcccccga ctggacgaga gggattgtcc gggaaactgg | 1140 |
| acgtggccag aaaactccca gcagactcca atgtgccagg cttgggggaa ccccttgccc | 1200 |

-continued

```
gagctcaagt gtctaaagga tggcactttc ccactgccca tcggggaatc agtgactgtc    1260
actcgagatc ttgagggcac ctacctctgt cgggccagga gcactcaagg ggaggtcacc    1320
cgcgaggtga ccgtgaatgt gctctccccc cggtatgaga ttgtcatcat cactgtggta    1380
gcagccgcag ccatactggg cactgcaggc ctcagcacgt acctctataa ccgccagcgg    1440
aagatcagga tatacagact acaacaggct caaaaaggga cccccatgaa accaaacaca    1500
caaaccacgc ctccc                                                    1515
```

<210> SEQ ID NO 6
<211> LENGTH: 505
<212> TYPE: PRT
<213> ORGANISM: Homo sapiens

<400> SEQUENCE: 6

```
Gln Thr Ser Val Ser Pro Ser Lys Val Ile Leu Pro Arg Gly Gly Ser
  1               5                  10                  15

Val Leu Val Thr Cys Ser Thr Ser Cys Asp Gln Pro Lys Leu Leu Gly
                 20                  25                  30

Ile Glu Thr Pro Leu Pro Lys Lys Glu Leu Leu Leu Pro Gly Asn Asn
             35                  40                  45

Arg Lys Val Tyr Glu Leu Ser Asn Val Gln Glu Asp Ser Gln Pro Met
 50                  55                  60

Cys Tyr Ser Asn Cys Pro Asp Gly Gln Ser Thr Ala Lys Thr Phe Leu
 65                  70                  75                  80

Thr Val Tyr Trp Thr Pro Glu Arg Val Glu Leu Ala Pro Leu Pro Ser
                 85                  90                  95

Trp Gln Pro Val Gly Lys Asn Leu Thr Leu Arg Cys Gln Val Glu Gly
                100                 105                 110

Gly Ala Pro Arg Ala Asn Leu Thr Val Val Leu Leu Arg Gly Glu Lys
            115                 120                 125

Glu Leu Lys Arg Glu Pro Ala Val Gly Glu Pro Ala Glu Val Thr Thr
130                 135                 140

Thr Val Leu Val Arg Arg Asp His His Gly Ala Asn Phe Ser Cys Arg
145                 150                 155                 160

Thr Glu Leu Asp Leu Arg Pro Gln Gly Leu Glu Leu Phe Glu Asn Thr
                165                 170                 175

Ser Ala Pro Tyr Gln Leu Gln Thr Phe Val Leu Pro Ala Thr Pro Pro
            180                 185                 190

Gln Leu Val Ser Pro Arg Val Leu Glu Val Asp Thr Gln Gly Thr Val
        195                 200                 205

Val Cys Ser Leu Asp Gly Leu Phe Pro Val Ser Glu Ala Gln Val His
210                 215                 220

Leu Ala Leu Gly Asp Gln Arg Leu Asn Pro Thr Val Thr Tyr Gly Asn
225                 230                 235                 240

Asp Ser Phe Ser Ala Lys Ala Ser Val Ser Val Thr Ala Glu Asp Glu
                245                 250                 255

Gly Thr Gln Arg Leu Thr Cys Ala Val Ile Leu Gly Asn Gln Ser Gln
            260                 265                 270

Glu Thr Leu Gln Thr Val Thr Ile Tyr Ser Phe Pro Ala Pro Asn Val
        275                 280                 285

Ile Leu Thr Lys Pro Glu Val Ser Glu Gly Thr Glu Val Thr Val Lys
    290                 295                 300

Cys Glu Ala His Pro Arg Ala Lys Val Thr Leu Asn Gly Val Pro Ala
```

```
                305                 310                 315                 320
Gln Pro Leu Gly Pro Arg Ala Gln Leu Leu Lys Ala Thr Pro Glu
                325                 330                 335

Asp Asn Gly Arg Ser Phe Ser Cys Ser Ala Thr Leu Glu Val Ala Gly
                340                 345                 350

Gln Leu Ile His Lys Asn Gln Thr Arg Glu Leu Arg Val Leu Tyr Gly
                355                 360                 365

Pro Arg Leu Asp Glu Arg Asp Cys Pro Gly Asn Trp Thr Trp Pro Glu
            370                 375                 380

Asn Ser Gln Gln Thr Pro Met Cys Gln Ala Trp Gly Asn Pro Leu Pro
385                 390                 395                 400

Glu Leu Lys Cys Leu Lys Asp Gly Thr Phe Pro Leu Pro Ile Gly Glu
                405                 410                 415

Ser Val Thr Val Thr Arg Asp Leu Glu Gly Thr Tyr Leu Cys Arg Ala
                420                 425                 430

Arg Ser Thr Gln Gly Glu Val Thr Arg Glu Val Thr Val Asn Val Leu
            435                 440                 445

Ser Pro Arg Tyr Glu Ile Val Ile Ile Thr Val Ala Ala Ala Val
450                 455                 460

Ile Met Gly Thr Ala Gly Leu Ser Thr Tyr Leu Tyr Asn Arg Gln Arg
465                 470                 475                 480

Lys Ile Lys Lys Tyr Arg Leu Gln Gln Ala Gln Lys Gly Thr Pro Met
                485                 490                 495

Lys Pro Asn Thr Gln Ala Thr Pro Pro
            500                 505

<210> SEQ ID NO 7
<211> LENGTH: 254
<212> TYPE: PRT
<213> ORGANISM: Homo sapiens

<400> SEQUENCE: 7

Ser Asp Glu Lys Val Phe Glu Val His Val Arg Pro Lys Lys Leu Ala
1               5                   10                  15

Val Glu Pro Lys Gly Ser Leu Glu Val Asn Cys Ser Thr Thr Cys Asn
                20                  25                  30

Gln Pro Glu Val Gly Gly Leu Glu Thr Ser Leu Asp Lys Ile Leu Leu
            35                  40                  45

Asp Glu Gln Ala Gln Trp Lys His Tyr Leu Val Ser Asn Ile Ser His
50                  55                  60

Asp Thr Val Leu Gln Cys His Phe Thr Cys Ser Gly Lys Gln Glu Ser
65                  70                  75                  80

Met Asn Ser Asn Val Ser Val Tyr Gln Pro Pro Arg Gln Val Ile Leu
                85                  90                  95

Thr Leu Gln Pro Thr Leu Val Ala Val Gly Lys Ser Phe Thr Ile Glu
            100                 105                 110

Cys Arg Val Pro Thr Val Glu Pro Leu Asp Ser Leu Thr Leu Phe Leu
        115                 120                 125

Phe Arg Gly Asn Glu Thr Leu His Tyr Glu Thr Phe Gly Lys Ala Ala
    130                 135                 140

Pro Ala Pro Gln Glu Ala Thr Ala Thr Phe Asn Ser Thr Ala Asp Arg
145                 150                 155                 160

Glu Asp Gly His Arg Asn Phe Ser Cys Leu Ala Val Leu Asp Leu Met
                165                 170                 175
```

Ser Arg Gly Gly Asn Ile Phe His Lys His Ser Ala Pro Lys Met Leu
            180                 185                 190

Glu Ile Tyr Glu Pro Val Ser Asp Ser Gln Met Val Ile Ile Val Thr
        195                 200                 205

Val Val Ser Val Leu Leu Ser Leu Phe Val Thr Ser Val Leu Leu Cys
    210                 215                 220

Phe Ile Phe Gly Gln His Leu Arg Gln Gln Arg Met Gly Thr Tyr Gly
225                 230                 235                 240

Val Arg Ala Ala Trp Arg Arg Leu Pro Gln Ala Phe Arg Pro
                245                 250

<210> SEQ ID NO 8
<211> LENGTH: 518
<212> TYPE: PRT
<213> ORGANISM: Homo sapiens

<400> SEQUENCE: 8

Gln Glu Phe Leu Leu Arg Val Glu Pro Gln Asn Pro Val Leu Ser Ala
1               5                   10                  15

Gly Gly Ser Leu Phe Val Asn Cys Ser Thr Asp Cys Pro Ser Ser Glu
            20                  25                  30

Lys Ile Ala Leu Glu Thr Ser Leu Ser Lys Glu Leu Val Ala Ser Gly
        35                  40                  45

Met Gly Trp Ala Ala Phe Asn Leu Ser Asn Val Thr Gly Asn Ser Arg
    50                  55                  60

Ile Leu Cys Ser Val Tyr Cys Asn Gly Ser Gln Ile Thr Gly Ser Ser
65                  70                  75                  80

Asn Ile Thr Val Tyr Gly Leu Pro Glu Arg Val Glu Leu Ala Pro Leu
                85                  90                  95

Pro Pro Trp Gln Pro Val Gly Gln Asn Phe Thr Leu Arg Cys Gln Val
            100                 105                 110

Glu Gly Gly Ser Pro Arg Thr Ser Leu Thr Val Val Leu Leu Arg Trp
        115                 120                 125

Glu Glu Glu Leu Ser Arg Gln Pro Ala Val Glu Glu Pro Ala Glu Val
    130                 135                 140

Thr Ala Thr Val Leu Ala Ser Arg Asp Asp His Gly Ala Pro Phe Ser
145                 150                 155                 160

Cys Arg Thr Glu Leu Asp Met Gln Pro Gln Gly Leu Gly Leu Phe Val
                165                 170                 175

Asn Thr Ser Ala Pro Arg Gln Leu Arg Thr Phe Val Leu Pro Val Thr
            180                 185                 190

Pro Pro Arg Leu Val Ala Pro Arg Phe Leu Glu Val Glu Thr Ser Trp
        195                 200                 205

Pro Val Asp Cys Thr Leu Asp Gly Leu Phe Pro Ala Ser Glu Ala Gln
    210                 215                 220

Val Tyr Leu Ala Leu Gly Asp Gln Met Leu Asn Ala Thr Val Met Asn
225                 230                 235                 240

His Gly Asp Thr Leu Thr Ala Thr Ala Thr Ala Thr Ala Arg Ala Asp
                245                 250                 255

Gln Glu Gly Ala Arg Glu Ile Val Cys Asn Val Thr Leu Gly Gly Glu
            260                 265                 270

Arg Arg Glu Ala Arg Glu Asn Leu Thr Val Phe Ser Phe Leu Gly Pro
        275                 280                 285

Ile Val Asn Leu Ser Glu Pro Thr Ala His Glu Gly Ser Thr Val Thr
    290                 295                 300

```
Val Ser Cys Met Ala Gly Ala Arg Val Gln Val Thr Leu Asp Gly Val
305                 310                 315                 320

Pro Ala Ala Ala Pro Gly Gln Pro Ala Gln Leu Gln Leu Asn Ala Thr
                325                 330                 335

Glu Ser Asp Asp Gly Arg Ser Phe Phe Cys Ser Ala Thr Leu Glu Val
            340                 345                 350

Asp Gly Glu Phe Leu His Arg Asn Ser Ser Val Gln Leu Arg Val Leu
        355                 360                 365

Tyr Gly Pro Lys Ile Asp Arg Ala Thr Cys Pro Gln His Leu Lys Trp
370                 375                 380

Lys Asp Lys Thr Arg His Val Leu Gln Cys Gln Ala Arg Gly Asn Pro
385                 390                 395                 400

Tyr Pro Glu Leu Arg Cys Leu Lys Glu Gly Ser Ser Arg Glu Val Pro
                405                 410                 415

Val Gly Ile Pro Phe Phe Val Asn Val Thr His Asn Gly Thr Tyr Gln
            420                 425                 430

Cys Gln Ala Ser Ser Ser Arg Gly Lys Tyr Thr Leu Val Val Val Met
        435                 440                 445

Asp Ile Glu Ala Gly Ser Ser His Phe Val Pro Val Phe Val Ala Val
    450                 455                 460

Leu Leu Thr Leu Gly Val Val Thr Ile Val Leu Ala Leu Met Tyr Val
465                 470                 475                 480

Phe Arg Glu His Gln Arg Ser Gly Ser Tyr His Val Arg Glu Glu Ser
                485                 490                 495

Thr Tyr Leu Pro Leu Thr Ser Met Gln Pro Thr Glu Ala Met Gly Glu
            500                 505                 510

Glu Pro Ser Arg Ala Glu
        515

<210> SEQ ID NO 9
<211> LENGTH: 1212
<212> TYPE: DNA
<213> ORGANISM: Homo sapiens

<400> SEQUENCE: 9
atgagtgact ccaaggaacc aagactgcag cagctgggcc tcctggagga ggaacagctg      60
agaggccttg gattccgaca gactcgagga tacaagagct tagcagggtg tcttggccat     120
ggtcccctgg tgctgcaact cctctccttc acgctcttgg ctgggctcct tgtccaagtg     180
tccaaggtcc ccagctccat aagtcaggaa caatccaggc aagacgcgat ctaccagaac     240
ctgacccagc ttaaagctgc agtgggtgag ctctcagaga atccaagctg caggagatc      300 taccaggagc tgacccagct gaaggctgca gtgggtgagc ttccagagaa atctaagctg     360
caggagatct accaggagct gacccggctg aaggctgcag tgggtgagct tccagagaaa     420
tctaagctgc aggagatcta ccaggagctg acctggctga aggctgcagt gggtgagctt     480
ccagagaaat ctaagatgca ggagatctac caggagctga ctcggctgaa ggctgcagtg     540
ggtgagcttc agagaaatc taagcagcag gagatctacc aggagctgac ccggctgaag     600
gctgcagtgg gtgagcttcc agagaaatct aagcagcagg agatctacca ggagctgacc     660
cggctgaagg ctgcagtggg tgagcttcca gagaaatcta agcagcagga gatctaccag     720
gagctgaccc agctgaaggc tgcagtggaa cgcctgtgcc accctgtcc ctgggaatgg      780 acattcttcc aaggaaactg ttacttcatg tctaactccc agcggaactg gcacgactcc     840
```

```
atcaccgcct gcaaagaagt gggggcccag ctcgtcgtaa tcaaaagtgc tgaggagcag      900
aacttcctac agctgcagtc ttccagaagt aaccgcttca cctggatggg actttcagat      960
ctaaatcagg aaggcacgtg gcaatgggtg gacggctcac ctctgttgcc cagcttcaag     1020
cagtattgga acagaggaga gcccaacaac gttggggagg aagactgcgc ggaatttagt     1080
ggcaatggct ggaacgacga caaatgtaat cttgccaaat tctggatctg caaaaagtcc     1140
gcagcctcct gctccaggga tgaagaacag tttctttctc agcccctgc  caccccaaac     1200 ccccctcctg cg                                                         1212

<210> SEQ ID NO 10
<211> LENGTH: 1212
<212> TYPE: DNA
<213> ORGANISM: Pan troglodytes

<400> SEQUENCE: 10
atgagtgact ccaaggaacc aagactgcag cagctgggcc tcctggagga ggaacagctg       60
agaggccttg gattccgaca gactcgaggc tacaagagct tagcagggtg tcttggccat      120
ggtcccctgg tgctgcaact cctctccttc acgctcttgg ctgggctcct tgtccaagtg      180
tccaaggtcc ccagctccat aagtcaggaa gaatccaggc aagacgtgat ctaccagaac      240
ctgacccagc ttaaagctgc agtgggtgag ctctcagaga atccaagct  gcaggagatc      300 taccaggagc tgacccagct gaaggctgca gtgggtgagc ttccagagaa atctaagcag      360
caggagatct accaggagct gacccggctg aaggctgcag tgggtgagct tccagagaaa      420
tctaagatgc aggagatcta ccaggagctg actcggctga aggctgcagt gggtgagctt      480
ccagagaaat ctaagatgca ggagatctac caggagctga ctcggctgaa ggctgcagtg      540
ggtgagcttc agagaaatc  taagcagcag gagatctacc aggagctgac ccagctgaag      600
gctgcagtgg gtgagcttcc agagaaatct aagcagcagg agatctacca ggagctgacc      660
cagctgaagg ctgcagtggg tgagcttcca gagaaatcta agcagcagga gatctaccag      720
gagctgaccc ggctgaaggc tgcagtggaa cgcctgtgcc gccgctgccc ctgggaatgg      780
acattcttcc aaggaaactg ttacttcatg tctaactccc agcggaactg gcacgactcc      840
atcactgcct gcaaagaagt gggggcccag ctcgtcgtaa tcaaaagtgc tgaggagcag      900
aacttcctac agctgcagtc ttccagaagt aaccgcttca cctggatggg actttcagat      960
ctaaatgagg aaggcatgtg gcaatgggtg gacggctcac ctctgttgcc cagcttcaac     1020
cagtaytgga acagaggaga gcccaacaac gttggggagg aagactgcgc ggaatttagt     1080
ggcaatggct ggaatgacga caaatgtaat cttgccaaat tctggatctg caaaaagtcc     1140
gcagcctcct gctccaggga tgaagaacag tttctttctc agcccctgc  caccccaaac     1200 ccccctcctg cg                                                         1212

<210> SEQ ID NO 11
<211> LENGTH: 1212
<212> TYPE: DNA
<213> ORGANISM: Gorilla gorilla

<400> SEQUENCE: 11
atgagtgact ccaaggaacc aagactgcag cagctgggcc tcctggagga ggaacagctg       60
agaggccttg gattccgaca gactcgaggc tacaagagct tagcagggtg tcttggccat      120
ggtcccctgg tgctgcaact cctctccttc acgctcttgg ctgcgctcct tgtccaagtg      180
tccaaggtcc ccagctccat aagtcaggaa caatccaggc aagacgcgat ctaccagaac      240
```

```
ctgacccagt ttaaagctgc agtgggtgag ctctcagaga atccaagct gcaggagatc      300 tatcaggagc tgacccagct gaaggctgca gtgggtgagc ttccagagaa atctaagcag      360
caggagatct accaggagct gagccagctg aaggctgcag tgggtgagct tccagagaaa      420
tctaagcagc aggagatcta ccaggagctg acccggctga aggctgcagt gggtgagctt      480
ccagagaaat ctaagcagca ggagatctac caggagctga cccggctgaa ggctgcagtg      540
ggtgagcttc agagaaatc taagcagcag gagatctacc aggagctgag ccagctgaag      600
gctgcagtgg gtgagcttcc agagaaatct aagcagcagg agatctacca ggagctgagc      660
cagctgaagg ctgcagtggg tgagcttcca gagaaatcta agcagcagga gatctaccag      720
gagctgaccc agctgaaggc tgcagtggaa cgcctgtgcc gccgctgccc ctgggaatgg      780
acattcttcc aaggaaactg ttacttcatg tctaactccc agcggaactg gcacgactcc      840
atcaccgcct gccaagaagt gggggcccag ctcgtcgtaa tcaaaagtgc tgaggagcag      900
aacttcctac agctgcagtc ttccagaagt aaccgcttca cctggatggg actttcagat      960
ctaaatcatg aaggcacgtg gcaatgggtg gacggctcac ctctgttgcc cagcttcgag     1020
cagtattgga acagaggaga gcccaacaac gttggggagg aagactgcgc ggaatttagt     1080
ggcaatggct ggaacgatga caaatgtaat cttgccaaat ctggatctg caaaaagtct     1140 gcagcctcct gctccaggga tgaagaacag tttctttctc cagcctctgc caccccaaac     1200
ccccctcctg cg                                                        1212
```

<210> SEQ ID NO 12
<211> LENGTH: 105
<212> TYPE: PRT
<213> ORGANISM: Pan troglodytes

<400> SEQUENCE: 12

```
Ser Leu Gln Cys Tyr Asn Cys Pro Asn Pro Thr Ala Asp Cys Lys Thr
1               5                   10                  15

Ala Val Asn Cys Ser Ser Asp Phe Asp Ala Cys Leu Ile Thr Lys Ala
            20                  25                  30

Gly Leu Gln Val Tyr Asn Lys Cys Trp Lys Phe Glu His Cys Asn Phe
        35                  40                  45

Asn Asp Val Thr Thr Arg Leu Arg Glu Asn Glu Leu Tyr Tyr Cys
    50                  55                  60

Cys Lys Lys Asp Leu Cys Asn Phe Asn Glu Gln Leu Glu Asn Gly Gly
65                  70                  75                  80

Thr Ser Leu Ser Glu Lys Thr Val Leu Leu Val Thr Pro Phe Leu
                85                  90                  95

Ala Ala Ala Ala Trp Ser Leu His Pro
            100                 105
```

<210> SEQ ID NO 13
<211> LENGTH: 121
<212> TYPE: PRT
<213> ORGANISM: Pan troglodytes

<400> SEQUENCE: 13

```
Ser Leu Gln Cys Tyr Asn Cys Pro Asn Pro Thr Ala Asp Cys Lys Thr
1               5                   10                  15

Ala Val Asn Cys Ser Ser Asp Phe Asp Ala Cys Leu Ile Thr Lys Ala
            20                  25                  30

Gly Leu Gln Val Tyr Asn Lys Cys Trp Lys Leu Glu His Cys Asn Phe
```

```
                35                  40                  45
Lys Asp Leu Thr Thr Arg Leu Arg Glu Asn Glu Leu Thr Tyr Tyr Cys
 50                  55                  60

Cys Lys Lys Asp Leu Cys Asn Phe Asn Glu Gln Leu Glu Asn Gly Gly
 65                  70                  75                  80

Asn Glu Gln Leu Glu Asn Gly Gly Asn Glu Gln Leu Glu Asn Gly Gly
                 85                  90                  95

Thr Ser Leu Ser Glu Lys Thr Val Leu Leu Arg Val Thr Pro Phe Leu
                100                 105                 110

Ala Ala Ala Ala Trp Ser Leu His Pro
                115                 120

<210> SEQ ID NO 14
<211> LENGTH: 5140
<212> TYPE: DNA
<213> ORGANISM: Homo sapiens

<400> SEQUENCE: 14
ctccagacct acccagaaag atgcccggat ggatcctgca gctccgtggc ttttctggga      60
agcagcggcc cctgctctca agagaccctg gctcctgatg gtggcccccaa ggttgccagc   120 tggtgctagg gactcaggac agtttcccag aaaaggccaa gcgggcagcc cctccagggg    180
ccgggtgagg aagctggggg gtgcggaggc cacactgggt ccctgaaccc cctgcttggt    240
tacagtgcag ctcctcaagt ccacagacgt gggccggcac agcctcctgt acctgaagga   300
aatcggccgt ggctggttcg ggaaggtgtt cctgggggag gtgaactctg gcatcagcag   360
tgcccaggtg gtggtgaagg agctgcaggc tagtgccagc gtgcaggagc agatgcagtt   420
cctggaggag gtgcagccct acagggccct gaagcacagc aacctgctcc agtgcctggc   480
ccagtgcgcc gaggtgacgc cctacctgct ggtgatggag ttctgcccac tgggggacct   540
caagggctac ctgcgagct gccgggtggc ggagtccatg gctcccgacc ccggacccct    600
gcagcgcatg gcctgtgagg tggcctgtgg cgtcctgcac cttcatcgca caatttcgt    660 gcacagcgac ctggccctgc ggaactgcct gctcacggct gacctgacgg tgaagattgg   720
tgactatggc ctggctcact gcaagtacag agaggactac ttcgtgactg ccgaccagct   780
gtgggtgcct ctgcgctgga tcgcgccaga gctggtggac gaggtgcata gcaacctgct   840
cgtcgtggac cagaccaaga gcgggaatgt gtggtccctg ggcgtgacca tctgggagct   900
cttttagctg gcacgcagc cctatcccca gcactcggac cagcaggtgc tggcgtacac    960
ggtccgggag cagcagctca agctgcccaa gccccagctg cagctgaccc tgtcggaccg  1020
ctggtacgag gtgatgcagt tctgctggct gcagcccgag cagcggccca cagccgagga  1080
ggtgcacctg ctgctgtcct acctgtgtgc caagggcgcc accgaagcag aggaggagtt  1140
tgaacgcgcc tggcgctctc tgcggcccgg cggggcggc gtgggcccg gcccggtgc    1200 ggcggggccc atgctgggcg cgtggtgga gctcgccgct gcctcgtcct tcccgctgct  1260
ggagcagttc gcgggcgacg gcttccacgc ggacggcgac gacgtgctga cggtgaccga  1320
gaccagccga ggcctcaatt ttgagtacaa gtgggaggcg ggccgcggcg cggaggcctt  1380
cccggccacg ctgagccctg ccgcaccgc acgcctgcag gagctgtgcg ccccgacgg   1440 cgcgccccccg ggcgtggttc cggtgctcag cgcgcacagc ccgtcgctgg cagcgagta   1500 cttcatccgc ctagaggagg ccgcacccgc cgcggccac gacccctgact gcgccggctg  1560 cgccccccagt ccacctgcca ccgcggacca ggacgacgac tctgacggca gcaccgccgc  1620
```

```
ctcgctggcc atggagccgc tgctgggcca cgggccaccc gtcgacgtcc cctggggccg      1680
cggcgaccac taccctcgca gaagcttggc gcgggacccg ctctgcccct cacgctctcc      1740
ctcgccctcg gcggggcccc tgagtctggc ggagggagga gcggaggatg cagactgggg      1800
cgtggccgcc ttctgtcctg ccttcttcga ggacccactg ggcacgtccc ctttggggag      1860
ctcaggggcg cccccgctgc cgctgactgg cgaggatgag ctagaggagg tgggagcgcg      1920
gagggccgcc cagcgcgggc actggcgctc aacgtgtca gccaacaaca acagcggcag      1980
ccgctgtcca gagtcctggg accccgtctc tgcgggctgc cacgctgagg gctgccccag      2040
tccaaagcag accccacggg cctcccccga gccggggtac cctggagagc ctctgcttgg      2100
gctccaggca gcctctgccc aggagccagg ctgctgcccc ggcctccctc atctatgctc      2160
tgcccagggc ctggcacctg ctccctgcct ggttacaccc tcctggacag agacagccag      2220
tagtgggggt gaccacccgc aggcagagcc caagcttgcc acggaggctg agggcactac      2280
cggacccgc ctgccccttc cttccgtccc ctccccatcc caggagggag ccccacttcc      2340
ctcggaggag gccagtgccc ccgacgcccc tgatgccctg cctgactctc ccacgcctgc      2400
tactggtggc gaggtgtctg ccatcaagct ggcttctgcc ctgaatggca gcagcagctc      2460
tcccgaggtg gaggcaccca gcagtgagga tgaggacacg gctgaggcca cctcaggcat      2520
cttcaccgac acgtccagcg acggcctgca ggccaggagg ccggatgtgg tgccagcctt      2580
ccgctctctg cagaagcagg tggggacccc cgactccctg gactccctgg acatcccgtc      2640
ctcagccagt gatggtggct atgaggtctt cagcccgtcg ccactggcc cctctggagg      2700
gcagccgcga gcgctggaca gtggctatga caccgagaac tatgagtccc ctgagtttgt      2760
gctcaaggag gcgcaggaag ggtgtgagcc ccaggccttt gcggagctgg cctcagaggg      2820
tgagggcccc gggcccgaga cacggctctc cacctccctc agtggcctca acgagaagaa      2880
tccctaccga gactctgcct acttctcaga cctcgaggct gaggccgagg ccacctcagg      2940
cccagagaag aagtgcggcg gggaccgagc ccccgggcca gagctgggcc tgccgagcac      3000
tgggcagccg tctgagcagg tctgtctcag gcctggggtt ccggggagg cacaaggctc      3060
tggcccccggg gaggtgctgc ccccactgct gcagcttgaa gggtcctccc cagagcccag      3120
cacctgcccc tcgggcctgg tcccagagcc tccggagccc caaggcccag ccaaggtgcg      3180
gcctgggccc agcccagct gctcccagtt tttcctgctg accccggttc cgctgagatc      3240
agaaggcaac agctctgagt tccaggggcc cccaggactg ttgtcagggc cggccccaca      3300
aaagcggatg ggggggcccag gcaccccag agccccactc cgcctggctc tgcccggcct      3360
ccctgcggcc ttggagggcc ggccggagga ggaggaggag gacagtgagg acagcgacga      3420
gtctgacgag gagctccgct gctacagcgt ccaggagcct agcgaggaca gcgaagagga      3480
ggcgccggcg gtgcccgtgg tggtggctga gagccagagc gcgcgcaacc tgcgcagcct      3540
gctcaagatg cccagcctgc tgtccgagac cttctgcgag gacctggaac gcaagaagaa      3600
ggccgtgtcc ttcttcgacg acgtcaccgt ctacctcttt gaccaggaaa gccccacccg      3660
ggagctcggg gagcccttcc cgggcgccaa ggaatcgccc cctacgttcc ttaggggag      3720
ccccggctct cccagcgccc caaccggcc gcagcaggct gatggctccc caaatggctc      3780
cacagcggaa gagggtggtg ggttcgcgtg ggacgacgac tttcccgctga tgacggccaa      3840
ggcagccttc gccatggccc tagacccggc cgcacccgcc ccggctgcgc ccacgcccac      3900
gcccgctccc ttctcgcgct tcacggtgtc gcccgcgccc acgtcccgct tctccatcac      3960
gcacgtgtct gactcggacg ccgagtccaa gagaggacct gaagctggtg ccgggggtga      4020
```

-continued

```
gagtaaagag gcttgagacc tgggcagctc ctgcccctca aggctggcgt caccggagcc    4080
cctgccaggc agcagcgagg atggtgaccg agaaggtggg gaccacgtcc tggtggctgt    4140
tggcagcaga ttcaggtgcc tctgccccac gcggtgtcct ggagaagccc gtgggatgag    4200
aggccctgga tggtagatcg gccatgctcc gccccagagg cagaattcgt ctgggctttt    4260
aggcttgctg ctagccccctg ggggcgcctg agccacagt gggtgtctgt acacacatac    4320
acactcaaaa ggggccagtg ccctgggca cggcggcccc caccctctgc cctgcctgcc    4380
tggcctcgga ggacccgcat gccccatccg gcagctcctc cggtgtgctc acaggacact    4440
taaaccagga cgaggcatgg ccccgagaca ctggcaggtt tgtgagcctc ttcccacccc    4500
ctgtgccccc accttgcct ggttcctggt ggctcaggc aaggagtggc cctgggcgcc    4560
cgtgtcggtc ctgtttccgc tgcccttatc tcaaagtccg tggctgtttc cccttcactg    4620
actcagctag acccgtaagc ccaccttcc cacagggaac aggctgctcc cacctgggtc    4680
ccgctgtggc cacggtgggc agcccaaaag atcagggtg gagggcttc caggctgtac    4740 tcctgccccg tgggcccgt tctagaggtg cccttggcag gaccgtgcag gcagctcccc    4800
tctgtggggc agtatctggt cctgtgcccc agctgccaaa ggagagtggg ggccatgccc    4860
cgcagtcagt gttgggggc tcctgcctac agggagaggg atggtgggga aggggtggag    4920
ctgggggcag ggcagcacag ggaatatttt tgtaactaac taactgctgt ggttggagcg    4980
aatggaagtt gggtgatttt aagttattgt tgccaaagag atgtaaagtt tattgttgct    5040 tcgcagggg atttgttttg tgttttgttt gaggcttaga acgctggtgc aatgttttct    5100
tgttccttgt tttttaagag aaatgaagct aagaaaaag                          5140
```

<210> SEQ ID NO 15
<211> LENGTH: 5140
<212> TYPE: DNA
<213> ORGANISM: Homo sapiens
<220> FEATURE:
<221> NAME/KEY: CDS
<222> LOCATION: (413)..(4036)

<400> SEQUENCE: 15

```
ctccagacct acccagaaag atgcccggat ggatcctgca gctccgtggc ttttctggga    60
agcagcggcc cctgctctca agagaccctg gctcctgatg gtggccccaa ggttgccagc    120
tggtgctagg gactcaggac agtttcccag aaaaggccaa gcgggcagcc cctccagggg    180
ccgggtgagg aagctggggg gtgcggaggc cacactgggt ccctgaaccc cctgcttggt    240
tacagtgcag ctcctcaagt ccacagacgt gggccggcac agcctcctgt acctgaagga    300
aatcggccgt ggctggttcg ggaaggtgtt cctgggggag gtgaactctg gcatcagcag    360
tgcccaggtg gtggtgaagg agctgcaggc tagtgccagc gtgcaggagc ag atg cag   418
                                                          Met Gln
                                                            1 ttc ctg gag gag gtg cag ccc tac agg gcc ctg aag cac agc aac ctg     466
Phe Leu Glu Glu Val Gln Pro Tyr Arg Ala Leu Lys His Ser Asn Leu
    5                   10                  15 ctc cag tgc ctg gcc cag tgc gcc gag gtg acg ccc tac ctg ctg gtg     514
Leu Gln Cys Leu Ala Gln Cys Ala Glu Val Thr Pro Tyr Leu Leu Val
 20                  25                  30 atg gag ttc tgc cca ctg ggg gac ctc aag ggc tac ctg cgg agc tgc     562
Met Glu Phe Cys Pro Leu Gly Asp Leu Lys Gly Tyr Leu Arg Ser Cys
 35                  40                  45                  50 cgg gtg gcg gag tcc atg gct ccc gac ccc cgg acc ctg cag cgc atg     610
```

-continued

```
                Arg Val Ala Glu Ser Met Ala Pro Asp Pro Arg Thr Leu Gln Arg Met
                             55                  60                  65 gcc tgt gag gtg gcc tgt ggc gtc ctg cac ctt cat cgc aac aat ttc        658
Ala Cys Glu Val Ala Cys Gly Val Leu His Leu His Arg Asn Asn Phe
             70                  75                  80 gtg cac agc gac ctg gcc ctg cgg aac tgc ctg ctc acg gct gac ctg        706
Val His Ser Asp Leu Ala Leu Arg Asn Cys Leu Leu Thr Ala Asp Leu
             85                  90                  95 acg gtg aag att ggt gac tat ggc ctg gct cac tgc aag tac aga gag        754
Thr Val Lys Ile Gly Asp Tyr Gly Leu Ala His Cys Lys Tyr Arg Glu
        100                 105                 110 gac tac ttc gtg act gcc gac cag ctg tgg gtg cct ctg cgc tgg atc        802
Asp Tyr Phe Val Thr Ala Asp Gln Leu Trp Val Pro Leu Arg Trp Ile
115                 120                 125                 130 gcg cca gag ctg gtg gac gag gtg cat agc aac ctg ctc gtc gtg gac        850
Ala Pro Glu Leu Val Asp Glu Val His Ser Asn Leu Leu Val Val Asp
                135                 140                 145 cag acc aag agc ggg aat gtg tgg tcc ctg ggc gtg acc atc tgg gag        898
Gln Thr Lys Ser Gly Asn Val Trp Ser Leu Gly Val Thr Ile Trp Glu
            150                 155                 160 ctc ttt gag ctg ggc acg cag ccc tat ccc cag cac tcg gac cag cag        946
Leu Phe Glu Leu Gly Thr Gln Pro Tyr Pro Gln His Ser Asp Gln Gln
        165                 170                 175 gtg ctg gcg tac acg gtc cgg gag cag cag ctc aag ctg ccc aag ccc        994
Val Leu Ala Tyr Thr Val Arg Glu Gln Gln Leu Lys Leu Pro Lys Pro
        180                 185                 190 cag ctg cag ctg acc ctg tcg gac cgc tgg tac gag gtg atg cag ttc       1042
Gln Leu Gln Leu Thr Leu Ser Asp Arg Trp Tyr Glu Val Met Gln Phe
195                 200                 205                 210 tgc tgg ctg cag ccc gag cag cgg ccc aca gcc gag gag gtg cac ctg       1090
Cys Trp Leu Gln Pro Glu Gln Arg Pro Thr Ala Glu Glu Val His Leu
                215                 220                 225 ctg ctg tcc tac ctg tgt gcc aag ggc gcc acc gaa gca gag gag gag       1138
Leu Leu Ser Tyr Leu Cys Ala Lys Gly Ala Thr Glu Ala Glu Glu Glu
            230                 235                 240 ttt gaa cgg cgc tgg cgc tct ctg cgg ccc ggc ggg ggc ggc gtg ggg       1186
Phe Glu Arg Arg Trp Arg Ser Leu Arg Pro Gly Gly Gly Gly Val Gly
        245                 250                 255 ccc ggg ccc ggt gcg gcg ggg ccc atg ctg ggc ggc gtg gtg gag ctc       1234
Pro Gly Pro Gly Ala Ala Gly Pro Met Leu Gly Gly Val Val Glu Leu
        260                 265                 270 gcc gct gcc tcg tcc ttc ccg ctg ctg gag cag ttc gcg ggc gac ggc       1282
Ala Ala Ala Ser Ser Phe Pro Leu Leu Glu Gln Phe Ala Gly Asp Gly
275                 280                 285                 290 ttc cac gcg gac ggc gac gac gtg ctg acg gtg acc gag acc agc cga       1330
Phe His Ala Asp Gly Asp Asp Val Leu Thr Val Thr Glu Thr Ser Arg
                295                 300                 305 ggc ctc aat ttt gag tac aag tgg gag gcg ggc cgc ggc gcg gag gcc       1378
Gly Leu Asn Phe Glu Tyr Lys Trp Glu Ala Gly Arg Gly Ala Glu Ala
            310                 315                 320 ttc ccg gcc acg ctg agc cct ggc cgc acc gca cgc ctg cag gag ctg       1426
Phe Pro Ala Thr Leu Ser Pro Gly Arg Thr Ala Arg Leu Gln Glu Leu
        325                 330                 335 tgc gcc ccc gac ggc gcg ccc ccg ggc gtg gtt ccg gtg ctc agc gcg       1474
Cys Ala Pro Asp Gly Ala Pro Pro Gly Val Val Pro Val Leu Ser Ala
        340                 345                 350 cac agc ccg tcg ctg ggc agc gag tac ttc atc cgc cta gag gag gcc       1522
His Ser Pro Ser Leu Gly Ser Glu Tyr Phe Ile Arg Leu Glu Glu Ala
355                 360                 365                 370
```

```
gca ccc gcc gcc ggc cac gac cct gac tgc gcc ggc tgc gcc ccc agt    1570
Ala Pro Ala Ala Gly His Asp Pro Asp Cys Ala Gly Cys Ala Pro Ser
            375                 380                 385 cca cct gcc acc gcg gac cag gac gac gac tct gac ggc agc acc gcc    1618
Pro Pro Ala Thr Ala Asp Gln Asp Asp Asp Ser Asp Gly Ser Thr Ala
                390                 395                 400 gcc tcg ctg gcc atg gag ccg ctg ctg ggc cac ggg cca ccc gtc gac    1666
Ala Ser Leu Ala Met Glu Pro Leu Leu Gly His Gly Pro Pro Val Asp
            405                 410                 415 gtc ccc tgg ggc cgc ggc gac cac tac cct cgc aga agc ttg gcg cgg    1714
Val Pro Trp Gly Arg Gly Asp His Tyr Pro Arg Arg Ser Leu Ala Arg
        420                 425                 430 gac ccg ctc tgc ccc tca cgc tct ccc tcg ccc tcg gcg ggg ccc ctg    1762
Asp Pro Leu Cys Pro Ser Arg Ser Pro Ser Pro Ser Ala Gly Pro Leu
435                 440                 445                 450 agt ctg gcg gag gga gga gcg gag gat gca gac tgg ggc gtg gcc gcc    1810
Ser Leu Ala Glu Gly Gly Ala Glu Asp Ala Asp Trp Gly Val Ala Ala
                455                 460                 465 ttc tgt cct gcc ttc ttc gag gac cca ctg ggc acg tcc cct ttg ggg    1858
Phe Cys Pro Ala Phe Phe Glu Asp Pro Leu Gly Thr Ser Pro Leu Gly
            470                 475                 480 agc tca ggg gcg ccc ccg ctg ccg ctg act ggc gag gat gag cta gag    1906
Ser Ser Gly Ala Pro Pro Leu Pro Leu Thr Gly Glu Asp Glu Leu Glu
        485                 490                 495 gag gtg gga gcg cgg agg gcc gcc cag cgc ggg cac tgg cgc tcc aac    1954
Glu Val Gly Ala Arg Arg Ala Ala Gln Arg Gly His Trp Arg Ser Asn
    500                 505                 510 gtg tca gcc aac aac aac agc ggc agc cgc tgt cca gag tcc tgg gac    2002
Val Ser Ala Asn Asn Asn Ser Gly Ser Arg Cys Pro Glu Ser Trp Asp
515                 520                 525                 530 ccc gtc tct gcg ggc tgc cac gct gag ggc tgc ccc agt cca aag cag    2050
Pro Val Ser Ala Gly Cys His Ala Glu Gly Cys Pro Ser Pro Lys Gln
                535                 540                 545 acc cca cgg gcc tcc ccc gag ccg ggg tac cct gga gag cct ctg ctt    2098
Thr Pro Arg Ala Ser Pro Glu Pro Gly Tyr Pro Gly Glu Pro Leu Leu
            550                 555                 560 ggg ctc cag gca gcc tct gcc cag gag cca ggc tgc tgc ccc ggc ctc    2146
Gly Leu Gln Ala Ala Ser Ala Gln Glu Pro Gly Cys Cys Pro Gly Leu
        565                 570                 575 cct cat cta tgc tct gcc cag ggc ctg gca cct gct ccc tgc ctg gtt    2194
Pro His Leu Cys Ser Ala Gln Gly Leu Ala Pro Ala Pro Cys Leu Val
580                 585                 590 aca ccc tcc tgg aca gag aca gcc agt agt ggg ggt gac cac ccg cag    2242
Thr Pro Ser Trp Thr Glu Thr Ala Ser Ser Gly Gly Asp His Pro Gln
595                 600                 605                 610 gca gag ccc aag ctt gcc acg gag gct gag ggc act acc gga ccc cgc    2290
Ala Glu Pro Lys Leu Ala Thr Glu Ala Glu Gly Thr Thr Gly Pro Arg
            615                 620                 625 ctg ccc ctt cct tcc gtc ccc tcc cca tcc cag gag gga gcc cca ctt    2338
Leu Pro Leu Pro Ser Val Pro Ser Pro Ser Gln Glu Gly Ala Pro Leu
        630                 635                 640 ccc tcg gag gag gcc agt gcc ccc gac gcc cct gat gcc ctg cct gac    2386
Pro Ser Glu Glu Ala Ser Ala Pro Asp Ala Pro Asp Ala Leu Pro Asp
    645                 650                 655 tct ccc acg cct gct act ggt ggc gag gtg tct gcc atc aag ctg gct    2434
Ser Pro Thr Pro Ala Thr Gly Gly Glu Val Ser Ala Ile Lys Leu Ala
                660                 665                 670 tct gcc ctg aat ggc agc agc agc tct ccc gag gtg gag gca ccc agc    2482
Ser Ala Leu Asn Gly Ser Ser Ser Ser Pro Glu Val Glu Ala Pro Ser
675                 680                 685                 690
```

-continued

| | | |
|---|---|---|
| agt gag gat gag gac acg gct gag gcc acc tca ggc atc ttc acc gac<br>Ser Glu Asp Glu Asp Thr Ala Glu Ala Thr Ser Gly Ile Phe Thr Asp<br>                            695                            700                            705 | 2530 |
| acg tcc agc gac ggc ctg cag gcc agg agg ccg gat gtg gtg cca gcc<br>Thr Ser Ser Asp Gly Leu Gln Ala Arg Arg Pro Asp Val Val Pro Ala<br>            710                              715                            720 | 2578 |
| ttc cgc tct ctg cag aag cag gtg ggg acc ccc gac tcc ctg gac tcc<br>Phe Arg Ser Leu Gln Lys Gln Val Gly Thr Pro Asp Ser Leu Asp Ser<br>                   725                            730                           735 | 2626 |
| ctg gac atc ccg tcc tca gcc agt gat ggt ggc tat gag gtc ttc agc<br>Leu Asp Ile Pro Ser Ser Ala Ser Asp Gly Gly Tyr Glu Val Phe Ser<br>        740                          745                            750 | 2674 |
| ccg tcg gcc act ggc ccc tct gga ggg cag ccg cga gcg ctg gac agt<br>Pro Ser Ala Thr Gly Pro Ser Gly Gly Gln Pro Arg Ala Leu Asp Ser<br>755                        760                            765                            770 | 2722 |
| ggc tat gac acc gag aac tat gag tcc cct gag ttt gtg ctc aag gag<br>Gly Tyr Asp Thr Glu Asn Tyr Glu Ser Pro Glu Phe Val Leu Lys Glu<br>                   775                            780                           785 | 2770 |
| gcg cag gaa ggg tgt gag ccc cag gcc ttt gcg gag ctg gcc tca gag<br>Ala Gln Glu Gly Cys Glu Pro Gln Ala Phe Ala Glu Leu Ala Ser Glu<br>            790                              795                            800 | 2818 |
| ggt gag ggc ccc ggg ccc gag aca cgg ctc tcc acc tcc ctc agt ggc<br>Gly Glu Gly Pro Gly Pro Glu Thr Arg Leu Ser Thr Ser Leu Ser Gly<br>                 805                            810                           815 | 2866 |
| ctc aac gag aag aat ccc tac cga gac tct gcc tac ttc tca gac ctc<br>Leu Asn Glu Lys Asn Pro Tyr Arg Asp Ser Ala Tyr Phe Ser Asp Leu<br>820                        825                            830 | 2914 |
| gag gct gag gcc gag gcc acc tca ggc cca gag aag aag tgc ggc ggg<br>Glu Ala Glu Ala Glu Ala Thr Ser Gly Pro Glu Lys Lys Cys Gly Gly<br>835                        840                            845                           850 | 2962 |
| gac cga gcc ccc ggg cca gag ctg ggc ctg ccg agc act ggg cag ccg<br>Asp Arg Ala Pro Gly Pro Glu Leu Gly Leu Pro Ser Thr Gly Gln Pro<br>                   855                            860                           865 | 3010 |
| tct gag cag gtc tgt ctc agg cct ggg gtt tcc ggg gag gca caa ggc<br>Ser Glu Gln Val Cys Leu Arg Pro Gly Val Ser Gly Glu Ala Gln Gly<br>            870                              875                            880 | 3058 |
| tct ggc ccc ggg gag gtg ctg ccc cca ctg ctg cag ctt gaa ggg tcc<br>Ser Gly Pro Gly Glu Val Leu Pro Pro Leu Leu Gln Leu Glu Gly Ser<br>                   885                            890                           895 | 3106 |
| tcc cca gag ccc agc acc tgc ccc tcg ggc ctg gtc cca gag cct ccg<br>Ser Pro Glu Pro Ser Thr Cys Pro Ser Gly Leu Val Pro Glu Pro Pro<br>900                        905                            910 | 3154 |
| gag ccc caa ggc cca gcc aag gtg cgg cct ggg ccc agc ccc agc tgc<br>Glu Pro Gln Gly Pro Ala Lys Val Arg Pro Gly Pro Ser Pro Ser Cys<br>915                        920                            925                           930 | 3202 |
| tcc cag ttt ttc ctg ctg acc ccg gtt ccg ctg aga tca gaa ggc aac<br>Ser Gln Phe Phe Leu Leu Thr Pro Val Pro Leu Arg Ser Glu Gly Asn<br>                   935                            940                           945 | 3250 |
| agc tct gag ttc cag ggg ccc cca gga ctg ttg tca ggg ccg gcc cca<br>Ser Ser Glu Phe Gln Gly Pro Pro Gly Leu Leu Ser Gly Pro Ala Pro<br>            950                              955                           960 | 3298 |
| caa aag cgg atg ggg ggc cca ggc acc ccc aga gcc cca ctc cgc ctg<br>Gln Lys Arg Met Gly Gly Pro Gly Thr Pro Arg Ala Pro Leu Arg Leu<br>965                        970                            975 | 3346 |
| gct ctg ccc ggc ctc cct gcg gcc ttg gag ggc cgg ccg gag gag gag<br>Ala Leu Pro Gly Leu Pro Ala Ala Leu Glu Gly Arg Pro Glu Glu Glu<br>        980                        985                            990 | 3394 |
| gag gag gac agt gag gac    agc gac gag tct gac    gag gag ctc cgc<br>Glu Glu Asp Ser Glu Asp    Ser Asp Glu Ser Asp    Glu Glu Leu Arg | 3439 |

```
                                                                                    -continued
995                  1000                    1005 tgc tac agc gtc cag gag cct agc gag gac agc gaa gag gag gcg       3484
Cys Tyr Ser Val Gln Glu Pro Ser Glu Asp Ser Glu Glu Glu Ala
1010                 1015                   1020 ccg gcg gtg ccc gtg gtg gct gag agc cag agc gcg cgc aac           3529
Pro Ala Val Pro Val Val Ala Glu Ser Gln Ser Ala Arg Asn
1025                 1030                   1035 ctg cgc agc ctg ctc aag atg ccc agc ctg ctg tcc gag acc ttc       3574
Leu Arg Ser Leu Leu Lys Met Pro Ser Leu Leu Ser Glu Thr Phe
1040                 1045                   1050 tgc gag gac ctg gaa cgc aag aag aag gcc gtg tcc ttc ttc gac       3619
Cys Glu Asp Leu Glu Arg Lys Lys Lys Ala Val Ser Phe Phe Asp
1055                 1060                   1065 gac gtc acc gtc tac ctc ttt gac cag gaa agc ccc acc cgg gag       3664
Asp Val Thr Val Tyr Leu Phe Asp Gln Glu Ser Pro Thr Arg Glu
1070                 1075                   1080 ctc ggg gag ccc ttc ccg ggc gcc aag gaa tcg ccc cct acg ttc       3709
Leu Gly Glu Pro Phe Pro Gly Ala Lys Glu Ser Pro Pro Thr Phe
1085                 1090                   1095 ctt agg ggg agc ccc ggc tct ccc agc gcc ccc aac cgg ccg cag       3754
Leu Arg Gly Ser Pro Gly Ser Pro Ser Ala Pro Asn Arg Pro Gln
1100                 1105                   1110 cag gct gat ggc tcc cca aat ggc tcc aca gcg gaa gag ggt ggt       3799
Gln Ala Asp Gly Ser Pro Asn Gly Ser Thr Ala Glu Glu Gly Gly
1115                 1120                   1125 ggg ttc gcg tgg gac gac gac ttc ccg ctg atg acg gcc aag gca       3844
Gly Phe Ala Trp Asp Asp Asp Phe Pro Leu Met Thr Ala Lys Ala
1130                 1135                   1140 gcc ttc gcc atg gcc cta gac ccg gcc gca ccc gcc ccg gct gcg       3889
Ala Phe Ala Met Ala Leu Asp Pro Ala Ala Pro Ala Pro Ala Ala
1145                 1150                   1155 ccc acg ccc acg ccc gct ccc ttc tcg cgc ttc acg gtg tcg ccc       3934
Pro Thr Pro Thr Pro Ala Pro Phe Ser Arg Phe Thr Val Ser Pro
1160                 1165                   1170 gcg ccc acg tcc cgc ttc tcc atc acg cac gtg tct gac tcg gac       3979
Ala Pro Thr Ser Arg Phe Ser Ile Thr His Val Ser Asp Ser Asp
1175                 1180                   1185 gcc gag tcc aag aga gga cct gaa gct ggt gcc ggg ggt gag agt       4024
Ala Glu Ser Lys Arg Gly Pro Glu Ala Gly Ala Gly Gly Glu Ser
1190                 1195                   1200 aaa gag gct tga gacctgggca gctcctgccc ctcaaggctg gcgtcaccgg       4076
Lys Glu Ala
1205 agcccctgcc aggcagcagc gaggatggtg accgagaagg tggggaccac gtcctggtgg    4136 ctgttggcag cagattcagg tgcctctgcc ccacgcggtg tcctggagaa gcccgtggga    4196 tgagaggccc tggatggtag atcggccatg ctccgcccca gaggcagaat tcgtctgggc    4256 ttttaggctt gctgctagcc cctgggggcg cctggagcca cagtgggtgt ctgtacacac    4316 atacacactc aaaagggggcc agtgcccctg ggcacggcgg cccccaccct ctgccctgcc    4376 tgcctggcct cggaggaccc gcatgcccca tccggcagct cctccggtgt gctcacagga    4436 cacttaaacc aggacgaggc atggccccga cacactggca ggtttgtgag cctcttccca    4496 cccctgtgc ccccaccctt gcctggttcc tggtggctca gggcaaggag tggccctggg    4556 cgcccgtgtc ggtcctgttt ccgctgccct tatctcaaag tccgtggctg ttttcccttc    4616 actgactcag ctagacccgt aagcccaccc ttcccacagg gaacaggctg ctcccacctg    4676 ggtcccgctg tggccacggt gggcagccca aaagatcagg ggtggagggg cttccaggct    4736
```

-continued

```
gtactcctgc cccgtgggcc ccgttctaga ggtgcccttg gcaggaccgt gcaggcagct    4796 ccctctgtg gggcagtatc tggtcctgtg ccccagctgc caaaggagag tgggggccat    4856
gccccgcagt cagtgttggg gggctcctgc ctacagggag agggatggtg gggaaggggt    4916
ggagctgggg gcagggcagc acagggaata ttttgtaac taactaactg ctgtggttgg    4976
agcgaatgga agttgggtga ttttaagtta ttgttgccaa agagatgtaa agtttattgt    5036
tgcttcgcag ggggatttgt tttgtgtttt gtttgaggct tagaacgctg gtgcaatgtt    5096
ttcttgttcc ttgttttta agagaaatga agctaagaaa aaag                     5140
```

<210> SEQ ID NO 16
<211> LENGTH: 1207
<212> TYPE: PRT
<213> ORGANISM: Homo sapiens

<400> SEQUENCE: 16

```
Met Gln Phe Leu Glu Glu Val Gln Pro Tyr Arg Ala Leu Lys His Ser
1               5                   10                  15

Asn Leu Leu Gln Cys Leu Ala Gln Cys Ala Glu Val Thr Pro Tyr Leu
            20                  25                  30

Leu Val Met Glu Phe Cys Pro Leu Gly Asp Leu Lys Gly Tyr Leu Arg
        35                  40                  45

Ser Cys Arg Val Ala Glu Ser Met Ala Pro Asp Pro Arg Thr Leu Gln
    50                  55                  60

Arg Met Ala Cys Glu Val Ala Cys Gly Val Leu His Leu His Arg Asn
65                  70                  75                  80

Asn Phe Val His Ser Asp Leu Ala Leu Arg Asn Cys Leu Leu Thr Ala
                85                  90                  95

Asp Leu Thr Val Lys Ile Gly Asp Tyr Gly Leu Ala His Cys Lys Tyr
            100                 105                 110

Arg Glu Asp Tyr Phe Val Thr Ala Asp Gln Leu Trp Val Pro Leu Arg
        115                 120                 125

Trp Ile Ala Pro Glu Leu Val Asp Glu Val His Ser Asn Leu Leu Val
    130                 135                 140

Val Asp Gln Thr Lys Ser Gly Asn Val Trp Ser Leu Gly Val Thr Ile
145                 150                 155                 160

Trp Glu Leu Phe Glu Leu Gly Thr Gln Pro Tyr Pro Gln His Ser Asp
                165                 170                 175

Gln Gln Val Leu Ala Tyr Thr Val Arg Glu Gln Leu Lys Leu Pro
            180                 185                 190

Lys Pro Gln Leu Gln Leu Thr Leu Ser Asp Arg Trp Tyr Glu Val Met
        195                 200                 205

Gln Phe Cys Trp Leu Gln Pro Glu Gln Arg Pro Thr Ala Glu Glu Val
    210                 215                 220

His Leu Leu Leu Ser Tyr Leu Cys Ala Lys Gly Ala Thr Glu Ala Glu
225                 230                 235                 240

Glu Glu Phe Glu Arg Arg Trp Arg Ser Leu Arg Pro Gly Gly Gly Gly
                245                 250                 255

Val Gly Pro Gly Pro Gly Ala Ala Gly Pro Met Leu Gly Gly Val Val
            260                 265                 270

Glu Leu Ala Ala Ala Ser Ser Phe Pro Leu Leu Glu Gln Phe Ala Gly
        275                 280                 285

Asp Gly Phe His Ala Asp Gly Asp Asp Val Leu Thr Val Thr Glu Thr
    290                 295                 300
```

```
Ser Arg Gly Leu Asn Phe Glu Tyr Lys Trp Glu Ala Gly Arg Ala
305                 310                 315                 320

Glu Ala Phe Pro Ala Thr Leu Ser Pro Gly Arg Thr Ala Arg Leu Gln
            325                 330                 335

Glu Leu Cys Ala Pro Asp Gly Ala Pro Pro Gly Val Val Pro Val Leu
            340                 345                 350

Ser Ala His Ser Pro Ser Leu Gly Ser Glu Tyr Phe Ile Arg Leu Glu
            355                 360                 365

Glu Ala Pro Ala Ala Gly His Asp Pro Asp Cys Ala Gly Cys Ala
370                 375                 380

Pro Ser Pro Pro Ala Thr Ala Asp Gln Asp Asp Ser Asp Gly Ser
385                 390                 395                 400

Thr Ala Ala Ser Leu Ala Met Glu Pro Leu Gly His Gly Pro Pro
                405                 410                 415

Val Asp Val Pro Trp Gly Arg Gly Asp His Tyr Pro Arg Arg Ser Leu
            420                 425                 430

Ala Arg Asp Pro Leu Cys Pro Ser Arg Ser Pro Ser Pro Ser Ala Gly
            435                 440                 445

Pro Leu Ser Leu Ala Glu Gly Gly Ala Glu Asp Ala Asp Trp Gly Val
450                 455                 460

Ala Ala Phe Cys Pro Ala Phe Phe Glu Asp Pro Leu Gly Thr Ser Pro
465                 470                 475                 480

Leu Gly Ser Ser Gly Ala Pro Pro Leu Pro Leu Thr Gly Glu Asp Glu
                485                 490                 495

Leu Glu Glu Val Gly Ala Arg Arg Ala Ala Gln Arg Gly His Trp Arg
            500                 505                 510

Ser Asn Val Ser Ala Asn Asn Ser Gly Ser Arg Cys Pro Glu Ser
            515                 520                 525

Trp Asp Pro Val Ser Ala Gly Cys His Ala Glu Gly Cys Pro Ser Pro
530                 535                 540

Lys Gln Thr Pro Arg Ala Ser Pro Glu Pro Gly Tyr Pro Gly Glu Pro
545                 550                 555                 560

Leu Leu Gly Leu Gln Ala Ala Ser Ala Gln Glu Pro Gly Cys Cys Pro
                565                 570                 575

Gly Leu Pro His Leu Cys Ser Ala Gln Gly Leu Ala Pro Ala Pro Cys
            580                 585                 590

Leu Val Thr Pro Ser Trp Thr Glu Thr Ala Ser Ser Gly Gly Asp His
            595                 600                 605

Pro Gln Ala Glu Pro Lys Leu Ala Thr Glu Ala Glu Gly Thr Thr Gly
    610                 615                 620

Pro Arg Leu Pro Leu Pro Ser Val Pro Ser Pro Ser Gln Glu Gly Ala
625                 630                 635                 640

Pro Leu Pro Ser Glu Glu Ala Ser Ala Pro Asp Ala Pro Asp Ala Leu
                645                 650                 655

Pro Asp Ser Pro Thr Pro Ala Thr Gly Gly Glu Val Ser Ala Ile Lys
            660                 665                 670

Leu Ala Ser Ala Leu Asn Gly Ser Ser Ser Pro Glu Val Glu Ala
            675                 680                 685

Pro Ser Ser Glu Asp Glu Asp Thr Ala Glu Ala Thr Ser Gly Ile Phe
    690                 695                 700

Thr Asp Thr Ser Ser Asp Gly Leu Gln Ala Arg Arg Pro Asp Val Val
705                 710                 715                 720
```

-continued

```
Pro Ala Phe Arg Ser Leu Gln Lys Gln Val Gly Thr Pro Asp Ser Leu
            725                 730                 735

Asp Ser Leu Asp Ile Pro Ser Ser Ala Ser Asp Gly Gly Tyr Glu Val
            740                 745                 750

Phe Ser Pro Ser Ala Thr Gly Pro Ser Gly Gln Pro Arg Ala Leu
            755                 760             765

Asp Ser Gly Tyr Asp Thr Glu Asn Tyr Glu Ser Pro Glu Phe Val Leu
            770                 775                 780

Lys Glu Ala Gln Glu Gly Cys Glu Pro Gln Ala Phe Ala Glu Leu Ala
785                 790                 795                 800

Ser Glu Gly Glu Gly Pro Gly Pro Glu Thr Arg Leu Ser Thr Ser Leu
                805                 810                 815

Ser Gly Leu Asn Glu Lys Asn Pro Tyr Arg Asp Ser Ala Tyr Phe Ser
            820                 825                 830

Asp Leu Glu Ala Glu Ala Glu Ala Thr Ser Gly Pro Glu Lys Lys Cys
            835                 840                 845

Gly Gly Asp Arg Ala Pro Gly Pro Glu Leu Gly Leu Pro Ser Thr Gly
            850                 855                 860

Gln Pro Ser Glu Gln Val Cys Leu Arg Pro Gly Val Ser Gly Glu Ala
865                 870                 875                 880

Gln Gly Ser Gly Pro Gly Glu Val Leu Pro Leu Leu Gln Leu Glu
                885                 890                 895

Gly Ser Ser Pro Glu Pro Ser Thr Cys Pro Ser Gly Leu Val Pro Glu
                900                 905                 910

Pro Pro Glu Pro Gln Gly Pro Ala Lys Val Arg Pro Gly Pro Ser Pro
            915                 920                 925

Ser Cys Ser Gln Phe Phe Leu Leu Thr Pro Val Pro Leu Arg Ser Glu
            930                 935                 940

Gly Asn Ser Ser Glu Phe Gln Gly Pro Pro Gly Leu Leu Ser Gly Pro
945                 950                 955                 960

Ala Pro Gln Lys Arg Met Gly Gly Pro Gly Thr Pro Arg Ala Pro Leu
            965                 970                 975

Arg Leu Ala Leu Pro Gly Leu Pro Ala Ala Leu Glu Gly Arg Pro Glu
            980                 985                 990

Glu Glu Glu Glu Asp Ser Glu Asp  Ser Asp Glu Ser Asp  Glu Glu Leu
            995                 1000                1005

Arg Cys  Tyr Ser Val Gln Glu  Pro Ser Glu Asp Ser  Glu Glu Glu
    1010                1015                1020

Ala Pro  Ala Val Pro Val Val  Val Ala Glu Ser Gln  Ser Ala Arg
    1025                1030                1035

Asn Leu  Arg Ser Leu Leu Lys  Met Pro Ser Leu Leu  Ser Glu Thr
    1040                1045                1050

Phe Cys  Glu Asp Leu Glu Arg  Lys Lys Lys Ala Val  Ser Phe Phe
    1055                1060                1065

Asp Asp  Val Thr Val Tyr Leu  Phe Asp Gln Glu Ser  Pro Thr Arg
    1070                1075                1080

Glu Leu  Gly Glu Pro Phe Pro  Gly Ala Lys Glu Ser  Pro Pro Thr
    1085                1090                1095

Phe Leu  Arg Gly Ser Pro Gly  Ser Pro Ser Ala Pro  Asn Arg Pro
    1100                1105                1110

Gln Gln  Ala Asp Gly Ser Pro  Asn Gly Ser Thr Ala  Glu Glu Gly
    1115                1120                1125

Gly Gly  Phe Ala Trp Asp Asp  Asp Phe Pro Leu Met  Thr Ala Lys
```

-continued

```
             1130                1135                1140
Ala Ala Phe Ala Met Ala Leu Asp Pro Ala Pro Ala Pro Ala
    1145                1150                1155

Ala Pro Thr Pro Thr Pro Ala Pro Phe Ser Arg Phe Thr Val Ser
1160                1165                1170

Pro Ala Pro Thr Ser Arg Phe Ser Ile Thr His Val Ser Asp Ser
    1175                1180                1185

Asp Ala Glu Ser Lys Arg Gly Pro Glu Ala Gly Ala Gly Gly Glu
    1190                1195                1200

Ser Lys Glu Ala
    1205

<210> SEQ ID NO 17
<211> LENGTH: 1803
<212> TYPE: DNA
<213> ORGANISM: Pan troglodytes

<400> SEQUENCE: 17
gctccctgcc tggttacacc ctcctggaca gagacagccg gtagtggggg tgaccacccg      60
caggcagagc ccaagcttgc cacggaggct gagggcactg ccggaccctg tctgccccTt     120
ccttccgtcc cctccccatc ccaggaggga gccccacttc cctcggagga ggccagtgcc    180
cctgacgccc ctgatgccct gcctgactct cccatgcctg ctactggtgg cgaggtgtct    240
gccatcaagc tggcttctgt cctgaatggc agcagcagct ccccgaggt ggaggcaccc     300 agcagcgagg atgaggacac ggctgaggcc acctcaggca tcttcaccga cacgtccagc    360
gacggcctgc aggccgagag gctggatgtg gtgccagcct ccgctctct gcagaagcag     420 gtggggaccc ccgactccct ggactccctg gacatcccat cctcagccag tgatggtggc    480
tatgaggtct tcagcccgtc ggccactggc ccctctggag gcagccccg agcgctggac     540 agtggctatg acaccgagaa ctatgagtcc cctgagtttg tgctcaagga ggcgcaggaa    600
gggtgtgagc cccaggcctt tgaggagctg gcctcagagg gtgagggccc cggccccggg    660
cccgagacgc ggctctccac ctccctcagt ggcctcaacg agaagaatcc ctaccgagac    720
tctgcctact ctcagacct ggaggctgag gccgaggccg aggccacctc aggcccagag     780
aagaagtgcg gcggggacca agccccgggg ccagagctgg acctgccgag cactgggcag    840
ccgtctgagc aggtctccct caggcctggg gtttccgggg aggcacaagg ctctggcccc    900
ggggaggtgc tgccccact gctgcggctt gaaggatcct cccagagcc cagcacctgc      960 ccctcgggcc tggtcccaga gcctccggag ccccaaggcc cagccgaggt gcggcctggg    1020
cccagcccca gctgctccca gttttctcctg ctgaccccgg ttccgctgag atcagaaggc   1080
aacagctctg agttccaggg gcccccagga ctgttgtcag ggccggcccc acaaaagcgg    1140 atgggggggcc taggcacccc cagagcccca ctccgcctgg ctctgcccgg cctccctgcg   1200
gccttggagg gccggccgga ggaggaggag gaggacagtg aggacagcgg cgagtctgac    1260
gaggagctcc gctgctacag cgtccaggag cctagcgagg acagcgaaga ggaggcgccg    1320
gcggtgcccg tggtggtggc tgagagccag agcgcgcgca acctgcgcag cctgctcaag    1380
atgcccagcc tgctgtccga ggccttctgc gaggacctgg aacgcaagaa gaaggccgtg    1440
tccttcttcg acgacgtcac cgtctacctc tttgaccagg aaagcccac ctgggagctc    1500 ggggagccct tccgggcgc caaggaatcg cccccacgt tccttagggg gagccccggc     1560
tctcccagcg ccccccaaccg gccgcagcag gctgatggct cccaaatgg ctccacagcg    1620
```

| | |
|---|---|
| gaagagggtg gtgggttcgc gtgggacgac gacttcccgc tgatgccggc caaggcagcc | 1680 |
| ttcgccatgg ccctagaccc ggccgcaccc gccccggctg cgcccacgcc cgctcccttc | 1740 |
| tcgcgcttca cggtgtcgcc cgcgcccacg tccacgtccc gcttctccat cacgcacgtg | 1800 |
| tct | 1803 |

<210> SEQ ID NO 18
<211> LENGTH: 1785
<212> TYPE: DNA
<213> ORGANISM: Gorilla gorilla

<400> SEQUENCE: 18

| | |
|---|---|
| gctccctgcc tggttacacc ctcctggaca gagacagacg gtagtggggg tgaccacccg | 60 |
| caggcagagc ccaagcttgc cacggaggct gagggcactg ccggaccccg cctgcccctt | 120 |
| ccttccgtcc cctccccatc ccaggaggga gccccacttc cctcggagga ggccagtgcc | 180 |
| cccgacgccc tgatgccct gcctgactcg cccacgcctg ctactggtgg cgaggtgtct | 240 |
| gccaccaagc tggcttccgc cctgaatggc agcagcagct ctcccgaggt ggaggcaccc | 300 |
| agcagtgagg atgaggacac ggctgaggca acctcaggca tcttcaccga cacgtccagc | 360 |
| gacggcctgc aggccgagag gcaggatgtg gtgccagcct ccactctct gcagaagcag | 420 |
| gtggggaccc ccgactccct ggactccctg gacatcccgt cctcagccag tgatggtggc | 480 |
| tatgaggtct tcagcccgtc ggccacgggc ccctctggag ggcagccccg agcgctggac | 540 |
| agtggctatg acaccgagaa ctatgagtcc cctgagtttg tgctcaagga ggcgcaggaa | 600 |
| gggtgtgagc cccaggcctt tgcggagctg gcctcagagg gcgagggccc cgggcccgag | 660 |
| acgcggctct ccacctccct cagtggcctc aacgagaaga tccctaccg agattctgcc | 720 |
| tacttctcag acctggaggc tgaggccgag gctacctcag gcccagagaa gaagtgcggt | 780 |
| ggggaccaag cccccgggcc agagctgggc ctgccgagca ctgggcagcc gtctgagcag | 840 |
| gtctccctca gtcctggggt ttccgtggag gcacaaggct ctggccccgg ggaggtgctg | 900 |
| cccccactgc tgcggcttga agggtcctcc ccagagccca gcacctgccc ctcgggcctg | 960 |
| gtcccagagc ctccggagcc ccaaggccca gcgaggtgc ggcctgggcc cagccccagc | 1020 |
| tgctcccagt ttttcctgct gaccccggtt ccgctgagat cagaaggcaa cagctctgag | 1080 |
| ttccaggggc cccaggact gttgtcaggg ccggccccac aaaagcggat gggggggccca | 1140 |
| ggcaccccca gagcccccaca ccgcctggct ctgcccggcc tccctgcggc cttggagggc | 1200 |
| cggccggagg aggaggagga ggacagtgag gacagcgacg agtctgacga ggagctccgc | 1260 |
| tgctacagcg tccaggagcc tagcgaggac agcgaagagg aggcgccggc ggtgcccgtg | 1320 |
| gtggtggctg agagccagag cgcgcgcaac ctgcgcagcc tgctcaagat gcccagcctg | 1380 |
| ctgtccgagg ccttctgcga ggacctggaa cgcaagaaga aggccgtgtc cttcttcgac | 1440 |
| gacgtcaccg tctacctctt tgaccaggaa agccccaccc gggagctcgg ggagcccttc | 1500 |
| ccgggcgcca aggaatcgcc ccccacgttc cttaggggga gccccggctc ttccagcgcc | 1560 |
| cccaaccggc cgcagcaggc tgatggctcc ccaaatggct ccacagcgga agagggtggt | 1620 |
| gggttcgcgt gggacgacga cttcccgctg atgccggcca aggcagcctt cgccatggcc | 1680 |
| ctagacccgg ccgcacccgc cccggctgcg cccacgcccg ctcccttctc gcgcttcacg | 1740 |
| gtgtcgcccg cgcccacgtc ccgcttctcc atcacgcacg tgtct | 1785 |

<210> SEQ ID NO 19
<211> LENGTH: 24

```
<212> TYPE: DNA
<213> ORGANISM: Pan troglodytes

<400> SEQUENCE: 19
ggtgagggcc ccggccccgg gccc                                              24

<210> SEQ ID NO 20
<211> LENGTH: 18
<212> TYPE: DNA
<213> ORGANISM: Homo sapiens

<400> SEQUENCE: 20
ggtgagggcc ccgggccc                                                     18

<210> SEQ ID NO 21
<211> LENGTH: 18
<212> TYPE: DNA
<213> ORGANISM: Gorilla gorilla

<400> SEQUENCE: 21
ggcgagggcc ccgggccc                                                     18

<210> SEQ ID NO 22
<211> LENGTH: 24
<212> TYPE: DNA
<213> ORGANISM: Pan troglodytes

<400> SEQUENCE: 22
ctggaggctg aggccgaggc cgag                                              24

<210> SEQ ID NO 23
<211> LENGTH: 18
<212> TYPE: DNA
<213> ORGANISM: Homo sapiens

<400> SEQUENCE: 23
ctcgaggctg aggccgag                                                     18

<210> SEQ ID NO 24
<211> LENGTH: 18
<212> TYPE: DNA
<213> ORGANISM: Gorilla gorilla

<400> SEQUENCE: 24
ctggaggctg aggccgag                                                     18

<210> SEQ ID NO 25
<211> LENGTH: 18
<212> TYPE: DNA
<213> ORGANISM: Pan troglodytes

<400> SEQUENCE: 25
cccacgcccg ctcccttc                                                     18

<210> SEQ ID NO 26
<211> LENGTH: 24
<212> TYPE: DNA
<213> ORGANISM: Homo sapiens

<400> SEQUENCE: 26
cccacgccca cgcccgctcc cttc                                              24

<210> SEQ ID NO 27
```

<210> SEQ ID NO 27
<211> LENGTH: 18
<212> TYPE: DNA
<213> ORGANISM: Gorilla gorilla

<400> SEQUENCE: 27
cccacgcccg ctcccttc                                                    18

<210> SEQ ID NO 28
<211> LENGTH: 24
<212> TYPE: DNA
<213> ORGANISM: Pan troglodytes

<400> SEQUENCE: 28
cccacgtcca cgtcccgctt ctcc                                             24

<210> SEQ ID NO 29
<211> LENGTH: 18
<212> TYPE: DNA
<213> ORGANISM: Homo sapiens

<400> SEQUENCE: 29
cccacgtccc gcttctcc                                                    18

<210> SEQ ID NO 30
<211> LENGTH: 18
<212> TYPE: DNA
<213> ORGANISM: Gorilla gorilla

<400> SEQUENCE: 30
cccacgtccc gcttctcc                                                    18

<210> SEQ ID NO 31
<211> LENGTH: 1335
<212> TYPE: DNA
<213> ORGANISM: Pan troglodytes

<400> SEQUENCE: 31
atggcagtga caactcgttt gacatggttg catgaaaaga tcctgcaaaa tcatttthgga      60 gggaagcggc ttagccttct ctataagggt agtgtccatg gattccataa tggagttttg     120
cttgacagat gttgtaatca agggcctact ctaacagtga tttatagtga agatcatatt     180
attggagcat atgcagaaga gggttaccag gmaagaaagt atgcttccat catccttttt     240
gcacttcaag agactaaaat ttcagaatgg aaactaggac tatatacacc agaaacactg     300
ttttgttgtg acgttgcaaa atataactcc ccaactaatt tccagataga tggaagaaat     360
agaaaagtga ttatggactt aaagacaatg gaaaatcttg gacttgctca aaattgtact     420
atctctattc aggattatga agtttttcga tgcgaagatt cactggacga agaaagata      480 aaagggtca ttgagctcag gaagagctta ctgtctgcct tgagaactta tgaaccatat     540
ggatccctgg ttcaacaaat acgaattctg ctgctgggtc aattggagc tgggaagtct     600 agcttttca actcagtgag gtctgttttc caagggcatg taacgcatca ggctttggtg     660
ggcactaata caactgggat atctgagaag tataggacat actctattag agacgggaaa     720
gatggcaaat acctgccatt tattctgtgt gactcactgg ggctgagtga aaagaaggc     780 ggcctgtgca tggatgacat atcctacatc ttgaacggta acattcgtga tagataccag     840
tttaatccca tggaatcaat caaattaaat catcatgact acattgattc cccatcgctg     900
aaggacagaa ttcattgtgt ggcatttgta tttgatgcca gctctattga atacttctcc     960
tctcagatga tagtaaagat caaaagaatt cgaagggagt tggtaaacgc tggtgtggta    1020

```
catgtggctt tgctcactca tgtggatagc atggatctga ttacaaaagg tgaccttata    1080
gaaatagaga gatgtgtgcc tgtgaggtcc aagctagagg aagtccaaag aaaacttgga    1140
tttgctcttt ctgacatctc ggtggttagc aattattcct ctgagtggga gctggaccct    1200
gtaaaggatg ttctaattct ttctgctctg agacgaatgc tatgggctgc agatgacttc    1260
ttagaggatt tgcctttga gcaaataggg aatctaaggg aggaaattat caactgtgca    1320
caaggaaaaa aatag                                                     1335

<210> SEQ ID NO 32
<211> LENGTH: 1335
<212> TYPE: DNA
<213> ORGANISM: Pan troglodytes
<220> FEATURE:
<221> NAME/KEY: CDS
<222> LOCATION: (1)..(1335)
<220> FEATURE:
<221> NAME/KEY: misc_feature
<222> LOCATION: (71)..(71)
<223> OTHER INFORMATION: Xaa = Glu or Ala
<220> FEATURE:
<221> NAME/KEY: misc_feature
<222> LOCATION: (212)..(212)
<223> OTHER INFORMATION: m is A or C

<400> SEQUENCE: 32 atg gca gtg aca act cgt ttg aca tgg ttg cat gaa aag atc ctg caa      48
Met Ala Val Thr Thr Arg Leu Thr Trp Leu His Glu Lys Ile Leu Gln
1               5                   10                  15 aat cat ttt gga ggg aag cgg ctt agc ctt ctc tat aag ggt agt gtc      96
Asn His Phe Gly Gly Lys Arg Leu Ser Leu Leu Tyr Lys Gly Ser Val
            20                  25                  30 cat gga ttc cat aat gga gtt ttg ctt gac aga tgt tgt aat caa ggg     144
His Gly Phe His Asn Gly Val Leu Leu Asp Arg Cys Cys Asn Gln Gly
        35                  40                  45 cct act cta aca gtg att tat agt gaa gat cat att att gga gca tat     192
Pro Thr Leu Thr Val Ile Tyr Ser Glu Asp His Ile Ile Gly Ala Tyr
    50                  55                  60 gca gaa gag ggt tac cag gma aga aag tat gct tcc atc atc ctt ttt     240
Ala Glu Glu Gly Tyr Gln Xaa Arg Lys Tyr Ala Ser Ile Ile Leu Phe
65                  70                  75                  80 gca ctt caa gag act aaa att tca gaa tgg aaa cta gga cta tat aca     288
Ala Leu Gln Glu Thr Lys Ile Ser Glu Trp Lys Leu Gly Leu Tyr Thr
                85                  90                  95 cca gaa aca ctg ttt tgt tgt gac gtt gca aaa tat aac tcc cca act     336
Pro Glu Thr Leu Phe Cys Cys Asp Val Ala Lys Tyr Asn Ser Pro Thr
            100                 105                 110 aat ttc cag ata gat gga aga aat aga aaa gtg att atg gac tta aag     384
Asn Phe Gln Ile Asp Gly Arg Asn Arg Lys Val Ile Met Asp Leu Lys
        115                 120                 125 aca atg gaa aat ctt gga ctt gct caa aat tgt act atc tct att cag     432
Thr Met Glu Asn Leu Gly Leu Ala Gln Asn Cys Thr Ile Ser Ile Gln
    130                 135                 140 gat tat gaa gtt ttt cga tgc gaa gat tca ctg gac gaa aga aag ata     480
Asp Tyr Glu Val Phe Arg Cys Glu Asp Ser Leu Asp Glu Arg Lys Ile
145                 150                 155                 160 aaa ggg gtc att gag ctc agg aag agc tta ctg tct gcc ttg aga act     528
Lys Gly Val Ile Glu Leu Arg Lys Ser Leu Leu Ser Ala Leu Arg Thr
                165                 170                 175 tat gaa cca tat gga tcc ctg gtt caa caa ata cga att ctg ctg ctg     576
Tyr Glu Pro Tyr Gly Ser Leu Val Gln Gln Ile Arg Ile Leu Leu Leu
            180                 185                 190
```

```
ggt cca att gga gct ggg aag tct agc ttt ttc aac tca gtg agg tct      624
Gly Pro Ile Gly Ala Gly Lys Ser Ser Phe Phe Asn Ser Val Arg Ser
        195                 200                 205 gtt ttc caa ggg cat gta acg cat cag gct ttg gtg ggc act aat aca      672
Val Phe Gln Gly His Val Thr His Gln Ala Leu Val Gly Thr Asn Thr
    210                 215                 220 act ggg ata tct gag aag tat agg aca tac tct att aga gac ggg aaa      720
Thr Gly Ile Ser Glu Lys Tyr Arg Thr Tyr Ser Ile Arg Asp Gly Lys
225                 230                 235                 240 gat ggc aaa tac ctg cca ttt att ctg tgt gac tca ctg ggg ctg agt      768
Asp Gly Lys Tyr Leu Pro Phe Ile Leu Cys Asp Ser Leu Gly Leu Ser
                245                 250                 255 gag aaa gaa ggc ggc ctg tgc atg gat gac ata tcc tac atc ttg aac      816
Glu Lys Glu Gly Gly Leu Cys Met Asp Asp Ile Ser Tyr Ile Leu Asn
        260                 265                 270 ggt aac att cgt gat aga tac cag ttt aat ccc atg gaa tca atc aaa      864
Gly Asn Ile Arg Asp Arg Tyr Gln Phe Asn Pro Met Glu Ser Ile Lys
    275                 280                 285 tta aat cat cat gac tac att gat tcc cca tcg ctg aag gac aga att      912
Leu Asn His His Asp Tyr Ile Asp Ser Pro Ser Leu Lys Asp Arg Ile
290                 295                 300 cat tgt gtg gca ttt gta ttt gat gcc agc tct att gaa tac ttc tcc      960
His Cys Val Ala Phe Val Phe Asp Ala Ser Ser Ile Glu Tyr Phe Ser
305                 310                 315                 320 tct cag atg ata gta aag atc aaa aga att cga agg gag ttg gta aac     1008
Ser Gln Met Ile Val Lys Ile Lys Arg Ile Arg Arg Glu Leu Val Asn
                325                 330                 335 gct ggt gtg gta cat gtg gct ttg ctc act cat gtg gat agc atg gat     1056
Ala Gly Val Val His Val Ala Leu Leu Thr His Val Asp Ser Met Asp
        340                 345                 350 ctg att aca aaa ggt gac ctt ata gaa ata gag aga tgt gtg cct gtg     1104
Leu Ile Thr Lys Gly Asp Leu Ile Glu Ile Glu Arg Cys Val Pro Val
    355                 360                 365 agg tcc aag cta gag gaa gtc caa aga aaa ctt gga ttt gct ctt tct     1152
Arg Ser Lys Leu Glu Glu Val Gln Arg Lys Leu Gly Phe Ala Leu Ser
370                 375                 380 gac atc tcg gtg gtt agc aat tat tcc tct gag tgg gag ctg gac cct     1200
Asp Ile Ser Val Val Ser Asn Tyr Ser Ser Glu Trp Glu Leu Asp Pro
385                 390                 395                 400 gta aag gat gtt cta att ctt tct gct ctg aga cga atg cta tgg gct     1248
Val Lys Asp Val Leu Ile Leu Ser Ala Leu Arg Arg Met Leu Trp Ala
                405                 410                 415 gca gat gac ttc tta gag gat ttg cct ttt gag caa ata ggg aat cta     1296
Ala Asp Asp Phe Leu Glu Asp Leu Pro Phe Glu Gln Ile Gly Asn Leu
        420                 425                 430 agg gag gaa att atc aac tgt gca caa gga aaa aaa tag                 1335
Arg Glu Glu Ile Ile Asn Cys Ala Gln Gly Lys Lys
    435                 440
```

<210> SEQ ID NO 33
<211> LENGTH: 444
<212> TYPE: PRT
<213> ORGANISM: Pan troglodytes
<220> FEATURE:
<221> NAME/KEY: misc_feature
<222> LOCATION: (71)..(71)
<223> OTHER INFORMATION: The 'Xaa' at location 71 stands for Glu, or Ala.

<400> SEQUENCE: 33

Met Ala Val Thr Thr Arg Leu Thr Trp Leu His Glu Lys Ile Leu Gln

```
  1               5                10               15
Asn His Phe Gly Gly Lys Arg Leu Ser Leu Leu Tyr Lys Gly Ser Val
              20                  25                  30
His Gly Phe His Asn Gly Val Leu Leu Asp Arg Cys Cys Asn Gln Gly
              35                  40              45
Pro Thr Leu Thr Val Ile Tyr Ser Glu Asp His Ile Ile Gly Ala Tyr
        50                  55              60
Ala Glu Glu Gly Tyr Gln Xaa Arg Lys Tyr Ala Ser Ile Ile Leu Phe
65                  70              75                      80
Ala Leu Gln Glu Thr Lys Ile Ser Glu Trp Lys Leu Gly Leu Tyr Thr
                85                  90                  95
Pro Glu Thr Leu Phe Cys Cys Asp Val Ala Lys Tyr Asn Ser Pro Thr
                100                 105             110
Asn Phe Gln Ile Asp Gly Arg Asn Arg Lys Val Ile Met Asp Leu Lys
            115                 120             125
Thr Met Glu Asn Leu Gly Leu Ala Gln Asn Cys Thr Ile Ser Ile Gln
    130                 135             140
Asp Tyr Glu Val Phe Arg Cys Glu Asp Ser Leu Asp Glu Arg Lys Ile
145                 150             155                 160
Lys Gly Val Ile Glu Leu Arg Lys Ser Leu Leu Ser Ala Leu Arg Thr
                165             170                 175
Tyr Glu Pro Tyr Gly Ser Leu Val Gln Gln Ile Arg Ile Leu Leu Leu
            180             185                 190
Gly Pro Ile Gly Ala Gly Lys Ser Ser Phe Phe Asn Ser Val Arg Ser
            195                 200             205
Val Phe Gln Gly His Val Thr His Gln Ala Leu Val Gly Thr Asn Thr
    210                 215             220
Thr Gly Ile Ser Glu Lys Tyr Arg Thr Tyr Ser Ile Arg Asp Gly Lys
225                 230                 235                 240
Asp Gly Lys Tyr Leu Pro Phe Ile Leu Cys Asp Ser Leu Gly Leu Ser
                245                 250             255
Glu Lys Glu Gly Gly Leu Cys Met Asp Asp Ile Ser Tyr Ile Leu Asn
            260                 265             270
Gly Asn Ile Arg Asp Arg Tyr Gln Phe Asn Pro Met Glu Ser Ile Lys
        275                 280             285
Leu Asn His His Asp Tyr Ile Asp Ser Pro Ser Leu Lys Asp Arg Ile
        290                 295             300
His Cys Val Ala Phe Val Phe Asp Ala Ser Ser Ile Glu Tyr Phe Ser
305                 310                 315                 320
Ser Gln Met Ile Val Lys Ile Lys Arg Ile Arg Arg Glu Leu Val Asn
                325                 330                 335
Ala Gly Val Val His Val Ala Leu Leu Thr His Val Asp Ser Met Asp
                340                 345             350
Leu Ile Thr Lys Gly Asp Leu Ile Glu Ile Glu Arg Cys Val Pro Val
            355                 360             365
Arg Ser Lys Leu Glu Glu Val Gln Arg Lys Leu Gly Phe Ala Leu Ser
    370                 375             380
Asp Ile Ser Val Val Ser Asn Tyr Ser Ser Glu Trp Glu Leu Asp Pro
385                 390             395                 400
Val Lys Asp Val Leu Ile Leu Ser Ala Leu Arg Arg Met Leu Trp Ala
            405                 410                 415
Ala Asp Asp Phe Leu Glu Asp Leu Pro Phe Glu Gln Ile Gly Asn Leu
            420                 425                 430
```

Arg Glu Glu Ile Ile Asn Cys Ala Gln Gly Lys Lys
        435                 440

<210> SEQ ID NO 34
<211> LENGTH: 1335
<212> TYPE: DNA
<213> ORGANISM: Homo sapiens

<400> SEQUENCE: 34

| | |
|---|---|
| atggcagtga caactcgttt gacatggttg cacgaaaaga tcctgcaaaa tcattttgga | 60 |
| gggaagcggc ttagccttct ctataagggt agtgtccatg gattccgtaa tggagttttg | 120 |
| cttgacagat gttgtaatca agggcctact ctaacagtga tttatagtga agatcatatt | 180 |
| attggagcat atgcagaaga gagttaccag gaaggaaagt atgcttccat catccttttt | 240 |
| gcacttcaag atactaaaat ttcagaatgg aaactaggac tatgtacacc agaaacactg | 300 |
| ttttgttgtg atgttacaaa atataactcc ccaactaatt tccagataga tggaagaaat | 360 |
| agaaaagtga ttatggactt aaagacaatg gaaaatcttg gacttgctca aaattgtact | 420 |
| atctctattc aggattatga agtttttcga tgcgaagatt cactggatga agaaagata | 480 |
| aaaggggtca ttgagctcag gaagagctta ctgtctgcct tgagaactta tgaaccatat | 540 |
| ggatccctgg ttcaacaaat acgaattctc ctcctgggtc aattggagc tcccaagtcc | 600 |
| agcttttca actcagtgag gtctgttttc aagggcatg taacgcatca ggctttggtg | 660 |
| ggcactaata caactgggat atctgagaag tataggacat actctattag agacgggaaa | 720 |
| gatggcaaat acctgccgtt tattctgtgt gactcactgg ggctgagtga aaagaaggc | 780 |
| ggcctgtgca gggatgacat attctatatc ttgaacggta acattcgtga tagataccag | 840 |
| tttaatccca tggaatcaat caaattaaat catcatgact acattgattc cccatcgctg | 900 |
| aaggacagaa tcattgtgt ggcatttgta tttgatgcca gctctattca atacttctcc | 960 |
| tctcagatga tagtaaagat caaaagaatt caaagggagt tggtaaacgc tggtgtggta | 1020 |
| catgtggctt tgctcactca tgtggatagc atggatttga ttacaaaagg tgaccttata | 1080 |
| gaaatagaga gatgtgagcc tgtgaggtcc aagctagagg aagtccaaag aaaacttgga | 1140 |
| tttgctcttt ctgacatctc ggtggttagc aattattcct ctgagtggga gctggaccct | 1200 |
| gtaaaggatg ttctaattct ttctgctctg agacgaatgc tatgggctgc agatgacttc | 1260 |
| ttagaggatt tgccttttga gcaaataggg aatctaaggg aggaaattat caactgtgca | 1320 |
| caaggaaaaa aatag | 1335 |

<210> SEQ ID NO 35
<211> LENGTH: 1335
<212> TYPE: DNA
<213> ORGANISM: Homo sapiens
<220> FEATURE:
<221> NAME/KEY: CDS
<222> LOCATION: (1)..(1335)

<400> SEQUENCE: 35

| | |
|---|---|
| atg gca gtg aca act cgt ttg aca tgg ttg cac gaa aag atc ctg caa | 48 |
| Met Ala Val Thr Thr Arg Leu Thr Trp Leu His Glu Lys Ile Leu Gln | |
| 1               5                   10                  15 | |
| aat cat ttt gga ggg aag cgg ctt agc ctt ctc tat aag ggt agt gtc | 96 |
| Asn His Phe Gly Gly Lys Arg Leu Ser Leu Leu Tyr Lys Gly Ser Val | |
|             20                  25                  30 | |
| cat gga ttc cgt aat gga gtt ttg ctt gac aga tgt tgt aat caa ggg | 144 |
| His Gly Phe Arg Asn Gly Val Leu Leu Asp Arg Cys Cys Asn Gln Gly | |

```
                35                    40                     45
cct act cta aca gtg att tat agt gaa gat cat att att gga gca tat        192
Pro Thr Leu Thr Val Ile Tyr Ser Glu Asp His Ile Ile Gly Ala Tyr
    50                    55                    60 gca gaa gag agt tac cag gaa gga aag tat gct tcc atc atc ctt ttt        240
Ala Glu Glu Ser Tyr Gln Glu Gly Lys Tyr Ala Ser Ile Ile Leu Phe
65                    70                    75                    80 gca ctt caa gat act aaa att tca gaa tgg aaa cta gga cta tgt aca        288
Ala Leu Gln Asp Thr Lys Ile Ser Glu Trp Lys Leu Gly Leu Cys Thr
                    85                    90                    95 cca gaa aca ctg ttt tgt tgt gat gtt aca aaa tat aac tcc cca act        336
Pro Glu Thr Leu Phe Cys Cys Asp Val Thr Lys Tyr Asn Ser Pro Thr
                100                   105                   110 aat ttc cag ata gat gga aga aat aga aaa gtg att atg gac tta aag        384
Asn Phe Gln Ile Asp Gly Arg Asn Arg Lys Val Ile Met Asp Leu Lys
            115                   120                   125 aca atg gaa aat ctt gga ctt gct caa aat tgt act atc tct att cag        432
Thr Met Glu Asn Leu Gly Leu Ala Gln Asn Cys Thr Ile Ser Ile Gln
130                   135                   140 gat tat gaa gtt ttt cga tgc gaa gat tca ctg gat gaa aga aag ata        480
Asp Tyr Glu Val Phe Arg Cys Glu Asp Ser Leu Asp Glu Arg Lys Ile
145                   150                   155                   160 aaa ggg gtc att gag ctc agg aag agc tta ctg tct gcc ttg aga act        528
Lys Gly Val Ile Glu Leu Arg Lys Ser Leu Leu Ser Ala Leu Arg Thr
                165                   170                   175 tat gaa cca tat gga tcc ctg gtt caa caa ata cga att ctc ctc ctg        576
Tyr Glu Pro Tyr Gly Ser Leu Val Gln Gln Ile Arg Ile Leu Leu Leu
                180                   185                   190 ggt cca att gga gct ccc aag tcc agc ttt ttc aac tca gtg agg tct        624
Gly Pro Ile Gly Ala Pro Lys Ser Ser Phe Phe Asn Ser Val Arg Ser
            195                   200                   205 gtt ttc caa ggg cat gta acg cat cag gct ttg gtg ggc act aat aca        672
Val Phe Gln Gly His Val Thr His Gln Ala Leu Val Gly Thr Asn Thr
210                   215                   220 act ggg ata tct gag aag tat agg aca tac tct att aga gac ggg aaa        720
Thr Gly Ile Ser Glu Lys Tyr Arg Thr Tyr Ser Ile Arg Asp Gly Lys
225                   230                   235                   240 gat ggc aaa tac ctg ccg ttt att ctg tgt gac tca ctg ggg ctg agt        768
Asp Gly Lys Tyr Leu Pro Phe Ile Leu Cys Asp Ser Leu Gly Leu Ser
                245                   250                   255 gag aaa gaa ggc ggc ctg tgc agg gat gac ata ttc tat atc ttg aac        816
Glu Lys Glu Gly Gly Leu Cys Arg Asp Asp Ile Phe Tyr Ile Leu Asn
                260                   265                   270 ggt aac att cgt gat aga tac cag ttt aat ccc atg gaa tca atc aaa        864
Gly Asn Ile Arg Asp Arg Tyr Gln Phe Asn Pro Met Glu Ser Ile Lys
            275                   280                   285 tta aat cat cat gac tac att gat tcc cca tcg ctg aag gac aga att        912
Leu Asn His His Asp Tyr Ile Asp Ser Pro Ser Leu Lys Asp Arg Ile
290                   295                   300 cat tgt gtg gca ttt gta ttt gat gcc agc tct att caa tac ttc tcc        960
His Cys Val Ala Phe Val Phe Asp Ala Ser Ser Ile Gln Tyr Phe Ser
305                   310                   315                   320 tct cag atg ata gta aag atc aaa aga att caa agg gag ttg gta aac       1008
Ser Gln Met Ile Val Lys Ile Lys Arg Ile Gln Arg Glu Leu Val Asn
                325                   330                   335 gct ggt gtg gta cat gtg gct ttg ctc act cat gtg gat agc atg gat       1056
Ala Gly Val Val His Val Ala Leu Leu Thr His Val Asp Ser Met Asp
                340                   345                   350 ttg att aca aaa ggt gac ctt ata gaa ata gag aga tgt gag cct gtg       1104
```

```
Leu Ile Thr Lys Gly Asp Leu Ile Glu Ile Glu Arg Cys Glu Pro Val
            355                 360                 365 agg tcc aag cta gag gaa gtc caa aga aaa ctt gga ttt gct ctt tct      1152
Arg Ser Lys Leu Glu Glu Val Gln Arg Lys Leu Gly Phe Ala Leu Ser
        370                 375                 380 gac atc tcg gtg gtt agc aat tat tcc tct gag tgg gag ctg gac cct      1200
Asp Ile Ser Val Val Ser Asn Tyr Ser Ser Glu Trp Glu Leu Asp Pro
385                 390                 395                 400 gta aag gat gtt cta att ctt tct gct ctg aga cga atg cta tgg gct      1248
Val Lys Asp Val Leu Ile Leu Ser Ala Leu Arg Arg Met Leu Trp Ala
                405                 410                 415 gca gat gac ttc tta gag gat ttg cct ttt gag caa ata ggg aat cta      1296
Ala Asp Asp Phe Leu Glu Asp Leu Pro Phe Glu Gln Ile Gly Asn Leu
            420                 425                 430 agg gag gaa att atc aac tgt gca caa gga aaa aaa tag                  1335
Arg Glu Glu Ile Ile Asn Cys Ala Gln Gly Lys Lys
        435                 440

<210> SEQ ID NO 36
<211> LENGTH: 444
<212> TYPE: PRT
<213> ORGANISM: Homo sapiens

<400> SEQUENCE: 36

Met Ala Val Thr Thr Arg Leu Thr Trp Leu His Glu Lys Ile Leu Gln
1               5                   10                  15

Asn His Phe Gly Gly Lys Arg Leu Ser Leu Leu Tyr Lys Gly Ser Val
            20                  25                  30

His Gly Phe Arg Asn Gly Val Leu Leu Asp Arg Cys Cys Asn Gln Gly
        35                  40                  45

Pro Thr Leu Thr Val Ile Tyr Ser Glu Asp His Ile Ile Gly Ala Tyr
    50                  55                  60

Ala Glu Glu Ser Tyr Gln Glu Gly Lys Tyr Ala Ser Ile Ile Leu Phe
65                  70                  75                  80

Ala Leu Gln Asp Thr Lys Ile Ser Glu Trp Lys Leu Gly Leu Cys Thr
                85                  90                  95

Pro Glu Thr Leu Phe Cys Cys Asp Val Thr Lys Tyr Asn Ser Pro Thr
            100                 105                 110

Asn Phe Gln Ile Asp Gly Arg Asn Arg Lys Val Ile Met Asp Leu Lys
        115                 120                 125

Thr Met Glu Asn Leu Gly Leu Ala Gln Asn Cys Thr Ile Ser Ile Gln
    130                 135                 140

Asp Tyr Glu Val Phe Arg Cys Glu Asp Ser Leu Asp Glu Arg Lys Ile
145                 150                 155                 160

Lys Gly Val Ile Glu Leu Arg Lys Ser Leu Leu Ser Ala Leu Arg Thr
                165                 170                 175

Tyr Glu Pro Tyr Gly Ser Leu Val Gln Gln Ile Arg Ile Leu Leu Leu
            180                 185                 190

Gly Pro Ile Gly Ala Pro Lys Ser Ser Phe Phe Asn Ser Val Arg Ser
        195                 200                 205

Val Phe Gln Gly His Val Thr His Gln Ala Leu Val Gly Thr Asn Thr
    210                 215                 220

Thr Gly Ile Ser Glu Lys Tyr Arg Thr Tyr Ser Ile Arg Asp Gly Lys
225                 230                 235                 240

Asp Gly Lys Tyr Leu Pro Phe Ile Leu Cys Asp Ser Leu Gly Leu Ser
                245                 250                 255
```

```
Glu Lys Glu Gly Gly Leu Cys Arg Asp Asp Ile Phe Tyr Ile Leu Asn
            260                 265                 270
Gly Asn Ile Arg Asp Arg Tyr Gln Phe Asn Pro Met Glu Ser Ile Lys
        275                 280                 285
Leu Asn His His Asp Tyr Ile Asp Ser Pro Ser Leu Lys Asp Arg Ile
    290                 295                 300
His Cys Val Ala Phe Val Phe Asp Ala Ser Ser Ile Gln Tyr Phe Ser
305                 310                 315                 320
Ser Gln Met Ile Val Lys Ile Lys Arg Ile Gln Arg Glu Leu Val Asn
                325                 330                 335
Ala Gly Val Val His Val Ala Leu Leu Thr His Val Asp Ser Met Asp
            340                 345                 350
Leu Ile Thr Lys Gly Asp Leu Ile Glu Ile Glu Arg Cys Glu Pro Val
        355                 360                 365
Arg Ser Lys Leu Glu Glu Val Gln Arg Lys Leu Gly Phe Ala Leu Ser
    370                 375                 380
Asp Ile Ser Val Val Ser Asn Tyr Ser Ser Glu Trp Glu Leu Asp Pro
385                 390                 395                 400
Val Lys Asp Val Leu Ile Leu Ser Ala Leu Arg Arg Met Leu Trp Ala
                405                 410                 415
Ala Asp Asp Phe Leu Glu Asp Leu Pro Phe Glu Gln Ile Gly Asn Leu
            420                 425                 430
Arg Glu Glu Ile Ile Asn Cys Ala Gln Gly Lys Lys
        435                 440

<210> SEQ ID NO 37
<211> LENGTH: 1590
<212> TYPE: DNA
<213> ORGANISM: Pan troglodytes

<400> SEQUENCE: 37
atgagccagg acaccgaggt ggatatgaag gaggtggagc tgaatgagtt agagcccgag      60
aagcagccga tgaacgcggc gtctggggcg gccatgtccc tggcgggagc cgagaagaat     120
ggtctggtga agatcaaggt ggcggaagac gaggcggagg cggcagccgc ggctaagttc     180
acgggcctgt ccaaggagga gctgctgaag gtggcaggca gccccggctg ggtacgcacc     240
cgctgggcac tgctgctgct cttctggctc ggctggctcg gcatgctggc gggtgccgtg     300
gtcataatcg tgcgggcgcc gcgttgtcgc gagctaccgg cgcagaagtg gtggcacacg     360
ggcgccctct accgcatcgg cgaccttcag gccttccagg ccacggcgc gggcaacctg      420
gcgggtctga gggcgtctc cgattacctg agctctctga aggtgaaggg ccttgtgctg      480
ggcccaattc acaagaacca gaaggatgat gtcgctcaga ctgacttgct gcagatcgac     540
cccaattttg gctccaagga agattttgac agtctcttgc aatcggctaa aaaaagagc      600
atccgtgtca ttctggacct tactcccaac taccggggtg agaactcgtg gttctccact     660
caggttgaca ctgtggccac caaggtgaag gatgctctgg agttttggct gcaagctggc     720
gtggatgggt tccaggttcg ggacatagag aatctgaagg atgcatcctc attttttggct   780
gagtggcaaa acatcaccaa gggcttcagt gaagacaggc tcttgattgc ggggactaac     840
tcctccgacc ttcagcagat cctgagccta ctcgaatcca acaaagactt gctgttgact     900
agctcatacc tgtctgattc tggttctact ggggagcata caaaatccct agtcacacag     960
tatttgaatg ccactggcaa tcactggtgc agctggagtt tgtctcaggc aaggctcctg    1020
acttccttct tgccggctca acttctccga ctctaccagc tgatgctctt caccctgcca    1080
```

-continued

```
gggacccctg ttttcagcta cggggatgag attggcctgg atgcggctgc ccttcctgga    1140
cagcctatgg aggctccagt catgctgtgg gatgagtcca gcttccctga catcccaggg    1200
gctgtaagtg ccaacatgac tgtgaagggc cagagtgaag accctggctc cctcctttcc    1260
ttgttccggc ggctgagtga ccagcggagt aaggagcgct ccctactgca tggggacttc    1320
cacgcgttct ccgctgggcc tggactcttc tcctatatcc gccactggga ccagaatgag    1380
cgttttctgg tagtgcttaa cttttgggat gtgggcctct cggctggact gcaggcctcc    1440
gacctgcctg ccagcgccag cctgccagcc aaggctgacc tcctgctcag cacccagcca    1500
ggccgtgagg agggctcccc tcttgagctg gaacgcctga aactggagcc tcacgaaggg    1560
ctgctgctcc gcttccccta cgcggcctga                                    1590
```

<210> SEQ ID NO 38
<211> LENGTH: 1590
<212> TYPE: DNA
<213> ORGANISM: Pan troglodytes
<220> FEATURE:
<221> NAME/KEY: CDS
<222> LOCATION: (1)..(1590)

<400> SEQUENCE: 38

```
atg agc cag gac acc gag gtg gat atg aag gag gtg gag ctg aat gag    48
Met Ser Gln Asp Thr Glu Val Asp Met Lys Glu Val Glu Leu Asn Glu
1               5                   10                  15 tta gag ccc gag aag cag ccg atg aac gcg gcg tct ggg gcg gcc atg    96
Leu Glu Pro Glu Lys Gln Pro Met Asn Ala Ala Ser Gly Ala Ala Met
            20                  25                  30 tcc ctg gcg gga gcc gag aag aat ggt ctg gtg aag atc aag gtg gcg    144
Ser Leu Ala Gly Ala Glu Lys Asn Gly Leu Val Lys Ile Lys Val Ala
        35                  40                  45 gaa gac gag gcg gag gcg gca gcc gcg gct aag ttc acg ggc ctg tcc    192
Glu Asp Glu Ala Glu Ala Ala Ala Ala Lys Phe Thr Gly Leu Ser
    50                  55                  60 aag gag gag ctg ctg aag gtg gca ggc agc ccc ggc tgg gta cgc acc    240
Lys Glu Glu Leu Leu Lys Val Ala Gly Ser Pro Gly Trp Val Arg Thr
65                  70                  75                  80 cgc tgg gca ctg ctg ctc ttc tgg ctc ggc tgg ctc ggc atg ctg        288
Arg Trp Ala Leu Leu Leu Phe Trp Leu Gly Trp Leu Gly Met Leu
                85                  90                  95 gcg ggt gcc gtg gtc ata atc gtg cgg gcg ccg cgt tgt cgc gag cta    336
Ala Gly Ala Val Val Ile Ile Val Arg Ala Pro Arg Cys Arg Glu Leu
            100                 105                 110 ccg gcg cag aag tgg tgg cac acg ggc gcc ctc tac cgc atc ggc gac    384
Pro Ala Gln Lys Trp Trp His Thr Gly Ala Leu Tyr Arg Ile Gly Asp
        115                 120                 125 ctt cag gcc ttc cag ggc cac ggc gcg ggc aac ctg gcg ggt ctg aag    432
Leu Gln Ala Phe Gln Gly His Gly Ala Gly Asn Leu Ala Gly Leu Lys
    130                 135                 140 ggg cgt ctc gat tac ctg agc tct ctg aag gtg aag ggc ctt gtg ctg    480
Gly Arg Leu Asp Tyr Leu Ser Ser Leu Lys Val Lys Gly Leu Val Leu
145                 150                 155                 160 ggc cca att cac aag aac cag aag gat gat gtc gct cag act gac ttg    528
Gly Pro Ile His Lys Asn Gln Lys Asp Asp Val Ala Gln Thr Asp Leu
                165                 170                 175 ctg cag atc gac ccc aat ttt ggc tcc aag gaa gat ttt gac agt ctc    576
Leu Gln Ile Asp Pro Asn Phe Gly Ser Lys Glu Asp Phe Asp Ser Leu
            180                 185                 190 ttg caa tcg gct aaa aaa aag agc atc cgt gtc att ctg gac ctt act    624
Leu Gln Ser Ala Lys Lys Lys Ser Ile Arg Val Ile Leu Asp Leu Thr
```

-continued

```
                Leu Gln Ser Ala Lys Lys Ser Ile Arg Val Ile Leu Asp Leu Thr
                        195                 200                 205 ccc aac tac cgg ggt gag aac tcg tgg ttc tcc act cag gtt gac act         672
Pro Asn Tyr Arg Gly Glu Asn Ser Trp Phe Ser Thr Gln Val Asp Thr
    210                 215                 220 gtg gcc acc aag gtg aag gat gct ctg gag ttt tgg ctg caa gct ggc         720
Val Ala Thr Lys Val Lys Asp Ala Leu Glu Phe Trp Leu Gln Ala Gly
225                 230                 235                 240 gtg gat ggg ttc cag gtt cgg gac ata gag aat ctg aag gat gca tcc         768
Val Asp Gly Phe Gln Val Arg Asp Ile Glu Asn Leu Lys Asp Ala Ser
                245                 250                 255 tca ttt ttg gct gag tgg caa aac atc acc aag ggc ttc agt gaa gac         816
Ser Phe Leu Ala Glu Trp Gln Asn Ile Thr Lys Gly Phe Ser Glu Asp
            260                 265                 270 agg ctc ttg att gcg ggg act aac tcc tcc gac ctt cag cag atc ctg         864
Arg Leu Leu Ile Ala Gly Thr Asn Ser Ser Asp Leu Gln Gln Ile Leu
        275                 280                 285 agc cta ctc gaa tcc aac aaa gac ttg ctg ttg act agc tca tac ctg         912
Ser Leu Leu Glu Ser Asn Lys Asp Leu Leu Leu Thr Ser Ser Tyr Leu
    290                 295                 300 tct gat tct ggt tct act ggg gag cat aca aaa tcc cta gtc aca cag         960
Ser Asp Ser Gly Ser Thr Gly Glu His Thr Lys Ser Leu Val Thr Gln
305                 310                 315                 320 tat ttg aat gcc act ggc aat cac tgg tgc agc tgg agt ttg tct cag        1008
Tyr Leu Asn Ala Thr Gly Asn His Trp Cys Ser Trp Ser Leu Ser Gln
                325                 330                 335 gca agg ctc ctg act tcc ttc ttg ccg gct caa ctt ctc cga ctc tac        1056
Ala Arg Leu Leu Thr Ser Phe Leu Pro Ala Gln Leu Leu Arg Leu Tyr
            340                 345                 350 cag ctg atg ctc ttc acc ctg cca ggg acc cct gtt ttc agc tac ggg        1104
Gln Leu Met Leu Phe Thr Leu Pro Gly Thr Pro Val Phe Ser Tyr Gly
        355                 360                 365 gat gag att ggc ctg gat gcg gct gcc ctt cct gga cag cct atg gag        1152
Asp Glu Ile Gly Leu Asp Ala Ala Ala Leu Pro Gly Gln Pro Met Glu
    370                 375                 380 gct cca gtc atg ctg tgg gat gag tcc agc ttc cct gac atc cca ggg        1200
Ala Pro Val Met Leu Trp Asp Glu Ser Ser Phe Pro Asp Ile Pro Gly
385                 390                 395                 400 gct gta agt gcc aac atg act gtg aag ggc cag agt gaa gac cct ggc        1248
Ala Val Ser Ala Asn Met Thr Val Lys Gly Gln Ser Glu Asp Pro Gly
                405                 410                 415 tcc ctc ctt tcc ttg ttc cgg cgg ctg agt gac cag cgg agt aag gag        1296
Ser Leu Leu Ser Leu Phe Arg Arg Leu Ser Asp Gln Arg Ser Lys Glu
            420                 425                 430 cgc tcc cta ctg cat ggg gac ttc cac gcg ttc tcc gct ggg cct gga        1344
Arg Ser Leu Leu His Gly Asp Phe His Ala Phe Ser Ala Gly Pro Gly
        435                 440                 445 ctc ttc tcc tat atc cgc cac tgg gac cag aat gag cgt ttt ctg gta        1392
Leu Phe Ser Tyr Ile Arg His Trp Asp Gln Asn Glu Arg Phe Leu Val
    450                 455                 460 gtg ctt aac ttt ggg gat gtg ggc ctc tcg gct gga ctg cag gcc tcc        1440
Val Leu Asn Phe Gly Asp Val Gly Leu Ser Ala Gly Leu Gln Ala Ser
465                 470                 475                 480 gac ctg cct gcc agc gcc agc ctg cca gcc aag gct gac ctc ctg ctc        1488
Asp Leu Pro Ala Ser Ala Ser Leu Pro Ala Lys Ala Asp Leu Leu Leu
                485                 490                 495 agc acc cag cca ggc cgt gag gag ggc tcc cct ctt gag ctg gaa cgc        1536
Ser Thr Gln Pro Gly Arg Glu Glu Gly Ser Pro Leu Glu Leu Glu Arg
            500                 505                 510
```

```
ctg aaa ctg gag cct cac gaa ggg ctg ctg ctc cgc ttc ccc tac gcg      1584
Leu Lys Leu Glu Pro His Glu Gly Leu Leu Leu Arg Phe Pro Tyr Ala
        515                 520                 525 gcc tga                                                               1590
Ala
```

<210> SEQ ID NO 39
<211> LENGTH: 529
<212> TYPE: PRT
<213> ORGANISM: Pan troglodytes

<400> SEQUENCE: 39

```
Met Ser Gln Asp Thr Glu Val Asp Met Lys Glu Val Glu Leu Asn Glu
1               5                   10                  15

Leu Glu Pro Glu Lys Gln Pro Met Asn Ala Ala Ser Gly Ala Ala Met
            20                  25                  30

Ser Leu Ala Gly Ala Glu Lys Asn Gly Leu Val Lys Ile Lys Val Ala
        35                  40                  45

Glu Asp Glu Ala Glu Ala Ala Ala Ala Lys Phe Thr Gly Leu Ser
    50                  55                  60

Lys Glu Glu Leu Leu Lys Val Ala Gly Ser Pro Gly Trp Val Arg Thr
65                  70                  75                  80

Arg Trp Ala Leu Leu Leu Leu Phe Trp Leu Gly Trp Leu Gly Met Leu
                85                  90                  95

Ala Gly Ala Val Val Ile Ile Val Arg Ala Pro Arg Cys Arg Glu Leu
            100                 105                 110

Pro Ala Gln Lys Trp Trp His Thr Gly Ala Leu Tyr Arg Ile Gly Asp
        115                 120                 125

Leu Gln Ala Phe Gln Gly His Gly Ala Gly Asn Leu Ala Gly Leu Lys
    130                 135                 140

Gly Arg Leu Asp Tyr Leu Ser Ser Leu Lys Val Lys Gly Leu Val Leu
145                 150                 155                 160

Gly Pro Ile His Lys Asn Gln Lys Asp Val Ala Gln Thr Asp Leu
                165                 170                 175

Leu Gln Ile Asp Pro Asn Phe Gly Ser Lys Glu Asp Phe Asp Ser Leu
            180                 185                 190

Leu Gln Ser Ala Lys Lys Lys Ser Ile Arg Val Ile Leu Asp Leu Thr
        195                 200                 205

Pro Asn Tyr Arg Gly Glu Asn Ser Trp Phe Ser Thr Gln Val Asp Thr
    210                 215                 220

Val Ala Thr Lys Val Lys Asp Ala Leu Glu Phe Trp Leu Gln Ala Gly
225                 230                 235                 240

Val Asp Gly Phe Gln Val Arg Asp Ile Glu Asn Leu Lys Asp Ala Ser
                245                 250                 255

Ser Phe Leu Ala Glu Trp Gln Asn Ile Thr Lys Gly Phe Ser Glu Asp
            260                 265                 270

Arg Leu Leu Ile Ala Gly Thr Asn Ser Ser Asp Leu Gln Gln Ile Leu
        275                 280                 285

Ser Leu Leu Glu Ser Asn Lys Asp Leu Leu Leu Thr Ser Ser Tyr Leu
    290                 295                 300

Ser Asp Ser Gly Ser Thr Gly Glu His Thr Lys Ser Leu Val Thr Gln
305                 310                 315                 320

Tyr Leu Asn Ala Thr Gly Asn His Trp Cys Ser Trp Ser Leu Ser Gln
                325                 330                 335

Ala Arg Leu Leu Thr Ser Phe Leu Pro Ala Gln Leu Leu Arg Leu Tyr
```

```
                340             345             350
Gln Leu Met Leu Phe Thr Leu Pro Gly Thr Pro Val Phe Ser Tyr Gly
            355                 360                 365
Asp Glu Ile Gly Leu Asp Ala Ala Leu Pro Gly Gln Pro Met Glu
        370                 375                 380
Ala Pro Val Met Leu Trp Asp Glu Ser Ser Phe Pro Asp Ile Pro Gly
385                 390                 395                 400
Ala Val Ser Ala Asn Met Thr Val Lys Gly Gln Ser Glu Asp Pro Gly
                405                 410                 415
Ser Leu Leu Ser Leu Phe Arg Arg Leu Ser Asp Gln Arg Ser Lys Glu
            420                 425                 430
Arg Ser Leu Leu His Gly Asp Phe His Ala Phe Ser Ala Gly Pro Gly
        435                 440                 445
Leu Phe Ser Tyr Ile Arg His Trp Asp Gln Asn Glu Arg Phe Leu Val
    450                 455                 460
Val Leu Asn Phe Gly Asp Val Gly Leu Ser Ala Gly Leu Gln Ala Ser
465                 470                 475                 480
Asp Leu Pro Ala Ser Ala Ser Leu Pro Ala Lys Ala Asp Leu Leu Leu
                485                 490                 495
Ser Thr Gln Pro Gly Arg Glu Glu Gly Ser Pro Leu Glu Leu Glu Arg
            500                 505                 510
Leu Lys Leu Glu Pro His Glu Gly Leu Leu Leu Arg Phe Pro Tyr Ala
        515                 520                 525
Ala

<210> SEQ ID NO 40
<211> LENGTH: 1861
<212> TYPE: DNA
<213> ORGANISM: Homo sapiens

<400> SEQUENCE: 40 gggggggag atgcagtagc cgaaaactgc gcggaggcac gagaggccgg ggagagcgtt    60
ctgggtccga gggtccaggt aggggttgag ccaccatctg accgcaagct gcgtcgtgtc   120
gccttctctg caggcaccat gagccaggac accgaggtgg atatgaagga ggtggagctg   180
aatgagttag agcccgagaa gcagccgatg aacgcggcgt ctggggcggc catgtccctg   240
gcggaagccg agaagaatgg tctggtgaag atcaaggtgg cggaagacga ggcggaggcg   300
gcagccgcgg ctaagttcac gggcctgtcc aaggaggagc tgctgaaggt ggcaggcagc   360
cccggctggg tacgcacccg ctgggcactg ctgctgctct tctggctcgg ctggctcggc   420
atgcttgctg gtgccgtggt gataatcgtg cgagcgccgc gttgtcgcga gctaccggcg   480
cagaagtggt ggcacacggg cccctctac cgcatcggcg accttcaggc cttccagggc   540
cacgcgcgg caacctggc gggtctgaag ggcgtctcg attacctgag ctctctgaag   600
gtgaagggcc ttgtgctggg tccaattcac aagaaccaga aggatgatgt cgctcagact   660
gacttgctgc agatcgaccc caattttggc tccaaggaag attttgacag tctcttgcaa   720
tcggctaaaa aaagagcat ccgtgtcatt ctggaccta ctcccaacta ccggggtgac   780
aactcgtggt tctccactca ggttgacact gtggccacca aggtgaagga tgctctggag   840
ttttggctgc aagctggcgt ggatgggttc caggttcggg acatagagaa tctgaaggat   900
gcatcctcat tcttggctga gtggcaaaat atcaccaagg gcttcagtgg agacaggctc   960
ttgattgcgg ggactaactc ctccgacctt cagcagatcc tgagcctact cgaatccaac  1020
```

| | |
|---|---|
| aaagacttgc tgttgactag ctcatacctg tctgattctg gttctactcc ccagcataca | 1080 |
| aaatccctag tcacacagta tttgaatgcc actggcaatc gctggtgcag ctggagtttg | 1140 |
| tctcaggcaa ggctcctgac ttccttcttg ccggctcaac ttctccgact ctaccagctg | 1200 |
| atgctcttca ccctgccagg gaccctctt ttcagctacg gggatgagat tggcctggat | 1260 |
| gcagctgccc ttcctccaca gcctatggag gctccagtca tgctgtggga tgagtccagc | 1320 |
| ttccctgaca tcccaggggc tgtaagtgcc aacatgactg tgaagggcca gagtgaagac | 1380 |
| cctggctccc tcctttcctt gttccggcgg ctgagtgacc agcggagtaa ggagcgctcc | 1440 |
| ctactgcatg gggacttcca cgcgttctcc gctgggcctg gactcttctc ctatatccgc | 1500 |
| cactgggacc agaatgagcg tttctggta gtgcttaact ttggggatgt gggcctctcg | 1560 |
| gctggactgc aggcctccga cctgcctgcc agcgccagcc tgccagccaa ggctgacctc | 1620 |
| ctgctcagca cccagccagg ccgtgaggag ggctcccctc ctgagctggg acgcctgaaa | 1680 |
| ctggagcctc acgaagggct gctgctccgc ttccctacg cggcctgacc tcagcctgac | 1740 |
| atggacccac tacccttctc ctttccttcc caggccttt ggcttctgat tttttttctc | 1800 |
| ttttttaaaa caaacaaaca aactgttgca gattatgagt gaaccccaaa tagggtgttt | 1860 |
| t | 1861 |

```
<210> SEQ ID NO 41
<211> LENGTH: 1861
<212> TYPE: DNA
<213> ORGANISM: Homo sapiens
<220> FEATURE:
<221> NAME/KEY: CDS
<222> LOCATION: (139)..(1728)

<400> SEQUENCE: 41
```

| | |
|---|---|
| gggggggag atgcagtagc cgaaaactgc gcggaggcac gagaggccgg ggagagcgtt | 60 |
| ctgggtccga gggtccaggt aggggttgag ccaccatctg accgcaagct gcgtcgtgtc | 120 |
| gccttctctg caggcacc atg agc cag gac acc gag gtg gat atg aag gag<br>                           Met Ser Gln Asp Thr Glu Val Asp Met Lys Glu<br>                            1                5                    10 | 171 |
| gtg gag ctg aat gag tta gag ccc gag aag cag ccg atg aac gcg gcg<br>Val Glu Leu Asn Glu Leu Glu Pro Glu Lys Gln Pro Met Asn Ala Ala<br>        15                    20                  25 | 219 |
| tct ggg gcg gcc atg tcc ctg gcg gaa gcc gag aag aat ggt ctg gtg<br>Ser Gly Ala Ala Met Ser Leu Ala Glu Ala Glu Lys Asn Gly Leu Val<br>     30                  35                  40 | 267 |
| aag atc aag gtg gcg gaa gac gag gcg gag gcg gca gcc gcg gct aag<br>Lys Ile Lys Val Ala Glu Asp Glu Ala Glu Ala Ala Ala Ala Ala Lys<br>45                  50                  55 | 315 |
| ttc acg ggc ctg tcc aag gag gag ctg ctg aag gtg gca ggc agc ccc<br>Phe Thr Gly Leu Ser Lys Glu Glu Leu Leu Lys Val Ala Gly Ser Pro<br>60                  65                  70                  75 | 363 |
| ggc tgg gta cgc acc cgc tgg gca ctg ctg ctc ttc tgg ctc ggc<br>Gly Trp Val Arg Thr Arg Trp Ala Leu Leu Leu Phe Trp Leu Gly<br>              80                  85                  90 | 411 |
| tgg ctc ggc atg ctt gct ggt gcc gtg gtg ata atc gtg cga gcg ccg<br>Trp Leu Gly Met Leu Ala Gly Ala Val Val Ile Ile Val Arg Ala Pro<br>         95                  100                 105 | 459 |
| cgt tgt cgc gag cta ccg gcg cag aag tgg tgg cac acg ggc ccc ctc<br>Arg Cys Arg Glu Leu Pro Ala Gln Lys Trp Trp His Thr Gly Pro Leu<br>            110                 115                 120 | 507 |
| tac cgc atc ggc gac ctt cag gcc ttc cag ggc cac ggc gcg ggc aac<br>Tyr Arg Ile Gly Asp Leu Gln Ala Phe Gln Gly His Gly Ala Gly Asn | 555 |

-continued

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 125 |     |     |     |     | 130 |     |     |     |     | 135 |     |     |      |
| ctg | gcg | ggt | ctg | aag | ggg | cgt | ctc | gat | tac | ctg | agc | tct | ctg | aag | gtg | 603  |
| Leu | Ala | Gly | Leu | Lys | Gly | Arg | Leu | Asp | Tyr | Leu | Ser | Ser | Leu | Lys | Val |      |
| 140 |     |     |     | 145 |     |     |     |     | 150 |     |     |     |     | 155 |     |      |
| aag | ggc | ctt | gtg | ctg | ggt | cca | att | cac | aag | aac | cag | aag | gat | gat | gtc | 651  |
| Lys | Gly | Leu | Val | Leu | Gly | Pro | Ile | His | Lys | Asn | Gln | Lys | Asp | Asp | Val |      |
|     |     |     |     | 160 |     |     |     |     | 165 |     |     |     |     | 170 |     |      |
| gct | cag | act | gac | ttg | ctg | cag | atc | gac | ccc | aat | ttt | ggc | tcc | aag | gaa | 699  |
| Ala | Gln | Thr | Asp | Leu | Leu | Gln | Ile | Asp | Pro | Asn | Phe | Gly | Ser | Lys | Glu |      |
|     |     |     | 175 |     |     |     |     | 180 |     |     |     |     | 185 |     |     |      |
| gat | ttt | gac | agt | ctc | ttg | caa | tcg | gct | aaa | aaa | aag | agc | atc | cgt | gtc | 747  |
| Asp | Phe | Asp | Ser | Leu | Leu | Gln | Ser | Ala | Lys | Lys | Lys | Ser | Ile | Arg | Val |      |
|     |     | 190 |     |     |     |     | 195 |     |     |     |     | 200 |     |     |     |      |
| att | ctg | gac | ctt | act | ccc | aac | tac | cgg | ggt | gac | aac | tcg | tgg | ttc | tcc | 795  |
| Ile | Leu | Asp | Leu | Thr | Pro | Asn | Tyr | Arg | Gly | Asp | Asn | Ser | Trp | Phe | Ser |      |
|     | 205 |     |     |     |     | 210 |     |     |     |     | 215 |     |     |     |     |      |
| act | cag | gtt | gac | act | gtg | gcc | acc | aag | gtg | aag | gat | gct | ctg | gag | ttt | 843  |
| Thr | Gln | Val | Asp | Thr | Val | Ala | Thr | Lys | Val | Lys | Asp | Ala | Leu | Glu | Phe |      |
| 220 |     |     |     |     | 225 |     |     |     |     | 230 |     |     |     |     | 235 |      |
| tgg | ctg | caa | gct | ggc | gtg | gat | ggg | ttc | cag | gtt | cgg | gac | ata | gag | aat | 891  |
| Trp | Leu | Gln | Ala | Gly | Val | Asp | Gly | Phe | Gln | Val | Arg | Asp | Ile | Glu | Asn |      |
|     |     |     |     | 240 |     |     |     |     | 245 |     |     |     |     | 250 |     |      |
| ctg | aag | gat | gca | tcc | tca | ttc | ttg | gct | gag | tgg | caa | aat | atc | acc | aag | 939  |
| Leu | Lys | Asp | Ala | Ser | Ser | Phe | Leu | Ala | Glu | Trp | Gln | Asn | Ile | Thr | Lys |      |
|     |     |     | 255 |     |     |     |     | 260 |     |     |     |     | 265 |     |     |      |
| ggc | ttc | agt | gga | gac | agg | ctc | ttg | att | gcg | ggg | act | aac | tcc | tcc | gac | 987  |
| Gly | Phe | Ser | Gly | Asp | Arg | Leu | Leu | Ile | Ala | Gly | Thr | Asn | Ser | Ser | Asp |      |
|     |     | 270 |     |     |     |     | 275 |     |     |     |     | 280 |     |     |     |      |
| ctt | cag | cag | atc | ctg | agc | cta | ctc | gaa | tcc | aac | aaa | gac | ttg | ctg | ttg | 1035 |
| Leu | Gln | Gln | Ile | Leu | Ser | Leu | Leu | Glu | Ser | Asn | Lys | Asp | Leu | Leu | Leu |      |
|     | 285 |     |     |     |     | 290 |     |     |     |     | 295 |     |     |     |     |      |
| act | agc | tca | tac | ctg | tct | gat | tct | ggt | tct | act | ccc | cag | cat | aca | aaa | 1083 |
| Thr | Ser | Ser | Tyr | Leu | Ser | Asp | Ser | Gly | Ser | Thr | Pro | Gln | His | Thr | Lys |      |
| 300 |     |     |     |     | 305 |     |     |     |     | 310 |     |     |     |     | 315 |      |
| tcc | cta | gtc | aca | cag | tat | ttg | aat | gcc | act | ggc | aat | cgc | tgg | tgc | agc | 1131 |
| Ser | Leu | Val | Thr | Gln | Tyr | Leu | Asn | Ala | Thr | Gly | Asn | Arg | Trp | Cys | Ser |      |
|     |     |     |     | 320 |     |     |     |     | 325 |     |     |     |     | 330 |     |      |
| tgg | agt | ttg | tct | cag | gca | agg | ctc | ctg | act | tcc | ttc | ttg | ccg | gct | caa | 1179 |
| Trp | Ser | Leu | Ser | Gln | Ala | Arg | Leu | Leu | Thr | Ser | Phe | Leu | Pro | Ala | Gln |      |
|     |     |     | 335 |     |     |     |     | 340 |     |     |     |     | 345 |     |     |      |
| ctt | ctc | cga | ctc | tac | cag | ctg | atg | ctc | ttc | acc | ctg | cca | ggg | acc | cct | 1227 |
| Leu | Leu | Arg | Leu | Tyr | Gln | Leu | Met | Leu | Phe | Thr | Leu | Pro | Gly | Thr | Pro |      |
|     |     | 350 |     |     |     |     | 355 |     |     |     |     | 360 |     |     |     |      |
| ctt | ttc | agc | tac | ggg | gat | gag | att | ggc | ctg | gat | gca | gct | gcc | ctt | cct | 1275 |
| Leu | Phe | Ser | Tyr | Gly | Asp | Glu | Ile | Gly | Leu | Asp | Ala | Ala | Ala | Leu | Pro |      |
|     | 365 |     |     |     |     | 370 |     |     |     |     | 375 |     |     |     |     |      |
| cca | cag | cct | atg | gag | gct | cca | gtc | atg | ctg | tgg | gat | gag | tcc | agc | ttc | 1323 |
| Pro | Gln | Pro | Met | Glu | Ala | Pro | Val | Met | Leu | Trp | Asp | Glu | Ser | Ser | Phe |      |
| 380 |     |     |     |     | 385 |     |     |     |     | 390 |     |     |     |     | 395 |      |
| cct | gac | atc | cca | ggg | gct | gta | agt | gcc | aac | atg | act | gtg | aag | ggc | cag | 1371 |
| Pro | Asp | Ile | Pro | Gly | Ala | Val | Ser | Ala | Asn | Met | Thr | Val | Lys | Gly | Gln |      |
|     |     |     |     | 400 |     |     |     |     | 405 |     |     |     |     | 410 |     |      |
| agt | gaa | gac | cct | ggc | tcc | ctc | ctt | tcc | ttg | ttc | cgg | cgg | ctg | agt | gac | 1419 |
| Ser | Glu | Asp | Pro | Gly | Ser | Leu | Leu | Ser | Leu | Phe | Arg | Arg | Leu | Ser | Asp |      |
|     |     |     | 415 |     |     |     |     | 420 |     |     |     |     | 425 |     |     |      |
| cag | cgg | agt | aag | gag | cgc | tcc | cta | ctg | cat | ggg | gac | ttc | cac | gcg | ttc | 1467 |
| Gln | Arg | Ser | Lys | Glu | Arg | Ser | Leu | Leu | His | Gly | Asp | Phe | His | Ala | Phe |      |
|     |     | 430 |     |     |     |     | 435 |     |     |     |     | 440 |     |     |     |      |
| tcc | gct | ggg | cct | gga | ctc | ttc | tcc | tat | atc | cgc | cac | tgg | gac | cag | aat | 1515 |

```
Ser Ala Gly Pro Gly Leu Phe Ser Tyr Ile Arg His Trp Asp Gln Asn
    445                 450                 455 gag cgt ttt ctg gta gtg ctt aac ttt ggg gat gtg ggc ctc tcg gct      1563
Glu Arg Phe Leu Val Val Leu Asn Phe Gly Asp Val Gly Leu Ser Ala
460                 465                 470                 475 gga ctg cag gcc tcc gac ctg cct gcc agc gcc agc ctg cca gcc aag      1611
Gly Leu Gln Ala Ser Asp Leu Pro Ala Ser Ala Ser Leu Pro Ala Lys
                480                 485                 490 gct gac ctc ctg ctc agc acc cag cca ggc cgt gag gag ggc tcc cct      1659
Ala Asp Leu Leu Leu Ser Thr Gln Pro Gly Arg Glu Glu Gly Ser Pro
            495                 500                 505 cct gag ctg gga cgc ctg aaa ctg gag cct cac gaa ggg ctg ctg ctc      1707
Pro Glu Leu Gly Arg Leu Lys Leu Glu Pro His Glu Gly Leu Leu Leu
        510                 515                 520 cgc ttc ccc tac gcg gcc tga cctcagcctg acatggaccc actacccttc        1758
Arg Phe Pro Tyr Ala Ala
    525 tcctttcctt cccaggccct ttggcttctg attttttttc tcttttttaa aacaaacaaa   1818 caaactgttg cagattatga gtgaaccca aatagggtgt ttt                      1861

<210> SEQ ID NO 42
<211> LENGTH: 529
<212> TYPE: PRT
<213> ORGANISM: Homo sapiens

<400> SEQUENCE: 42

Met Ser Gln Asp Thr Glu Val Asp Met Lys Glu Val Glu Leu Asn Glu
1               5                   10                  15

Leu Glu Pro Glu Lys Gln Pro Met Asn Ala Ala Ser Gly Ala Ala Met
            20                  25                  30

Ser Leu Ala Glu Ala Glu Lys Asn Gly Leu Val Lys Ile Lys Val Ala
        35                  40                  45

Glu Asp Glu Ala Glu Ala Ala Ala Ala Lys Phe Thr Gly Leu Ser
    50                  55                  60

Lys Glu Glu Leu Leu Lys Val Ala Gly Ser Pro Gly Trp Val Arg Thr
65                  70                  75                  80

Arg Trp Ala Leu Leu Leu Leu Phe Trp Leu Gly Trp Leu Gly Met Leu
                85                  90                  95

Ala Gly Ala Val Val Ile Ile Val Arg Ala Pro Arg Cys Arg Glu Leu
            100                 105                 110

Pro Ala Gln Lys Trp Trp His Thr Gly Pro Leu Tyr Arg Ile Gly Asp
        115                 120                 125

Leu Gln Ala Phe Gln Gly His Gly Ala Gly Asn Leu Ala Gly Leu Lys
    130                 135                 140

Gly Arg Leu Asp Tyr Leu Ser Ser Leu Lys Val Lys Gly Leu Val Leu
145                 150                 155                 160

Gly Pro Ile His Lys Asn Gln Lys Asp Asp Val Ala Gln Thr Asp Leu
                165                 170                 175

Leu Gln Ile Asp Pro Asn Phe Gly Ser Lys Glu Asp Phe Asp Ser Leu
            180                 185                 190

Leu Gln Ser Ala Lys Lys Lys Ser Ile Arg Val Ile Leu Asp Leu Thr
        195                 200                 205

Pro Asn Tyr Arg Gly Asp Asn Ser Trp Phe Ser Thr Gln Val Asp Thr
    210                 215                 220

Val Ala Thr Lys Val Lys Asp Ala Leu Glu Phe Trp Leu Gln Ala Gly
225                 230                 235                 240
```

```
Val Asp Gly Phe Gln Val Arg Asp Ile Glu Asn Leu Lys Asp Ala Ser
            245                 250                 255

Ser Phe Leu Ala Glu Trp Gln Asn Ile Thr Lys Gly Phe Ser Gly Asp
            260                 265                 270

Arg Leu Leu Ile Ala Gly Thr Asn Ser Ser Asp Leu Gln Gln Ile Leu
            275                 280                 285

Ser Leu Leu Glu Ser Asn Lys Asp Leu Leu Thr Ser Ser Tyr Leu
            290                 295                 300

Ser Asp Ser Gly Ser Thr Pro Gln His Thr Lys Ser Leu Val Thr Gln
305                 310                 315                 320

Tyr Leu Asn Ala Thr Gly Asn Arg Trp Cys Ser Trp Ser Leu Ser Gln
            325                 330                 335

Ala Arg Leu Leu Thr Ser Phe Leu Pro Ala Gln Leu Leu Arg Leu Tyr
            340                 345                 350

Gln Leu Met Leu Phe Thr Leu Pro Gly Thr Pro Leu Phe Ser Tyr Gly
            355                 360                 365

Asp Glu Ile Gly Leu Asp Ala Ala Leu Pro Pro Gln Pro Met Glu
370                 375                 380

Ala Pro Val Met Leu Trp Asp Glu Ser Ser Phe Pro Asp Ile Pro Gly
385                 390                 395                 400

Ala Val Ser Ala Asn Met Thr Val Lys Gly Gln Ser Glu Asp Pro Gly
            405                 410                 415

Ser Leu Leu Ser Leu Phe Arg Arg Leu Ser Asp Gln Arg Ser Lys Glu
            420                 425                 430

Arg Ser Leu Leu His Gly Asp Phe His Ala Phe Ser Ala Gly Pro Gly
            435                 440                 445

Leu Phe Ser Tyr Ile Arg His Trp Asp Gln Asn Glu Arg Phe Leu Val
            450                 455                 460

Val Leu Asn Phe Gly Asp Val Gly Leu Ser Ala Gly Leu Gln Ala Ser
465                 470                 475                 480

Asp Leu Pro Ala Ser Ala Ser Leu Pro Ala Lys Ala Asp Leu Leu Leu
            485                 490                 495

Ser Thr Gln Pro Gly Arg Glu Glu Gly Ser Pro Glu Leu Gly Arg
            500                 505                 510

Leu Lys Leu Glu Pro His Glu Gly Leu Leu Leu Arg Phe Pro Tyr Ala
            515                 520                 525

Ala
```

<210> SEQ ID NO 43
<211> LENGTH: 1437
<212> TYPE: DNA
<213> ORGANISM: Pan troglodytes

<400> SEQUENCE: 43

| | | |
|---|---|---|
| atgagtacaa atggtgatga tcatcaggtc aaggatagtc tggagcaatt gagatgtcac | 60 |
| tttacatggg agttatccat tgatgacgat gaaatgcctg atttagaaaa cagagtcttg | 120 |
| gatcagattg aattcctaga caccaaatac aatgtgggaa tacacaacct actagcctat | 180 |
| gtgaaacacc tgaaaggcca gaatgaggaa gccctgaaga gcttaaaaga agctgaaaac | 240 |
| ttaatgcagg aagaacatga caaccaagca atgtgagga gtctggtgac ctggggcaac | 300 |
| tttgcctgga tgtattacca catgggcaga ctggcagaag cccagactta cctggacaag | 360 |
| gtggagaaca tttgcaagaa gctttcaat cccttccgct atagaatgga gtgtccagaa | 420 |

-continued

```
atagactgtg aggaaggatg ggccttgctg aagtgtggag gaaagaatta tgaacgggcc      480
aaggcctgct ttgaaaaggt gcttgaagtg gaccctgaaa accctgaatc cagcgctggg      540
tatgcgatct ctgcctatcg cctggatggc tttaaattag ccacaaaaaa tcacatacca      600
ttttctttgc ttcccctaag gcaggctgtc cgtttaaatc cggacaatgg atatatgaag      660
gttctccttg ccctgaagct tcaggatgaa ggacaggaag ctgaaggaga aaagtacatt      720
gaagaagctc tagccaacat gtcctcacag acctatgtct ttcgatatgc agccaagttt      780
taccgaagaa aaggctctgt ggataaagct cttgagttat tagaaaaggc cttgcaggaa      840
acacccactt ctgtcttact gcatcaccag atagggcttt gctacaaggc acaaatgatc      900
caaatcaagg aggctacaaa agggcagcct agagggcaga acagagaaaa gctagacaaa      960
atgataagat cagccatatt tcattttgaa tctgcagtgg aaaaaaagcc cacatttgag     1020
gtggctcatc tagacctggc aagaatgtat atagaagcag gcaatcacag aaaagctgaa     1080
gagagttttc gaaaaatgtt atgcatgaaa ccagtggtag aagaaacaat gcaagacata     1140
catttccact atggtcggtt tcaggaattt caaaagaaat ctgacgtcaa tgcaattatc     1200
cattatttaa aagctataaa aatagaacag gcatcattag caaggataaa agtatcaat     1260 tctttgaaga aattggtttt aaggaaactt cggagaaagg cattagatct ggaaagcttg     1320
agcctccttg ggttcgtcta caaattggaa ggaaatatga atgaagccct ggagtactat     1380
gagcgggccc tgagactggc tgctgacttc gagaactctg tgagacaagg tccttag       1437
```

<210> SEQ ID NO 44
<211> LENGTH: 1437
<212> TYPE: DNA
<213> ORGANISM: Pan troglodytes
<220> FEATURE:
<221> NAME/KEY: CDS
<222> LOCATION: (1)..(1437)

<400> SEQUENCE: 44

| atg | agt | aca | aat | ggt | gat | gat | cat | cag | gtc | aag | gat | agt | ctg | gag | caa |    48 |
|-----|-----|-----|-----|-----|-----|-----|-----|-----|-----|-----|-----|-----|-----|-----|-----|-------|
| Met | Ser | Thr | Asn | Gly | Asp | Asp | His | Gln | Val | Lys | Asp | Ser | Leu | Glu | Gln |       |
| 1   |     |     |     | 5   |     |     |     |     | 10  |     |     |     |     | 15  |     |       |

| ttg | aga | tgt | cac | ttt | aca | tgg | gag | tta | tcc | att | gat | gac | gat | gaa | atg |    96 |
|-----|-----|-----|-----|-----|-----|-----|-----|-----|-----|-----|-----|-----|-----|-----|-----|-------|
| Leu | Arg | Cys | His | Phe | Thr | Trp | Glu | Leu | Ser | Ile | Asp | Asp | Asp | Glu | Met |       |
|     |     |     | 20  |     |     |     |     | 25  |     |     |     |     | 30  |     |     |       |

| cct | gat | tta | gaa | aac | aga | gtc | ttg | gat | cag | att | gaa | ttc | cta | gac | acc |   144 |
|-----|-----|-----|-----|-----|-----|-----|-----|-----|-----|-----|-----|-----|-----|-----|-----|-------|
| Pro | Asp | Leu | Glu | Asn | Arg | Val | Leu | Asp | Gln | Ile | Glu | Phe | Leu | Asp | Thr |       |
|     |     | 35  |     |     |     |     | 40  |     |     |     |     | 45  |     |     |     |       |

| aaa | tac | aat | gtg | gga | ata | cac | aac | cta | cta | gcc | tat | gtg | aaa | cac | ctg |   192 |
|-----|-----|-----|-----|-----|-----|-----|-----|-----|-----|-----|-----|-----|-----|-----|-----|-------|
| Lys | Tyr | Asn | Val | Gly | Ile | His | Asn | Leu | Leu | Ala | Tyr | Val | Lys | His | Leu |       |
| 50  |     |     |     |     | 55  |     |     |     |     | 60  |     |     |     |     |     |       |

| aaa | ggc | cag | aat | gag | gaa | gcc | ctg | aag | agc | tta | aaa | gaa | gct | gaa | aac |   240 |
|-----|-----|-----|-----|-----|-----|-----|-----|-----|-----|-----|-----|-----|-----|-----|-----|-------|
| Lys | Gly | Gln | Asn | Glu | Glu | Ala | Leu | Lys | Ser | Leu | Lys | Glu | Ala | Glu | Asn |       |
| 65  |     |     |     |     | 70  |     |     |     |     | 75  |     |     |     |     | 80  |       |

| tta | atg | cag | gaa | gaa | cat | gac | aac | caa | gca | aat | gtg | agg | agt | ctg | gtg |   288 |
|-----|-----|-----|-----|-----|-----|-----|-----|-----|-----|-----|-----|-----|-----|-----|-----|-------|
| Leu | Met | Gln | Glu | Glu | His | Asp | Asn | Gln | Ala | Asn | Val | Arg | Ser | Leu | Val |       |
|     |     |     |     | 85  |     |     |     |     | 90  |     |     |     |     | 95  |     |       |

| acc | tgg | ggc | aac | ttt | gcc | tgg | atg | tat | tac | cac | atg | ggc | aga | ctg | gca |   336 |
|-----|-----|-----|-----|-----|-----|-----|-----|-----|-----|-----|-----|-----|-----|-----|-----|-------|
| Thr | Trp | Gly | Asn | Phe | Ala | Trp | Met | Tyr | Tyr | His | Met | Gly | Arg | Leu | Ala |       |
|     |     |     | 100 |     |     |     |     | 105 |     |     |     |     | 110 |     |     |       |

| gaa | gcc | cag | act | tac | ctg | gac | aag | gtg | gag | aac | att | tgc | aag | aag | ctt |   384 |
|-----|-----|-----|-----|-----|-----|-----|-----|-----|-----|-----|-----|-----|-----|-----|-----|-------|
| Glu | Ala | Gln | Thr | Tyr | Leu | Asp | Lys | Val | Glu | Asn | Ile | Cys | Lys | Lys | Leu |       |
|     |     | 115 |     |     |     |     | 120 |     |     |     |     | 125 |     |     |     |       |

| tca | aat | ccc | ttc | cgc | tat | aga | atg | gag | tgt | cca | gaa | ata | gac | tgt | gag |   432 |
|-----|-----|-----|-----|-----|-----|-----|-----|-----|-----|-----|-----|-----|-----|-----|-----|-------|
| Ser | Asn | Pro | Phe | Arg | Tyr | Arg | Met | Glu | Cys | Pro | Glu | Ile | Asp | Cys | Glu |       |

```
            130                 135                 140
gaa gga tgg gcc ttg ctg aag tgt gga gga aag aat tat gaa cgg gcc      480
Glu Gly Trp Ala Leu Leu Lys Cys Gly Gly Lys Asn Tyr Glu Arg Ala
145                 150                 155                 160 aag gcc tgc ttt gaa aag gtg ctt gaa gtg gac cct gaa aac cct gaa      528
Lys Ala Cys Phe Glu Lys Val Leu Glu Val Asp Pro Glu Asn Pro Glu
                165                 170                 175 tcc agc gct ggg tat gcg atc tct gcc tat cgc ctg gat ggc ttt aaa      576
Ser Ser Ala Gly Tyr Ala Ile Ser Ala Tyr Arg Leu Asp Gly Phe Lys
            180                 185                 190 tta gcc aca aaa aat cac ata cca ttt tct ttg ctt ccc cta agg cag      624
Leu Ala Thr Lys Asn His Ile Pro Phe Ser Leu Leu Pro Leu Arg Gln
        195                 200                 205 gct gtc cgt tta aat ccg gac aat gga tat atg aag gtt ctc ctt gcc      672
Ala Val Arg Leu Asn Pro Asp Asn Gly Tyr Met Lys Val Leu Leu Ala
    210                 215                 220 ctg aag ctt cag gat gaa gga cag gaa gct gaa gga gaa aag tac att      720
Leu Lys Leu Gln Asp Glu Gly Gln Glu Ala Glu Gly Glu Lys Tyr Ile
225                 230                 235                 240 gaa gaa gct cta gcc aac atg tcc tca cag acc tat gtc ttt cga tat      768
Glu Glu Ala Leu Ala Asn Met Ser Ser Gln Thr Tyr Val Phe Arg Tyr
                245                 250                 255 gca gcc aag ttt tac cga aga aaa ggc tct gtg gat aaa gct ctt gag      816
Ala Ala Lys Phe Tyr Arg Arg Lys Gly Ser Val Asp Lys Ala Leu Glu
            260                 265                 270 tta tta gaa aag gcc ttg cag gaa aca ccc act tct gtc tta ctg cat      864
Leu Leu Glu Lys Ala Leu Gln Glu Thr Pro Thr Ser Val Leu Leu His
        275                 280                 285 cac cag ata ggg ctt tgc tac aag gca caa atg atc caa atc aag gag      912
His Gln Ile Gly Leu Cys Tyr Lys Ala Gln Met Ile Gln Ile Lys Glu
    290                 295                 300 gct aca aaa ggg cag cct aga ggg cag aac aga gaa aag cta gac aaa      960
Ala Thr Lys Gly Gln Pro Arg Gly Gln Asn Arg Glu Lys Leu Asp Lys
305                 310                 315                 320 atg ata aga tca gcc ata ttt cat ttt gaa tct gca gtg gaa aaa aag     1008
Met Ile Arg Ser Ala Ile Phe His Phe Glu Ser Ala Val Glu Lys Lys
                325                 330                 335 ccc aca ttt gag gtg gct cat cta gac ctg gca aga atg tat ata gaa     1056
Pro Thr Phe Glu Val Ala His Leu Asp Leu Ala Arg Met Tyr Ile Glu
            340                 345                 350 gca ggc aat cac aga aaa gct gaa gag agt ttt cga aaa atg tta tgc     1104
Ala Gly Asn His Arg Lys Ala Glu Glu Ser Phe Arg Lys Met Leu Cys
        355                 360                 365 atg aaa cca gtg gta gaa gaa aca atg caa gac ata cat ttc cac tat     1152
Met Lys Pro Val Val Glu Glu Thr Met Gln Asp Ile His Phe His Tyr
    370                 375                 380 ggt cgg ttt cag gaa ttt caa aag aaa tct gac gtc aat gca att atc     1200
Gly Arg Phe Gln Glu Phe Gln Lys Lys Ser Asp Val Asn Ala Ile Ile
385                 390                 395                 400 cat tat tta aaa gct ata aaa ata gaa cag gca tca tta gca agg gat     1248
His Tyr Leu Lys Ala Ile Lys Ile Glu Gln Ala Ser Leu Ala Arg Asp
                405                 410                 415 aaa agt atc aat tct ttg aag aaa ttg gtt tta agg aaa ctt cgg aga     1296
Lys Ser Ile Asn Ser Leu Lys Lys Leu Val Leu Arg Lys Leu Arg Arg
            420                 425                 430 aag gca tta gat ctg gaa agc ttg agc ctc ctt ggg ttc gtc tac aaa     1344
Lys Ala Leu Asp Leu Glu Ser Leu Ser Leu Leu Gly Phe Val Tyr Lys
        435                 440                 445 ttg gaa gga aat atg aat gaa gcc ctg gag tac tat gag cgg gcc ctg     1392
Leu Glu Gly Asn Met Asn Glu Ala Leu Glu Tyr Tyr Glu Arg Ala Leu
```

```
Leu Glu Gly Asn Met Asn Glu Ala Leu Glu Tyr Tyr Glu Arg Ala Leu
            450                 455                 460 aga ctg gct gct gac ttc gag aac tct gtg aga caa ggt cct tag          1437
Arg Leu Ala Ala Asp Phe Glu Asn Ser Val Arg Gln Gly Pro
465                 470                 475

<210> SEQ ID NO 45
<211> LENGTH: 478
<212> TYPE: PRT
<213> ORGANISM: Pan troglodytes

<400> SEQUENCE: 45

Met Ser Thr Asn Gly Asp Asp His Gln Val Lys Asp Ser Leu Glu Gln
1               5                   10                  15

Leu Arg Cys His Phe Thr Trp Glu Leu Ser Ile Asp Asp Glu Met
            20                  25                  30

Pro Asp Leu Glu Asn Arg Val Leu Asp Gln Ile Glu Phe Leu Asp Thr
            35                  40                  45

Lys Tyr Asn Val Gly Ile His Asn Leu Leu Ala Tyr Val Lys His Leu
        50                  55                  60

Lys Gly Gln Asn Glu Glu Ala Leu Lys Ser Leu Lys Glu Ala Glu Asn
65                  70                  75                  80

Leu Met Gln Glu Glu His Asp Asn Gln Ala Asn Val Arg Ser Leu Val
                85                  90                  95

Thr Trp Gly Asn Phe Ala Trp Met Tyr Tyr His Met Gly Arg Leu Ala
            100                 105                 110

Glu Ala Gln Thr Tyr Leu Asp Lys Val Glu Asn Ile Cys Lys Lys Leu
        115                 120                 125

Ser Asn Pro Phe Arg Tyr Arg Met Glu Cys Pro Glu Ile Asp Cys Glu
    130                 135                 140

Glu Gly Trp Ala Leu Leu Lys Cys Gly Gly Lys Asn Tyr Glu Arg Ala
145                 150                 155                 160

Lys Ala Cys Phe Glu Lys Val Leu Glu Val Asp Pro Glu Asn Pro Glu
                165                 170                 175

Ser Ser Ala Gly Tyr Ala Ile Ser Ala Tyr Arg Leu Asp Gly Phe Lys
            180                 185                 190

Leu Ala Thr Lys Asn His Ile Pro Phe Ser Leu Leu Pro Leu Arg Gln
        195                 200                 205

Ala Val Arg Leu Asn Pro Asp Asn Gly Tyr Met Lys Val Leu Leu Ala
    210                 215                 220

Leu Lys Leu Gln Asp Glu Gly Gln Glu Ala Glu Gly Glu Lys Tyr Ile
225                 230                 235                 240

Glu Glu Ala Leu Ala Asn Met Ser Ser Gln Thr Tyr Val Phe Arg Tyr
                245                 250                 255

Ala Ala Lys Phe Tyr Arg Arg Lys Gly Ser Val Asp Lys Ala Leu Glu
            260                 265                 270

Leu Leu Glu Lys Ala Leu Gln Glu Thr Pro Thr Ser Val Leu Leu His
        275                 280                 285

His Gln Ile Gly Leu Cys Tyr Lys Ala Gln Met Ile Gln Ile Lys Glu
    290                 295                 300

Ala Thr Lys Gly Gln Pro Arg Gly Gln Asn Arg Glu Lys Leu Asp Lys
305                 310                 315                 320

Met Ile Arg Ser Ala Ile Phe His Phe Glu Ser Ala Val Glu Lys Lys
                325                 330                 335

Pro Thr Phe Glu Val Ala His Leu Asp Leu Ala Arg Met Tyr Ile Glu
```

```
                  340             345             350
Ala Gly Asn His Arg Lys Ala Glu Glu Ser Phe Arg Lys Met Leu Cys
            355             360             365

Met Lys Pro Val Val Glu Thr Met Gln Asp Ile His Phe His Tyr
370             375             380

Gly Arg Phe Gln Glu Phe Gln Lys Lys Ser Asp Val Asn Ala Ile Ile
385             390             395             400

His Tyr Leu Lys Ala Ile Lys Ile Glu Gln Ala Ser Leu Ala Arg Asp
                405             410             415

Lys Ser Ile Asn Ser Leu Lys Lys Leu Val Leu Arg Lys Leu Arg Arg
            420             425             430

Lys Ala Leu Asp Leu Glu Ser Leu Ser Leu Leu Gly Phe Val Tyr Lys
            435             440             445

Leu Glu Gly Asn Met Asn Glu Ala Leu Glu Tyr Tyr Glu Arg Ala Leu
        450             455             460

Arg Leu Ala Ala Asp Phe Glu Asn Ser Val Arg Gln Gly Pro
465             470             475

<210> SEQ ID NO 46
<211> LENGTH: 1642
<212> TYPE: DNA
<213> ORGANISM: Homo sapiens

<400> SEQUENCE: 46
ccagatctca gaggagcctg gctaagcaaa accctgcaga acggctgcct aatttacagc       60
aaccatgagt acaaatggtg atgatcatca ggtcaaggat agtctggagc aattgagatg      120
tcactttaca tgggagttat ccattgatga cgatgaaatg cctgatttag aaaacagagt      180
cttggatcag attgaattcc tagacaccaa atacagtgtg gaatacaca acctactagc       240
ctatgtgaaa cacctgaaag gccagaatga ggaagccctg aagagcttaa agaagctga       300
aaacttaatg caggaagaac atgacaacca agcaaatgtg aggagtctgg tgacctgggg      360
caactttgcc tggatgtatt accacatggg cagactggca gaagcccaga cttacctgga      420
caaggtggag aacatttgca agaagctttc aaatcccttc cgctatagaa tggagtgtcc      480
agaaatagac tgtgaggaag gatgggcctt gctgaagtgt ggaggaaaga attatgaacg      540
ggccaaggcc tgctttgaaa aggtgcttga agtggaccct gaaaaccctg aatccagcgc      600
tgggtatgcg atctctgcct atcgcctgga tggctttaaa ttagccacaa aaaatcacaa      660
gccatttct ttgcttcccc taaggcaggc tgtccgctta aatccagaca atggatatat       720
taaggttctc cttgccctga agcttcagga tgaaggacag gaagctgaag gagaaaagta      780
cattgaagaa gctctagcca acatgtcctc acagacctat gtctttcgat atgcagccaa      840
gtttaccga agaaaaggct ctgtggataa agctcttgag ttattaaaaa aggccttgca       900
ggaaacaccc acttctgtct tactgcatca ccagataggg ctttgctaca aggcacaaat      960
gatccaaatc aaggaggcta caaagggca gcctagaggg cagaacagag aaaagctaga     1020
caaaatgata agatcagcca tatttcattt tgaatctgca gtggaaaaaa agcccacatt     1080
tgaggtggct catctagacc tggcaagaat gtatatagaa gcaggcaatc acagaaaagc     1140
tgaagagaat tttcaaaaat tgttatgcat gaaccagtg gtagaagaaa caatgcaaga     1200
catacatttc tactatggtc ggtttcagga atttcaaaag aaatctgacg tcaatgcaat     1260
tatccattat ttaaaagcta taaaaataga acaggcatca ttaacaaggg ataaaagtat     1320
caattctttg aagaaattgg ttttaaggaa acttcggaga aaggcattag atctggaaag     1380
```

-continued

```
cttgagcctc cttgggttcg tctataaatt ggaaggaaat atgaatgaag ccctggagta    1440
ctatgagcgg gccctgagac tggctgctga ctttgagaac tctgtgagac aaggtcctta    1500
ggcacccaga tatcagccac tttcacattt catttcattt tatgctaaca tttactaatc    1560
atcttttctg cttactgttt tcagaaacat tataattcac tgtaatgatg taattcttga    1620
ataataaatc tgacaaaata tt                                              1642

<210> SEQ ID NO 47
<211> LENGTH: 1642
<212> TYPE: DNA
<213> ORGANISM: Homo sapiens
<220> FEATURE:
<221> NAME/KEY: CDS
<222> LOCATION: (65)..(1501)

<400> SEQUENCE: 47
ccagatctca gaggagcctg gctaagcaaa accctgcaga acggctgcct aatttacagc      60 aacc atg agt aca aat ggt gat gat cat cag gtc aag gat agt ctg gag     109
     Met Ser Thr Asn Gly Asp Asp His Gln Val Lys Asp Ser Leu Glu
       1               5                  10                  15 caa ttg aga tgt cac ttt aca tgg gag tta tcc att gat gac gat gaa     157
Gln Leu Arg Cys His Phe Thr Trp Glu Leu Ser Ile Asp Asp Asp Glu
                 20                  25                  30 atg cct gat tta gaa aac aga gtc ttg gat cag att gaa ttc cta gac     205
Met Pro Asp Leu Glu Asn Arg Val Leu Asp Gln Ile Glu Phe Leu Asp
             35                  40                  45 acc aaa tac agt gtg gga ata cac aac cta cta gcc tat gtg aaa cac     253
Thr Lys Tyr Ser Val Gly Ile His Asn Leu Leu Ala Tyr Val Lys His
         50                  55                  60 ctg aaa ggc cag aat gag gaa gcc ctg aag agc tta aaa gaa gct gaa     301
Leu Lys Gly Gln Asn Glu Glu Ala Leu Lys Ser Leu Lys Glu Ala Glu
     65                  70                  75 aac tta atg cag gaa gaa cat gac aac caa gca aat gtg agg agt ctg     349
Asn Leu Met Gln Glu Glu His Asp Asn Gln Ala Asn Val Arg Ser Leu
 80                  85                  90                  95 gtg acc tgg ggc aac ttt gcc tgg atg tat tac cac atg ggc aga ctg     397
Val Thr Trp Gly Asn Phe Ala Trp Met Tyr Tyr His Met Gly Arg Leu
                100                 105                 110 gca gaa gcc cag act tac ctg gac aag gtg gag aac att tgc aag aag     445
Ala Glu Ala Gln Thr Tyr Leu Asp Lys Val Glu Asn Ile Cys Lys Lys
            115                 120                 125 ctt tca aat ccc ttc cgc tat aga atg gag tgt cca gaa ata gac tgt     493
Leu Ser Asn Pro Phe Arg Tyr Arg Met Glu Cys Pro Glu Ile Asp Cys
        130                 135                 140 gag gaa gga tgg gcc ttg ctg aag tgt gga gga aag aat tat gaa cgg     541
Glu Glu Gly Trp Ala Leu Leu Lys Cys Gly Gly Lys Asn Tyr Glu Arg
    145                 150                 155 gcc aag gcc tgc ttt gaa aag gtg ctt gaa gtg gac cct gaa aac cct     589
Ala Lys Ala Cys Phe Glu Lys Val Leu Glu Val Asp Pro Glu Asn Pro
160                 165                 170                 175 gaa tcc agc gct ggg tat gcg atc tct gcc tat cgc ctg gat ggc ttt     637
Glu Ser Ser Ala Gly Tyr Ala Ile Ser Ala Tyr Arg Leu Asp Gly Phe
                180                 185                 190 aaa tta gcc aca aaa aat cac aag cca ttt tct ttg ctt ccc cta agg     685
Lys Leu Ala Thr Lys Asn His Lys Pro Phe Ser Leu Leu Pro Leu Arg
            195                 200                 205 cag gct gtc cgc tta aat cca gac aat gga tat att aag gtt ctc ctt     733
Gln Ala Val Arg Leu Asn Pro Asp Asn Gly Tyr Ile Lys Val Leu Leu
        210                 215                 220
```

```
gcc ctg aag ctt cag gat gaa gga cag gaa gct gaa gga gaa aag tac    781
Ala Leu Lys Leu Gln Asp Glu Gly Gln Glu Ala Glu Gly Glu Lys Tyr
    225                 230                 235 att gaa gaa gct cta gcc aac atg tcc tca cag acc tat gtc ttt cga    829
Ile Glu Glu Ala Leu Ala Asn Met Ser Ser Gln Thr Tyr Val Phe Arg
240                 245                 250                 255 tat gca gcc aag ttt tac cga aga aaa ggc tct gtg gat aaa gct ctt    877
Tyr Ala Ala Lys Phe Tyr Arg Arg Lys Gly Ser Val Asp Lys Ala Leu
                260                 265                 270 gag tta tta aaa aag gcc ttg cag gaa aca ccc act tct gtc tta ctg    925
Glu Leu Leu Lys Lys Ala Leu Gln Glu Thr Pro Thr Ser Val Leu Leu
        275                 280                 285 cat cac cag ata ggg ctt tgc tac aag gca caa atg atc caa atc aag    973
His His Gln Ile Gly Leu Cys Tyr Lys Ala Gln Met Ile Gln Ile Lys
    290                 295                 300 gag gct aca aaa ggg cag cct aga ggg cag aac aga gaa aag cta gac   1021
Glu Ala Thr Lys Gly Gln Pro Arg Gly Gln Asn Arg Glu Lys Leu Asp
305                 310                 315 aaa atg ata aga tca gcc ata ttt cat ttt gaa tct gca gtg gaa aaa   1069
Lys Met Ile Arg Ser Ala Ile Phe His Phe Glu Ser Ala Val Glu Lys
320                 325                 330                 335 aag ccc aca ttt gag gtg gct cat cta gac ctg gca aga atg tat ata   1117
Lys Pro Thr Phe Glu Val Ala His Leu Asp Leu Ala Arg Met Tyr Ile
                340                 345                 350 gaa gca ggc aat cac aga aaa gct gag gag aat ttt caa aaa ttg tta   1165
Glu Ala Gly Asn His Arg Lys Ala Glu Glu Asn Phe Gln Lys Leu Leu
            355                 360                 365 tgc atg aaa cca gtg gta gaa gaa aca atg caa gac ata cat ttc tac   1213
Cys Met Lys Pro Val Val Glu Glu Thr Met Gln Asp Ile His Phe Tyr
        370                 375                 380 tat ggt cgg ttt cag gaa ttt caa aag aaa tct gac gtc aat gca att   1261
Tyr Gly Arg Phe Gln Glu Phe Gln Lys Lys Ser Asp Val Asn Ala Ile
    385                 390                 395 atc cat tat tta aaa gct ata aaa ata gaa cag gca tca tta aca agg   1309
Ile His Tyr Leu Lys Ala Ile Lys Ile Glu Gln Ala Ser Leu Thr Arg
400                 405                 410                 415 gat aaa agt atc aat tct ttg aag aaa ttg gtt tta agg aaa ctt cgg   1357
Asp Lys Ser Ile Asn Ser Leu Lys Lys Leu Val Leu Arg Lys Leu Arg
                420                 425                 430 aga aag gca tta gat ctg gaa agc ttg agc ctc ctt ggg ttc gtc tat   1405
Arg Lys Ala Leu Asp Leu Glu Ser Leu Ser Leu Leu Gly Phe Val Tyr
            435                 440                 445 aaa ttg gaa gga aat atg aat gaa gcc ctg gag tac tat gag cgg gcc   1453
Lys Leu Glu Gly Asn Met Asn Glu Ala Leu Glu Tyr Tyr Glu Arg Ala
        450                 455                 460 ctg aga ctg gct gct gac ttt gag aac tct gtg aga caa ggt cct tag   1501
Leu Arg Leu Ala Ala Asp Phe Glu Asn Ser Val Arg Gln Gly Pro
    465                 470                 475 gcacccagat atcagccact ttcacatttc atttcatttt atgctaacat ttactaatca   1561
tcttttctgc ttactgtttt cagaaacatt ataattcact gtaatgatgt aattcttgaa   1621
taataaatct gacaaaatat t                                              1642

<210> SEQ ID NO 48
<211> LENGTH: 478
<212> TYPE: PRT
<213> ORGANISM: Homo sapiens

<400> SEQUENCE: 48
```

```
Met Ser Thr Asn Gly Asp Asp His Gln Val Lys Asp Ser Leu Glu Gln
1               5                   10                  15

Leu Arg Cys His Phe Thr Trp Glu Leu Ser Ile Asp Asp Glu Met
        20                  25                  30

Pro Asp Leu Glu Asn Arg Val Leu Asp Gln Ile Glu Phe Leu Asp Thr
            35                  40                  45

Lys Tyr Ser Val Gly Ile His Asn Leu Leu Ala Tyr Val Lys His Leu
50                      55                  60

Lys Gly Gln Asn Glu Glu Ala Leu Lys Ser Leu Lys Glu Ala Glu Asn
65                  70                  75                  80

Leu Met Gln Glu Glu His Asp Asn Gln Ala Asn Val Arg Ser Leu Val
                85                  90                  95

Thr Trp Gly Asn Phe Ala Trp Met Tyr Tyr His Met Gly Arg Leu Ala
            100                 105                 110

Glu Ala Gln Thr Tyr Leu Asp Lys Val Glu Asn Ile Cys Lys Lys Leu
        115                 120                 125

Ser Asn Pro Phe Arg Tyr Arg Met Glu Cys Pro Glu Ile Asp Cys Glu
    130                 135                 140

Glu Gly Trp Ala Leu Leu Lys Cys Gly Gly Lys Asn Tyr Glu Arg Ala
145                 150                 155                 160

Lys Ala Cys Phe Glu Lys Val Leu Glu Val Asp Pro Glu Asn Pro Glu
                165                 170                 175

Ser Ser Ala Gly Tyr Ala Ile Ser Ala Tyr Arg Leu Asp Gly Phe Lys
            180                 185                 190

Leu Ala Thr Lys Asn His Lys Pro Phe Ser Leu Leu Pro Leu Arg Gln
        195                 200                 205

Ala Val Arg Leu Asn Pro Asp Asn Gly Tyr Ile Lys Val Leu Leu Ala
    210                 215                 220

Leu Lys Leu Gln Asp Glu Gly Gln Glu Ala Glu Gly Glu Lys Tyr Ile
225                 230                 235                 240

Glu Glu Ala Leu Ala Asn Met Ser Ser Gln Thr Tyr Val Phe Arg Tyr
                245                 250                 255

Ala Ala Lys Phe Tyr Arg Arg Lys Gly Ser Val Asp Lys Ala Leu Glu
            260                 265                 270

Leu Leu Lys Lys Ala Leu Gln Glu Thr Pro Thr Ser Val Leu Leu His
        275                 280                 285

His Gln Ile Gly Leu Cys Tyr Lys Ala Gln Met Ile Gln Ile Lys Glu
    290                 295                 300

Ala Thr Lys Gly Gln Pro Arg Gly Gln Asn Arg Glu Lys Leu Asp Lys
305                 310                 315                 320

Met Ile Arg Ser Ala Ile Phe His Phe Glu Ser Ala Val Glu Lys Lys
                325                 330                 335

Pro Thr Phe Glu Val Ala His Leu Asp Leu Ala Arg Met Tyr Ile Glu
            340                 345                 350

Ala Gly Asn His Arg Lys Ala Glu Glu Asn Phe Gln Lys Leu Leu Cys
        355                 360                 365

Met Lys Pro Val Val Glu Glu Thr Met Gln Asp Ile His Phe Tyr Tyr
    370                 375                 380

Gly Arg Phe Gln Glu Phe Gln Lys Lys Ser Asp Val Asn Ala Ile Ile
385                 390                 395                 400

His Tyr Leu Lys Ala Ile Lys Ile Glu Gln Ala Ser Leu Thr Arg Asp
                405                 410                 415

Lys Ser Ile Asn Ser Leu Lys Lys Leu Val Leu Arg Lys Leu Arg Arg
```

```
                420             425             430
Lys Ala Leu Asp Leu Glu Ser Leu Ser Leu Leu Gly Phe Val Tyr Lys
        435                 440                 445

Leu Glu Gly Asn Met Asn Glu Ala Leu Glu Tyr Tyr Glu Arg Ala Leu
    450                 455                 460

Arg Leu Ala Ala Asp Phe Glu Asn Ser Val Arg Gln Gly Pro
465                 470                 475
```

<210> SEQ ID NO 49
<211> LENGTH: 1341
<212> TYPE: DNA
<213> ORGANISM: Pan troglodytes

<400> SEQUENCE: 49

```
atggatttct cagtaaaggt agacatagag aaggaggtga cctgcccat  ctgcctggag    60
ctcctgacag aacctctgag cctagattgt ggccacagct tctgccaagc ctgcatcact   120
acaaagatca aggagtcagt gatcatctca agaggggaaa gcagctgtcc tgtgtgtcag   180
accagattcc agcctgggaa cctccgacct aatcggcatc tggccaacat agttgagaga   240
gtcaaagagg tcaagatgag cccacaggag gggcagaaga gagatgtctg tgagcaccat   300
ggaaaaaaac tccagatctt ctgtaaggag gatggaaaag tcatttgctg ggtttgtgaa   360
ctgtctccgg aacaccaagg tcaccaaaca ttccgcataa acgaggtggt caaggaatgt   420
caggaaaagc tgcaggtagc cctgcagagg ctgataaagg aggatcaaga ggctgagaag   480
ctggaagatg acatcagaca agagagaacc gcctggaaga attatatcca gatcgagaga   540
cagaagattc tgaaagggtt caatgaaatg agagtcatct ggacaatga  ggagcagaga   600
gagctgcaaa agctggagga aggtgaggtg aatgtgctgg ataacctggc agcagctaca   660
gaccagctgg tccagcagag gcaggatgcc agcacgctca tctcagatct ccagcggagg   720
ttgaggggat cgtcagtaga gatgctgcag gatgtgattg acgtcatgaa aaggagtgaa   780
agctggacat tgaagaagcc aaaatctgtt tccaagaaac taaagagtgt attccgagta   840
ccagatctga gtgggatgct gcaagttctt aaagagctga cagatgtcca gtactactgg   900
gtggacgtga tgctgaatcc aggcagtgcc acttcgaatg ttgctatttc tgtggatcag   960
agacaagtga aaactgtacg cacctgcaca tttaagaatt caaatccatg tgatttttct  1020
gcttttggtg tcttcggctg ccaatatttc tcttcgggga atattactg  ggaagtagat  1080
gtgtctggaa agattgcctg gatcctgggc gtacacagta aaataagtag tctgaataaa  1140
aggaagagct ctgggtttgc ttttgatcca agtgtaaatt attcaaaagt ttactccaaa  1200
tatagacctc aatatggcta ctgggttata ggattacaga atacatgtga atataatgct  1260
tttgaggact cctcctcttc tgatcccaag gttttgactc tctttatggc cgtgctccct  1320
gtcgtattgg ggttttccta g                                            1341
```

<210> SEQ ID NO 50
<211> LENGTH: 1341
<212> TYPE: DNA
<213> ORGANISM: Pan troglodytes

<400> SEQUENCE: 50

```
atggatttct cagtaaaggt agacatagag aaggaggtga cctgcccat  ctgcctggag    60
ctcctgacag aacctctgag cctagattgt ggccacagct tctgccaagc ctgcatcact   120
acaaagatca aggagtcagt gatcatctca agaggggaaa gcagctgtcc tgtgtgtcag   180
```

-continued

| | |
|---|---|
| accagattcc agcctgggaa cctccgacct aatcggcatc tggccaacat agttgagaga | 240 |
| gtcaaagagg tcaagatgag cccacaggag gggcagaaga gagatgtctg tgagcaccat | 300 |
| ggaaaaaaac tccagatctt ctgtaaggag gatggaaaag tcatttgctg ggtttgtgaa | 360 |
| ctgtctccgg aacaccaagg tcaccaaaca ttccgcataa acgaggtggt caaggaatgt | 420 |
| caggaaaagc tgcaggtagc cctgcagagg ctgataaagg aggatcaaga ggctgagaag | 480 |
| ctggaagatg acatcagaca agagagaacc gcctggaaga attatatcca gatcgagaga | 540 |
| cagaagattc tgaaagggtt caatgaaatg agagtcatct tggacaatga ggagcagaga | 600 |
| gagctgcaaa agctggagga aggtgaggtg aatgtgctgg ataacctggc agcagctaca | 660 |
| gaccagctgg tccagcagag gcaggatgcc agcacgctca tctcagatct ccagcggagg | 720 |
| ttgaggggat cgtcagtaga gatgctgcag gatgtgattg acgtcatgaa aaggagtgaa | 780 |
| agctggacat tgaagaagcc aaaatctgtt ccaagaaac taaagagtgt attccgagta | 840 |
| ccagatctga gtgggatgct gcaagttctt aaagagctga cagatgtcca gtactactgg | 900 |
| gtggacgtga tgctgaatcc aggcagtgcc acttcgaatg ttgctatttc tgtggatcag | 960 |
| agacaagtga aaactgtacg cacctgcaca tttaagaatt caaatccatg tgattttctct | 1020 |
| gcttttggtg tcttcggctg ccaatatttc tcttcgggga atattactg ggaagtagat | 1080 |
| gtgtctggaa agattgcctg gatcctgggc gtacacagta aaataagtag tctgaataaa | 1140 |
| aggaagagct ctgggtttgc ttttgatcca agtgtaaatt attcaaaagt ttactccaaa | 1200 |
| tatagacctc aatatggcta ctgggttata ggattacaga atacatgtga atataatgct | 1260 |
| tttgaggact cctcctcttc tgatcccaag gttttgactc tctttatggc tgtgctccct | 1320 |
| gtcgtattgg ggttttccta g | 1341 |

<210> SEQ ID NO 51
<211> LENGTH: 2811
<212> TYPE: DNA
<213> ORGANISM: Homo sapiens

<400> SEQUENCE: 51

| | |
|---|---|
| gaattcggca cgagctcttc tcccctgatt caagactcct ctgctttgga ctgaagcact | 60 |
| gcaggagttt gtgaccaaga acttcaagag tcaagacaga aggaagccaa gggagcagtg | 120 |
| caatggattt ctcagtaaag gtagacatag agaaggaggt gacctgcccc atctgcctgg | 180 |
| agctcctgac agaacctctg agcctagatt gtggccacag cttctgccaa gcctgcatca | 240 |
| ctgcaaagat caaggagtca gtgatcatct caagagggga agcagctgt cctgtgtgtc | 300 |
| agaccagatt ccagcctggg aacctccgac ctaatcggca tctggccaac atagttgaga | 360 |
| gagtcaaaga ggtcaagatg agcccacagg agggggcagaa gagagatgtc tgtgagcacc | 420 |
| atggaaaaaa actccagatc ttctgtaagg aggatggaaa agtcatttgc tgggtttgtg | 480 |
| aactgtctca ggaacaccaa ggtcaccaaa cattccgcat aaacgaggtg gtcaaggaat | 540 |
| gtcaggaaaa gctgcaggta gccctgcaga ggctgataaa ggaggatcaa gaggctgaga | 600 |
| agctggaaga tgacatcaga caagagagaa ccgcctggaa gatcgagaga cagaagattc | 660 |
| tgaaagggtt caatgaaatg agagtcatct tggacaatga ggagcagaga gagctgcaaa | 720 |
| agctggagga aggtgaggtg aatgtgctgg acaacctggc agcagctaca gaccagctgg | 780 |
| tccagcagag gcaggatgcc agcacgctca tctcagatct ccagcggagg ttgacgggat | 840 |
| cgtcagtaga gatgctgcag gatgtgattg acgtcatgaa aaggagtgaa agctggacat | 900 |
| tgaagaagcc aaaatctgtt ccaagaaac taaagagtgt attccgagta ccagatctga | 960 |

-continued

```
gtgggatgct gcaagttctt aaagagctga cagatgtcca gtactactgg gtggacgtga    1020
tgctgaatcc aggcagtgcc acttcgaatg ttgctatttc tgtggatcag agacaagtga    1080
aaactgtacg cacctgcaca tttaagaatt caaatccatg tgattttcct gcttttggtg    1140
tcttcggctg ccaatatttc tcttcgggga atattactg ggaagtagat gtgtctggaa     1200
agattgcctg gatcctgggc gtacacagta aaataagtag tctgaataaa aggaagagct    1260
ctgggtttgc ttttgatcca agtgtaaatt attcaaaagt ttactccaga tatagacctc    1320
aatatggcta ctgggttata ggattacaga atacatgtga atataatgct tttgaggact    1380
cctcctcttc tgatcccaag gttttgactc tctttatggc tgtgctccct gtcgtattgg    1440
ggttttccta gactatgagg caggcattgt ctcattttc aatgtcacaa accacggacg     1500
actcatctac aagttctctg gatgtcgctt ttctcgacct gcttatccgt atttcaatcc    1560
ttggaactgc ctagtcccca tgactgtgtg cccaccgagc tcctgagtgt tctcattcct    1620
ttacccactt ctgcatagta gcccttctgt gagactcaga ttctgcacct gagttcatct    1680
ctactgagac catctcttcc tttctttccc cttcttttac ttagaatgtc tttgtattca    1740
tttgctaggg cttccatagc aaagcatcat agattgctga tttaaactgt aattgtattg    1800
ccgtactgtg ggctgaaatc ccaaatctag attccagcag agttggttct ttctgaggtc    1860
tgcaaggaag ggctctgttc catgcctctc tccttggctt gtagaaggca tcttgtccct    1920
atgactcttc acattgtctt tatgtacatc tctgtgccca agttttccct ttttattaag    1980
acaccagtca tactggcctc agggcccacc gctaatgcct aatgaaatc attttaacat     2040 tatattgtgt acaaagacct tatttccaaa taagataata tttggaggta ttgggaataa    2100
aatttgagga aggcgatttc actcataaca atcttaccct ttcttgcaag agatgcttgt    2160
acattatttt cctaatacct tggtttcact agtagtaaac attattattt tttttatatt    2220
tgcaaaggaa acatatctaa tccttcctat agaaagaaca gtattgctgt aattcctttc    2280
cttttcttcc tcatttcctc tgccccttaa aagattgaag aaagagaaac ttgtcaactc    2340
atatccacgt tatctagcaa agtcataaga atctatcact aagtaatgta tccttcagaa    2400
tgtgttggtt taccagtgac acccccatatt catcacaaaa ttaaagcaag aagtccatag   2460 taatttatt gctaatagtg gattttttaat gctcagagtt tctgaggtca aattttatct    2520
tttcacttac aagctctatg atcttaaata atttacttaa tgtattttgg tgtattttcc    2580
tcaaattaat attggtgttc aagactatat ctaattcctc tgatcacttt gagaaacaaa    2640
cttttattaa atgtaaggca cttttctatg aattttaaat ataaaataa atattgttct     2700 gattattact gaaaagatgt cagccatttc aatgtcttgg gaaacaattt tttgtttttg    2760
ttctgttttc ttttttgcttc aataaaacaa tagctggctc taaaaaaaaa a            2811
```

<210> SEQ ID NO 52
<211> LENGTH: 2811
<212> TYPE: DNA
<213> ORGANISM: Homo sapiens
<220> FEATURE:
<221> NAME/KEY: CDS
<222> LOCATION: (123)..(1451)

<400> SEQUENCE: 52

```
gaattcggca cgagctcttc tcccctgatt caagactcct ctgctttgga ctgaagcact     60
gcaggagttt gtgaccaaga acttcaagag tcaagacaga aggaagccaa gggagcagtg    120 ca atg gat ttc tca gta aag gta gac ata gag aag gag gtg acc tgc       167
```

-continued

```
    Met Asp Phe Ser Val Lys Val Asp Ile Glu Lys Glu Val Thr Cys
    1               5                   10                  15 ccc atc tgc ctg gag ctc ctg aca gaa cct ctg agc cta gat tgt ggc      215
Pro Ile Cys Leu Glu Leu Leu Thr Glu Pro Leu Ser Leu Asp Cys Gly
            20                  25                  30 cac agc ttc tgc caa gcc tgc atc act gca aag atc aag gag tca gtg      263
His Ser Phe Cys Gln Ala Cys Ile Thr Ala Lys Ile Lys Glu Ser Val
                35                  40                  45 atc atc tca aga ggg gaa agc agc tgt cct gtg tgt cag acc aga ttc      311
Ile Ile Ser Arg Gly Glu Ser Ser Cys Pro Val Cys Gln Thr Arg Phe
            50                  55                  60 cag cct ggg aac ctc cga cct aat cgg cat ctg gcc aac ata gtt gag      359
Gln Pro Gly Asn Leu Arg Pro Asn Arg His Leu Ala Asn Ile Val Glu
65                  70                  75 aga gtc aaa gag gtc aag atg agc cca cag gag ggg cag aag aga gat      407
Arg Val Lys Glu Val Lys Met Ser Pro Gln Glu Gly Gln Lys Arg Asp
80                  85                  90                  95 gtc tgt gag cac cat gga aaa aaa ctc cag atc ttc tgt aag gag gat      455
Val Cys Glu His His Gly Lys Lys Leu Gln Ile Phe Cys Lys Glu Asp
                100                 105                 110 gga aaa gtc att tgc tgg gtt tgt gaa ctg tct cag gaa cac caa ggt      503
Gly Lys Val Ile Cys Trp Val Cys Glu Leu Ser Gln Glu His Gln Gly
            115                 120                 125 cac caa aca ttc cgc ata aac gag gtg gtc aag gaa tgt cag gaa aag      551
His Gln Thr Phe Arg Ile Asn Glu Val Val Lys Glu Cys Gln Glu Lys
        130                 135                 140 ctg cag gta gcc ctg cag agg ctg ata aag gag gat caa gag gct gag      599
Leu Gln Val Ala Leu Gln Arg Leu Ile Lys Glu Asp Gln Glu Ala Glu
145                 150                 155 aag ctg gaa gat gac atc aga caa gag aga acc gcc tgg aag atc gag      647
Lys Leu Glu Asp Asp Ile Arg Gln Glu Arg Thr Ala Trp Lys Ile Glu
160                 165                 170                 175 aga cag aag att ctg aaa ggg ttc aat gaa atg aga gtc atc ttg gac      695
Arg Gln Lys Ile Leu Lys Gly Phe Asn Glu Met Arg Val Ile Leu Asp
                180                 185                 190 aat gag gag cag aga gag ctg caa aag ctg gag gaa ggt gag gtg aat      743
Asn Glu Glu Gln Arg Glu Leu Gln Lys Leu Glu Glu Gly Glu Val Asn
            195                 200                 205 gtg ctg gac aac ctg gca gca gct aca gac cag ctg gtc cag cag agg      791
Val Leu Asp Asn Leu Ala Ala Ala Thr Asp Gln Leu Val Gln Gln Arg
        210                 215                 220 cag gat gcc agc acg ctc atc tca gat ctc cag cgg agg ttg acg gga      839
Gln Asp Ala Ser Thr Leu Ile Ser Asp Leu Gln Arg Arg Leu Thr Gly
    225                 230                 235 tcg tca gta gag atg ctg cag gat gtg att gac gtc atg aaa agg agt      887
Ser Ser Val Glu Met Leu Gln Asp Val Ile Asp Val Met Lys Arg Ser
240                 245                 250                 255 gaa agc tgg aca ttg aag aag cca aaa tct gtt tcc aag aaa cta aag      935
Glu Ser Trp Thr Leu Lys Lys Pro Lys Ser Val Ser Lys Lys Leu Lys
                260                 265                 270 agt gta ttc cga gta cca gat ctg agt ggg atg ctg caa gtt ctt aaa      983
Ser Val Phe Arg Val Pro Asp Leu Ser Gly Met Leu Gln Val Leu Lys
            275                 280                 285 gag ctg aca gat gtc cag tac tac tgg gtg gac gtg atg ctg aat cca     1031
Glu Leu Thr Asp Val Gln Tyr Tyr Trp Val Asp Val Met Leu Asn Pro
        290                 295                 300 ggc agt gcc act tcg aat gtt gct att tct gtg gat cag aga caa gtg     1079
Gly Ser Ala Thr Ser Asn Val Ala Ile Ser Val Asp Gln Arg Gln Val
    305                 310                 315
```

```
aaa act gta cgc acc tgc aca ttt aag aat tca aat cca tgt gat ttt     1127
Lys Thr Val Arg Thr Cys Thr Phe Lys Asn Ser Asn Pro Cys Asp Phe
320                 325                 330                 335 tct gct ttt ggt gtc ttc ggc tgc caa tat ttc tct tcg ggg aaa tat     1175
Ser Ala Phe Gly Val Phe Gly Cys Gln Tyr Phe Ser Ser Gly Lys Tyr
                340                 345                 350 tac tgg gaa gta gat gtg tct gga aag att gcc tgg atc ctg ggc gta     1223
Tyr Trp Glu Val Asp Val Ser Gly Lys Ile Ala Trp Ile Leu Gly Val
            355                 360                 365 cac agt aaa ata agt agt ctg aat aaa agg aag agc tct ggg ttt gct     1271
His Ser Lys Ile Ser Ser Leu Asn Lys Arg Lys Ser Ser Gly Phe Ala
        370                 375                 380 ttt gat cca agt gta aat tat tca aaa gtt tac tcc aga tat aga cct     1319
Phe Asp Pro Ser Val Asn Tyr Ser Lys Val Tyr Ser Arg Tyr Arg Pro
385                 390                 395 caa tat ggc tac tgg gtt ata gga tta cag aat aca tgt gaa tat aat     1367
Gln Tyr Gly Tyr Trp Val Ile Gly Leu Gln Asn Thr Cys Glu Tyr Asn
400                 405                 410                 415 gct ttt gag gac tcc tcc tct tct gat ccc aag gtt ttg act ctc ttt     1415
Ala Phe Glu Asp Ser Ser Ser Ser Asp Pro Lys Val Leu Thr Leu Phe
                420                 425                 430 atg gct gtg ctc cct gtc gta ttg ggg ttt tcc tag actatgaggc         1461
Met Ala Val Leu Pro Val Val Leu Gly Phe Ser
                435                 440 aggcattgtc tcattttca atgtcacaaa ccacggacga ctcatctaca agttctctgg    1521
atgtcgcttt tctcgacctg cttatccgta tttcaatcct tggaactgcc tagtccccat   1581
gactgtgtgc ccaccgagct cctgagtgtt ctcattcctt tacccacttc tgcatagtag   1641
cccttctgtg agactcagat tctgcacctg agttcatctc tactgagacc atctcttcct   1701
ttctttcccc ttcttttact tagaatgtct ttgtattcat ttgctagggc ttccatagca   1761
aagcatcata gattgctgat ttaaactgta attgtattgc cgtactgtgg gctgaaatcc   1821
caaatctaga ttccagcaga gttggttctt tctgaggtct gcaaggaagg gctctgttcc   1881
atgcctctct ccttggcttg tagaaggcat cttgtcccta tgactcttca cattgtcttt   1941
atgtacatct ctgtgcccaa gttttccctt tttattaaga caccagtcat actggcctca   2001
gggcccaccg ctaatgcctt aatgaaatca ttttaacatt atattgtgta caaagacctt   2061
atttccaaat aagataatat ttggaggtat tgggaataaa atttgaggaa ggcgatttca   2121
ctcataacaa tcttaccctt tcttgcaaga gatgcttgta cattattttc ctaatacctt   2181
ggtttcacta gtagtaaaca ttattatttt ttttatattt gcaaaggaaa catatctaat   2241
ccttcctata gaaagaacag tattgctgta attccttttc ttttcttcct catttcctct   2301
gccccttaaa agattgaaga aagagaaact tgtcaactca tatccacgtt atctagcaaa   2361
gtcataagaa tctatcacta agtaatgtat ccttcagaat gtgttggttt accagtgaca   2421
ccccatattc atcacaaaat taaagcaaga agtccatagt aatttatttg ctaatagtgg   2481 attttttaatg ctcagagttt ctgaggtcaa attttatctt ttcacttaca agctctatga  2541
tcttaaataa tttacttaat gtattttggt gtattttcct caaattaata ttggtgttca   2601
agactatatc taattcctct gatcactttg agaaacaaac ttttattaaa tgtaaggcac   2661
ttttctatga attttaaata taaaaataaa tattgttctg attattactg aaaagatgtc   2721
agccatttca atgtcttggg aaacaatttt ttgttttttgt tctgttttct ttttgcttca   2781
ataaaacaat agctggctct aaaaaaaaaa                                     2811
```

-continued

<210> SEQ ID NO 53
<211> LENGTH: 442
<212> TYPE: PRT
<213> ORGANISM: Homo sapiens

<400> SEQUENCE: 53

```
Met Asp Phe Ser Val Lys Val Asp Ile Glu Lys Glu Val Thr Cys Pro
1               5                   10                  15
Ile Cys Leu Glu Leu Leu Thr Glu Pro Leu Ser Leu Asp Cys Gly His
            20                  25                  30
Ser Phe Cys Gln Ala Cys Ile Thr Ala Lys Ile Lys Glu Ser Val Ile
        35                  40                  45
Ile Ser Arg Gly Glu Ser Ser Cys Pro Val Cys Gln Thr Arg Phe Gln
    50                  55                  60
Pro Gly Asn Leu Arg Pro Asn Arg His Leu Ala Asn Ile Val Glu Arg
65                  70                  75                  80
Val Lys Glu Val Lys Met Ser Pro Gln Glu Gly Gln Lys Arg Asp Val
                85                  90                  95
Cys Glu His His Gly Lys Lys Leu Gln Ile Phe Cys Lys Glu Asp Gly
            100                 105                 110
Lys Val Ile Cys Trp Val Cys Glu Leu Ser Gln Glu His Gln Gly His
        115                 120                 125
Gln Thr Phe Arg Ile Asn Glu Val Val Lys Glu Cys Gln Glu Lys Leu
    130                 135                 140
Gln Val Ala Leu Gln Arg Leu Ile Lys Glu Asp Gln Glu Ala Glu Lys
145                 150                 155                 160
Leu Glu Asp Asp Ile Arg Gln Glu Arg Thr Ala Trp Lys Ile Glu Arg
                165                 170                 175
Gln Lys Ile Leu Lys Gly Phe Asn Glu Met Arg Val Ile Leu Asp Asn
            180                 185                 190
Glu Glu Gln Arg Glu Leu Gln Lys Leu Glu Glu Gly Glu Val Asn Val
        195                 200                 205
Leu Asp Asn Leu Ala Ala Ala Thr Asp Gln Leu Val Gln Gln Arg Gln
    210                 215                 220
Asp Ala Ser Thr Leu Ile Ser Asp Leu Gln Arg Arg Leu Thr Gly Ser
225                 230                 235                 240
Ser Val Glu Met Leu Gln Asp Val Ile Asp Val Met Lys Arg Ser Glu
                245                 250                 255
Ser Trp Thr Leu Lys Lys Pro Lys Ser Val Ser Lys Lys Leu Lys Ser
            260                 265                 270
Val Phe Arg Val Pro Asp Leu Ser Gly Met Leu Gln Val Leu Lys Glu
        275                 280                 285
Leu Thr Asp Val Gln Tyr Tyr Trp Val Asp Val Met Leu Asn Pro Gly
    290                 295                 300
Ser Ala Thr Ser Asn Val Ala Ile Ser Val Asp Gln Arg Gln Val Lys
305                 310                 315                 320
Thr Val Arg Thr Cys Thr Phe Lys Asn Ser Asn Pro Cys Asp Phe Ser
                325                 330                 335
Ala Phe Gly Val Phe Gly Cys Gln Tyr Phe Ser Ser Gly Lys Tyr Tyr
            340                 345                 350
Trp Glu Val Asp Val Ser Gly Lys Ile Ala Trp Ile Leu Gly Val His
        355                 360                 365
Ser Lys Ile Ser Ser Leu Asn Lys Arg Lys Ser Ser Gly Phe Ala Phe
    370                 375                 380
```

-continued

```
Asp Pro Ser Val Asn Tyr Ser Lys Val Tyr Ser Arg Tyr Arg Pro Gln
385                 390                 395                 400

Tyr Gly Tyr Trp Val Ile Gly Leu Gln Asn Thr Cys Glu Tyr Asn Ala
            405                 410                 415

Phe Glu Asp Ser Ser Ser Ser Asp Pro Lys Val Leu Thr Leu Phe Met
        420                 425                 430

Ala Val Leu Pro Val Val Leu Gly Phe Ser
        435                 440
```

<210> SEQ ID NO 54
<211> LENGTH: 825
<212> TYPE: DNA
<213> ORGANISM: Homo sapiens

<400> SEQUENCE: 54

| | | |
|---|---|---|
| atgtcctctt tcggttacag gaccctgact gtggccctct tcaccctgat ctgctgtcca | 60 |
| ggatcggatg agaaggtatt cgaggtacac gtgaggccaa agaagctggc ggttgagccc | 120 |
| aaagggtccc tcgaggtcaa ctgcagcacc acctgtaacc agcctgaagt gggtggtctg | 180 |
| gagacctctc tagataagat tctgctggac gaacaggctc agtggaaaca ttacttggtc | 240 |
| tcaaacatct cccatgacac ggtcctccaa tgccacttca cctgctccgg gaagcaggag | 300 |
| tcaatgaatt ccaacgtcag cgtgtaccag cctccaaggc aggtcatcct gacactgcaa | 360 |
| cccactttgg tggctgtggg caagtccttc accattgagt gcagggtgcc caccgtggag | 420 |
| cccctggaca gcctcaccct cttcctgttc cgtggcaatg agactctgca ctatgagacc | 480 |
| ttcgggaagg cagcccctgc tccgcaggag gccacagcca cattcaacag cacggctgac | 540 |
| agagaggatg gccaccgcaa cttctcctgc ctggctgtgc tggacttgat gtctcgcggt | 600 |
| ggcaacatct ttcacaaaca ctcagccccg aagatgttgg agatctatga gcctgtgtcg | 660 |
| gacagccaga tggtcatcat agtcacggtg gtgtcggtgt tgctgtccct gttcgtgaca | 720 |
| tctgtcctgc tctgcttcat cttcggccag cacttgcgcc agcagcggat gggcacctac | 780 |
| ggggtgcgag cggcttggag gaggctgccc caggccttcc ggcca | 825 |

<210> SEQ ID NO 55
<211> LENGTH: 825
<212> TYPE: DNA
<213> ORGANISM: Homo sapiens
<220> FEATURE:
<221> NAME/KEY: CDS
<222> LOCATION: (1)..(825)

<400> SEQUENCE: 55

```
atg tcc tct ttc ggt tac agg acc ctg act gtg gcc ctc ttc acc ctg      48
Met Ser Ser Phe Gly Tyr Arg Thr Leu Thr Val Ala Leu Phe Thr Leu
1               5                   10                  15 atc tgc tgt cca gga tcg gat gag aag gta ttc gag gta cac gtg agg      96
Ile Cys Cys Pro Gly Ser Asp Glu Lys Val Phe Glu Val His Val Arg
            20                  25                  30 cca aag aag ctg gcg gtt gag ccc aaa ggg tcc ctc gag gtc aac tgc     144
Pro Lys Lys Leu Ala Val Glu Pro Lys Gly Ser Leu Glu Val Asn Cys
        35                  40                  45 agc acc acc tgt aac cag cct gaa gtg ggt ggt ctg gag acc tct cta     192
Ser Thr Thr Cys Asn Gln Pro Glu Val Gly Gly Leu Glu Thr Ser Leu
    50                  55                  60 gat aag att ctg ctg gac gaa cag gct cag tgg aaa cat tac ttg gtc     240
Asp Lys Ile Leu Leu Asp Glu Gln Ala Gln Trp Lys His Tyr Leu Val
65                  70                  75                  80
```

-continued

```
tca aac atc tcc cat gac acg gtc ctc caa tgc cac ttc acc tgc tcc       288
Ser Asn Ile Ser His Asp Thr Val Leu Gln Cys His Phe Thr Cys Ser
                85                  90                  95 ggg aag cag gag tca atg aat tcc aac gtc agc gtg tac cag cct cca       336
Gly Lys Gln Glu Ser Met Asn Ser Asn Val Ser Val Tyr Gln Pro Pro
            100                 105                 110 agg cag gtc atc ctg aca ctg caa ccc act ttg gtg gct gtg ggc aag       384
Arg Gln Val Ile Leu Thr Leu Gln Pro Thr Leu Val Ala Val Gly Lys
        115                 120                 125 tcc ttc acc att gag tgc agg gtg ccc acc gtg gag ccc ctg gac agc       432
Ser Phe Thr Ile Glu Cys Arg Val Pro Thr Val Glu Pro Leu Asp Ser
130                 135                 140 ctc acc ctc ttc ctg ttc cgt ggc aat gag act ctg cac tat gag acc       480
Leu Thr Leu Phe Leu Phe Arg Gly Asn Glu Thr Leu His Tyr Glu Thr
145                 150                 155                 160 ttc ggg aag gca gcc cct gct ccg cag gag gcc aca gcc aca ttc aac       528
Phe Gly Lys Ala Ala Pro Ala Pro Gln Glu Ala Thr Ala Thr Phe Asn
                165                 170                 175 agc acg gct gac aga gag gat ggc cac cgc aac ttc tcc tgc ctg gct       576
Ser Thr Ala Asp Arg Glu Asp Gly His Arg Asn Phe Ser Cys Leu Ala
            180                 185                 190 gtg ctg gac ttg atg tct cgc ggt ggc aac atc ttt cac aaa cac tca       624
Val Leu Asp Leu Met Ser Arg Gly Gly Asn Ile Phe His Lys His Ser
        195                 200                 205 gcc ccg aag atg ttg gag atc tat gag cct gtg tcg gac agc cag atg       672
Ala Pro Lys Met Leu Glu Ile Tyr Glu Pro Val Ser Asp Ser Gln Met
210                 215                 220 gtc atc ata gtc acg gtg gtg tcg gtg ttg ctg tcc ctg ttc gtg aca       720
Val Ile Ile Val Thr Val Val Ser Val Leu Leu Ser Leu Phe Val Thr
225                 230                 235                 240 tct gtc ctg ctc tgc ttc atc ttc ggc cag cac ttg cgc cag cag cgg       768
Ser Val Leu Leu Cys Phe Ile Phe Gly Gln His Leu Arg Gln Gln Arg
                245                 250                 255 atg ggc acc tac ggg gtg cga gcg gct tgg agg agg ctg ccc cag gcc       816
Met Gly Thr Tyr Gly Val Arg Ala Ala Trp Arg Arg Leu Pro Gln Ala
            260                 265                 270 ttc cgg cca                                                           825
Phe Arg Pro
        275
```

<210> SEQ ID NO 56
<211> LENGTH: 275
<212> TYPE: PRT
<213> ORGANISM: Homo sapiens

<400> SEQUENCE: 56

Met Ser Ser Phe Gly Tyr Arg Thr Leu Thr Val Ala Leu Phe Thr Leu
1               5                   10                  15

Ile Cys Cys Pro Gly Ser Asp Glu Lys Val Phe Glu Val His Val Arg
            20                  25                  30

Pro Lys Lys Leu Ala Val Glu Pro Lys Gly Ser Leu Glu Val Asn Cys
        35                  40                  45

Ser Thr Thr Cys Asn Gln Pro Glu Val Gly Gly Leu Glu Thr Ser Leu
50                  55                  60

Asp Lys Ile Leu Leu Asp Glu Gln Ala Gln Trp Lys His Tyr Leu Val
65                  70                  75                  80

Ser Asn Ile Ser His Asp Thr Val Leu Gln Cys His Phe Thr Cys Ser
                85                  90                  95

Gly Lys Gln Glu Ser Met Asn Ser Asn Val Ser Val Tyr Gln Pro Pro

```
                100             105             110
Arg Gln Val Ile Leu Thr Leu Gln Pro Thr Leu Val Ala Val Gly Lys
            115                 120                 125
Ser Phe Thr Ile Glu Cys Arg Val Pro Thr Val Glu Pro Leu Asp Ser
        130                 135                 140
Leu Thr Leu Phe Leu Phe Arg Gly Asn Glu Thr Leu His Tyr Glu Thr
145                 150                 155                 160
Phe Gly Lys Ala Ala Pro Ala Pro Gln Glu Ala Thr Ala Thr Phe Asn
                165                 170                 175
Ser Thr Ala Asp Arg Glu Asp Gly His Arg Asn Phe Ser Cys Leu Ala
            180                 185                 190
Val Leu Asp Leu Met Ser Arg Gly Gly Asn Ile Phe His Lys His Ser
        195                 200                 205
Ala Pro Lys Met Leu Glu Ile Tyr Glu Pro Val Ser Asp Ser Gln Met
    210                 215                 220
Val Ile Ile Val Thr Val Ser Val Leu Leu Ser Leu Phe Val Thr
225                 230                 235                 240
Ser Val Leu Leu Cys Phe Ile Phe Gly Gln His Leu Arg Gln Gln Arg
                245                 250                 255
Met Gly Thr Tyr Gly Val Arg Ala Ala Trp Arg Arg Leu Pro Gln Ala
            260                 265                 270
Phe Arg Pro
    275

<210> SEQ ID NO 57
<211> LENGTH: 825
<212> TYPE: DNA
<213> ORGANISM: Pan troglodytes

<400> SEQUENCE: 57
atgtcctctt tcagttacag gaccctgact gtggccctct tcgccctgat ctgctgtcca    60
ggatcggatg agaaggtatt cgaggtacac gtgaggccaa agaagctggc ggttgagccc   120
aaagggtccc tcaaggtcaa ctgcagcacc acctgtaacc agcctgaagt gggtggtctg   180
gagacctctc tagataagat tctgctggac gaacaggctc agtggaaaca ttacttggtc   240
tcaaacatct cccatgacac ggtcctccaa tgccacttca cctgctccgg aagcaggag    300 tcaatgaatt ccaacgtcag cgtgtaccag cctccaaggc aggtcatcct gacactgcaa   360
cccactttgg tggctgtggg caagtccttc accattgagt gcagggtgcc caccgtggag   420
cccctggaca gcctcaccct cttcctgttc cgtggcaatg agactctgca ctatgagacc   480
ttcgggaagg cagcccctgc tccgcaggag gccacagtca cattcaacag cacggctgac   540
agagacgatg gccaccgcaa cttctcctgc ctggctgtgc tggacttgat gtctcgcggt   600
ggcaacatct tcacaaaaca ctcagccccg aagatgttgg agatctatga gcctgtgtcg   660
gacagccaga tggtcatcat agtcacggtg gtgtcggtgt tgctgtccct gttcgtgaca   720
tctgtcctgc tctgcttcat cttcggccag cacttgcgcc agcagcggat gggcacctac   780
ggggtgcgag cggcttggag gaggctgccc caggccttcc ggcca                   825

<210> SEQ ID NO 58
<211> LENGTH: 825
<212> TYPE: DNA
<213> ORGANISM: Pan troglodytes
<220> FEATURE:
<221> NAME/KEY: CDS
<222> LOCATION: (1)..(825)
```

<400> SEQUENCE: 58

```
atg tcc tct ttc agt tac agg acc ctg act gtg gcc ctc ttc gcc ctg      48
Met Ser Ser Phe Ser Tyr Arg Thr Leu Thr Val Ala Leu Phe Ala Leu
1               5                   10                  15 atc tgc tgt cca gga tcg gat gag aag gta ttc gag gta cac gtg agg      96
Ile Cys Cys Pro Gly Ser Asp Glu Lys Val Phe Glu Val His Val Arg
            20                  25                  30 cca aag aag ctg gcg gtt gag ccc aaa ggg tcc ctc aag gtc aac tgc     144
Pro Lys Lys Leu Ala Val Glu Pro Lys Gly Ser Leu Lys Val Asn Cys
        35                  40                  45 agc acc acc tgt aac cag cct gaa gtg ggt ggt ctg gag acc tct cta     192
Ser Thr Thr Cys Asn Gln Pro Glu Val Gly Gly Leu Glu Thr Ser Leu
    50                  55                  60 gat aag att ctg ctg gac gaa cag gct cag tgg aaa cat tac ttg gtc     240
Asp Lys Ile Leu Leu Asp Glu Gln Ala Gln Trp Lys His Tyr Leu Val
65                  70                  75                  80 tca aac atc tcc cat gac acg gtc ctc caa tgc cac ttc acc tgc tcc     288
Ser Asn Ile Ser His Asp Thr Val Leu Gln Cys His Phe Thr Cys Ser
                85                  90                  95 ggg aag cag gag tca atg aat tcc aac gtc agc gtg tac cag cct cca     336
Gly Lys Gln Glu Ser Met Asn Ser Asn Val Ser Val Tyr Gln Pro Pro
            100                 105                 110 agg cag gtc atc ctg aca ctg caa ccc act ttg gtg gct gtg ggc aag     384
Arg Gln Val Ile Leu Thr Leu Gln Pro Thr Leu Val Ala Val Gly Lys
        115                 120                 125 tcc ttc acc att gag tgc agg gtg ccc acc gtg gag ccc ctg gac agc     432
Ser Phe Thr Ile Glu Cys Arg Val Pro Thr Val Glu Pro Leu Asp Ser
    130                 135                 140 ctc acc ctc ttc ctg ttc cgt ggc aat gag act ctg cac tat gag acc     480
Leu Thr Leu Phe Leu Phe Arg Gly Asn Glu Thr Leu His Tyr Glu Thr
145                 150                 155                 160 ttc ggg aag gca gcc cct gct ccg cag gag gcc aca gtc aca ttc aac     528
Phe Gly Lys Ala Ala Pro Ala Pro Gln Glu Ala Thr Val Thr Phe Asn
                165                 170                 175 agc acg gct gac aga gac gat ggc cac cgc aac ttc tcc tgc ctg gct     576
Ser Thr Ala Asp Arg Asp Asp Gly His Arg Asn Phe Ser Cys Leu Ala
            180                 185                 190 gtg ctg gac ttg atg tct cgc ggt ggc aac atc ttt cac aaa cac tca     624
Val Leu Asp Leu Met Ser Arg Gly Gly Asn Ile Phe His Lys His Ser
        195                 200                 205 gcc ccg aag atg ttg gag atc tat gag cct gtg tcg gac agc cag atg     672
Ala Pro Lys Met Leu Glu Ile Tyr Glu Pro Val Ser Asp Ser Gln Met
    210                 215                 220 gtc atc ata gtc acg gtg gtg tcg gtg ttg ctg tcc ctg ttc gtg aca     720
Val Ile Ile Val Thr Val Val Ser Val Leu Leu Ser Leu Phe Val Thr
225                 230                 235                 240 tct gtc ctg ctc tgc ttc atc ttc ggc cag cac ttg cgc cag cag cgg     768
Ser Val Leu Leu Cys Phe Ile Phe Gly Gln His Leu Arg Gln Gln Arg
                245                 250                 255 atg ggc acc tac ggg gtg cga gcg gct tgg agg agg ctg ccc cag gcc     816
Met Gly Thr Tyr Gly Val Arg Ala Ala Trp Arg Arg Leu Pro Gln Ala
            260                 265                 270 ttc cgg cca                                                          825
Phe Arg Pro
        275

<210> SEQ ID NO 59
<211> LENGTH: 275
<212> TYPE: PRT
```

-continued

<213> ORGANISM: Pan troglodytes

<400> SEQUENCE: 59

```
Met Ser Ser Phe Ser Tyr Arg Thr Leu Thr Val Ala Leu Phe Ala Leu
1               5                   10                  15

Ile Cys Cys Pro Gly Ser Asp Glu Lys Val Phe Glu Val His Val Arg
            20                  25                  30

Pro Lys Lys Leu Ala Val Glu Pro Lys Gly Ser Leu Lys Val Asn Cys
        35                  40                  45

Ser Thr Thr Cys Asn Gln Pro Glu Val Gly Gly Leu Glu Thr Ser Leu
    50                  55                  60

Asp Lys Ile Leu Leu Asp Glu Gln Ala Gln Trp Lys His Tyr Leu Val
65                  70                  75                  80

Ser Asn Ile Ser His Asp Thr Val Leu Gln Cys His Phe Thr Cys Ser
                85                  90                  95

Gly Lys Gln Glu Ser Met Asn Ser Asn Val Ser Val Tyr Gln Pro Pro
            100                 105                 110

Arg Gln Val Ile Leu Thr Leu Gln Pro Thr Leu Val Ala Val Gly Lys
        115                 120                 125

Ser Phe Thr Ile Glu Cys Arg Val Pro Thr Val Glu Pro Leu Asp Ser
    130                 135                 140

Leu Thr Leu Phe Leu Phe Arg Gly Asn Glu Thr Leu His Tyr Glu Thr
145                 150                 155                 160

Phe Gly Lys Ala Ala Pro Ala Pro Gln Glu Ala Thr Val Thr Phe Asn
                165                 170                 175

Ser Thr Ala Asp Arg Asp Asp Gly His Arg Asn Phe Ser Cys Leu Ala
            180                 185                 190

Val Leu Asp Leu Met Ser Arg Gly Gly Asn Ile Phe His Lys His Ser
        195                 200                 205

Ala Pro Lys Met Leu Glu Ile Tyr Glu Pro Val Ser Asp Ser Gln Met
    210                 215                 220

Val Ile Ile Val Thr Val Val Ser Val Leu Leu Ser Leu Phe Val Thr
225                 230                 235                 240

Ser Val Leu Leu Cys Phe Ile Phe Gly Gln His Leu Arg Gln Gln Arg
                245                 250                 255

Met Gly Thr Tyr Gly Val Arg Ala Ala Trp Arg Arg Leu Pro Gln Ala
            260                 265                 270

Phe Arg Pro
        275
```

<210> SEQ ID NO 60
<211> LENGTH: 825
<212> TYPE: DNA
<213> ORGANISM: Gorilla gorilla

<400> SEQUENCE: 60

```
atgtcctctt tcggttacag gacactgact gtggccctct tcgccctgat ctgctgtcca      60
ggatctgatg agaaggtatt tgaggtacac gtgaggccaa agaagctggc ggttgagccc     120
aaagcgtccc tcgaggtcaa ctgcagcacc acctgtaacc agcctgaagt gggtggtctg     180
gagacctctc tagataagat tctgctggac gaacaggctc agtggaaaca ttacttggtc     240
tcaaacatct cccatgacac ggtcctccaa tgccacttca cctgctccgg gaagcaggag     300
tcaatgaatt ccaacgtcag cgtgtaccag cctccaaggc aggtcatcct gacactgcaa     360
cccactttgg tggctgtggg caagtccttc accattgagt gcagggtgcc caccgtggag     420
```

-continued

| | |
|---|---|
| ccctggaca gcctcaccct cttcctgttc cgtggcaatg agactctgca caatcagacc | 480 |
| ttcgggaagg cagcccctgc tctgcaggag gccacagcca cattcaacag cacggctgac | 540 |
| agagaggatg gccaccgcaa cttctcctgc ctggctgtgc tggacttgat atctcgcggt | 600 |
| ggcaacatct ttcaggaaca ctcagcccca aagatgttgg agatctatga gcctgtgtcg | 660 |
| gacagccaga tggtcatcat agtcacggtg gtgtcggtgt tgctgtccct gttcgtgaca | 720 |
| tctgtcctgc tctgcttcat cttcggccag cacttgcgcc agcagcggat gggcacctat | 780 |
| ggggtgcgag cggcttggag gaggctgccc caggccttcc ggcca | 825 |

<210> SEQ ID NO 61
<211> LENGTH: 825
<212> TYPE: DNA
<213> ORGANISM: Gorilla gorilla
<220> FEATURE:
<221> NAME/KEY: CDS
<222> LOCATION: (1)..(825)

<400> SEQUENCE: 61

| | |
|---|---|
| atg tcc tct ttc ggt tac agg aca ctg act gtg gcc ctc ttc gcc ctg<br>Met Ser Ser Phe Gly Tyr Arg Thr Leu Thr Val Ala Leu Phe Ala Leu<br>1                  5                      10                  15 | 48 |
| atc tgc tgt cca gga tct gat gag aag gta ttt gag gta cac gtg agg<br>Ile Cys Cys Pro Gly Ser Asp Glu Lys Val Phe Glu Val His Val Arg<br>                    20                      25                      30 | 96 |
| cca aag aag ctg gcg gtt gag ccc aaa gcg tcc ctc gag gtc aac tgc<br>Pro Lys Lys Leu Ala Val Glu Pro Lys Ala Ser Leu Glu Val Asn Cys<br>                35                      40                      45 | 144 |
| agc acc acc tgt aac cag cct gaa gtg ggt ggt ctg gag acc tct cta<br>Ser Thr Thr Cys Asn Gln Pro Glu Val Gly Gly Leu Glu Thr Ser Leu<br>50                    55                      60 | 192 |
| gat aag att ctg ctg gac gaa cag gct cag tgg aaa cat tac ttg gtc<br>Asp Lys Ile Leu Leu Asp Glu Gln Ala Gln Trp Lys His Tyr Leu Val<br>65                    70                      75                      80 | 240 |
| tca aac atc tcc cat gac acg gtc ctc caa tgc cac ttc acc tgc tcc<br>Ser Asn Ile Ser His Asp Thr Val Leu Gln Cys His Phe Thr Cys Ser<br>                    85                      90                      95 | 288 |
| ggg aag cag gag tca atg aat tcc aac gtc agc gtg tac cag cct cca<br>Gly Lys Gln Glu Ser Met Asn Ser Asn Val Ser Val Tyr Gln Pro Pro<br>                100                    105                    110 | 336 |
| agg cag gtc atc ctg aca ctg caa ccc act ttg gtg gct gtg ggc aag<br>Arg Gln Val Ile Leu Thr Leu Gln Pro Thr Leu Val Ala Val Gly Lys<br>                    115                    120                    125 | 384 |
| tcc ttc acc att gag tgc agg gtg ccc acc gtg gag ccc ctg gac agc<br>Ser Phe Thr Ile Glu Cys Arg Val Pro Thr Val Glu Pro Leu Asp Ser<br>130                   135                    140 | 432 |
| ctc acc ctc ttc ctg ttc cgt ggc aat gag act ctg cac aat cag acc<br>Leu Thr Leu Phe Leu Phe Arg Gly Asn Glu Thr Leu His Asn Gln Thr<br>145                   150                    155                    160 | 480 |
| ttc ggg aag gca gcc cct gct ctg cag gag gcc aca gcc aca ttc aac<br>Phe Gly Lys Ala Ala Pro Ala Leu Gln Glu Ala Thr Ala Thr Phe Asn<br>                    165                    170                    175 | 528 |
| agc acg gct gac aga gag gat ggc cac cgc aac ttc tcc tgc ctg gct<br>Ser Thr Ala Asp Arg Glu Asp Gly His Arg Asn Phe Ser Cys Leu Ala<br>                    180                    185                    190 | 576 |
| gtg ctg gac ttg ata tct cgc ggt ggc aac atc ttt cag gaa cac tca<br>Val Leu Asp Leu Ile Ser Arg Gly Gly Asn Ile Phe Gln Glu His Ser<br>                    195                    200                    205 | 624 |
| gcc cca aag atg ttg gag atc tat gag cct gtg tcg gac agc cag atg<br>Ala Pro Lys Met Leu Glu Ile Tyr Glu Pro Val Ser Asp Ser Gln Met | 672 |

```
Ala Pro Lys Met Leu Glu Ile Tyr Glu Pro Val Ser Asp Ser Gln Met
    210                 215                 220 gtc atc ata gtc acg gtg gtg tcg gtg ttg ctg tcc ctg ttc gtg aca    720
Val Ile Ile Val Thr Val Val Ser Val Leu Leu Ser Leu Phe Val Thr
225                 230                 235                 240 tct gtc ctg ctc tgc ttc atc ttc ggc cag cac ttg cgc cag cag cgg    768
Ser Val Leu Leu Cys Phe Ile Phe Gly Gln His Leu Arg Gln Gln Arg
                245                 250                 255 atg ggc acc tat ggg gtg cga gcg gct tgg agg agg ctg ccc cag gcc    816
Met Gly Thr Tyr Gly Val Arg Ala Ala Trp Arg Arg Leu Pro Gln Ala
                260                 265                 270 ttc cgg cca                                                        825
Phe Arg Pro
        275

<210> SEQ ID NO 62
<211> LENGTH: 275
<212> TYPE: PRT
<213> ORGANISM: Gorilla gorilla

<400> SEQUENCE: 62

Met Ser Ser Phe Gly Tyr Arg Thr Leu Thr Val Ala Leu Phe Ala Leu
1               5                   10                  15

Ile Cys Cys Pro Gly Ser Asp Glu Lys Val Phe Glu Val His Val Arg
                20                  25                  30

Pro Lys Lys Leu Ala Val Glu Pro Lys Ala Ser Leu Glu Val Asn Cys
            35                  40                  45

Ser Thr Thr Cys Asn Gln Pro Glu Val Gly Gly Leu Glu Thr Ser Leu
        50                  55                  60

Asp Lys Ile Leu Leu Asp Glu Gln Ala Gln Trp Lys His Tyr Leu Val
65                  70                  75                  80

Ser Asn Ile Ser His Asp Thr Val Leu Gln Cys His Phe Thr Cys Ser
                85                  90                  95

Gly Lys Gln Glu Ser Met Asn Ser Asn Val Ser Val Tyr Gln Pro Pro
                100                 105                 110

Arg Gln Val Ile Leu Thr Leu Gln Pro Thr Leu Val Ala Val Gly Lys
            115                 120                 125

Ser Phe Thr Ile Glu Cys Arg Val Pro Thr Val Glu Pro Leu Asp Ser
130                 135                 140

Leu Thr Leu Phe Leu Phe Arg Gly Asn Glu Thr Leu His Asn Gln Thr
145                 150                 155                 160

Phe Gly Lys Ala Ala Pro Ala Leu Gln Glu Ala Thr Ala Thr Phe Asn
                165                 170                 175

Ser Thr Ala Asp Arg Glu Asp Gly His Arg Asn Phe Ser Cys Leu Ala
            180                 185                 190

Val Leu Asp Leu Ile Ser Arg Gly Asn Ile Phe Gln Glu His Ser
            195                 200                 205

Ala Pro Lys Met Leu Glu Ile Tyr Glu Pro Val Ser Asp Ser Gln Met
    210                 215                 220

Val Ile Ile Val Thr Val Val Ser Val Leu Leu Ser Leu Phe Val Thr
225                 230                 235                 240

Ser Val Leu Leu Cys Phe Ile Phe Gly Gln His Leu Arg Gln Gln Arg
                245                 250                 255

Met Gly Thr Tyr Gly Val Arg Ala Ala Trp Arg Arg Leu Pro Gln Ala
                260                 265                 270

Phe Arg Pro
```

<210> SEQ ID NO 63
<211> LENGTH: 762
<212> TYPE: DNA
<213> ORGANISM: Macaca mulatta

<400> SEQUENCE: 63

```
tctgatgaga aggcattcga ggtacatatg aggctagaga agctgatagt aaagcccaag      60
gagtccttcg aggtcaactg cagcaccacc tgtaaccagc ctgaagtggg tggtctggag     120
acttctctaa ataagattct gctgctcgaa cagactcagt ggaagcatta cttgatctca     180
aacatctccc atgacacggt cctctggtgc cacttcacct gctctgggaa gcagaagtca     240
atgagttcca acgtcagcgt gtaccagcct ccaaggcagg tcttcctcac actgcagccc     300
acttgggtgg ccgtgggcaa gtccttcacc atcgagtgca gggtgcccgc cgtggagccc     360
ctggacagcc tcaccctcag cctgctccgt ggcagtgaga ctctgcacag tcagaccttc     420
gggaaggcag cccctgccct gcaggaggcc acagccacat tcagcagcat ggctcacaga     480
gaggacggcc accacaactt ctcctgcctg gctgtgctgg acttgatgtc tcgcggtggc     540
gaagtcttct gcacacactc agccccgaag atgctggaga tctatgagcc cgtgccggac     600
agccagatgg tcatcatcgt cacagtggtg tcagtgttgc tgttcctgtt cgtgacatct     660
gtcctgctct gcttcatctt cagccagcac tggcgccagc ggcggatggg cacctacggg     720
gtgcgagcgg cttggaggag gctaccccag gccttccggc ca                       762
```

<210> SEQ ID NO 64
<211> LENGTH: 762
<212> TYPE: DNA
<213> ORGANISM: Macaca mulatta
<220> FEATURE:
<221> NAME/KEY: CDS
<222> LOCATION: (1)..(762)

<400> SEQUENCE: 64

```
tct gat gag aag gca ttc gag gta cat atg agg cta gag aag ctg ata       48
Ser Asp Glu Lys Ala Phe Glu Val His Met Arg Leu Glu Lys Leu Ile
1               5                   10                  15 gta aag ccc aag gag tcc ttc gag gtc aac tgc agc acc acc tgt aac       96
Val Lys Pro Lys Glu Ser Phe Glu Val Asn Cys Ser Thr Thr Cys Asn
            20                  25                  30 cag cct gaa gtg ggt ggt ctg gag act tct cta aat aag att ctg ctg      144
Gln Pro Glu Val Gly Gly Leu Glu Thr Ser Leu Asn Lys Ile Leu Leu
        35                  40                  45 ctc gaa cag act cag tgg aag cat tac ttg atc tca aac atc tcc cat      192
Leu Glu Gln Thr Gln Trp Lys His Tyr Leu Ile Ser Asn Ile Ser His
    50                  55                  60 gac acg gtc ctc tgg tgc cac ttc acc tgc tct ggg aag cag aag tca      240
Asp Thr Val Leu Trp Cys His Phe Thr Cys Ser Gly Lys Gln Lys Ser
65                  70                  75                  80 atg agt tcc aac gtc agc gtg tac cag cct cca agg cag gtc ttc ctc      288
Met Ser Ser Asn Val Ser Val Tyr Gln Pro Pro Arg Gln Val Phe Leu
                85                  90                  95 aca ctg cag ccc act tgg gtg gcc gtg ggc aag tcc ttc acc atc gag      336
Thr Leu Gln Pro Thr Trp Val Ala Val Gly Lys Ser Phe Thr Ile Glu
            100                 105                 110 tgc agg gtg ccc gcc gtg gag ccc ctg gac agc ctc acc ctc agc ctg      384
Cys Arg Val Pro Ala Val Glu Pro Leu Asp Ser Leu Thr Leu Ser Leu
        115                 120                 125
```

-continued

| | |
|---|---|
| ctc cgt ggc agt gag act ctg cac agt cag acc ttc ggg aag gca gcc<br>Leu Arg Gly Ser Glu Thr Leu His Ser Gln Thr Phe Gly Lys Ala Ala<br>130             135                 140 | 432 |
| cct gcc ctg cag gag gcc aca gcc aca ttc agc agc atg gct cac aga<br>Pro Ala Leu Gln Glu Ala Thr Ala Thr Phe Ser Ser Met Ala His Arg<br>145                 150                 155                 160 | 480 |
| gag gac ggc cac cac aac ttc tcc tgc ctg gct gtg ctg gac ttg atg<br>Glu Asp Gly His His Asn Phe Ser Cys Leu Ala Val Leu Asp Leu Met<br>                165                 170                 175 | 528 |
| tct cgc ggt ggc gaa gtc ttc tgc aca cac tca gcc ccg aag atg ctg<br>Ser Arg Gly Gly Glu Val Phe Cys Thr His Ser Ala Pro Lys Met Leu<br>            180                 185                 190 | 576 |
| gag atc tat gag ccc gtg ccg gac agc cag atg gtc atc atc gtc aca<br>Glu Ile Tyr Glu Pro Val Pro Asp Ser Gln Met Val Ile Ile Val Thr<br>        195                 200                 205 | 624 |
| gtg gtg tca gtg ttg ctg ttc ctg ttc gtg aca tct gtc ctg ctc tgc<br>Val Val Ser Val Leu Leu Phe Leu Phe Val Thr Ser Val Leu Leu Cys<br>    210                 215                 220 | 672 |
| ttc atc ttc agc cag cac tgg cgc cag cgg cgg atg ggc acc tac ggg<br>Phe Ile Phe Ser Gln His Trp Arg Gln Arg Arg Met Gly Thr Tyr Gly<br>225                 230                 235                 240 | 720 |
| gtg cga gcg gct tgg agg agg cta ccc cag gcc ttc cgg cca<br>Val Arg Ala Ala Trp Arg Arg Leu Pro Gln Ala Phe Arg Pro<br>                245                 250 | 762 |

<210> SEQ ID NO 65
<211> LENGTH: 254
<212> TYPE: PRT
<213> ORGANISM: Macaca mulatta

<400> SEQUENCE: 65

Ser Asp Glu Lys Ala Phe Glu Val His Met Arg Leu Glu Lys Leu Ile
1               5                   10                  15

Val Lys Pro Lys Glu Ser Phe Glu Val Asn Cys Ser Thr Thr Cys Asn
            20                  25                  30

Gln Pro Glu Val Gly Gly Leu Glu Thr Ser Leu Asn Lys Ile Leu Leu
        35                  40                  45

Leu Glu Gln Thr Gln Trp Lys His Tyr Leu Ile Ser Asn Ile Ser His
    50                  55                  60

Asp Thr Val Leu Trp Cys His Phe Thr Cys Ser Gly Lys Gln Lys Ser
65                  70                  75                  80

Met Ser Ser Asn Val Ser Val Tyr Gln Pro Pro Arg Gln Val Phe Leu
                85                  90                  95

Thr Leu Gln Pro Thr Trp Val Ala Val Gly Lys Ser Phe Thr Ile Glu
            100                 105                 110

Cys Arg Val Pro Ala Val Glu Pro Leu Asp Ser Leu Thr Leu Ser Leu
        115                 120                 125

Leu Arg Gly Ser Glu Thr Leu His Ser Gln Thr Phe Gly Lys Ala Ala
    130                 135                 140

Pro Ala Leu Gln Glu Ala Thr Ala Thr Phe Ser Ser Met Ala His Arg
145                 150                 155                 160

Glu Asp Gly His His Asn Phe Ser Cys Leu Ala Val Leu Asp Leu Met
                165                 170                 175

Ser Arg Gly Gly Glu Val Phe Cys Thr His Ser Ala Pro Lys Met Leu
            180                 185                 190

Glu Ile Tyr Glu Pro Val Pro Asp Ser Gln Met Val Ile Ile Val Thr
        195                 200                 205

-continued

```
Val Val Ser Val Leu Phe Leu Phe Val Thr Ser Val Leu Leu Cys
    210                 215                 220

Phe Ile Phe Ser Gln His Trp Arg Gln Arg Met Gly Thr Tyr Gly
225                 230                 235                 240

Val Arg Ala Ala Trp Arg Arg Leu Pro Gln Ala Phe Arg Pro
                245                 250
```

<210> SEQ ID NO 66
<211> LENGTH: 1608
<212> TYPE: DNA
<213> ORGANISM: Pan troglodytes

<400> SEQUENCE: 66

| | | | | | |
|---|---|---|---|---|---|
| agggcctgct | ggactctgct | ggtctgctgt | ctgctgaccc | caggtgtcca | ggggcaggag | 60 |
| ttccttttgc | gggtggagcc | ccagaaccct | gtgctctctg | ctggagggtc | cctgtttgtg | 120 |
| aactgcagta | ctgattgtcc | cagctctgag | aaaatcgcct | ggagacgtc | cctatcaaag | 180 |
| gagctggtgg | ccagtggcat | gggctgggca | gccttcaatc | tcagcaacgt | gactggcaac | 240 |
| agtcggatcc | tctgctcagt | gtactgcaat | ggctcccaga | taacaggctc | ctctaacatc | 300 |
| accgtgtaca | ggctcccgga | gcgtgtggag | ctggcacccc | tgcctccttg | gcagcgggtg | 360 |
| ggccagaact | tcaccctgcg | ctgccaagtg | gagggtgggt | cgccccggac | cagcctcacg | 420 |
| gtggtgctgc | ttcgctggga | ggaggagctg | agccggcagc | ccgcagtgga | ggagccagcg | 480 |
| gaggtcactg | ccactgtgct | ggccagcaga | gacgaccacg | gagccccttt | ctcatgccgc | 540 |
| acagaactgg | acatgcagcc | caggggctg | ggactgttcg | tgaacacctc | agccccccgc | 600 |
| cagctccgaa | cctttgtcct | gcccgtgacc | ccccgcgcc | tcgtggcccc | ccggttcttg | 660 |
| gaggtggaaa | cgtcgtggcc | ggtggactgc | accctagacg | gcttttttcc | agcctcagag | 720 |
| gcccaggtct | acctggcgct | gggggaccag | atgctgaatg | cgacagtcat | gaaccacggg | 780 |
| gacacgctaa | cggccacagc | cacagccacg | gcgcgcgcgg | atcaggaggg | tgcccgggag | 840 |
| atcgtctgca | acgtgaccct | aggggggcgag | agacgggagg | cccgggagaa | cttgacggtc | 900 |
| tttagcttcc | taggacccac | tgtgaacctc | agcgagccca | ccgcccctga | gggtccaca | 960 |
| gtgaccgtga | gttgcatggc | tgggctcga | gtccaggtca | cgctggacgg | agttccggcc | 1020 |
| gcggccccgg | ggcagccagc | tcaacttcag | ctaaatgcta | ccgagagtga | cgacagacgc | 1080 |
| agcttcttct | gcagtgccac | tctcgaggtg | gacggcgagt | tcttgcacag | gaacagtagc | 1140 |
| gtccagctgc | gagtcctgta | tggtcccaaa | attgaccgag | ccacatgccc | ccagcacttg | 1200 |
| aaatggaaag | ataaaacgac | acacgtcctg | cagtgccaag | ccagggggcaa | cccgtacccc | 1260 |
| gagctgcggt | gtttgaagga | aggctccagc | cgggaggtgc | cggtggggat | cccgttcttc | 1320 |
| gtcaacgtaa | cacataatgg | tacttatcag | tgccaagcgt | ccagctcacg | aggcaaatac | 1380 |
| accctggtcg | tggtgatgga | cattgaggct | gggagctccc | actttgtccc | cgtcttcgtg | 1440 |
| gcggtgttac | tgaccctggg | cgtggtgact | atcgtactgg | ccttaatgta | cgtcttcagg | 1500 |
| gagcacaaac | ggagcggcag | ttaccatgtt | agggaggaga | gcacctatct | gccccctcacg | 1560 |
| tctatgcagc | cgacacaagc | aatgggggaa | gaaccgtcca | gagctgag | | 1608 |

<210> SEQ ID NO 67
<211> LENGTH: 1608
<212> TYPE: DNA
<213> ORGANISM: Pan troglodytes
<220> FEATURE:
<221> NAME/KEY: CDS
<222> LOCATION: (1)..(1608)

```
<400> SEQUENCE: 67 agg gcc tgc tgg act ctg ctg gtc tgc tgt ctg ctg acc cca ggt gtc        48
Arg Ala Cys Trp Thr Leu Leu Val Cys Cys Leu Leu Thr Pro Gly Val
 1               5                  10                  15 cag ggg cag gag ttc ctt ttg cgg gtg gag ccc cag aac cct gtg ctc        96
Gln Gly Gln Glu Phe Leu Leu Arg Val Glu Pro Gln Asn Pro Val Leu
             20                  25                  30 tct gct gga ggg tcc ctg ttt gtg aac tgc agt act gat tgt ccc agc       144
Ser Ala Gly Gly Ser Leu Phe Val Asn Cys Ser Thr Asp Cys Pro Ser
         35                  40                  45 tct gag aaa atc gcc ttg gag acg tcc cta tca aag gag ctg gtg gcc       192
Ser Glu Lys Ile Ala Leu Glu Thr Ser Leu Ser Lys Glu Leu Val Ala
     50                  55                  60 agt ggc atg ggc tgg gca gcc ttc aat ctc agc aac gtg act ggc aac       240
Ser Gly Met Gly Trp Ala Ala Phe Asn Leu Ser Asn Val Thr Gly Asn
 65                  70                  75                  80 agt cgg atc ctc tgc tca gtg tac tgc aat ggc tcc cag ata aca ggc       288
Ser Arg Ile Leu Cys Ser Val Tyr Cys Asn Gly Ser Gln Ile Thr Gly
                 85                  90                  95 tcc tct aac atc acc gtg tac agg ctc ccg gag cgt gtg gag ctg gca       336
Ser Ser Asn Ile Thr Val Tyr Arg Leu Pro Glu Arg Val Glu Leu Ala
            100                 105                 110 ccc ctg cct cct tgg cag cgg gtg ggc cag aac ttc acc ctg cgc tgc       384
Pro Leu Pro Pro Trp Gln Arg Val Gly Gln Asn Phe Thr Leu Arg Cys
        115                 120                 125 caa gtg gag ggt ggg tcg ccc cgg acc agc ctc acg gtg gtg ctg ctt       432
Gln Val Glu Gly Gly Ser Pro Arg Thr Ser Leu Thr Val Val Leu Leu
    130                 135                 140 cgc tgg gag gag gag ctg agc cgg cag ccc gca gtg gag gag cca gcg       480
Arg Trp Glu Glu Glu Leu Ser Arg Gln Pro Ala Val Glu Glu Pro Ala
145                 150                 155                 160 gag gtc act gcc act gtg ctg gcc agc aga gac gac cac gga gcc cct       528
Glu Val Thr Ala Thr Val Leu Ala Ser Arg Asp Asp His Gly Ala Pro
                165                 170                 175 ttc tca tgc cgc aca gaa ctg gac atg cag ccc cag ggg ctg gga ctg       576
Phe Ser Cys Arg Thr Glu Leu Asp Met Gln Pro Gln Gly Leu Gly Leu
            180                 185                 190 ttc gtg aac acc tca gcc ccc gcc cag ctc cga acc ttt gtc ctg ccc       624
Phe Val Asn Thr Ser Ala Pro Arg Gln Leu Arg Thr Phe Val Leu Pro
        195                 200                 205 gtg acc ccc cgc ctc gtg gcc ccc cgg ttc ttg gag gtg gaa acg           672
Val Thr Pro Pro Arg Leu Val Ala Pro Arg Phe Leu Glu Val Glu Thr
    210                 215                 220 tcg tgg ccg gtg gac tgc acc cta gac ggg ctt ttt cca gcc tca gag       720
Ser Trp Pro Val Asp Cys Thr Leu Asp Gly Leu Phe Pro Ala Ser Glu
225                 230                 235                 240 gcc cag gtc tac ctg gcg ctg ggg gac cag atg ctg aat gca aca gtc       768
Ala Gln Val Tyr Leu Ala Leu Gly Asp Gln Met Leu Asn Ala Thr Val
                245                 250                 255 atg aac cac ggg gac acg cta acg gcc aca gcc aca gcc acg gcg cgc       816
Met Asn His Gly Asp Thr Leu Thr Ala Thr Ala Thr Ala Thr Ala Arg
            260                 265                 270 gcg gat cag gag ggt gcc cgg gag atc gtc tgc aac gtg acc cta ggg       864
Ala Asp Gln Glu Gly Ala Arg Glu Ile Val Cys Asn Val Thr Leu Gly
        275                 280                 285 ggc gag aga cgg gag gcc cgg gag aac ttg acg gtc ttt agc ttc cta       912
Gly Glu Arg Arg Glu Ala Arg Glu Asn Leu Thr Val Phe Ser Phe Leu
    290                 295                 300
```

| | | |
|---|---|---|
| gga ccc act gtg aac ctc agc gag ccc acc gcc cct gag ggg tcc aca<br>Gly Pro Thr Val Asn Leu Ser Glu Pro Thr Ala Pro Glu Gly Ser Thr<br>305                      310                    315                 320 | | 960 |
| gtg acc gtg agt tgc atg gct ggg gct cga gtc cag gtc acg ctg gac<br>Val Thr Val Ser Cys Met Ala Gly Ala Arg Val Gln Val Thr Leu Asp<br>                    325                    330                    335 | | 1008 |
| gga gtt ccg gcc gcg gcc ccg ggg cag cca gct caa ctt cag cta aat<br>Gly Val Pro Ala Ala Ala Pro Gly Gln Pro Ala Gln Leu Gln Leu Asn<br>             340                    345                    350 | | 1056 |
| gct acc gag agt gac gac aga cgc agc ttc ttc tgc agt gcc act ctc<br>Ala Thr Glu Ser Asp Asp Arg Arg Ser Phe Phe Cys Ser Ala Thr Leu<br>           355                    360                    365 | | 1104 |
| gag gtg gac ggc gag ttc ttg cac agg aac agt agc gtc cag ctg cga<br>Glu Val Asp Gly Glu Phe Leu His Arg Asn Ser Ser Val Gln Leu Arg<br>370                      375                    380 | | 1152 |
| gtc ctg tat ggt ccc aaa att gac cga gcc aca tgc ccc cag cac ttg<br>Val Leu Tyr Gly Pro Lys Ile Asp Arg Ala Thr Cys Pro Gln His Leu<br>385                      390                    395               400 | | 1200 |
| aaa tgg aaa gat aaa acg aca cac gtc ctg cag tgc caa gcc agg ggc<br>Lys Trp Lys Asp Lys Thr Thr His Val Leu Gln Cys Gln Ala Arg Gly<br>                    405                    410                    415 | | 1248 |
| aac ccg tac ccc gag ctg cgg tgt ttg aag gaa ggc tcc agc cgg gag<br>Asn Pro Tyr Pro Glu Leu Arg Cys Leu Lys Glu Gly Ser Ser Arg Glu<br>             420                    425                    430 | | 1296 |
| gtg ccg gtg ggg atc ccg ttc ttc gtc aac gta aca cat aat ggt act<br>Val Pro Val Gly Ile Pro Phe Phe Val Asn Val Thr His Asn Gly Thr<br>           435                    440                    445 | | 1344 |
| tat cag tgc caa gcg tcc agc tca cga ggc aaa tac acc ctg gtc gtg<br>Tyr Gln Cys Gln Ala Ser Ser Ser Arg Gly Lys Tyr Thr Leu Val Val<br>450                      455                    460 | | 1392 |
| gtg atg gac att gag gct ggg agc tcc cac ttt gtc ccc gtc ttc gtg<br>Val Met Asp Ile Glu Ala Gly Ser Ser His Phe Val Pro Val Phe Val<br>465                      470                    475               480 | | 1440 |
| gcg gtg tta ctg acc ctg ggc gtg gtg act atc gta ctg gcc tta atg<br>Ala Val Leu Leu Thr Leu Gly Val Val Thr Ile Val Leu Ala Leu Met<br>                    485                    490                    495 | | 1488 |
| tac gtc ttc agg gag cac aaa cgg agc ggc agt tac cat gtt agg gag<br>Tyr Val Phe Arg Glu His Lys Arg Ser Gly Ser Tyr His Val Arg Glu<br>             500                    505                    510 | | 1536 |
| gag agc acc tat ctg ccc ctc acg tct atg cag ccg aca caa gca atg<br>Glu Ser Thr Tyr Leu Pro Leu Thr Ser Met Gln Pro Thr Gln Ala Met<br>           515                    520                    525 | | 1584 |
| ggg gaa gaa ccg tcc aga gct gag<br>Gly Glu Glu Pro Ser Arg Ala Glu<br>    530                    535 | | 1608 |

<210> SEQ ID NO 68
<211> LENGTH: 536
<212> TYPE: PRT
<213> ORGANISM: Pan troglodytes

<400> SEQUENCE: 68

Arg Ala Cys Trp Thr Leu Leu Val Cys Cys Leu Leu Thr Pro Gly Val
1                  5                    10                   15

Gln Gly Gln Glu Phe Leu Leu Arg Val Glu Pro Gln Asn Pro Val Leu
             20                    25                    30

Ser Ala Gly Gly Ser Leu Phe Val Asn Cys Ser Thr Asp Cys Pro Ser
        35                    40                    45

Ser Glu Lys Ile Ala Leu Glu Thr Ser Leu Ser Lys Glu Leu Val Ala
  50                    55                    60

-continued

```
Ser Gly Met Gly Trp Ala Ala Phe Asn Leu Ser Asn Val Thr Gly Asn
 65                  70                  75                  80

Ser Arg Ile Leu Cys Ser Val Tyr Cys Asn Gly Ser Gln Ile Thr Gly
                 85                  90                  95

Ser Ser Asn Ile Thr Val Tyr Arg Leu Pro Glu Arg Val Glu Leu Ala
                100                 105                 110

Pro Leu Pro Pro Trp Gln Arg Val Gly Gln Asn Phe Thr Leu Arg Cys
                115                 120                 125

Gln Val Glu Gly Gly Ser Pro Arg Thr Ser Leu Thr Val Val Leu Leu
            130                 135                 140

Arg Trp Glu Glu Glu Leu Ser Arg Gln Pro Ala Val Glu Glu Pro Ala
145                 150                 155                 160

Glu Val Thr Ala Thr Val Leu Ala Ser Arg Asp Asp His Gly Ala Pro
                165                 170                 175

Phe Ser Cys Arg Thr Glu Leu Asp Met Gln Pro Gln Gly Leu Gly Leu
                180                 185                 190

Phe Val Asn Thr Ser Ala Pro Arg Gln Leu Arg Thr Phe Val Leu Pro
                195                 200                 205

Val Thr Pro Pro Arg Leu Val Ala Pro Arg Phe Leu Glu Val Glu Thr
            210                 215                 220

Ser Trp Pro Val Asp Cys Thr Leu Asp Gly Leu Phe Pro Ala Ser Glu
225                 230                 235                 240

Ala Gln Val Tyr Leu Ala Leu Gly Asp Gln Met Leu Asn Ala Thr Val
                245                 250                 255

Met Asn His Gly Asp Thr Leu Thr Ala Thr Ala Thr Ala Thr Ala Arg
                260                 265                 270

Ala Asp Gln Glu Gly Ala Arg Glu Ile Val Cys Asn Val Thr Leu Gly
            275                 280                 285

Gly Glu Arg Arg Glu Ala Arg Glu Asn Leu Thr Val Phe Ser Phe Leu
290                 295                 300

Gly Pro Thr Val Asn Leu Ser Glu Pro Thr Ala Pro Glu Gly Ser Thr
305                 310                 315                 320

Val Thr Val Ser Cys Met Ala Gly Ala Arg Val Gln Val Thr Leu Asp
                325                 330                 335

Gly Val Pro Ala Ala Pro Gly Gln Pro Ala Gln Leu Gln Leu Asn
                340                 345                 350

Ala Thr Glu Ser Asp Asp Arg Arg Ser Phe Phe Cys Ser Ala Thr Leu
            355                 360                 365

Glu Val Asp Gly Glu Phe Leu His Arg Asn Ser Ser Val Gln Leu Arg
370                 375                 380

Val Leu Tyr Gly Pro Lys Ile Asp Arg Ala Thr Cys Pro Gln His Leu
385                 390                 395                 400

Lys Trp Lys Asp Lys Thr Thr His Val Leu Gln Cys Gln Ala Arg Gly
                405                 410                 415

Asn Pro Tyr Pro Glu Leu Arg Cys Leu Lys Glu Gly Ser Ser Arg Glu
                420                 425                 430

Val Pro Val Gly Ile Pro Phe Phe Val Asn Val Thr His Asn Gly Thr
            435                 440                 445

Tyr Gln Cys Gln Ala Ser Ser Arg Gly Lys Tyr Thr Leu Val Val
                450                 455                 460

Val Met Asp Ile Glu Ala Gly Ser Ser His Phe Val Pro Val Phe Val
465                 470                 475                 480
```

Ala Val Leu Leu Thr Leu Gly Val Val Thr Ile Val Leu Ala Leu Met
            485                 490                 495

Tyr Val Phe Arg Glu His Lys Arg Ser Gly Ser Tyr His Val Arg Glu
        500                 505                 510

Glu Ser Thr Tyr Leu Pro Leu Thr Ser Met Gln Pro Thr Gln Ala Met
        515                 520                 525

Gly Glu Glu Pro Ser Arg Ala Glu
        530                 535

<210> SEQ ID NO 69
<211> LENGTH: 1610
<212> TYPE: DNA
<213> ORGANISM: Pan troglodytes

<400> SEQUENCE: 69

| | | | | | |
|---|---|---|---|---|---|
| ccagggcctg | ctggactctg | ctggtctgct | gtctgctgac | cccaggtgtc | caggggcagg | 60 |
| agttcctttt | gcgggtggag | ccccagaacc | ctgtgctctc | tgctggaggg | tccctgtttg | 120 |
| tgaactgcag | tactgattgt | cccagctctg | agaaaatcgc | cttggagacg | tccctatcaa | 180 |
| aggagctggt | ggccagtggc | atgggctggg | cagccttcaa | tctcagcaac | gtgactggca | 240 |
| acagtcggat | cctctgctca | gtgtactgca | atggctccca | gataacaggc | tcctctaaca | 300 |
| tcaccgtgta | caggctcccg | gagcgtgtgg | agctggcacc | cctgcctcct | ggcagcgggg | 360 |
| tgggccagaa | cttcacccctg | cgctgccaag | tggagggtgg | gtcgccccgg | accagcctca | 420 |
| cggtggtgct | gcttcgctgg | gaggaggagc | tgagccggca | gcccgcagtg | gaggagccag | 480 |
| cggaggtcac | tgccactgtg | ctggccagca | gagacgacca | cggagcccct | ttctcatgcc | 540 |
| gcacagaact | ggacatgcag | ccccaggggc | tgggactgtt | cgtgaacacc | tcagcccccc | 600 |
| gccagctccg | aacctttgtc | ctgcccgtga | ccccccccgcg | cctcgtggcc | cccggttct | 660 |
| tggaggtgga | aacgtcgtgg | ccggtggact | gcaccctaga | cgggcttttt | ccagcctcag | 720 |
| aggcccaggt | ctacctggcg | ctgggggacc | agatgctgaa | tgcgacagtc | atgaaccacg | 780 |
| gggacacgct | aacggccaca | gccacagcca | cggcgcgcgc | ggatcaggag | ggtgcccggg | 840 |
| agatcgtctg | caacgtgacc | ctaggggggcg | agagacggga | ggcccgggag | aacttgacgg | 900 |
| tctttagctt | cctaggaccc | actgtgaacc | tcagcgagcc | caccgcccct | gagggtccca | 960 |
| cagtgaccgt | gagttgcatg | gctggggctc | gagtccaggt | cacgctggac | ggagttccgg | 1020 |
| ccgcggcccc | ggggcagcca | gctcaacttc | agctaaatgc | taccgagagt | gacgacagac | 1080 |
| gcagcttctt | ctgcagtgcc | actctcgagg | tggacggcga | gttcttgcac | aggaacagta | 1140 |
| gcgtccagct | gcgagtcctg | tatggtccca | aaattgaccg | agccacatgc | ccccagcact | 1200 |
| tgaaatggaa | agataaaacg | acacacgtcc | tgcagtgcca | agccagggc | aacccgtacc | 1260 |
| ccgagctgcg | gtgtttgaag | gaaggctcca | gcgggaggt | gccggtgggg | atcccgttct | 1320 |
| tcgtcaacgt | aacacataat | ggtacttatc | agtgccaagc | gtccagctca | cgaggcaaat | 1380 |
| acaccctggt | cgtggtgatg | gacattgagg | ctgggagctc | ccactttgtc | cccgtcttcg | 1440 |
| tggcggtgtt | actgaccctg | ggcgtggtga | ctatcgtact | ggccttaatg | tacgtcttca | 1500 |
| gggagcacaa | acggagcggc | agttaccatg | ttagggagga | gagcacctat | ctgcccctca | 1560 |
| cgtctatgca | gccgacagaa | gcaatggggg | aagaaccgtc | cagagctgag | | 1610 |

<210> SEQ ID NO 70
<211> LENGTH: 1610
<212> TYPE: DNA
<213> ORGANISM: Pan troglodytes -continued

```
<220> FEATURE:
<221> NAME/KEY: CDS
<222> LOCATION: (3)..(1610)

<400> SEQUENCE: 70 cc agg gcc tgc tgg act ctg ctg gtc tgc tgt ctg ctg acc cca ggt       47
   Arg Ala Cys Trp Thr Leu Leu Val Cys Cys Leu Leu Thr Pro Gly
   1               5                  10                  15 gtc cag ggg cag gag ttc ctt ttg cgg gtg gag ccc cag aac cct gtg      95
Val Gln Gly Gln Glu Phe Leu Leu Arg Val Glu Pro Gln Asn Pro Val
             20                  25                  30 ctc tct gct gga ggg tcc ctg ttt gtg aac tgc agt act gat tgt ccc     143
Leu Ser Ala Gly Gly Ser Leu Phe Val Asn Cys Ser Thr Asp Cys Pro
         35                  40                  45 agc tct gag aaa atc gcc ttg gag acg tcc cta tca aag gag ctg gtg     191
Ser Ser Glu Lys Ile Ala Leu Glu Thr Ser Leu Ser Lys Glu Leu Val
 50                  55                  60 gcc agt ggc atg ggc tgg gca gcc ttc aat ctc agc aac gtg act ggc     239
Ala Ser Gly Met Gly Trp Ala Ala Phe Asn Leu Ser Asn Val Thr Gly
 65                  70                  75 aac agt cgg atc ctc tgc tca gtg tac tgc aat ggc tcc cag ata aca     287
Asn Ser Arg Ile Leu Cys Ser Val Tyr Cys Asn Gly Ser Gln Ile Thr
80                  85                  90                  95 ggc tcc tct aac atc acc gtg tac agg ctc ccg gag cgt gtg gag ctg     335
Gly Ser Ser Asn Ile Thr Val Tyr Arg Leu Pro Glu Arg Val Glu Leu
                100                 105                 110 gca ccc ctg cct cct tgg cag cgg gtg ggc cag aac ttc acc ctg cgc     383
Ala Pro Leu Pro Pro Trp Gln Arg Val Gly Gln Asn Phe Thr Leu Arg
            115                 120                 125 tgc caa gtg gag ggt ggg tcg ccc cgg acc agc ctc acg gtg gtg ctg     431
Cys Gln Val Glu Gly Gly Ser Pro Arg Thr Ser Leu Thr Val Val Leu
        130                 135                 140 ctt cgc tgg gag gag gag ctg agc cgg cag ccc gca gtg gag gag cca     479
Leu Arg Trp Glu Glu Glu Leu Ser Arg Gln Pro Ala Val Glu Glu Pro
    145                 150                 155 gcg gag gtc act gcc act gtg ctg gcc agc aga gac gac cac gga gcc     527
Ala Glu Val Thr Ala Thr Val Leu Ala Ser Arg Asp Asp His Gly Ala
160                 165                 170                 175 cct ttc tca tgc cgc aca gaa ctg gac atg cag ccc cag ggg ctg gga     575
Pro Phe Ser Cys Arg Thr Glu Leu Asp Met Gln Pro Gln Gly Leu Gly
                180                 185                 190 ctg ttc gtg aac acc tca gcc ccc cgc cag ctc cga acc ttt gtc ctg     623
Leu Phe Val Asn Thr Ser Ala Pro Arg Gln Leu Arg Thr Phe Val Leu
            195                 200                 205 ccc gtg acc ccc cgc ctc gtg gcc ccc cgg ttc ttg gag gtg gaa         671
Pro Val Thr Pro Pro Arg Leu Val Ala Pro Arg Phe Leu Glu Val Glu
        210                 215                 220 acg tcg tgg ccg gtg gac tgc acc cta gac ggg ctt ttt cca gcc tca     719
Thr Ser Trp Pro Val Asp Cys Thr Leu Asp Gly Leu Phe Pro Ala Ser
    225                 230                 235 gag gcc cag gtc tac ctg gcg ctg ggg gac cag atg ctg aat gcg aca     767
Glu Ala Gln Val Tyr Leu Ala Leu Gly Asp Gln Met Leu Asn Ala Thr
240                 245                 250                 255 gtc atg aac cac ggg gac acg cta acg gcc aca gcc aca gcc acg gcg     815
Val Met Asn His Gly Asp Thr Leu Thr Ala Thr Ala Thr Ala Thr Ala
                260                 265                 270 cgc gcg gat cag gag ggt gcc cgg gag atc gtc tgc aac gtg acc cta     863
Arg Ala Asp Gln Glu Gly Ala Arg Glu Ile Val Cys Asn Val Thr Leu
            275                 280                 285 ggg ggc gag aga cgg gag gcc cgg gag aac ttg acg gtc ttt agc ttc     911
```

-continued

| | | | | | | | | | | | | | |
|---|---|---|---|---|---|---|---|---|---|---|---|---|---|
| Gly | Gly | Glu | Arg | Arg | Glu | Ala | Arg | Glu | Asn | Leu | Thr | Val | Phe Ser Phe |
| | | 290 | | | | 295 | | | | 300 | | | |

```
cta gga ccc act gtg aac ctc agc gag ccc acc gcc cct gag ggg tcc        959
Leu Gly Pro Thr Val Asn Leu Ser Glu Pro Thr Ala Pro Glu Gly Ser
305                 310                 315 aca gtg acc gtg agt tgc atg gct ggg gct cga gtc cag gtc acg ctg       1007
Thr Val Thr Val Ser Cys Met Ala Gly Ala Arg Val Gln Val Thr Leu
320                 325                 330                 335 gac gga gtt ccg gcc gcg gcc ccg ggg cag cca gct caa ctt cag cta       1055
Asp Gly Val Pro Ala Ala Ala Pro Gly Gln Pro Ala Gln Leu Gln Leu
                340                 345                 350 aat gct acc gag agt gac gac aga cgc agc ttc ttc tgc agt gcc act       1103
Asn Ala Thr Glu Ser Asp Asp Arg Arg Ser Phe Phe Cys Ser Ala Thr
            355                 360                 365 ctc gag gtg gac ggc gag ttc ttg cac agg aac agt agc gtc cag ctg       1151
Leu Glu Val Asp Gly Glu Phe Leu His Arg Asn Ser Ser Val Gln Leu
        370                 375                 380 cga gtc ctg tat ggt ccc aaa att gac cga gcc aca tgc ccc cag cac       1199
Arg Val Leu Tyr Gly Pro Lys Ile Asp Arg Ala Thr Cys Pro Gln His
    385                 390                 395 ttg aaa tgg aaa gat aaa acg aca cac gtc ctg cag tgc caa gcc agg       1247
Leu Lys Trp Lys Asp Lys Thr Thr His Val Leu Gln Cys Gln Ala Arg
400                 405                 410                 415 ggc aac ccg tac ccc gag ctg cgg tgt ttg aag gaa ggc tcc agc cgg       1295
Gly Asn Pro Tyr Pro Glu Leu Arg Cys Leu Lys Glu Gly Ser Ser Arg
                420                 425                 430 gag gtg ccg gtg ggg atc ccg ttc ttc gtc aac gta aca cat aat ggt       1343
Glu Val Pro Val Gly Ile Pro Phe Phe Val Asn Val Thr His Asn Gly
            435                 440                 445 act tat cag tgc caa gcg tcc agc tca cga ggc aaa tac acc ctg gtc       1391
Thr Tyr Gln Cys Gln Ala Ser Ser Ser Arg Gly Lys Tyr Thr Leu Val
        450                 455                 460 gtg gtg atg gac att gag gct ggg agc tcc cac ttt gtc ccc gtc ttc       1439
Val Val Met Asp Ile Glu Ala Gly Ser Ser His Phe Val Pro Val Phe
    465                 470                 475 gtg gcg gtg tta ctg acc ctg ggc gtg gtg act atc gta ctg gcc tta       1487
Val Ala Val Leu Leu Thr Leu Gly Val Val Thr Ile Val Leu Ala Leu
480                 485                 490                 495 atg tac gtc ttc agg gag cac aaa cgg agc ggc agt tac cat gtt agg       1535
Met Tyr Val Phe Arg Glu His Lys Arg Ser Gly Ser Tyr His Val Arg
                500                 505                 510 gag gag agc acc tat ctg ccc ctc acg tct atg cag ccg aca gaa gca       1583
Glu Glu Ser Thr Tyr Leu Pro Leu Thr Ser Met Gln Pro Thr Glu Ala
            515                 520                 525 atg ggg gaa gaa ccg tcc aga gct gag                                   1610
Met Gly Glu Glu Pro Ser Arg Ala Glu
        530                 535
```

<210> SEQ ID NO 71
<211> LENGTH: 536
<212> TYPE: PRT
<213> ORGANISM: Pan troglodytes

<400> SEQUENCE: 71

```
Arg Ala Cys Trp Thr Leu Leu Val Cys Cys Leu Leu Thr Pro Gly Val
1               5                   10                  15

Gln Gly Gln Glu Phe Leu Leu Arg Val Glu Pro Gln Asn Pro Val Leu
            20                  25                  30

Ser Ala Gly Gly Ser Leu Phe Val Asn Cys Ser Thr Asp Cys Pro Ser
        35                  40                  45
```

```
Ser Glu Lys Ile Ala Leu Glu Thr Ser Leu Ser Lys Glu Leu Val Ala
    50                  55                  60

Ser Gly Met Gly Trp Ala Phe Asn Leu Ser Asn Val Thr Gly Asn
65              70                  75                  80

Ser Arg Ile Leu Cys Ser Val Tyr Cys Asn Gly Ser Gln Ile Thr Gly
                85                  90                  95

Ser Ser Asn Ile Thr Val Tyr Arg Leu Pro Glu Arg Val Glu Leu Ala
            100                 105                 110

Pro Leu Pro Pro Trp Gln Arg Val Gly Gln Asn Phe Thr Leu Arg Cys
            115                 120                 125

Gln Val Glu Gly Gly Ser Pro Arg Thr Ser Leu Thr Val Val Leu Leu
            130                 135                 140

Arg Trp Glu Glu Glu Leu Ser Arg Gln Pro Ala Val Glu Glu Pro Ala
145                 150                 155                 160

Glu Val Thr Ala Thr Val Leu Ala Ser Arg Asp Asp His Gly Ala Pro
                165                 170                 175

Phe Ser Cys Arg Thr Glu Leu Asp Met Gln Pro Gln Gly Leu Gly Leu
            180                 185                 190

Phe Val Asn Thr Ser Ala Pro Arg Gln Leu Arg Thr Phe Val Leu Pro
        195                 200                 205

Val Thr Pro Pro Arg Leu Val Ala Pro Arg Phe Leu Glu Val Glu Thr
        210                 215                 220

Ser Trp Pro Val Asp Cys Thr Leu Asp Gly Leu Phe Pro Ala Ser Glu
225                 230                 235                 240

Ala Gln Val Tyr Leu Ala Leu Gly Asp Gln Met Leu Asn Ala Thr Val
            245                 250                 255

Met Asn His Gly Asp Thr Leu Thr Ala Thr Ala Thr Ala Arg
            260                 265                 270

Ala Asp Gln Glu Gly Ala Arg Glu Ile Val Cys Asn Val Thr Leu Gly
        275                 280                 285

Gly Glu Arg Arg Glu Ala Arg Glu Asn Leu Thr Val Phe Ser Phe Leu
    290                 295                 300

Gly Pro Thr Val Asn Leu Ser Glu Pro Thr Ala Pro Glu Gly Ser Thr
305                 310                 315                 320

Val Thr Val Ser Cys Met Ala Gly Ala Arg Val Gln Val Thr Leu Asp
                325                 330                 335

Gly Val Pro Ala Ala Ala Pro Gly Gln Pro Ala Gln Leu Gln Leu Asn
            340                 345                 350

Ala Thr Glu Ser Asp Asp Arg Arg Ser Phe Phe Cys Ser Ala Thr Leu
        355                 360                 365

Glu Val Asp Gly Glu Phe Leu His Arg Asn Ser Ser Val Gln Leu Arg
    370                 375                 380

Val Leu Tyr Gly Pro Lys Ile Asp Arg Ala Thr Cys Pro Gln His Leu
385                 390                 395                 400

Lys Trp Lys Asp Lys Thr Thr His Val Leu Gln Cys Gln Ala Arg Gly
                405                 410                 415

Asn Pro Tyr Pro Glu Leu Arg Cys Leu Lys Glu Gly Ser Ser Arg Glu
            420                 425                 430

Val Pro Val Gly Ile Pro Phe Phe Val Asn Val Thr His Asn Gly Thr
        435                 440                 445

Tyr Gln Cys Gln Ala Ser Ser Ser Arg Gly Lys Tyr Thr Leu Val Val
    450                 455                 460
```

-continued

```
Val Met Asp Ile Glu Ala Gly Ser Ser His Phe Val Pro Val Phe Val
465                 470                 475                 480

Ala Val Leu Leu Thr Leu Gly Val Val Thr Ile Val Leu Ala Leu Met
                485                 490                 495

Tyr Val Phe Arg Glu His Lys Arg Ser Gly Ser Tyr His Val Arg Glu
                500                 505                 510

Glu Ser Thr Tyr Leu Pro Leu Thr Ser Met Gln Pro Thr Glu Ala Met
            515                 520                 525

Gly Glu Glu Pro Ser Arg Ala Glu
        530                 535
```

<210> SEQ ID NO 72
<211> LENGTH: 1605
<212> TYPE: DNA
<213> ORGANISM: Gorilla gorilla

<400> SEQUENCE: 72

| | | | | | | |
|---|---|---|---|---|---|---|
| gcctgctgga | ctctgctgct | ctgctgtctg | ctgaccccag | tgtccaggg | gcaggagttc | 60 |
| cttttgcggg | tggagcccca | gaaccctgtg | ctctctgctg | gagggtccct | gtttgtgaac | 120 |
| tgcagtactg | attgtcccag | ctctgagaaa | atcgccttgg | agacgtccct | atcaaaggag | 180 |
| ctggtggcca | gtggcatggg | ctgggcagcc | ttcaatctca | gcaacgtgac | tggcaacagt | 240 |
| cggatcctct | gctcagtgta | ctgcaatggc | tcccagataa | caggctcctc | taacatcacc | 300 |
| gtgtacaggc | tcccggagcg | tgtggagctg | gcacccctgc | ctccttggca | gccggtgggc | 360 |
| cagaacttca | ccctgcgctg | ccaagtggag | ggtgggtcgc | cccggaccag | cctcacggtg | 420 |
| gtgctgcttc | gctgggagga | ggagctgagc | cggcagcccg | cagtggagga | gccagcggag | 480 |
| gtcactgccc | ctgtgctggc | cagcagaggc | gaccatggag | ccccttctc | atgccgcaca | 540 |
| gaactggaca | tgcagcccca | ggggctggga | ctgttcgtga | cacctcagc | ccccgccag | 600 |
| ctccgaacct | ttgtcctgcc | catgaccccc | ccgcgcctcg | tggccccccg | gttcttggag | 660 |
| gtggaaacgt | cgtggccggt | ggactgcacc | ctagacgggc | tttttccggc | ctcagaggcc | 720 |
| caggtctacc | tggcgctggg | ggaccagatg | ctgaatgcga | cagtcatgaa | ccacggggac | 780 |
| acgctaacgg | ccacagccac | agccacggcg | ctcgcggatc | aggagggtgc | ccgggagatc | 840 |
| gtctgcaacg | tgaccctagg | gggcgagaga | cggaggccc | gggagaactt | gacgatcttt | 900 |
| agcttcctag | gacccattgt | gaacctcagc | gagcccaccg | cccctgaggg | gtccacagtg | 960 |
| accgtgagtt | gcatggctgg | ggctcgagtc | caggtcacgc | tggacggagt | tccggccgcg | 1020 |
| gccccggggc | agccagctca | acttcagcta | aatgctaccg | agagtgacga | cggacgcagc | 1080 |
| ttcttctgca | gtgccactct | cgaggtggac | ggcgagttct | gcacaggaa | cagtagcgtc | 1140 |
| cagctgcgag | tcctgtatgg | tcccaaaatt | gaccgagcca | catgcccca | gcacttgaaa | 1200 |
| tggaaagata | aaacgacaca | cgtcctgcag | tgccaagcca | gggcaaccc | gtaccccgag | 1260 |
| ctgcggtgtt | tgaaggaagg | ctccagccgg | gaggtgccgg | tggggatccc | gttcttcgtc | 1320 |
| aacgtaacac | ataatggtac | ttatcagtgc | aagcgtcca | gctcacgagg | caaatacacc | 1380 |
| ctggtcgtgg | tgatggacat | tgaggctggg | agctcccact | tgtccccgt | cttcgtggcg | 1440 |
| gtgttactga | ccctgggcgt | ggtgactatc | gtactggcct | taatgtacgt | cttcagggag | 1500 |
| cacaaacgga | gcggcagtta | ccatgttagg | gaggagagca | cctatctgcc | cctcacgtct | 1560 |
| atgcagccga | cagaagcaat | ggggaagaa | ccgtccagag | ctgag | | 1605 |

<210> SEQ ID NO 73

<211> LENGTH: 1605
<212> TYPE: DNA
<213> ORGANISM: Gorilla gorilla
<220> FEATURE:
<221> NAME/KEY: CDS
<222> LOCATION: (1)..(1605)

<400> SEQUENCE: 73

```
gcc tgc tgg act ctg ctg ctc tgc tgt ctg ctg acc cca ggt gtc cag        48
Ala Cys Trp Thr Leu Leu Leu Cys Cys Leu Leu Thr Pro Gly Val Gln
1               5                   10                  15 ggg cag gag ttc ctt ttg cgg gtg gag ccc cag aac cct gtg ctc tct        96
Gly Gln Glu Phe Leu Leu Arg Val Glu Pro Gln Asn Pro Val Leu Ser
            20                  25                  30 gct gga ggg tcc ctg ttt gtg aac tgc agt act gat tgt ccc agc tct       144
Ala Gly Gly Ser Leu Phe Val Asn Cys Ser Thr Asp Cys Pro Ser Ser
        35                  40                  45 gag aaa atc gcc ttg gag acg tcc cta tca aag gag ctg gtg gcc agt       192
Glu Lys Ile Ala Leu Glu Thr Ser Leu Ser Lys Glu Leu Val Ala Ser
    50                  55                  60 ggc atg ggc tgg gca gcc ttc aat ctc agc aac gtg act ggc aac agt       240
Gly Met Gly Trp Ala Ala Phe Asn Leu Ser Asn Val Thr Gly Asn Ser
65                  70                  75                  80 cgg atc ctc tgc tca gtg tac tgc aat ggc tcc cag ata aca ggc tcc       288
Arg Ile Leu Cys Ser Val Tyr Cys Asn Gly Ser Gln Ile Thr Gly Ser
                85                  90                  95 tct aac atc acc gtg tac agg ctc ccg gag cgt gtg gag ctg gca ccc       336
Ser Asn Ile Thr Val Tyr Arg Leu Pro Glu Arg Val Glu Leu Ala Pro
            100                 105                 110 ctg cct cct tgg cag ccg gtg ggc cag aac ttc acc ctg cgc tgc caa       384
Leu Pro Pro Trp Gln Pro Val Gly Gln Asn Phe Thr Leu Arg Cys Gln
        115                 120                 125 gtg gag ggt ggg tcg ccc cgg acc agc ctc acg gtg gtg ctg ctt cgc       432
Val Glu Gly Gly Ser Pro Arg Thr Ser Leu Thr Val Val Leu Leu Arg
    130                 135                 140 tgg gag gag gag ctg agc cgg cag ccc gca gtg gag gag cca gcg gag       480
Trp Glu Glu Glu Leu Ser Arg Gln Pro Ala Val Glu Glu Pro Ala Glu
145                 150                 155                 160 gtc act gcc cct gtg ctg gcc agc aga ggc gac cat gga gcc cct ttc       528
Val Thr Ala Pro Val Leu Ala Ser Arg Gly Asp His Gly Ala Pro Phe
                165                 170                 175 tca tgc cgc aca gaa ctg gac atg cag ccc cag ggg ctg gga ctg ttc       576
Ser Cys Arg Thr Glu Leu Asp Met Gln Pro Gln Gly Leu Gly Leu Phe
            180                 185                 190 gtg aac acc tca gcc ccc cgc cag ctc cga acc ttt gtc ctg ccc atg       624
Val Asn Thr Ser Ala Pro Arg Gln Leu Arg Thr Phe Val Leu Pro Met
        195                 200                 205 acc ccc ccg cgc ctc gtg gcc ccc cgg ttc ttg gag gtg gaa acg tcg       672
Thr Pro Pro Arg Leu Val Ala Pro Arg Phe Leu Glu Val Glu Thr Ser
    210                 215                 220 tgg ccg gtg gac tgc acc cta gac ggg ctt ttt ccg gcc tca gag gcc       720
Trp Pro Val Asp Cys Thr Leu Asp Gly Leu Phe Pro Ala Ser Glu Ala
225                 230                 235                 240 cag gtc tac ctg gcg ctg ggg gac cag atg ctg aat gcg aca gtc atg       768
Gln Val Tyr Leu Ala Leu Gly Asp Gln Met Leu Asn Ala Thr Val Met
                245                 250                 255 aac cac ggg gac acg cta acg gcc aca gcc aca gcc acg gcg ctc gcg       816
Asn His Gly Asp Thr Leu Thr Ala Thr Ala Thr Ala Thr Ala Leu Ala
            260                 265                 270 gat cag gag ggt gcc cgg gag atc gtc tgc aac gtg acc cta ggg ggc       864
Asp Gln Glu Gly Ala Arg Glu Ile Val Cys Asn Val Thr Leu Gly Gly
```

-continued

```
                275                 280                 285
gag aga cgg gag gcc cgg gag aac ttg acg atc ttt agc ttc cta gga        912
Glu Arg Arg Glu Ala Arg Glu Asn Leu Thr Ile Phe Ser Phe Leu Gly
    290                 295                 300 ccc att gtg aac ctc agc gag ccc acc gcc cct gag ggg tcc aca gtg        960
Pro Ile Val Asn Leu Ser Glu Pro Thr Ala Pro Glu Gly Ser Thr Val
305                 310                 315                 320 acc gtg agt tgc atg gct ggg gct cga gtc cag gtc acg ctg gac gga       1008
Thr Val Ser Cys Met Ala Gly Ala Arg Val Gln Val Thr Leu Asp Gly
                325                 330                 335 gtt ccg gcc gcg gcc ccg ggg cag cca gct caa ctt cag cta aat gct       1056
Val Pro Ala Ala Ala Pro Gly Gln Pro Ala Gln Leu Gln Leu Asn Ala
            340                 345                 350 acc gag agt gac gac gga cgc agc ttc ttc tgc agt gcc act ctc gag       1104
Thr Glu Ser Asp Asp Gly Arg Ser Phe Phe Cys Ser Ala Thr Leu Glu
        355                 360                 365 gtg gac ggc gag ttc ttg cac agg aac agt agc gtc cag ctg cga gtc       1152
Val Asp Gly Glu Phe Leu His Arg Asn Ser Ser Val Gln Leu Arg Val
    370                 375                 380 ctg tat ggt ccc aaa att gac cga gcc aca tgc ccc cag cac ttg aaa       1200
Leu Tyr Gly Pro Lys Ile Asp Arg Ala Thr Cys Pro Gln His Leu Lys
385                 390                 395                 400 tgg aaa gat aaa acg aca cac gtc ctg cag tgc caa gcc agg ggc aac       1248
Trp Lys Asp Lys Thr Thr His Val Leu Gln Cys Gln Ala Arg Gly Asn
                405                 410                 415 ccg tac ccc gag ctg cgg tgt ttg aag gaa ggc tcc agc cgg gag gtg       1296
Pro Tyr Pro Glu Leu Arg Cys Leu Lys Glu Gly Ser Ser Arg Glu Val
            420                 425                 430 ccg gtg ggg atc ccg ttc ttc gtc aac gta aca cat aat ggt act tat       1344
Pro Val Gly Ile Pro Phe Phe Val Asn Val Thr His Asn Gly Thr Tyr
        435                 440                 445 cag tgc caa gcg tcc agc tca cga ggc aaa tac acc ctg gtc gtg gtg       1392
Gln Cys Gln Ala Ser Ser Ser Arg Gly Lys Tyr Thr Leu Val Val Val
    450                 455                 460 atg gac att gag gct ggg agc tcc cac ttt gtc ccc gtc ttc gtg gcg       1440
Met Asp Ile Glu Ala Gly Ser Ser His Phe Val Pro Val Phe Val Ala
465                 470                 475                 480 gtg tta ctg acc ctg ggc gtg gtg act atc gta ctg gcc tta atg tac       1488
Val Leu Leu Thr Leu Gly Val Val Thr Ile Val Leu Ala Leu Met Tyr
                485                 490                 495 gtc ttc agg gag cac aaa cgg agc ggc agt tac cat gtt agg gag gag       1536
Val Phe Arg Glu His Lys Arg Ser Gly Ser Tyr His Val Arg Glu Glu
            500                 505                 510 agc acc tat ctg ccc ctc acg tct atg cag ccg aca gaa gca atg ggg       1584
Ser Thr Tyr Leu Pro Leu Thr Ser Met Gln Pro Thr Glu Ala Met Gly
        515                 520                 525 gaa gaa ccg tcc aga gct gag                                           1605
Glu Glu Pro Ser Arg Ala Glu
    530                 535
```

<210> SEQ ID NO 74
<211> LENGTH: 535
<212> TYPE: PRT
<213> ORGANISM: Gorilla gorilla

<400> SEQUENCE: 74

```
Ala Cys Trp Thr Leu Leu Cys Cys Leu Leu Thr Pro Gly Val Gln
1               5                   10                  15

Gly Gln Glu Phe Leu Leu Arg Val Glu Pro Gln Asn Pro Val Leu Ser
                20                  25                  30
```

-continued

```
Ala Gly Gly Ser Leu Phe Val Asn Cys Ser Thr Asp Cys Pro Ser Ser
         35                  40                  45
Glu Lys Ile Ala Leu Glu Thr Ser Leu Ser Lys Glu Leu Val Ala Ser
     50                  55                  60
Gly Met Gly Trp Ala Ala Phe Asn Leu Ser Asn Val Thr Gly Asn Ser
 65                  70                  75                  80
Arg Ile Leu Cys Ser Val Tyr Cys Asn Gly Ser Gln Ile Thr Gly Ser
             85                  90                  95
Ser Asn Ile Thr Val Tyr Arg Leu Pro Glu Arg Val Glu Leu Ala Pro
            100                 105                 110
Leu Pro Pro Trp Gln Pro Val Gly Gln Asn Phe Thr Leu Arg Cys Gln
        115                 120                 125
Val Glu Gly Gly Ser Pro Arg Thr Ser Leu Thr Val Val Leu Leu Arg
    130                 135                 140
Trp Glu Glu Glu Leu Ser Arg Gln Pro Ala Val Glu Glu Pro Ala Glu
145                 150                 155                 160
Val Thr Ala Pro Val Leu Ala Ser Arg Gly Asp His Gly Ala Pro Phe
                165                 170                 175
Ser Cys Arg Thr Glu Leu Asp Met Gln Pro Gln Gly Leu Gly Leu Phe
            180                 185                 190
Val Asn Thr Ser Ala Pro Arg Gln Leu Arg Thr Phe Val Leu Pro Met
        195                 200                 205
Thr Pro Pro Arg Leu Val Ala Pro Arg Phe Leu Glu Val Glu Thr Ser
    210                 215                 220
Trp Pro Val Asp Cys Thr Leu Asp Gly Leu Phe Pro Ala Ser Glu Ala
225                 230                 235                 240
Gln Val Tyr Leu Ala Leu Gly Asp Gln Met Leu Asn Ala Thr Val Met
                245                 250                 255
Asn His Gly Asp Thr Leu Thr Ala Thr Ala Thr Ala Thr Ala Leu Ala
            260                 265                 270
Asp Gln Glu Gly Ala Arg Glu Ile Val Cys Asn Val Thr Leu Gly Gly
        275                 280                 285
Glu Arg Arg Glu Ala Arg Glu Asn Leu Thr Ile Phe Ser Phe Leu Gly
    290                 295                 300
Pro Ile Val Asn Leu Ser Glu Pro Thr Ala Pro Glu Gly Ser Thr Val
305                 310                 315                 320
Thr Val Ser Cys Met Ala Gly Ala Arg Val Gln Val Thr Leu Asp Gly
                325                 330                 335
Val Pro Ala Ala Ala Pro Gly Gln Pro Ala Gln Leu Gln Leu Asn Ala
            340                 345                 350
Thr Glu Ser Asp Asp Gly Arg Ser Phe Phe Cys Ser Ala Thr Leu Glu
        355                 360                 365
Val Asp Gly Glu Phe Leu His Arg Asn Ser Ser Val Gln Leu Arg Val
    370                 375                 380
Leu Tyr Gly Pro Lys Ile Asp Arg Ala Thr Cys Pro Gln His Leu Lys
385                 390                 395                 400
Trp Lys Asp Lys Thr Thr His Val Leu Gln Cys Gln Ala Arg Gly Asn
                405                 410                 415
Pro Tyr Pro Glu Leu Arg Cys Leu Lys Glu Gly Ser Ser Arg Glu Val
            420                 425                 430
Pro Val Gly Ile Pro Phe Phe Val Asn Val Thr His Asn Gly Thr Tyr
        435                 440                 445
```

```
Gln Cys Gln Ala Ser Ser Arg Gly Lys Tyr Thr Leu Val Val Val
    450             455                 460

Met Asp Ile Glu Ala Gly Ser Ser His Phe Val Pro Val Phe Val Ala
465                 470                 475                 480

Val Leu Leu Thr Leu Gly Val Val Thr Ile Val Leu Ala Leu Met Tyr
                485                 490                 495

Val Phe Arg Glu His Lys Arg Ser Gly Ser Tyr His Val Arg Glu Glu
            500                 505                 510

Ser Thr Tyr Leu Pro Leu Thr Ser Met Gln Pro Thr Glu Ala Met Gly
        515                 520                 525

Glu Glu Pro Ser Arg Ala Glu
        530             535

<210> SEQ ID NO 75
<211> LENGTH: 1614
<212> TYPE: DNA
<213> ORGANISM: Homo sapiens

<400> SEQUENCE: 75
tggcccaggg cctgctggac tctgctggtc tgctgtctgc tgaccccagg tgtccagggg      60
caggagttcc ttttgcgggt ggagcccag aaccctgtgc tctctgctgg agggtccctg     120
tttgtgaact gcagtactga ttgtcccagc tctgagaaaa tcgccttgga cgtccccta     180 tcaaaggagc tggtggccag tggcatgggc tgggcagcct tcaatctcag caacgtgact     240
ggcaacagtc ggatcctctg ctcagtgtac tgcaatggct cccagataac aggctccct     300 aacatcaccg tgtacgggct cccggagcgt gtggagctgg cacccctgcc tccttggcag     360
ccggtgggcc agaacttcac cctgcgctgc caagtggagg gtgggtcgcc ccggaccagc     420
ctcacggtgg tgctgcttcg ctgggaggag gagctgagcc ggcagcccgc agtggaggag     480
ccagcggagg tcactgccac tgtgctggcc agcagagacg accacggagc ccctttctca     540
tgccgcacag aactggacat gcagcccag gggctgggac tgttcgtgaa cacctcagcc     600
ccccgccagc tccgaacctt tgtcctgccc gtgaccccc cgcgcctcgt ggcccccgg      660 ttcttggagg tggaaacgtc gtggccggtg gactgcaccc tagacgggct ttttccagcc     720
tcagaggccc aggtctacct ggcgctgggg gaccagatgc tgaatgcgac agtcatgaac     780
cacggggaca cgctaacggc cacagccaca gccacggcgc gcgcggatca ggagggtgcc     840
cgggagatcg tctgcaacgt gaccctaggg gcgagagac gggaggcccg ggagaacttg     900 acggtctta gcttcctagg acccattgtg aacctcagcg agcccaccgc ccatgagggg     960
tccacagtga ccgtgagttg catggctggg gctcgagtcc aggtcacgct ggacggagtt    1020
ccggccgcgg ccccggggca gccagctcaa cttcagctaa atgctaccga gagtgacgac    1080
ggacgcagct tcttctgcag tgccactctc gaggtggacg gcgagttctt gcacaggaac    1140
agtagcgtcc agctgcgagt cctgtatggt cccaaaattg accgagccac atgccccag    1200 cacttgaaat ggaaagataa aacgagacac gtcctgcagt gccaagccag gggcaacccg    1260
taccccgagc tgcggtgttt gaaggaaggc tccagccggg aggtgccggt ggggatcccg    1320
ttcttcgtca acgtaacaca taatggtact tatcagtgcc aagcgtccag ctcacgaggc    1380
aaatacaccc tggtcgtggt gatggacatt gaggctggga gctcccactt tgtccccgtc    1440
ttcgtggcgg tgttactgac cctgggcgtg gtgactatcg tactggcctt aatgtacgtc    1500
ttcagggagc accaacggag cggcagttac catgttaggg aggagagcac ctatctgccc    1560
ctcacgtcta tgcagccgac agaagcaatg ggggaagaac cgtccagagc tgag          1614
```

<210> SEQ ID NO 76
<211> LENGTH: 1614
<212> TYPE: DNA
<213> ORGANISM: Homo sapiens
<220> FEATURE:
<221> NAME/KEY: CDS
<222> LOCATION: (1)..(1614)

<400> SEQUENCE: 76

| | | | | | | | | | | | | | | | | |
|---|---|---|---|---|---|---|---|---|---|---|---|---|---|---|---|---|
| tgg | ccc | agg | gcc | tgc | tgg | act | ctg | ctg | gtc | tgc | tgt | ctg | ctg | acc | cca | 48 |
| Trp | Pro | Arg | Ala | Cys | Trp | Thr | Leu | Leu | Val | Cys | Cys | Leu | Leu | Thr | Pro | |
| 1 | | | | 5 | | | | | 10 | | | | | 15 | | |
| ggt | gtc | cag | ggg | cag | gag | ttc | ctt | ttg | cgg | gtg | gag | ccc | cag | aac | cct | 96 |
| Gly | Val | Gln | Gly | Gln | Glu | Phe | Leu | Leu | Arg | Val | Glu | Pro | Gln | Asn | Pro | |
| | | | 20 | | | | | 25 | | | | | 30 | | | |
| gtg | ctc | tct | gct | gga | ggg | tcc | ctg | ttt | gtg | aac | tgc | agt | act | gat | tgt | 144 |
| Val | Leu | Ser | Ala | Gly | Gly | Ser | Leu | Phe | Val | Asn | Cys | Ser | Thr | Asp | Cys | |
| | | 35 | | | | | 40 | | | | | 45 | | | | |
| ccc | agc | tct | gag | aaa | atc | gcc | ttg | gag | acg | tcc | cta | tca | aag | gag | ctg | 192 |
| Pro | Ser | Ser | Glu | Lys | Ile | Ala | Leu | Glu | Thr | Ser | Leu | Ser | Lys | Glu | Leu | |
| | 50 | | | | | 55 | | | | | 60 | | | | | |
| gtg | gcc | agt | ggc | atg | ggc | tgg | gca | gcc | ttc | aat | ctc | agc | aac | gtg | act | 240 |
| Val | Ala | Ser | Gly | Met | Gly | Trp | Ala | Ala | Phe | Asn | Leu | Ser | Asn | Val | Thr | |
| 65 | | | | | 70 | | | | | 75 | | | | | 80 | |
| ggc | aac | agt | cgg | atc | ctc | tgc | tca | gtg | tac | tgc | aat | ggc | tcc | cag | ata | 288 |
| Gly | Asn | Ser | Arg | Ile | Leu | Cys | Ser | Val | Tyr | Cys | Asn | Gly | Ser | Gln | Ile | |
| | | | | 85 | | | | | 90 | | | | | 95 | | |
| aca | ggc | tcc | tct | aac | atc | acc | gtg | tac | ggg | ctc | ccg | gag | cgt | gtg | gag | 336 |
| Thr | Gly | Ser | Ser | Asn | Ile | Thr | Val | Tyr | Gly | Leu | Pro | Glu | Arg | Val | Glu | |
| | | | 100 | | | | | 105 | | | | | 110 | | | |
| ctg | gca | ccc | ctg | cct | cct | tgg | cag | ccg | gtg | ggc | cag | aac | ttc | acc | ctg | 384 |
| Leu | Ala | Pro | Leu | Pro | Pro | Trp | Gln | Pro | Val | Gly | Gln | Asn | Phe | Thr | Leu | |
| | | 115 | | | | | 120 | | | | | 125 | | | | |
| cgc | tgc | caa | gtg | gag | ggt | ggg | tcg | ccc | cgg | acc | agc | ctc | acg | gtg | gtg | 432 |
| Arg | Cys | Gln | Val | Glu | Gly | Gly | Ser | Pro | Arg | Thr | Ser | Leu | Thr | Val | Val | |
| | 130 | | | | | 135 | | | | | 140 | | | | | |
| ctg | ctt | cgc | tgg | gag | gag | gag | ctg | agc | cgg | cag | ccc | gca | gtg | gag | gag | 480 |
| Leu | Leu | Arg | Trp | Glu | Glu | Glu | Leu | Ser | Arg | Gln | Pro | Ala | Val | Glu | Glu | |
| 145 | | | | | 150 | | | | | 155 | | | | | 160 | |
| cca | gcg | gag | gtc | act | gcc | act | gtg | ctg | gcc | agc | aga | gac | gac | cac | gga | 528 |
| Pro | Ala | Glu | Val | Thr | Ala | Thr | Val | Leu | Ala | Ser | Arg | Asp | Asp | His | Gly | |
| | | | | 165 | | | | | 170 | | | | | 175 | | |
| gcc | cct | ttc | tca | tgc | cgc | aca | gaa | ctg | gac | atg | cag | ccc | cag | ggg | ctg | 576 |
| Ala | Pro | Phe | Ser | Cys | Arg | Thr | Glu | Leu | Asp | Met | Gln | Pro | Gln | Gly | Leu | |
| | | | 180 | | | | | 185 | | | | | 190 | | | |
| gga | ctg | ttc | gtg | aac | acc | tca | gcc | ccc | cgc | cag | ctc | cga | acc | ttt | gtc | 624 |
| Gly | Leu | Phe | Val | Asn | Thr | Ser | Ala | Pro | Arg | Gln | Leu | Arg | Thr | Phe | Val | |
| | | 195 | | | | | 200 | | | | | 205 | | | | |
| ctg | ccc | gtg | acc | ccc | ccg | cgc | ctc | gtg | gcc | ccc | cgg | ttc | ttg | gag | gtg | 672 |
| Leu | Pro | Val | Thr | Pro | Pro | Arg | Leu | Val | Ala | Pro | Arg | Phe | Leu | Glu | Val | |
| | 210 | | | | | 215 | | | | | 220 | | | | | |
| gaa | acg | tcg | tgg | ccg | gtg | gac | tgc | acc | cta | gac | ggg | ctt | ttt | cca | gcc | 720 |
| Glu | Thr | Ser | Trp | Pro | Val | Asp | Cys | Thr | Leu | Asp | Gly | Leu | Phe | Pro | Ala | |
| 225 | | | | | 230 | | | | | 235 | | | | | 240 | |
| tca | gag | gcc | cag | gtc | tac | ctg | gcg | ctg | ggg | gac | cag | atg | ctg | aat | gcg | 768 |
| Ser | Glu | Ala | Gln | Val | Tyr | Leu | Ala | Leu | Gly | Asp | Gln | Met | Leu | Asn | Ala | |
| | | | | 245 | | | | | 250 | | | | | 255 | | |
| aca | gtc | atg | aac | cac | ggg | gac | acg | cta | acg | gcc | aca | gcc | aca | gcc | acg | 816 |
| Thr | Val | Met | Asn | His | Gly | Asp | Thr | Leu | Thr | Ala | Thr | Ala | Thr | Ala | Thr | |
| | | | 260 | | | | | 265 | | | | | 270 | | | |

```
gcg cgc gcg gat cag gag ggt gcc cgg gag atc gtc tgc aac gtg acc      864
Ala Arg Ala Asp Gln Glu Gly Ala Arg Glu Ile Val Cys Asn Val Thr
            275                 280                 285 cta ggg ggc gag aga cgg gag gcc cgg gag aac ttg acg gtc ttt agc      912
Leu Gly Gly Glu Arg Arg Glu Ala Arg Glu Asn Leu Thr Val Phe Ser
    290                 295                 300 ttc cta gga ccc att gtg aac ctc agc gag ccc acc gcc cat gag ggg      960
Phe Leu Gly Pro Ile Val Asn Leu Ser Glu Pro Thr Ala His Glu Gly
305                 310                 315                 320 tcc aca gtg acc gtg agt tgc atg gct ggg gct cga gtc cag gtc acg     1008
Ser Thr Val Thr Val Ser Cys Met Ala Gly Ala Arg Val Gln Val Thr
            325                 330                 335 ctg gac gga gtt ccg gcc gcg gcc ccg ggg cag cca gct caa ctt cag     1056
Leu Asp Gly Val Pro Ala Ala Ala Pro Gly Gln Pro Ala Gln Leu Gln
    340                 345                 350 cta aat gct acc gag agt gac gac gga cgc agc ttc ttc tgc agt gcc     1104
Leu Asn Ala Thr Glu Ser Asp Asp Gly Arg Ser Phe Phe Cys Ser Ala
355                 360                 365 act ctc gag gtg gac ggc gag ttc ttg cac agg aac agt agc gtc cag     1152
Thr Leu Glu Val Asp Gly Glu Phe Leu His Arg Asn Ser Ser Val Gln
            370                 375                 380 ctg cga gtc ctg tat ggt ccc aaa att gac cga gcc aca tgc ccc cag     1200
Leu Arg Val Leu Tyr Gly Pro Lys Ile Asp Arg Ala Thr Cys Pro Gln
385                 390                 395                 400 cac ttg aaa tgg aaa gat aaa acg aga cac gtc ctg cag tgc caa gcc     1248
His Leu Lys Trp Lys Asp Lys Thr Arg His Val Leu Gln Cys Gln Ala
            405                 410                 415 agg ggc aac ccg tac ccc gag ctg cgg tgt ttg aag gaa ggc tcc agc     1296
Arg Gly Asn Pro Tyr Pro Glu Leu Arg Cys Leu Lys Glu Gly Ser Ser
    420                 425                 430 cgg gag gtg ccg gtg ggg atc ccg ttc ttc gtc aac gta aca cat aat     1344
Arg Glu Val Pro Val Gly Ile Pro Phe Phe Val Asn Val Thr His Asn
            435                 440                 445 ggt act tat cag tgc caa gcg tcc agc tca cga ggc aaa tac acc ctg     1392
Gly Thr Tyr Gln Cys Gln Ala Ser Ser Ser Arg Gly Lys Tyr Thr Leu
450                 455                 460 gtc gtg gtg atg gac att gag gct ggg agc tcc cac ttt gtc ccc gtc     1440
Val Val Val Met Asp Ile Glu Ala Gly Ser Ser His Phe Val Pro Val
465                 470                 475                 480 ttc gtg gcg gtg tta ctg acc ctg ggc gtg gtg act atc gta ctg gcc     1488
Phe Val Ala Val Leu Leu Thr Leu Gly Val Val Thr Ile Val Leu Ala
            485                 490                 495 tta atg tac gtc ttc agg gag cac caa cgg agc ggc agt tac cat gtt     1536
Leu Met Tyr Val Phe Arg Glu His Gln Arg Ser Gly Ser Tyr His Val
    500                 505                 510 agg gag gag agc acc tat ctg ccc ctc acg tct atg cag ccg aca gaa     1584
Arg Glu Glu Ser Thr Tyr Leu Pro Leu Thr Ser Met Gln Pro Thr Glu
            515                 520                 525 gca atg ggg gaa gaa ccg tcc aga gct gag                             1614
Ala Met Gly Glu Glu Pro Ser Arg Ala Glu
530                 535

<210> SEQ ID NO 77
<211> LENGTH: 538
<212> TYPE: PRT
<213> ORGANISM: Homo sapiens

<400> SEQUENCE: 77

Trp Pro Arg Ala Cys Trp Thr Leu Leu Val Cys Cys Leu Leu Thr Pro
1               5                   10                  15
```

```
Gly Val Gln Gly Gln Glu Phe Leu Leu Arg Val Glu Pro Gln Asn Pro
            20                  25                  30

Val Leu Ser Ala Gly Gly Ser Leu Phe Val Asn Cys Ser Thr Asp Cys
            35                  40                  45

Pro Ser Ser Glu Lys Ile Ala Leu Glu Thr Ser Leu Ser Lys Glu Leu
    50                  55                  60

Val Ala Ser Gly Met Gly Trp Ala Ala Phe Asn Leu Ser Asn Val Thr
65                  70                  75                  80

Gly Asn Ser Arg Ile Leu Cys Ser Val Tyr Cys Asn Gly Ser Gln Ile
                85                  90                  95

Thr Gly Ser Ser Asn Ile Thr Val Tyr Gly Leu Pro Glu Arg Val Glu
            100                 105                 110

Leu Ala Pro Leu Pro Pro Trp Gln Pro Val Gly Gln Asn Phe Thr Leu
            115                 120                 125

Arg Cys Gln Val Glu Gly Gly Ser Pro Arg Thr Ser Leu Thr Val Val
            130                 135                 140

Leu Leu Arg Trp Glu Glu Glu Leu Ser Arg Gln Pro Ala Val Glu Glu
145                 150                 155                 160

Pro Ala Glu Val Thr Ala Thr Val Leu Ala Ser Arg Asp Asp His Gly
                165                 170                 175

Ala Pro Phe Ser Cys Arg Thr Glu Leu Asp Met Gln Pro Gln Gly Leu
            180                 185                 190

Gly Leu Phe Val Asn Thr Ser Ala Pro Arg Gln Leu Arg Thr Phe Val
            195                 200                 205

Leu Pro Val Thr Pro Pro Arg Leu Val Ala Pro Arg Phe Leu Glu Val
            210                 215                 220

Glu Thr Ser Trp Pro Val Asp Cys Thr Leu Asp Gly Leu Phe Pro Ala
225                 230                 235                 240

Ser Glu Ala Gln Val Tyr Leu Ala Leu Gly Asp Gln Met Leu Asn Ala
                245                 250                 255

Thr Val Met Asn His Gly Asp Thr Leu Thr Ala Thr Ala Thr Ala Thr
            260                 265                 270

Ala Arg Ala Asp Gln Glu Gly Ala Arg Glu Ile Val Cys Asn Val Thr
            275                 280                 285

Leu Gly Gly Glu Arg Arg Glu Ala Arg Glu Asn Leu Thr Val Phe Ser
            290                 295                 300

Phe Leu Gly Pro Ile Val Asn Leu Ser Glu Pro Thr Ala His Glu Gly
305                 310                 315                 320

Ser Thr Val Thr Val Ser Cys Met Ala Gly Ala Arg Val Gln Val Thr
                325                 330                 335

Leu Asp Gly Val Pro Ala Ala Pro Gly Gln Pro Ala Gln Leu Gln
            340                 345                 350

Leu Asn Ala Thr Glu Ser Asp Asp Gly Arg Ser Phe Phe Cys Ser Ala
            355                 360                 365

Thr Leu Glu Val Asp Gly Glu Phe Leu His Arg Asn Ser Ser Val Gln
            370                 375                 380

Leu Arg Val Leu Tyr Gly Pro Lys Ile Asp Arg Ala Thr Cys Pro Gln
385                 390                 395                 400

His Leu Lys Trp Lys Asp Lys Thr Arg His Val Leu Gln Cys Gln Ala
                405                 410                 415

Arg Gly Asn Pro Tyr Pro Glu Leu Arg Cys Leu Lys Glu Gly Ser Ser
            420                 425                 430
```

-continued

```
Arg Glu Val Pro Val Gly Ile Pro Phe Phe Val Asn Val Thr His Asn
        435                 440                 445
Gly Thr Tyr Gln Cys Gln Ala Ser Ser Arg Gly Lys Tyr Thr Leu
    450                 455                 460
Val Val Val Met Asp Ile Glu Ala Gly Ser Ser His Phe Val Pro Val
465                 470                 475                 480
Phe Val Ala Val Leu Leu Thr Leu Gly Val Thr Ile Val Leu Ala
                485                 490                 495
Leu Met Tyr Val Phe Arg Glu His Gln Arg Ser Gly Ser Tyr His Val
            500                 505                 510
Arg Glu Glu Ser Thr Tyr Leu Pro Leu Thr Ser Met Gln Pro Thr Glu
        515                 520                 525
Ala Met Gly Glu Glu Pro Ser Arg Ala Glu
        530                 535
```

<210> SEQ ID NO 78
<211> LENGTH: 1650
<212> TYPE: DNA
<213> ORGANISM: pongo pygmaeus

<400> SEQUENCE: 78

| | |
|---|---|
| gggcctgctg gactctgctg gtctgctgtc tgctgacccc aggtgcccag gggcaggagt | 60 |
| tcctgctgcg ggtggagccc cagaaccctg tgctccctgc tggagggtcc ctgttggtga | 120 |
| actgcagtac tgattgtccc agctctaaga aaattgcctt ggagacgtcc ctatcaaagg | 180 |
| agctggtgga caatggcatg ggctgggcag ccttctacct cagcaacgtg actggcaaca | 240 |
| gtaggatcct ctgctcagtt tactgcaatg ctcccagat aataggctcc tctaacatca | 300 |
| ccgtgtacag gctcccggag cgcgtggagc tggcacccct gcctctttgg cagccggtgg | 360 |
| gccagaactt caccctgcgc tgccaagtgg agggtgggtc gccccggacc agcctcacgg | 420 |
| tggtgctgct cgctgggag gaggagctga gccggcaacc cgcagtggaa gagccagcgg | 480 |
| aggtcactgc cactgtgctg ccagcagag gccaccacgg agcccatttc tcatgccgca | 540 |
| cagaactgga catgcagccc caggggctgg gactgttcgt gaacacctca gcccccgcc | 600 |
| agctccgaac ctttgtcctg cccgtgaccc cccgcgcct agtggctccc cggttcttgg | 660 |
| aggcggaaac gtcgtggccg gtggactgca ccctagatgg gcttttccg gcctcagagg | 720 |
| cccaggtcta cctggcgctg ggggaccaga tgctgaatgc gacagtcgtg aaccacgggg | 780 |
| acacgctgac ggccacagcc acagccatgg cgcgcgcgga tcaggagggt gcccaggaga | 840 |
| tcgtctgcaa cgtgaccta gggggcgaga gacgggaggc ccgggagaac ttgacggtct | 900 |
| ttagcttcct aggacccatt ctgaatctca gcgagcccag cgcccctgag gggtccacag | 960 |
| tgaccgtgag ttgcatggct ggggctcgag tccaggtcac gctggacgga gttccggccg | 1020 |
| cggcccgggg gcagccagct caacttcagc taaatgctac cgagagtgac gacggacgca | 1080 |
| gcttcttctg cagtgccact ctcgaggtgg acggcgagtt ctttcacagg aacagtagcg | 1140 |
| tccagctgcg tgtcctgtat ggtcccaaaa ttgaccgagc acatgccccc agcacttga | 1200 |
| agtggaaaga taaaacgaga cacgtcctgc agtgccaagc caggggcaac ccgcaccccg | 1260 |
| agctgcgatg tttgaaggaa ggctccagcc gggaggtgcc ggtggggatc ccgttcttcg | 1320 |
| ttaatgtaac acataatggt acttatcagt gccaagcgtc cagctcacga ggcagataca | 1380 |
| ccctggtcgt ggtgatggac attgaggctg ggaactccca ctttgtcctc gtcttcttgg | 1440 |
| cggtgttagt gaccctgggc gtggtgactg tcgtagtggc cttaatgtac gtcttcaggg | 1500 |

-continued

```
agcacaaacg gagcggcagg taccatgtta ggcaggagag cacctctctg cccctcacgt    1560
ctatgcagcc gacagaggca atgggggaag aaccgtccac agctgagtga cgctcggatc    1620
cggggtcaaa gttggcgggg acttggctgt                                     1650
```

<210> SEQ ID NO 79
<211> LENGTH: 1650
<212> TYPE: DNA
<213> ORGANISM: Pongo pygmeaus
<220> FEATURE:
<221> NAME/KEY: CDS
<222> LOCATION: (3)..(1649)

<400> SEQUENCE: 79

```
gg gcc tgc tgg act ctg ctg gtc tgc tgt ctg ctg acc cca ggt gcc          47
   Ala Cys Trp Thr Leu Leu Val Cys Cys Leu Leu Thr Pro Gly Ala
   1               5                  10                  15 cag ggg cag gag ttc ctg ctg cgg gtg gag ccc cag aac cct gtg ctc         95
Gln Gly Gln Glu Phe Leu Leu Arg Val Glu Pro Gln Asn Pro Val Leu
                 20                  25                  30 cct gct gga ggg tcc ctg ttg gtg aac tgc agt act gat tgt ccc agc        143
Pro Ala Gly Gly Ser Leu Leu Val Asn Cys Ser Thr Asp Cys Pro Ser
         35                  40                  45 tct aag aaa att gcc ttg gag acg tcc cta tca aag gag ctg gtg gac        191
Ser Lys Lys Ile Ala Leu Glu Thr Ser Leu Ser Lys Glu Leu Val Asp
     50                  55                  60 aat ggc atg ggc tgg gca gcc ttc tac ctc agc aac gtg act ggc aac        239
Asn Gly Met Gly Trp Ala Ala Phe Tyr Leu Ser Asn Val Thr Gly Asn
 65                  70                  75 agt agg atc ctc tgc tca gtt tac tgc aat ggc tcc cag ata ata ggc        287
Ser Arg Ile Leu Cys Ser Val Tyr Cys Asn Gly Ser Gln Ile Ile Gly
 80                  85                  90                  95 tcc tct aac atc acc gtg tac agg ctc ccg gag cgc gtg gag ctg gca        335
Ser Ser Asn Ile Thr Val Tyr Arg Leu Pro Glu Arg Val Glu Leu Ala
                100                 105                 110 ccc ctg cct ctt tgg cag ccg gtg ggc cag aac ttc acc ctg cgc tgc        383
Pro Leu Pro Leu Trp Gln Pro Val Gly Gln Asn Phe Thr Leu Arg Cys
             115                 120                 125 caa gtg gag ggt ggg tcg ccc cgg acc agc ctc acg gtg gtg ctg ctt        431
Gln Val Glu Gly Gly Ser Pro Arg Thr Ser Leu Thr Val Val Leu Leu
         130                 135                 140 cgc tgg gag gag gag ctg agc cgg caa ccc gca gtg gaa gag cca gcg        479
Arg Trp Glu Glu Glu Leu Ser Arg Gln Pro Ala Val Glu Glu Pro Ala
    145                 150                 155 gag gtc act gcc act gtg ctg gcc agc aga ggc cac cac gga gcc cat        527
Glu Val Thr Ala Thr Val Leu Ala Ser Arg Gly His His Gly Ala His
160                 165                 170                 175 ttc tca tgc cgc aca gaa ctg gac atg cag ccc cag ggg ctg gga ctg        575
Phe Ser Cys Arg Thr Glu Leu Asp Met Gln Pro Gln Gly Leu Gly Leu
                180                 185                 190 ttc gtg aac acc tca gcc ccc cgc cag ctc gaa acc ttt gtc ctg ccc        623
Phe Val Asn Thr Ser Ala Pro Arg Gln Leu Arg Thr Phe Val Leu Pro
            195                 200                 205 gtg acc ccc ccg cgc cta gtg gct ccc cgg ttc ttg gag gcg gaa acg        671
Val Thr Pro Pro Arg Leu Val Ala Pro Arg Phe Leu Glu Ala Glu Thr
        210                 215                 220 tcg tgg ccg gtg gac tgc acc cta gat ggg ctt ttt ccg gcc tca gag        719
Ser Trp Pro Val Asp Cys Thr Leu Asp Gly Leu Phe Pro Ala Ser Glu
    225                 230                 235 gcc cag gtc tac ctg gcg ctg ggg gac cag atg ctg aat gcg aca gtc        767
Ala Gln Val Tyr Leu Ala Leu Gly Asp Gln Met Leu Asn Ala Thr Val
```

-continued

| | |
|---|---|
| gtg aac cac ggg gac acg ctg acg gcc aca gcc aca gcc atg gcg cgc<br>Val Asn His Gly Asp Thr Leu Thr Ala Thr Ala Thr Ala Met Ala Arg<br>260                         265                       270 | 815 |
| gcg gat cag gag ggt gcc cag gag atc gtc tgc aac gtg acc cta ggg<br>Ala Asp Gln Glu Gly Ala Gln Glu Ile Val Cys Asn Val Thr Leu Gly<br>          275                      280                       285 | 863 |
| ggc gag aga cgg gag gcc cgg gag aac ttg acg gtc ttt agc ttc cta<br>Gly Glu Arg Arg Glu Ala Arg Glu Asn Leu Thr Val Phe Ser Phe Leu<br>        290                      295                     300 | 911 |
| gga ccc att ctg aat ctc agc gag ccc agc gcc cct gag ggg tcc aca<br>Gly Pro Ile Leu Asn Leu Ser Glu Pro Ser Ala Pro Glu Gly Ser Thr<br>305                         310                       315 | 959 |
| gtg acc gtg agt tgc atg gct ggg gct cga gtc cag gtc acg ctg gac<br>Val Thr Val Ser Cys Met Ala Gly Ala Arg Val Gln Val Thr Leu Asp<br>320                       325                       330                335 | 1007 |
| gga gtt ccg gcc gcg gcc ccg ggg cag cca gct caa ctt cag cta aat<br>Gly Val Pro Ala Ala Ala Pro Gly Gln Pro Ala Gln Leu Gln Leu Asn<br>               340                       345                     350 | 1055 |
| gct acc gag agt gac gac gga cgc agc ttc ttc tgc agt gcc act ctc<br>Ala Thr Glu Ser Asp Asp Gly Arg Ser Phe Phe Cys Ser Ala Thr Leu<br>                  355                       360                     365 | 1103 |
| gag gtg gac ggc gag ttc ttt cac agg aac agt agc gtc cag ctg cgt<br>Glu Val Asp Gly Glu Phe Phe His Arg Asn Ser Ser Val Gln Leu Arg<br>        370                      375                     380 | 1151 |
| gtc ctg tat ggt ccc aaa att gac cga gcc aca tgc ccc cag cac ttg<br>Val Leu Tyr Gly Pro Lys Ile Asp Arg Ala Thr Cys Pro Gln His Leu<br>385                         390                       395 | 1199 |
| aag tgg aaa gat aaa acg aga cac gtc ctg cag tgc caa gcc agg ggc<br>Lys Trp Lys Asp Lys Thr Arg His Val Leu Gln Cys Gln Ala Arg Gly<br>400                       405                       410                415 | 1247 |
| aac ccg cac ccc gag ctg cga tgt ttg aag gaa ggc tcc agc cgg gag<br>Asn Pro His Pro Glu Leu Arg Cys Leu Lys Glu Gly Ser Ser Arg Glu<br>               420                       425                     430 | 1295 |
| gtg ccg gtg ggg atc ccg ttc ttc gtt aat gta aca cat aat ggt act<br>Val Pro Val Gly Ile Pro Phe Phe Val Asn Val Thr His Asn Gly Thr<br>                  435                       440                     445 | 1343 |
| tat cag tgc caa gcg tcc agc tca cga ggc aga tac acc ctg gtc gtg<br>Tyr Gln Cys Gln Ala Ser Ser Ser Arg Gly Arg Tyr Thr Leu Val Val<br>        450                      455                     460 | 1391 |
| gtg atg gac att gag gct ggg aac tcc cac ttt gtc ctc gtc ttc ttg<br>Val Met Asp Ile Glu Ala Gly Asn Ser His Phe Val Leu Val Phe Leu<br>465                         470                       475 | 1439 |
| gcg gtg tta gtg acc ctg ggc gtg gtg act gtc gta gtg gcc tta atg<br>Ala Val Leu Val Thr Leu Gly Val Val Thr Val Val Val Ala Leu Met<br>480                       485                       490                495 | 1487 |
| tac gtc ttc agg gag cac aaa cgg agc ggc agg tac cat gtt agg cag<br>Tyr Val Phe Arg Glu His Lys Arg Ser Gly Arg Tyr His Val Arg Gln<br>               500                       505                     510 | 1535 |
| gag agc acc tct ctg ccc ctc acg tct atg cag ccg aca gag gca atg<br>Glu Ser Thr Ser Leu Pro Leu Thr Ser Met Gln Pro Thr Glu Ala Met<br>                 515                      520                     525 | 1583 |
| ggg gaa gaa ccg tcc aca gct gag tga cgc tcg gat ccg ggg tca aag<br>Gly Glu Glu Pro Ser Thr Ala Glu     Arg Ser Asp Pro Gly Ser Lys<br>        530                      535                       540 | 1631 |
| ttg gcg ggg act tgg ctg t<br>Leu Ala Gly Thr Trp Leu<br>        545 | 1650 |

-continued

```
<210> SEQ ID NO 80
<211> LENGTH: 535
<212> TYPE: PRT
<213> ORGANISM: Pongo pygmeaus

<400> SEQUENCE: 80

Ala Cys Trp Thr Leu Val Cys Cys Leu Leu Thr Pro Gly Ala Gln
 1               5                  10                  15

Gly Gln Glu Phe Leu Leu Arg Val Glu Pro Gln Asn Pro Val Leu Pro
             20                  25                  30

Ala Gly Gly Ser Leu Leu Val Asn Cys Ser Thr Asp Cys Pro Ser Ser
         35                  40                  45

Lys Lys Ile Ala Leu Glu Thr Ser Leu Ser Lys Glu Leu Val Asp Asn
 50                  55                  60

Gly Met Gly Trp Ala Ala Phe Tyr Leu Ser Asn Val Thr Gly Asn Ser
 65                  70                  75                  80

Arg Ile Leu Cys Ser Val Tyr Cys Asn Gly Ser Gln Ile Ile Gly Ser
                 85                  90                  95

Ser Asn Ile Thr Val Tyr Arg Leu Pro Glu Arg Val Glu Leu Ala Pro
            100                 105                 110

Leu Pro Leu Trp Gln Pro Val Gly Gln Asn Phe Thr Leu Arg Cys Gln
            115                 120                 125

Val Glu Gly Gly Ser Pro Arg Thr Ser Leu Thr Val Val Leu Leu Arg
        130                 135                 140

Trp Glu Glu Glu Leu Ser Arg Gln Pro Ala Val Glu Glu Pro Ala Glu
145                 150                 155                 160

Val Thr Ala Thr Val Leu Ala Ser Arg Gly His His Gly Ala His Phe
                165                 170                 175

Ser Cys Arg Thr Glu Leu Asp Met Gln Pro Gln Gly Leu Gly Leu Phe
            180                 185                 190

Val Asn Thr Ser Ala Pro Arg Gln Leu Arg Thr Phe Val Leu Pro Val
            195                 200                 205

Thr Pro Pro Arg Leu Val Ala Pro Arg Phe Leu Glu Ala Glu Thr Ser
        210                 215                 220

Trp Pro Val Asp Cys Thr Leu Asp Gly Leu Phe Pro Ala Ser Glu Ala
225                 230                 235                 240

Gln Val Tyr Leu Ala Leu Gly Asp Gln Met Leu Asn Ala Thr Val Val
                245                 250                 255

Asn His Gly Asp Thr Leu Thr Ala Thr Ala Thr Ala Met Ala Arg Ala
            260                 265                 270

Asp Gln Glu Gly Ala Gln Glu Ile Val Cys Asn Val Thr Leu Gly Gly
        275                 280                 285

Glu Arg Arg Glu Ala Arg Glu Asn Leu Thr Val Phe Ser Phe Leu Gly
    290                 295                 300

Pro Ile Leu Asn Leu Ser Glu Pro Ser Ala Pro Glu Gly Ser Thr Val
305                 310                 315                 320

Thr Val Ser Cys Met Ala Gly Ala Arg Val Gln Val Thr Leu Asp Gly
                325                 330                 335

Val Pro Ala Ala Ala Pro Gly Gln Pro Ala Gln Leu Gln Leu Asn Ala
            340                 345                 350

Thr Glu Ser Asp Asp Gly Arg Ser Phe Phe Cys Ser Ala Thr Leu Glu
        355                 360                 365

Val Asp Gly Glu Phe Phe His Arg Asn Ser Ser Val Gln Leu Arg Val
    370                 375                 380
```

-continued

```
Leu Tyr Gly Pro Lys Ile Asp Arg Ala Thr Cys Pro Gln His Leu Lys
385                 390                 395                 400

Trp Lys Asp Lys Thr Arg His Val Leu Gln Cys Gln Ala Arg Gly Asn
            405                 410                 415

Pro His Pro Glu Leu Arg Cys Leu Lys Glu Gly Ser Ser Arg Glu Val
        420                 425                 430

Pro Val Gly Ile Pro Phe Phe Val Asn Val Thr His Asn Gly Thr Tyr
    435                 440                 445

Gln Cys Gln Ala Ser Ser Arg Gly Arg Tyr Thr Leu Val Val Val
450                 455                 460

Met Asp Ile Glu Ala Gly Asn Ser His Phe Val Leu Val Phe Leu Ala
465                 470                 475                 480

Val Leu Val Thr Leu Gly Val Val Thr Val Val Ala Leu Met Tyr
                485                 490                 495

Val Phe Arg Glu His Lys Arg Ser Gly Arg Tyr His Val Arg Gln Glu
            500                 505                 510

Ser Thr Ser Leu Pro Leu Thr Ser Met Gln Pro Thr Glu Ala Met Gly
        515                 520                 525

Glu Glu Pro Ser Thr Ala Glu
    530                 535

<210> SEQ ID NO 81
<211> LENGTH: 13
<212> TYPE: PRT
<213> ORGANISM: Pongo pygmeaus

<400> SEQUENCE: 81

Arg Ser Asp Pro Gly Ser Lys Leu Ala Gly Thr Trp Leu
1               5                   10

<210> SEQ ID NO 82
<211> LENGTH: 1554
<212> TYPE: DNA
<213> ORGANISM: Macaca mulatta

<400> SEQUENCE: 82
caggagttcc tgctgcgggt ggagccccag aaccctgtgt tcctgctgg agggtccctg      60
ttggtgaact gcagtactga ttgccccagc tctaagaaaa tcatcttgga gacgtcccta    120
tcaaaggagc tggtggacaa tggcacaggc tgggcagcct tccagctcag caacgtgact    180
ggcaacagtc ggatcctctg ttcagggtac tgcaatggct cccagataac aggcttctct    240
gacatcaccg tgtacagcct cccggagcgc gtggagctgg caccctgcc tccttggcag    300
ccggtgggcc agaacttgat cctgcgctgc caagtggaag tgggtcgcc ccgcaccagc    360
ctcacggtgg tgctgctccg ctgggagaag gagctgaccc ggcagccagc agtgggggag    420
ccagcagagg tcaataccac tgtgctgacc agcagagagg accacggagc ccatttctca    480
tgccgcacag aactggacat gaagcccag gggctggaac tcttccggaa cacctcagcc    540
ccccgccaac tccgaacctt tgccctgccg gtgaccccc cgcgcctcgt ggccccgg     600
ttcttggagg tggaaaagtc gtggccggtg aactgcactc tagatgggct ttttccagcc    660
tcagaggccc aggtctacct ggcactgggg accagatgc tgaatgcgac agtcatgaac    720
cacggggaca tgctaacggc cacagccaca gccacacgcg cgcagatca ggagggtgcg    780
cgggaaatcg tctgcaacgt gatcctaggg ggcgagagac tggagacccg ggagaacttg    840
acggtcttta gcttcctagg acccattctg aacctgagcg agcccagcgc ccccgagggg    900
```

-continued

```
tccacagtga ccgtgagctg catggctggg gctcgagtcc aggtaacgct ggacggagtt      960
ccagccgcgg ccccggggca gccagctcaa cttcagttaa atgctaccga gagtgacgac     1020
ggacgcaact tcttctgcag tgccactctc gaggtggacg gcgagttctt gtgtaggaac     1080
agtagcgtcc agctgcgtgt cctgtatggt cccaaaattg accgagccac atgccccag      1140 cacttgaagt ggaaagacaa aacgagacac gtcctgcagt gccaagccag ggcaacccg      1200 taccccagc tgcggtgttt gaaggaaggc tccaaccggg aggtgccggt ggggatcccg      1260
ttcttcgtca atgtaacaca taatggcact tatcaatgcc aagcgtccag ctcacgaggc     1320
aaatacaccc tggtcgtggt gatggatatt gaggctccga agtcccactt tgtccctgtc     1380
ttcttggcgg tgttagtgac cctgggcgtg gtgactgtcg tagtggcctt aatgtacgtc     1440
ttcaaggagc ataaacggag cggcaggtac catgttaggc aggagagcac ctctctgccc     1500
ctcacgtcta tgcagccgac agaggcaatg ggggaagaac cgtccagagc tgag           1554
```

<210> SEQ ID NO 83
<211> LENGTH: 1554
<212> TYPE: DNA
<213> ORGANISM: Macaca mulatta
<220> FEATURE:
<221> NAME/KEY: CDS
<222> LOCATION: (1)..(1554)

<400> SEQUENCE: 83

```
cag gag ttc ctg ctg cgg gtg gag ccc cag aac cct gtg ttt cct gct        48
Gln Glu Phe Leu Leu Arg Val Glu Pro Gln Asn Pro Val Phe Pro Ala
1               5                   10                  15 gga ggg tcc ctg ttg gtg aac tgc agt act gat tgc ccc agc tct aag        96
Gly Gly Ser Leu Leu Val Asn Cys Ser Thr Asp Cys Pro Ser Ser Lys
            20                  25                  30 aaa atc atc ttg gag acg tcc cta tca aag gag ctg gtg gac aat ggc       144
Lys Ile Ile Leu Glu Thr Ser Leu Ser Lys Glu Leu Val Asp Asn Gly
        35                  40                  45 aca ggc tgg gca gcc ttc cag ctc agc aac gtg act ggc aac agt cgg       192
Thr Gly Trp Ala Ala Phe Gln Leu Ser Asn Val Thr Gly Asn Ser Arg
    50                  55                  60 atc ctc tgt tca ggg tac tgc aat ggc tcc cag ata aca ggc ttc tct       240
Ile Leu Cys Ser Gly Tyr Cys Asn Gly Ser Gln Ile Thr Gly Phe Ser
65                  70                  75                  80 gac atc acc gtg tac agc ctc ccg gag cgc gtg gag ctg gca ccc ctg       288
Asp Ile Thr Val Tyr Ser Leu Pro Glu Arg Val Glu Leu Ala Pro Leu
                85                  90                  95 cct cct tgg cag ccg gtg ggc cag aac ttg atc ctg cgc tgc caa gtg       336
Pro Pro Trp Gln Pro Val Gly Gln Asn Leu Ile Leu Arg Cys Gln Val
            100                 105                 110 gaa ggt ggg tcg ccc cgc acc agc ctc acg gtg gtg ctg ctc cgc tgg       384
Glu Gly Gly Ser Pro Arg Thr Ser Leu Thr Val Val Leu Leu Arg Trp
        115                 120                 125 gag aag gag ctg acc cgg cag cca gca gtg ggg gag cca gca gag gtc       432
Glu Lys Glu Leu Thr Arg Gln Pro Ala Val Gly Glu Pro Ala Glu Val
    130                 135                 140 aat acc act gtg ctg acc agc aga gag gac cac gga gcc cat ttc tca       480
Asn Thr Thr Val Leu Thr Ser Arg Glu Asp His Gly Ala His Phe Ser
145                 150                 155                 160 tgc cgc aca gaa ctg gac atg aag ccc cag ggg ctg gaa ctc ttc cgg       528
Cys Arg Thr Glu Leu Asp Met Lys Pro Gln Gly Leu Glu Leu Phe Arg
                165                 170                 175 aac acc tca gcc ccc cgc caa ctc cga acc ttt gcc ctg ccg gtg acc       576
Asn Thr Ser Ala Pro Arg Gln Leu Arg Thr Phe Ala Leu Pro Val Thr
```

-continued

```
                     180                 185                 190
ccc ccg cgc ctc gtg gcc ccc cgg ttc ttg gag gtg gaa aag tcg tgg    624
Pro Pro Arg Leu Val Ala Pro Arg Phe Leu Glu Val Glu Lys Ser Trp
        195                 200                 205 ccg gtg aac tgc act cta gat ggg ctt ttt cca gcc tca gag gcc cag    672
Pro Val Asn Cys Thr Leu Asp Gly Leu Phe Pro Ala Ser Glu Ala Gln
    210                 215                 220 gtc tac ctg gca ctg ggg gac cag atg ctg aat gcg aca gtc atg aac    720
Val Tyr Leu Ala Leu Gly Asp Gln Met Leu Asn Ala Thr Val Met Asn
225                 230                 235                 240 cac ggg gac atg cta acg gcc aca gcc aca gcc aca gcg cgc gca gat    768
His Gly Asp Met Leu Thr Ala Thr Ala Thr Ala Thr Ala Arg Ala Asp
                245                 250                 255 cag gag ggt gcg cgg gaa atc gtc tgc aac gtg atc cta ggg ggc gag    816
Gln Glu Gly Ala Arg Glu Ile Val Cys Asn Val Ile Leu Gly Gly Glu
            260                 265                 270 aga ctg gag acc cgg gag aac ttg acg gtc ttt agc ttc cta gga ccc    864
Arg Leu Glu Thr Arg Glu Asn Leu Thr Val Phe Ser Phe Leu Gly Pro
        275                 280                 285 att ctg aac ctg agc gag ccc agc gcc ccc gag ggg tcc aca gtg acc    912
Ile Leu Asn Leu Ser Glu Pro Ser Ala Pro Glu Gly Ser Thr Val Thr
    290                 295                 300 gtg agc tgc atg gct ggg gct cga gtc cag gta acg ctg gac gga gtt    960
Val Ser Cys Met Ala Gly Ala Arg Val Gln Val Thr Leu Asp Gly Val
305                 310                 315                 320 cca gcc gcg gcc ccg ggg cag cca gct caa ctt cag tta aat gct acc   1008
Pro Ala Ala Ala Pro Gly Gln Pro Ala Gln Leu Gln Leu Asn Ala Thr
                325                 330                 335 gag agt gac gac gga cgc aac ttc ttc tgc agt gcc act ctc gag gtg   1056
Glu Ser Asp Asp Gly Arg Asn Phe Phe Cys Ser Ala Thr Leu Glu Val
            340                 345                 350 gac ggc gag ttc ttg tgt agg aac agt agc gtc cag ctg cgt gtc ctg   1104
Asp Gly Glu Phe Leu Cys Arg Asn Ser Ser Val Gln Leu Arg Val Leu
        355                 360                 365 tat ggt ccc aaa att gac cga gcc aca tgc ccc cag cac ttg aag tgg   1152
Tyr Gly Pro Lys Ile Asp Arg Ala Thr Cys Pro Gln His Leu Lys Trp
    370                 375                 380 aaa gac aaa acg aga cac gtc ctg cag tgc caa gcc agg ggc aac ccg   1200
Lys Asp Lys Thr Arg His Val Leu Gln Cys Gln Ala Arg Gly Asn Pro
385                 390                 395                 400 tac ccc cag ctg cgg tgt ttg aag gaa ggc tcc aac cgg gag gtg ccg   1248
Tyr Pro Gln Leu Arg Cys Leu Lys Glu Gly Ser Asn Arg Glu Val Pro
                405                 410                 415 gtg ggg atc ccg ttc ttc gtc aat gta aca cat aat ggc act tat caa   1296
Val Gly Ile Pro Phe Phe Val Asn Val Thr His Asn Gly Thr Tyr Gln
            420                 425                 430 tgc caa gcg tcc agc tca cga ggc aaa tac acc ctg gtc gtg gtg atg   1344
Cys Gln Ala Ser Ser Ser Arg Gly Lys Tyr Thr Leu Val Val Val Met
        435                 440                 445 gat att gag gct ccg aag tcc cac ttt gtc cct gtc ttc ttg gcg gtg   1392
Asp Ile Glu Ala Pro Lys Ser His Phe Val Pro Val Phe Leu Ala Val
    450                 455                 460 tta gtg acc ctg ggc gtg gtg act gtc gta gtg gcc tta atg tac gtc   1440
Leu Val Thr Leu Gly Val Val Thr Val Val Val Ala Leu Met Tyr Val
465                 470                 475                 480 ttc aag gag cat aaa cgg agc ggc agg tac cat gtt agg cag gag agc   1488
Phe Lys Glu His Lys Arg Ser Gly Arg Tyr His Val Arg Gln Glu Ser
                485                 490                 495 acc tct ctg ccc ctc acg tct atg cag ccg aca gag gca atg ggg gaa   1536
```

```
Thr Ser Leu Pro Leu Thr Ser Met Gln Pro Thr Glu Ala Met Gly Glu
            500                 505                 510 gaa ccg tcc aga gct gag                                                      1554
Glu Pro Ser Arg Ala Glu
        515
```

<210> SEQ ID NO 84
<211> LENGTH: 518
<212> TYPE: PRT
<213> ORGANISM: Macaca mulatta

<400> SEQUENCE: 84

```
Gln Glu Phe Leu Leu Arg Val Glu Pro Gln Asn Pro Val Phe Pro Ala
1               5                   10                  15

Gly Gly Ser Leu Leu Val Asn Cys Ser Thr Asp Cys Pro Ser Ser Lys
            20                  25                  30

Lys Ile Ile Leu Glu Thr Ser Leu Ser Lys Glu Leu Val Asp Asn Gly
        35                  40                  45

Thr Gly Trp Ala Ala Phe Gln Leu Ser Asn Val Thr Gly Asn Ser Arg
    50                  55                  60

Ile Leu Cys Ser Gly Tyr Cys Asn Gly Ser Gln Ile Thr Gly Phe Ser
65                  70                  75                  80

Asp Ile Thr Val Tyr Ser Leu Pro Glu Arg Val Glu Leu Ala Pro Leu
                85                  90                  95

Pro Pro Trp Gln Pro Val Gly Gln Asn Leu Ile Leu Arg Cys Gln Val
            100                 105                 110

Glu Gly Gly Ser Pro Arg Thr Ser Leu Thr Val Val Leu Leu Arg Trp
        115                 120                 125

Glu Lys Glu Leu Thr Arg Gln Pro Ala Val Gly Glu Pro Ala Glu Val
    130                 135                 140

Asn Thr Thr Val Leu Thr Ser Arg Glu Asp His Gly Ala His Phe Ser
145                 150                 155                 160

Cys Arg Thr Glu Leu Asp Met Lys Pro Gln Gly Leu Glu Leu Phe Arg
                165                 170                 175

Asn Thr Ser Ala Pro Arg Gln Leu Arg Thr Phe Ala Leu Pro Val Thr
            180                 185                 190

Pro Pro Arg Leu Val Ala Pro Arg Phe Leu Glu Val Glu Lys Ser Trp
        195                 200                 205

Pro Val Asn Cys Thr Leu Asp Gly Leu Phe Pro Ala Ser Glu Ala Gln
    210                 215                 220

Val Tyr Leu Ala Leu Gly Asp Gln Met Leu Asn Ala Thr Val Met Asn
225                 230                 235                 240

His Gly Asp Met Leu Thr Ala Thr Ala Thr Ala Arg Ala Asp
                245                 250                 255

Gln Glu Gly Ala Arg Glu Ile Val Cys Asn Val Ile Leu Gly Gly Glu
            260                 265                 270

Arg Leu Glu Thr Arg Glu Asn Leu Thr Val Phe Ser Phe Leu Gly Pro
        275                 280                 285

Ile Leu Asn Leu Ser Glu Pro Ser Ala Pro Glu Gly Ser Thr Val Thr
    290                 295                 300

Val Ser Cys Met Ala Gly Ala Arg Val Gln Val Thr Leu Asp Gly Val
305                 310                 315                 320

Pro Ala Ala Ala Pro Gly Gln Pro Ala Gln Leu Gln Leu Asn Ala Thr
                325                 330                 335

Glu Ser Asp Asp Gly Arg Asn Phe Phe Cys Ser Ala Thr Leu Glu Val
```

-continued

```
        340                 345                 350

Asp Gly Glu Phe Leu Cys Arg Asn Ser Ser Val Gln Leu Arg Val Leu
    355                 360                 365

Tyr Gly Pro Lys Ile Asp Arg Ala Thr Cys Pro Gln His Leu Lys Trp
    370                 375                 380

Lys Asp Lys Thr Arg His Val Leu Gln Cys Gln Ala Arg Gly Asn Pro
385                 390                 395                 400

Tyr Pro Gln Leu Arg Cys Leu Lys Glu Gly Ser Asn Arg Glu Val Pro
                405                 410                 415

Val Gly Ile Pro Phe Phe Val Asn Val Thr His Asn Gly Thr Tyr Gln
            420                 425                 430

Cys Gln Ala Ser Ser Ser Arg Gly Lys Tyr Thr Leu Val Val Val Met
        435                 440                 445

Asp Ile Glu Ala Pro Lys Ser His Phe Val Pro Val Phe Leu Ala Val
    450                 455                 460

Leu Val Thr Leu Gly Val Val Thr Val Val Val Ala Leu Met Tyr Val
465                 470                 475                 480

Phe Lys Glu His Lys Arg Ser Gly Arg Tyr His Val Arg Gln Glu Ser
                485                 490                 495

Thr Ser Leu Pro Leu Thr Ser Met Gln Pro Thr Glu Ala Met Gly Glu
            500                 505                 510

Glu Pro Ser Arg Ala Glu
        515
```

METHODS TO IDENTIFY POLYNUCLEOTIDE AND POLYPEPTIDE SEQUENCES WHICH MAY BE ASSOCIATED WITH PHYSIOLOGICAL AND MEDICAL CONDITIONS

CROSS-REFERENCE TO RELATED APPLICATIONS

This application is a continuation-in-part of U.S. Ser. No. 10/098,600, filed Mar. 14, 2002, now U.S. Pat. No. 6,866, 996 which is a continuation-in-part of U.S. Ser. No. 09/942, 252, filed Aug. 28, 2001, now abandoned which is a continuation-in-part of U.S. Ser. No. 09/591,435, filed Jun. 9, 2000, now U.S. Pat. No. 6,280,953, which is a continuation-in-part of U.S. patent application Ser. No. 09/240,915, filed Jan. 29, 1999, now U.S. Pat. No. 6,228,586, which claims priority from U.S. Provisional Patent Application Ser. No. 60/098,987, filed Sep. 2, 1998, and U.S. Provisional Patent Application Ser. No. 60/073,263, filed Jan. 30, 1998, each of which is incorporated herein in its entirety by reference. This application also claims the benefit of U.S. Provisional Patent Application Ser. No. 60/484,030, filed Jun. 30, 2003, and U.S. Provisional Patent Application Ser. No. 60/545,604, filed Feb. 17, 2004, each of which is incorporated herein in its entirety by reference.

TECHNICAL FIELD

This invention relates to using molecular and evolutionary techniques to identify polynucleotide and polypeptide sequences corresponding to evolved traits that may be relevant to human diseases or conditions, such as unique or enhanced human brain functions, longer human life spans, susceptibility or resistance to development of infectious disease (such as AIDS and hepatitis C), susceptibility or resistance to development of cancer, and aesthetic traits, such as hair growth, susceptibility or resistance to acne, or enhanced muscle mass.

BACKGROUND OF THE INVENTION

Humans differ from their closest evolutionary relatives, the non-human primates enhanced brain function (e.g., cognitive skills, etc.) compared to chimpanzees; (2) humans have a longer life-span than non-human primates; (3) chimpanzees are resistant to certain infectious diseases that afflict humans, such as AIDS and hepatitis C; (4) chimpanzees appear to have a lower incidence of certain cancers than humans; (5) chimpanzees do not suffer from acne or alopecia (baldness); (6) chimpanzees have a higher percentage of muscle to fat; (7) chimpanzees are more resistant to malaria; (8) chimpanzees are less susceptible to Alzheimer's disease; and (9) chimpanzees have a lower incidence of atherosclerosis. At the present time, the genes underlying the above human/chimpanzee differences are not known, nor, more importantly, are the specific changes that have evolved in these genes to provide these capabilities. Understanding the basis of these differences between humans and our close evolutionary relatives will provide useful information for developing effective treatments for related human conditions and diseases.

Classic evolution analysis, which compares mainly the anatomic features of animals, has revealed dramatic morphological and functional differences between human and non-human primates; yet, the human genome is known to share remarkable sequence similarities with that of other primates. For example, it is generally concluded that human DNA sequence is roughly 98.5% identical to chimpanzee DNA and only slightly less similar to gorilla DNA. McConkey and Goodman (1997) TIG 13:350–351. Given the relatively small percentage of genomic difference between humans and closely related primates, it is possible, if not likely, that a relatively small number of changes in genomic sequences may be responsible for traits of interest to human health and well-being, such as those listed above. Thus, it is desirable and feasible to identify the genes underlying these traits and to glean information from the evolved changes in the proteins they encode to develop treatments that could benefit human health and well-being. Identifying and characterizing these sequence changes is crucial in order to benefit from evolutionary solutions that have eliminated or minimized diseases or that provide unique or enhanced functions.

Recent developments in the human genome project have provided a tremendous amount of information on human gene sequences. Furthermore, the structures and activities of many human genes and their protein products have been studied either directly in human cells in culture or in several animal model systems, such as the nematode, fruit fly, zebrafish and mouse. These model systems have great advantages in being relatively simple, easy to manipulate, and having short generation times. Because the basic structures and biological activities of many important genes have been conserved throughout evolution, homologous genes can be identified in many species by comparing macromolecule sequences. Information obtained from lower species on important gene products and functional domains can be used to help identify the homologous genes or functional domains in humans. For example, the homeo domain with DNA binding activity first discovered in the fruit fly *Drosophila* was used to identify human homologues that possess similar activities.

Although comparison of homologous genes or proteins between human and a lower model organism may provide useful information with respect to evolutionarily conserved molecular sequences and functional features, this approach is of limited use in identifying genes whose sequences have changed due to natural selection. With the advent of the development of sophisticated algorithms and analytical methods, much more information can be teased out of DNA sequence changes. The most powerful of these methods, "$K_A/K_S$," involves pairwise comparisons between aligned protein-coding nucleotide sequences of the ratios of $$\frac{\text{nonsynonymous nucleotide substitutions per nonsynonymous site } (K_A)}{\text{synonymous substitutions per synonymous site } (K_S)}$$

(where nonsynonymous means substitutions that change the encoded amino acid and synonymous means substitutions that do not change the encoded amino acid). "$K_A/K_S$-type methods" includes this and similar methods. These methods have been used to demonstrate the occurrence of Darwinian molecular-level positive selection, resulting in amino acid differences in homologous proteins. Several groups have used such methods to document that a particular protein has evolved more rapidly than the neutral substitution rate, and thus supports the existence of Darwinian molecular-level positive selection. For example, McDonald and Kreitman (1991) *Nature* 351:652–654 propose a statistical test of neutral protein evolution hypothesis based on comparison of the number of amino acid replacement substitutions to synonymous substitutions in the coding region of a locus. When they apply this test to the Adh locus of three *Drosophila* species, they conclude that it shows instead that the locus has undergone adaptive fixation of selectively advantageous mutations and that selective fixation of adaptive mutations may be a viable alternative to the clocklike accumulation of neutral mutations as an explanation for most protein evolution. Jenkins et al. (1995) *Proc. R. Soc. Lond. B* 261:203–207 use the McDonald & Kreitman test to investigate whether adaptive evolution is occurring in sequences controlling transcription (non-coding sequences).

Nakashima et al. (1995) *Proc. Natl. Acad. Sci USA* 92:5606–5609, use the method of Miyata and Yasunaga to perform pairwise comparisons of the nucleotide sequences of ten PLA2 isozyme genes from two snake species; this method involves comparing the number of nucleotide substitutions per site for the noncoding regions including introns ($K_N$) and the $K_A$ and $K_S$. They conclude that the protein coding regions have been evolving at much higher rates than the noncoding regions including introns. The highly accelerated substitution rate is responsible for Darwinian molecular-level evolution of PLA2 isozyme genes to produce new physiological activities that must have provided strong selective advantage for catching prey or for defense against predators. Endo et al. (1996) *Mol. Biol. Evol.* 13(5):685–690 use the method of Nei and Gojobori, wherein $d_N$ is the number of nonsynonymous substitutions and $d_S$ is the number of synonymous substitutions, for the purpose of identifying candidate genes on which positive selection operates. Metz and Palumbi (1996) Mol. Biol. Evol. 13(2): 397–406 use the McDonald & Kreitman test as well as a method attributed to Nei and Gojobori, Nei and Jin, and Kumar, Tamura, and Nei; examining the average proportions of $P_n$, the replacement substitutions per replacement site, and $P_s$, the silent substitutions per silent site, to look for evidence of positive selection on binding genes in sea urchins to investigate whether they have rapidly evolved as a prelude to species formation. Goodwin et al. (1996) *Mol. Biol. Evol.* 13(2):346–358 uses similar methods to examine the evolution of a particular murine gene family and conclude that the methods provide important fundamental insights into how selection drives genetic divergence in an experimentally manipulatable system. Edwards et al. (1995) use degenerate primers to pull out MHC loci from various species of birds and an alligator species, which are then analyzed by the Nei and Gojobori methods ($d_N$:$d_S$ ratios) to extend MHC studies to nonmammalian vertebrates. Whitfield et al. (1993) *Nature* 364:713–715 use Ka/Ks analysis to look for directional selection in the regions flanking a conserved region in the SRY gene (that determines male sex). They suggest that the rapid evolution of SRY could be a significant cause of reproductive isolation, leading to new species. Wettsetin et al. (1996) *Mol. Biol. Evol.* 13(1):56–66 apply the MEGA program of Kumar, Tamura and Nei and phylogenetic analysis to investigate the diversification of MHC class I genes in squirrels and related rodents. Parham and Ohta (1996) *Science* 272:67–74 state that a population biology approach, including tests for selection as well as for gene conversion and neutral drift are required to analyze the generation and maintenance of human MHC class I polymorphism. Hughes (1997) *Mol. Biol. Evol.* 14(1):1–5 compared over one hundred orthologous immunoglobulin C2 domains between human and rodent, using the method of Nei and Gojobori ($d_N$:$d_S$ ratios) to test the hypothesis that proteins expressed in cells of the vertebrate immune system evolve unusually rapidly. Swanson and Vacquier (1998) *Science* 281:710–712 use $d_N$:$d_S$ ratios to demonstrate concerted evolution between the lysin and the egg receptor for lysin and discuss the role of such concerted evolution in forming new species (speciation).

Due to the distant evolutionary relationships between humans and these lower animals, the adaptively valuable genetic changes fixed by natural selection are often masked by the accumulation of neutral, random mutations over time. Moreover, some proteins evolve in an episodic manner; such episodic changes could be masked, leading to inconclusive results, if the two genomes compared are not close enough. Messier and Stewart (1997) *Nature* 385:151–154. In fact, studies have shown that the occurrence of adaptive selection in protein evolution is often underestimated when predominantly distantly related sequences are compared. Endo et al. (1996) *Mol. Biol. Evol.* 37:441–456; Messier and Stewart (1997) *Nature* 385:151–154.

Molecular evolution studies within the primate family have been reported, but these mainly focus on the comparison of a small number of known individual genes and gene products to assess the rates and patterns of molecular changes and to explore the evolutionary mechanisms responsible for such changes. See generally, Li, *Molecular Evolution*, Sinauer Associates, Sunderland, Mass., 1997. Furthermore, sequence comparison data are used for phylogenetic analysis, wherein the evolution history of primates is reconstructed based on the relative extent of sequence similarities among examined molecules from different primates. For example, the DNA and amino acid sequence data for the enzyme lysozyme from different primates were used to study protein evolution in primates and the occurrence of adaptive selection within specific lineages. Malcolm et al. (1990) *Nature* 345:86–89; Messier and Stewart (1997). Other genes that have been subjected to molecular evolution studies in primates include hemoglobin, cytochrome c oxidase, and major histocompatibility complex (MHC). Nei and Hughes in: *Evolution at the Molecular Level*, Sinauer Associates, Sunderland, Mass. 222–247, 1991; Lienert and Parham (1996) *Immunol. Cell Biol.* 74:349–356; Wu et al. (1997) *J. Mol. Evol.* 44:477–491. Many non-coding sequences have also been used in molecular phylogenetic analysis of primates. Li, *Molecular Evolution*, Sinauer Associates, Sunderland, Mass. 1997. For example, the genetic distances among primate lineages were estimated from orthologous non-coding nucleotide sequences of beta-type globin loci and their flanking regions, and the evolution tree constructed for the nucleotide sequence orthologues depicted a branching pattern that is largely congruent with the picture from phylogenetic analyses of morphological characters. Goodman et al. (1990) *J. Mol. Evol.* 30:260–266.

Zhou and Li (1996) *Mol. Biol. Evol.* 13(6):780–783 applied $K_A$/$K_S$ analysis to primate genes. It had previously been reported that gene conversion events likely have occurred in introns 2 and 4 between the red and green retinal pigment genes during human evolution. However, intron 4 sequences of the red and green retinal pigment genes from one European human were completely identical, suggesting a recent gene conversion event. In order to determine if the gene conversion event occurred in that individual, or a common ancestor of Europeans, or an even earlier hominid ancestor, the authors sequenced intron 4 of the red and green pigment gene from a male Asian human, a male chimpanzee, and a male baboon, and applied $K_A$/$K_S$ analysis. They observed that the divergence between the two genes is significantly lower in intron 4 than in surrounding exons, suggesting that strong natural selection has acted against sequence homogenization.

Wolinsky et al. (1996) *Science* 272:537–542 used comparisons of nonsynonymous to synonymous base substitutions to demonstrate that the HIV virus itself (i.e., not the host species) is subject to adaptive evolution within individual human patients. Their goal was simply to document the occurrence of positive selection in a short time frame (that of a human patient's course of disease). Niewiesk and Bangham (1996) *J Mol Evol* 42:452–458 used the $D_n/D_s$ approach to ask a related question about the HTLV-1 virus, i.e., what are the selective forces acting on the virus itself. Perhaps because of an insufficient sample size, they were unable to resolve the nature of the selective forces. In both of these cases, although $K_A/K_S$-type methods were used in relation to a human virus, no attempt was made to use these methods for therapeutic goals (as in the present application), but rather to pursue narrow academic goals.

As can be seen from the papers cited above, analytical methods of molecular evolution to identify rapidly evolving genes ($K_A/K_S$-type methods) can be applied to achieve many different purposes, most commonly to confirm the existence of Darwinian molecular-level positive selection, but also to assess the frequency of Darwinian molecular-level positive selection, to understand phylogenetic relationships, to elucidate mechanisms by which new species are formed, or to establish single or multiple origin for specific gene polymorphisms. What is clear is from the papers cited above and others in the literature is that none of the authors applied $K_A/K_S$-type methods to identify evolutionary solutions, specific evolved changes, that could be mimicked or used in the development of treatments to prevent or cure human conditions or diseases or to modulate unique or enhanced human functions. They have not used $K_A/K_S$ type analysis as a systematic tool for identifying human or non-human primate genes that contain evolutionarily significant sequence changes and exploiting such genes and the identified changes in the development of treatments for human conditions or diseases.

The identification of human genes that have evolved to confer unique or enhanced human functions compared to homologous chimpanzee genes could be applied to developing agents to modulate these unique human functions or to restore function when the gene is defective. The identification of the underlying chimpanzee (or other non-human primate) genes and the specific nucleotide changes that have evolved, and the further characterization of the physical and biochemical changes in the proteins encoded by these evolved genes, could provide valuable information, for example, on what determines susceptibility and resistance to infectious viruses, such as HIV and HCV, what determines susceptibility or resistance to the development of certain cancers, what determines susceptibility or resistance to acne, how hair growth can be controlled, and how to control the formation of muscle versus fat. This valuable information could be applied to developing agents that cause the human proteins to behave more like their chimpanzee homologues.

All references cited herein are hereby incorporated by reference in their entirety.

SUMMARY OF THE INVENTION

The present invention provides methods for identifying polynucleotide and polypeptide sequences having evolutionarily significant changes which are associated with physiological conditions, including medical conditions. The invention applies comparative primate genomics to identify specific gene changes which may be associated with, and thus responsible for, physiological conditions, such as medically or commercially relevant evolved traits, and using the information obtained from these evolved genes to develop human treatments. The non-human primate sequences employed in the methods described herein may be any non-human primate, and are preferably a member of the hominoid group, more preferably a chimpanzee, bonobo, gorilla and/or orangutan, and most preferably a chimpanzee.

In one preferred embodiment, a non-human primate polynucleotide or polypeptide has undergone natural selection that resulted in a positive evolutionarily significant change (i.e., the non-human primate polynucleotide or polypeptide has a positive attribute not present in humans). In this embodiment the positively selected polynucleotide or polypeptide may be associated with susceptibility or resistance to certain diseases or with other commercially relevant traits. Examples of this embodiment include, but are not limited to, polynucleotides and polypeptides that are positively selected in non-human primates, preferably chimpanzees, that may be associated with susceptibility or resistance to infectious diseases and cancer. An example of a commercially relevant trait may include aesthetic traits such as hair growth, muscle mass, susceptibility or resistance to acne. An example of the disease resistance/susceptibility embodiment includes polynucleotides and polypeptides associated with the susceptibility or resistance to HIV dissemination, propagation and/or development of AIDS. The present invention can thus be useful in gaining insight into the molecular mechanisms that underlie resistance to HIV dissemination, propagation and/or development of AIDS, providing information that can also be useful in discovering and/or designing agents such as drugs that prevent and/or delay development of AIDS. Specific genes that have been positively selected in chimpanzees that may relate to AIDS or other infectious diseases are ICAM-1, ICAM-2, ICAM-3, MIP-1-α, CD59 and DC-SIGN. 17-β-hydroxysteroid dehydrogenase Type IV is a specific gene has been positively selected in chimpanzees that may relate to cancer. Additionally, the p44 gene is a gene that has been positively selected in chimpanzees and is believed to contribute to their HCV resistance.

In another preferred embodiment, a human polynucleotide or polypeptide has undergone natural selection that resulted in a positive evolutionarily significant change (i.e., the human polynucleotide or polypeptide has a positive attribute not present in non-human primates). One example of this embodiment is that the polynucleotide or polypeptide may be associated with unique or enhanced functional capabilities of the human brain compared to non-human primates. Another is the longer life-span of humans compared to non-human primates. A third is a commercially important aesthetic trait (e.g., normal or enhanced breast development). The present invention can thus be useful in gaining insight into the molecular mechanisms that underlie unique or enhanced human functions or physiological traits, providing information which can also be useful in designing agents such as drugs that modulate such unique or enhanced human functions or traits, and in designing treatment of diseases or conditions related to humans. As an example, the present invention can thus be useful in gaining insight into the molecular mechanisms that underlie human cognitive function, providing information which can also be useful in designing agents such as drugs that enhance human brain function, and in designing treatment of diseases related to the human brain. A specific example of a human gene that has positive evolutionarily significant changes when compared to non-human primates is a tyrosine kinase gene, the KIAA0641 or NM_004920 gene.

Accordingly, in one aspect, the invention provides methods for identifying a polynucleotide sequence encoding a polypeptide, wherein said polypeptide may be associated with a physiological condition (such as a medically or commercially relevant positive evolutionarily significant change). The positive evolutionarily significant change can be found in humans or in non-human primates. In a preferred embodiment the invention provides a method for identifying a human AATYK polynucleotide sequence encoding a human AATYK polypeptide associated with an evolutionarily significant change. In another preferred embodiment, the invention provides a method for identifying a p44 polynucleotide and polypeptide that are associated with enhanced HCV resistance in chimpanzees relative to humans.

For any embodiment of this invention, the physiological condition may be any physiological condition, including those listed herein, such as, for example, disease (including susceptibility or resistance to disease) such as cancer, infectious disease (including viral diseases such as AIDS or HCV-associated chronic hepatitis); life span; brain function, including cognitive function or developmental sculpting; and aesthetic or cosmetic qualities, such as enhanced breast development.

In one aspect of the invention, methods are provided for identifying a polynucleotide sequence encoding a human polypeptide, wherein said polypeptide may be associated with a physiological condition that is present in human(s), comprising the steps of: a) comparing human protein-coding polynucleotide sequences to protein-coding polynucleotide sequences of a non-human primate, wherein the non-human primate does not have the physiological condition (or has it to a lesser degree); and b) selecting a human polynucleotide sequence that contains a nucleotide change as compared to corresponding sequence of the non-human primate, wherein said change is evolutionarily significant. In some embodiments, the human protein coding sequence (and/or the polypeptide encoded therein) may be associated with development and/or maintenance of a physiological condition or trait or a biological function. In some embodiments, the physiological condition or biological function may be life span, brain or cognitive function, or breast development (including adipose, gland and duct development). Methods used to assess the nucleotide change, and the nature(s) of the nucleotide change, are described herein, and apply to any and all embodiments. In a preferred embodiment, the method is a method for identifying a human AATYK polynucleotide sequence encoding a human AATYK polypeptide.

In other embodiments, methods are provided that comprise the steps of: (a) comparing human protein-coding nucleotide sequences to protein-coding nucleotide sequences of a non-human primate, preferably a chimpanzee, that is resistant to a particular medically relevant disease state, wherein the human protein coding sequence is or is believed to be associated with development of the disease; and (b) selecting a non-human polynucleotide sequence that contains at least one nucleotide change as compared to the corresponding sequence of the human, wherein the change is evolutionarily significant. The sequences identified by these methods may be further characterized and/or analyzed to confirm that they are associated with the development of the disease state or condition. The most preferred disease states that are applicable to these methods are cancer and infectious diseases, including AIDS, hepatitis C and leprosy. In one embodiment, chimpanzee polynucleotide sequences are compared to human polynucleotide sequences to identify a p44 sequence that is evolutionarily significant. The p44 protein is (or is believed to be) associated with the enhanced HCV resistance of chimpanzees relative to humans.

In another aspect, methods are provided for identifying an evolutionarily significant change in a human brain polypeptide-coding polynucleotide sequence, comprising the steps of a) comparing human brain polypeptide-coding polynucleotide sequences to corresponding sequences of a non-human primate; and b) selecting a human polynucleotide sequence that contains a nucleotide change as compared to corresponding sequence of the non-human primate, wherein said change is evolutionarily significant. In some embodiments, the human brain polypeptide coding nucleotide sequences correspond to human brain cDNAs. In preferred embodiments, the human brain polypeptide-coding polynucleotide sequence is an AATYK sequence.

Another aspect of the invention includes methods for identifying a positively selected human evolutionarily significant change. These methods comprise the steps of: (a) comparing human polypeptide-coding nucleotide sequences to polypeptide-coding nucleotide sequences of a non-human primate; and (b) selecting a human polynucleotide sequence that contains at least one (i.e., one or more) nucleotide change as compared to corresponding sequence of the non-human primate, wherein said change is evolutionarily significant. The sequences identified by this method may be further characterized and/or analyzed for their possible association with biologically or medically relevant functions or traits unique or enhanced in humans. In preferred embodiments, the human polypeptide-coding nucleotide sequence is an AATYK sequence.

Another embodiment of the present invention is a method for large scale sequence comparison between human polypeptide-coding polynucleotide sequences and the polypeptide-coding polynucleotide sequences from a non-human primate, e.g., chimpanzee, comprising: (a) aligning the human polynucleotide sequences with corresponding polynucleotide sequences from non-human primate according to sequence homology; and (b) identifying any nucleotide changes within the human sequences as compared to the homologous sequences from the non-human primate, wherein the changes are evolutionarily significant. In some embodiments, the protein coding sequences are from brain.

In some embodiments, a nucleotide change identified by any of the methods described herein is a non-synonymous substitution. In some embodiments, the evolutionary significance of the nucleotide change is determined according to the non-synonymous substitution rate ($K_A$) of the nucleotide sequence. In some embodiments, the evolutionarily significant changes are assessed by determining the $K_A/K_S$ ratio between the human gene and the homologous gene from non-human primate (such as chimpanzee), and preferably that ratio is at least about 0.75, more preferably greater than about 1 (unity) (i.e., at least about 1), more preferably at least about 1.25, more preferably at least about 1.50, and more preferably at least about 2.00. In other embodiments, once a positively selected gene has been identified between human and a non-human primate (such as chimpanzee or gorilla), further comparisons are performed with other non-human primates to confirm whether the human or the non-human primate (such as chimpanzee or gorilla) gene has undergone positive selection.

In another aspect, the invention provides methods for correlating an evolutionarily significant human nucleotide change to a physiological condition in a human (or humans), which comprise analyzing a functional effect (which includes determining the presence of a functional effect), if any, of (the presence or absence of) a polynucleotide sequence identified by any of the methods described herein, wherein presence of a functional effect indicates a correlation between the evolutionarily significant nucleotide change and the physiological condition. Alternatively, in these methods, a functional effect (if any) may be assessed using a polypeptide sequence (or a portion of the polypeptide sequence) encoded by a nucleotide sequence identified by any of the methods described herein.

In a preferred embodiment, the polynucleotide sequence or polypeptide sequence is a human or chimpanzee p44 polynucleotide sequence (SEQ ID NO. 34 OR 31) or polypeptide sequence (SEQ ID NO. 36 OR 33). In a more preferred embodiment, the p44 polynucleotide sequences are the exon 2 sequences having nucleotides 1–457 of SEQ ID NO:34 (human), and nucleotides 1–457 of SEQ ID NO:31 (chimpanzee), or fragments thereof containing the exon 2 evolutionarily significant chimpanzee nucleotides or the corresponding human nucleotides. Such fragments are preferably between 18 and 225 nucleotides in length.

The present invention also provides comparison of the identified polypeptides by physical and biochemical methods widely used in the art to determine the structural or biochemical consequences of the evolutionarily significant changes. Physical methods are meant to include methods that are used to examine structural changes to proteins encoded by genes found to have undergone adaptive evolution. Side-by-side comparison of the three-dimensional structures of a protein (either human or non-human primate) and the evolved homologous protein (either non-human primate or human, respectively) will provide valuable information for developing treatments for related human conditions and diseases. For example, using the methods of the present invention, the chimpanzee ICAM-1 gene was identified as having positive evolutionary changes compared to human ICAM-1. In a three-dimensional model of two functional domains of the human ICAM-1 protein it can be seen that five of the six amino acids that have been changed in chimpanzees are immediately adjacent to (i.e., physically touching) amino acid residues known to be crucial for binding to the ICAM-1 counter-receptor, LFA-1; in each case, the human amino acid has been replaced by a larger amino acid in the chimpanzee ICAM-1. Such information allows insight into designing appropriate therapeutic intervention(s). Accordingly, in another aspect, the invention provides methods for identifying a target site (which includes one or more target sites) which may be suitable for therapeutic intervention, comprising comparing a human polypeptide (or a portion of the polypeptide) encoded in a sequence identified by any of the methods described herein, with a corresponding non-human polypeptide (or a portion of the polypeptide), wherein a location of a molecular difference, if any, indicates a target site.

Likewise, human and chimpanzee p44 polypeptide computer models or x-ray crystallography structures can be compared to determine how the evolutionarily significant amino acid changes of the chimpanzee p44 exon 2 alter the protein's structure, and how agents might be designed to interact with human p44 in such a manner that permits it to mimic chimpanzee p44 structure and/or function.

In another aspect, the invention provides methods for identifying a target site (which includes one or more target sites) which may be suitable for therapeutic intervention, comprising comparing a human polypeptide (or a portion of the polypeptide) encoded in a sequence identified by any of the methods described herein, with a corresponding non-human primate polypeptide (or a portion of the polypeptide), wherein a location of a molecular difference, such as an amino acid difference, if any, indicates a target site. Target sites can also be nonsynonymous nucleotide changes observed between a positively selected polynucleotide identified by any of the methods described herein and its corresponding sequence in the human or non-human primate. In preferred embodiments, the target site is a site on a human p44 polypeptide.

Biochemical methods are meant to include methods that are used to examine functional differences, such as binding specificity, binding strength, or optimal binding conditions, for a protein encoded by a gene that has undergone adaptive evolution. Side-by-side comparison of biochemical characteristics of a protein (either human or non-human primate) and the evolved homologous protein (either non-human primate or human, respectively) will reveal valuable information for developing treatments for related human conditions and diseases.

In another aspect, the invention provides methods of identifying an agent which may modulate a physiological condition, said method comprising contacting an agent (i.e., at least one agent to be tested) with a cell that has been transfected with a polynucleotide sequence identified by any of the methods described herein, wherein an agent is identified by its ability to modulate function of the polynucleotide sequence. In other embodiments, the invention provides methods of identifying an agent which may modulate a physiological condition, said method comprising contacting an agent (i.e., at least one agent) to be tested with a polypeptide (or a fragment of a polypeptide and/or a composition comprising a polypeptide or fragment of a polypeptide) encoded in or within a polynucleotide identified by any of the methods described herein, wherein an agent is identified by its ability to modulate function of the polypeptide. In preferred embodiments of these methods the polynucleotide sequence is an evolutionarily significant chimpanzee p44 polynucleotide sequence or its corresponding human polynucleotide. In more preferred embodiments, the polynucleotide sequence is nucleotides 1–457 of SEQ ID NO:31 (chimpanzee), and nucleotides 1–458 of SEQ ID NO:34 (human), or fragments thereof containing preferably 18–225 nucleotides and at least one of the chimpanzee evolutionarily significant nucleotides or corresponding human nucleotides. The invention also provides agents which are identified using the screening methods described herein.

In another aspect, the invention provides methods of screening agents which may modulate the activity of the human polynucleotide or polypeptide to either modulate a unique or enhanced human function or trait or to mimic the non-human primate trait of interest, such as susceptibility or resistance to development of a disease, such as HCV-associated chronic hepatitis or AIDS. These methods comprise contacting a cell which has been transfected with a polynucleotide sequence with an agent to be tested, and identifying agents based on their ability to modulate function of the polynucleotide or contacting a polypeptide preparation with an agent to be tested and identifying agents based upon their ability to modulate function of the polypeptide. In preferred embodiments, the polynucleotide sequence is an evolutionarily significant chimpanzee p44 polynucleotide sequence or its corresponding human polynucleotide sequence. In more preferred embodiments, the polynucleotide sequence is nucleotides 1–457 of SEQ ID NO: 31 (chimpanzee), or nucleotides 1–457 of SEQ ID NO-34 (human), or fragments thereof containing preferably 18–225 nucleotides and at least one of the chimpanzee evolutionarily significant nucleotides or corresponding human nucleotides.

In another aspect of the invention, methods are provided for identifying candidate polynucleotides that may be associated with decreased resistance to development of a disease in humans, comprising comparing the human polynucleotide sequence with the corresponding non-human primate polynucleotide sequence to identify any nucleotide changes; and determining whether the human nucleotide changes are evolutionarily significant. It has been observed that human polynucleotides that are evolutionarily significant may, in some instances, be associated with increased susceptibility or decreased resistance to the development of human diseases such as cancer. As is described herein, the strongly positively selected BRCA1 gene's exon 11 is also the location of a number of mutations associated with breast, ovarian and/or prostate cancer. Thus, this phenomenon may represent a trade-off between enhanced development of one trait and loss or reduction in another trait in polynucleotides encoding polypeptides of multiple functions. In this way, identification of positively selected human polynucleotides can serve to identify a pool of genes that are candidates for susceptibility to human diseases.

Human candidate evolutionarily significant polynucleotides that are identified in this manner can be evaluated for their role in conferring susceptibility to diseases by analyzing the functional effect of the evolutionarily significant nucleotide change in the candidate polynucleotide in a suitable model system. The presence of a functional effect in the model system indicates a correlation between the nucleotide change in the candidate polynucleotide and the decreased resistance to development of the disease in humans. For example, if an evolutionarily significant polynucleotide containing all the evolutionarily significant nucleotide changes, or a similar polynucleotide with a lesser number of nucleotide changes, is found to increase the susceptibility to the disease at issue in a non-human primate model, this would be a functional effect that correlates the nucleotide change and the disease.

Alternatively, human candidate evolutionarily significant polynucleotides may, in some individuals, have mutations aside from the evolutionarily significant nucleotide changes, that confer the increased susceptibility to the disease. These mutations can be tested in a suitable model system for a functional effect, such as conversion to a neoplastic phenotype, to correlate the mutation to the disease.

Further, the subject method includes a diagnostic method to determine whether a human patient is predisposed to decreased resistance to the development of a disease, by assaying the patient's nucleic acids for the presence of a mutation in an evolutionarily significant polynucleotide, where the presence of the mutation in the polynucleotide has been determined by methods described herein as being diagnostic for decreased resistance to the development of the disease. In one embodiment, the polynucleotide is BRCA1 exon 11, and the disease is breast, prostate or ovarian cancer.

BRIEF DESCRIPTION OF THE DRAWINGS

Figure 2:
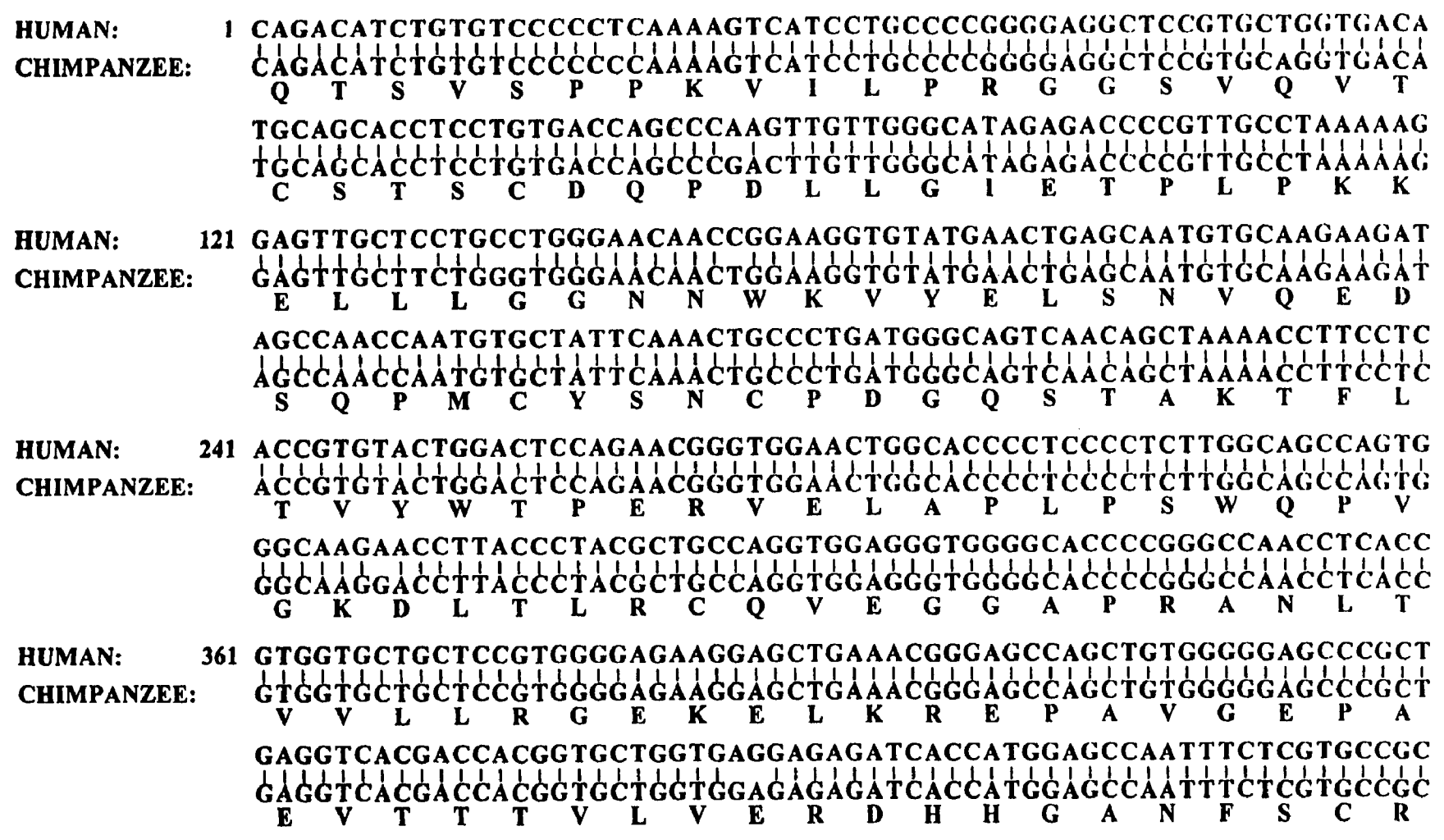
Figure 2:
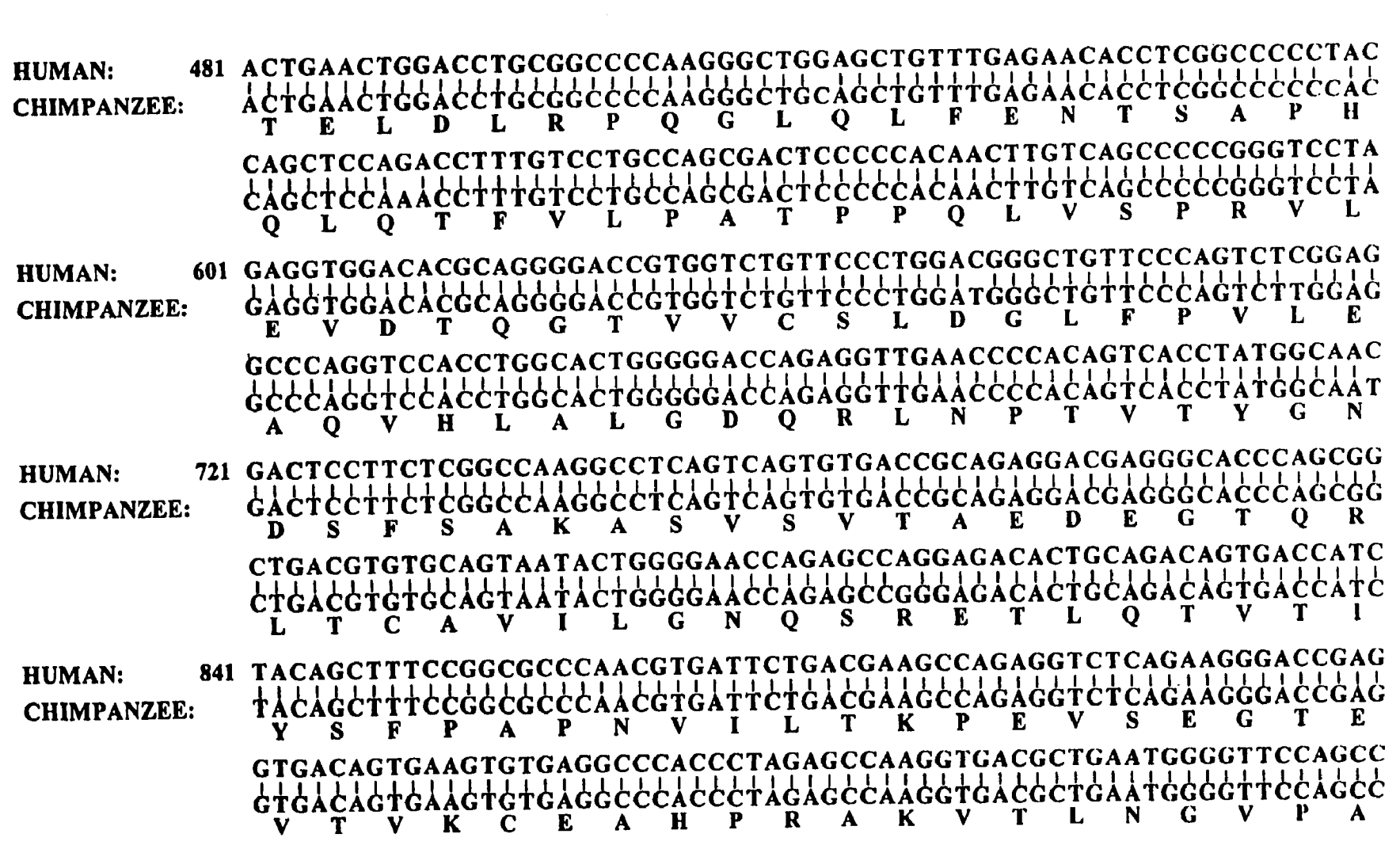

FIG. 2 (SEQ ID NOS:1–3) is a nucleotide sequence alignment between human and chimpanzee ICAM-1 sequences (GenBank® accession numbers X06990 and X86848, respectively). The amino acid translation of the chimpanzee sequence is shown below the alignment.

FIG. 3 shows the nucleotide sequence of gorilla ICAM-1 (SEQ ID NO:4).

FIG. 4 shows the nucleotide sequence of orangutan ICAM-1 (SEQ ID NO:5).

FIGS. 5(A)–(E) show the polypeptide sequence alignment of ICAM-1 from several primate species (SEQ ID NO:6).

FIGS. 6(A)–(B) show the polypeptide sequence alignment of ICAM-2 from several primate species (SEQ ID NO:7).

FIGS. 7(A)–(D) show the polypeptide sequence alignment of ICAM-3 from several primate species (SEQ ID NO:8).

FIG. 11 shows the coding sequence of human DC-SIGN (Genbank Acc. No. M98457) (SEQ. ID. NO. 9).

FIG. 12 shows the coding sequence of chimpanzee DC-SIGN (SEQ. ID. NO. 10).

FIG. 13 shows the coding sequence of gorilla DC-SIGN (SEQ. ID. NO. 11).

FIG. 14A shows the nucleotide sequence of the human AATYK gene. Start and stop codons are underlined (SEQ ID NO:14).

FIG. 14B shows an 1207 amino acid sequence of the human AATYK gene (SEQ ID NO:16).

FIG. 15A shows an 1806 base-pair region of the chimp AATYK gene (SEQ ID NO:17).

FIG. 15B shows an 1785 base-pair region of the gorilla AATYK gene (SEQ ID NO:18).

FIG. 16 shows a 1335 nucleotide region of the aligned chimpanzee (SEQ ID NO:31) and human (SEQ IS NO:34) p44 gene coding region. The underlined portion is exon 2, which was determined to be evolutionarily significant. Nonsynonymous differences between the two sequences are indicated in bold, synonymous differences in italics. Chimpanzee has a single heterozygous base (position 212), shown as M (IUPAC code for A or C. The C base represents a nonsynonymous difference from human, while A is identical to the same position in the human homolog. Thus, these two chimpanzee alleles differ slightly in the $K_A/K_S$ ratios relative to human p44.

DETAILED DESCRIPTION OF THE INVENTION

Figure 1:
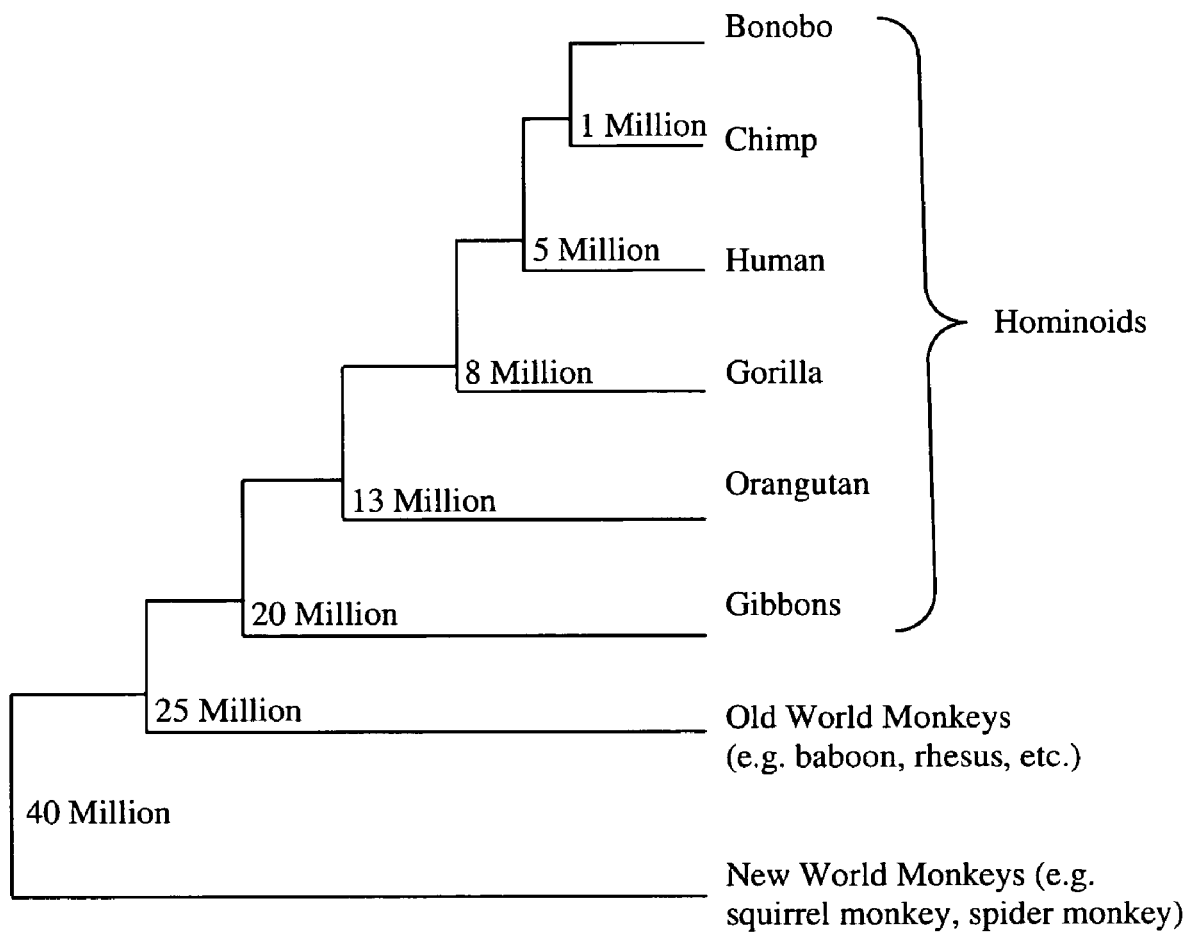
FIG. 1 depicts a phylogenetic tree for primates within the hominoid group. The branching orders are based on well-supported mitochondrial DNA phylogenies. Messier and Stewart (1997) *Nature* 385:151–154.
Figure 8:
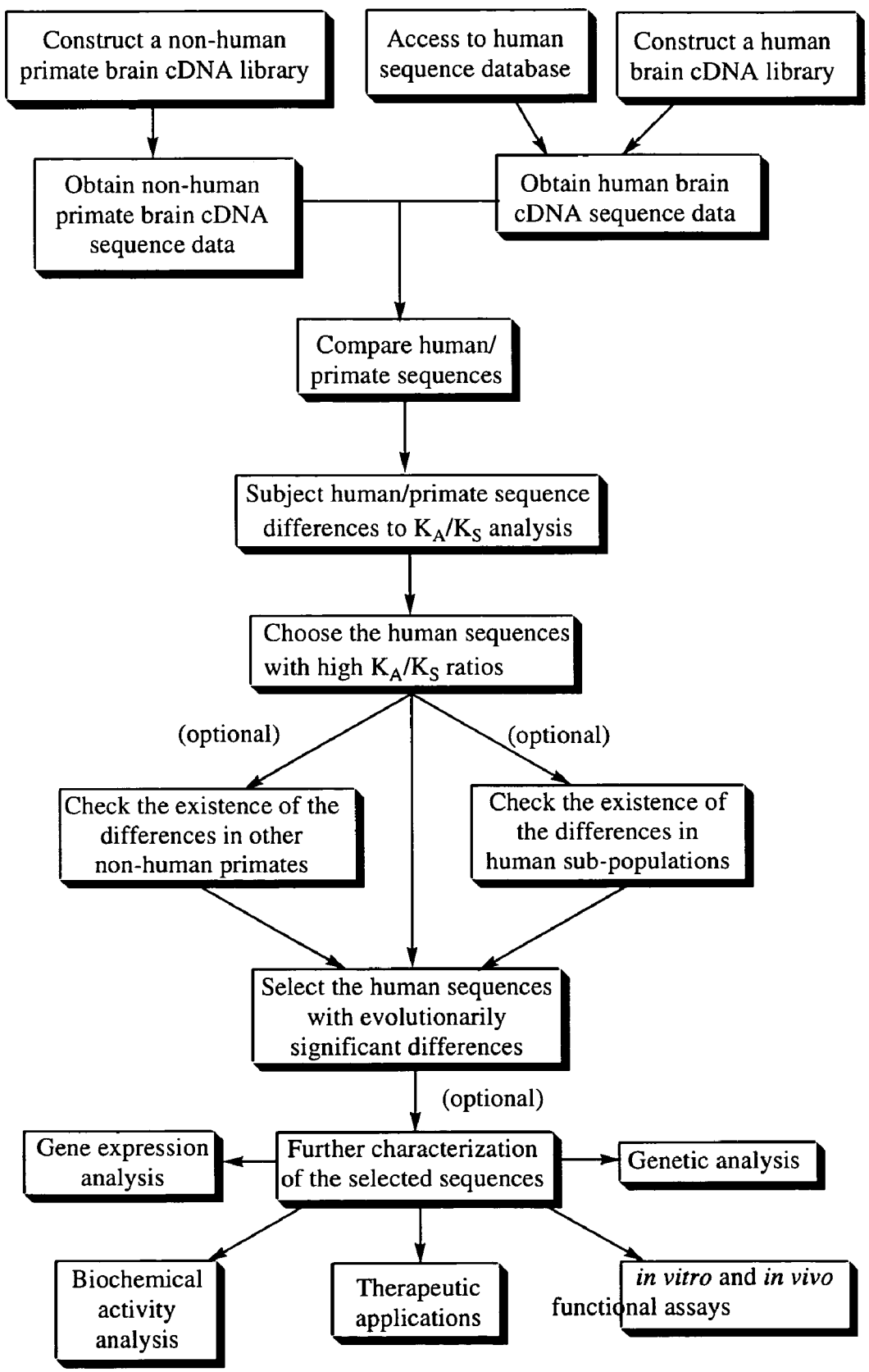
FIG. 8 depicts a schematic representation of a procedure for comparing human/primate brain polynucleotides, selecting sequences with evolutionarily significant changes, and further characterizing the selected sequences. The diagram of FIG. 8 illustrates a preferred embodiment of the invention and together with the description serves to explain the principles of the invention, along with elaboration and optional additional steps. It is understood that any human/primate polynucleotide sequence can be compared by a similar procedure and that the procedure is not limited to brain polynucleotides.

The present invention applies comparative genomics to identify specific gene changes which are associated with, and thus may contribute to or be responsible for, physiological conditions, such as medically or commercially relevant evolved traits. The invention comprises a comparative genomics approach to identify specific gene changes responsible for differences in functions and diseases distinguishing humans from other non-humans, particularly primates, and most preferably chimpanzees, including the two known species, common chimpanzees and bonobos (pygmy chimpanzees). For example, chimpanzees and humans are 98.5% identical at the DNA sequence level and the present invention can identify the adaptive molecular changes underlying differences between the species in a number of areas, including unique or enhanced human cognitive abilities or physiological traits and chimpanzee resistance to HCV, AIDS and certain cancers. Unlike traditional genomics, which merely identifies genes, the present invention provides exact information on evolutionary solutions that eliminate disease or provide unique or enhanced functions or traits. The present invention identifies genes that have evolved to confer an evolutionary advantage and the specific evolved changes.

The present invention results from the observation that human protein-coding polynucleotides may contain sequence changes that are found in humans but not in other evolutionarily closely related species such as non-human primates, as a result of adaptive selection during evolution.

The present invention further results from the observation that the genetic information of non-human primates may contain changes that are found in a particular non-human primate but not in humans, as a result of adaptive selection during evolution. In this embodiment, a non-human primate polynucleotide or polypeptide has undergone natural selection that resulted in a positive evolutionarily significant change (i.e., the non-human primate polynucleotide or polypeptide has a positive attribute not present in humans). In this embodiment the positively selected polynucleotide or polypeptide may be associated with susceptibility or resistance to certain diseases or other commercially relevant traits. Medically relevant examples of this embodiment include, but are not limited to, polynucleotides and polypeptides that are positively selected in non-human primates, preferably chimpanzees, that may be associated with susceptibility or resistance to infectious diseases and cancer. An example of this embodiment includes polynucleotides and polypeptides associated with the susceptibility or resistance to progression from HIV infection to development of AIDS. The present invention can thus be useful in gaining insight into the molecular mechanisms that underlie resistance to progression from HIV infection to development of AIDS, providing information that can also be useful in discovering and/or designing agents such as drugs that prevent and/or delay development of AIDS. Likewise, the present invention can be useful in gaining insight into the underlying mechanisms for HCV resistance in chimpanzees as compared to humans. Commercially relevant examples include, but are not limited to, polynucleotides and polypeptides that are positively selected in non-human primates that may be associated with aesthetic traits, such as hair growth, absence of acne or muscle mass.

Positively selected human evolutionarily significant changes in polynucleotide and polypeptide sequences may be attributed to human capabilities that provide humans with competitive advantages, particularly when compared to the closest evolutionary relative, chimpanzee, such as unique or enhanced human brain functions. The present invention identifies human genes that evolved to provide unique or enhanced human cognitive abilities and the actual protein changes that confer functional differences will be quite useful in therapeutic approaches to treat cognitive deficiencies as well as cognitive enhancement for the general population.

Other positively selected human evolutionarily significant changes include those sequences that may be attributed to human physiological traits or conditions that are enhanced or unique relative to close evolutionary relatives, such as the chimpanzee, including enhanced breast development. The present invention provides a method of determining whether a polynucleotide sequence in humans that may be associated with enhanced breast development has undergone an evolutionarily significant change relative to a corresponding polynucleotide sequence in a closely related non-human primate. The identification of evolutionarily significant changes in the human polynucleotide that is involved in the development of unique or enhanced human physiological traits is important in the development of agents or drugs that can modulate the activity or function of the human polynucleotide or its encoded polypeptide.

The practice of the present invention employs, unless otherwise indicated, conventional techniques of molecular biology, genetics and molecular evolution, which are within the skill of the art. Such techniques are explained fully in the literature, such as: "Molecular Cloning: A Laboratory Manual", second edition (Sambrook et al., 1989); "Oligonucleotide Synthesis" (M. J. Gait, ed., 1984); "Current Protocols in Molecular Biology" (F. M. Ausubel et al., eds., 1987); "PCR: The Polymerase Chain Reaction", (Mullis et al., eds., 1994); "Molecular Evolution", (Li, 1997).

Definitions

As used herein, a "polynucleotide" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified polynucleotides such as methylated and/or capped polynucleotides. The terms "polynucleotide" and "nucleotide sequence" are used interchangeably.

As used herein, a "gene" refers to a polynucleotide or portion of a polynucleotide comprising a sequence that encodes a protein. It is well understood in the art that a gene also comprises non-coding sequences, such as 5' and 3' flanking sequences (such as promoters, enhancers, repressors, and other regulatory sequences) as well as introns.

The terms "polypeptide," "peptide," and "protein" are used interchangeably herein to refer to polymers of amino acids of any length. These terms also include proteins that are post-translationally modified through reactions that include glycosylation, acetylation and phosphorylation.

A "physiological condition" is a term well-understood in the art and means any condition or state that can be measured and/or observed. A "physiological condition" includes, but is not limited to, a physical condition, such as degree of body fat, alopecia (baldness), acne or enhanced breast development; life-expectancy; disease states (which include susceptibility and/or resistance to diseases), such as cancer or infectious diseases. Examples of physiological conditions are provided below (see, e.g., definitions of "human medically relevant medical condition", "human commercially relevant condition", "medically relevant evolved trait", and "commercially relevant evolved trait") and throughout the specification, and it is understood that these terms and examples refer to a physiological condition. A physiological condition may be, but is not necessarily, the result of multiple factors, any of which in turn may be considered a physiological condition. A physiological condition which is "present" in a human or non-human primate occurs within a given population, and includes those physiological conditions which are unique and/or enhanced in a given population when compared to another population.

The terms "human medically relevant condition" or "human commercially relevant condition" are used herein to refer to human conditions for which medical or non-medical intervention is desired.

The term "medically relevant evolved trait" is used herein to refer to traits-that have evolved in humans or non-human primates whose analysis could provide information (e.g., physical or biochemical data) relevant to the development of a human medical treatment.

The term "commercially relevant evolved trait" is used herein to refer to traits that have evolved in humans or non-human primates whose analysis could provide information (e.g., physical or biochemical data) relevant to the development of a medical or non-medical product or treatment for human use.

The term "$K_A/K_S$-type methods" means methods that evaluate differences, frequently (but not always) shown as a ratio, between the number of nonsynonymous substitutions and synonymous substitutions in homologous genes (including the more rigorous methods that determine non-synonymous and synonymous sites). These methods are designated using several systems of nomenclature, including but not limited to $K_A/K_S$, $d_N/d_S$, $D_N/D_S$.

The terms "evolutionarily significant change" or "adaptive evolutionary change" refers to one or more nucleotide or peptide sequence change(s) between two species that may be attributed to a positive selective pressure. One method for determining the presence of an evolutionarily significant change is to apply a $K_A/K_S$-type analytical method, such as to measure a $K_A/K_S$ ratio. Typically, a $K_A/K_S$ ratio at least about 0.75, more preferably at least about 1.0, more preferably at least about 1.25, more preferably at least about 1.5 and most preferably at least about 2.0 indicates the action of positive selection and is considered to be an evolutionarily significant change.

Strictly speaking, only $K_A/K_S$ ratios greater than 1.0 are indicative of positive selection. It is commonly accepted that the ESTs in GenBank® and other public databases often suffer from some degree of sequencing error, and even a few incorrect nucleotides can influence $K_A/K_S$ scores. Thus, all pairwise comparisons that involve public ESTs must be undertaken with care. Due to the errors inherent in the publicly available databases, it is possible that these errors could depress a $K_A/K_S$ ratio below 1.0. For this reason, $K_A/K_S$ ratios between 0.75 and 1.0 should be examined carefully in order to determine whether or not a sequencing error has obscured evidence of positive selection. Such errors may be discovered through sequencing methods that are designed to be highly accurate.

The term "positive evolutionarily significant change" means an evolutionarily significant change in a particular species that results in an adaptive change that is positive as compared to other related species. Examples of positive evolutionarily significant changes are changes that have resulted in enhanced cognitive abilities or enhanced or unique physiological conditions in humans and adaptive changes in chimpanzees that have resulted in the ability of the chimpanzees infected with HIV or HCV to be resistant to progression of the infection.

The term "enhanced breast development" refers to the enlarged breasts observed in humans relative to non-human primates. The enlarged human breast has increased adipose, duct and/or gland tissue relative to other primates, and develops prior to first pregnancy and lactation.

The term "resistant" means that an organism, such as a chimpanzee, exhibits an ability to avoid, or diminish the extent of, a disease condition and/or development of the disease, preferably when compared to non-resistant organisms, typically humans. For example, a chimpanzee is resistant to certain impacts of HCV, HIV and other viral infections, and/or it does not develop the ultimate disease (chronic hepatitis or AIDS, respectively).

The term "susceptibility" means that an organism, such as a human, fails to avoid, or diminish the extent of, a disease condition and/or development of the disease condition, preferably when compared to an organism that is known to be resistant, such as a non-human primate, such as chimpanzee. For example, a human is susceptible to certain impacts of HCV, HIV and other viral infections and/or development of the ultimate disease (chronic hepatitis or AIDS).

It is understood that resistance and susceptibility vary from individual to individual, and that, for purposes of this invention, these terms also apply to a group of individuals within a species, and comparisons of resistance and susceptibility generally refer to overall, average differences between species, although intra-specific comparisons may be used.

The term "homologous" or "homologue" or "ortholog" is known and well understood in the art and refers to related sequences that share a common ancestor and is determined based on degree of sequence identity. These terms describe the relationship between a gene found in one species and the corresponding or equivalent gene in another species. For purposes of this invention homologous sequences are compared. "Homologous sequences" or "homologues" or "orthologs" are thought, believed, or known to be functionally related. A functional relationship may be indicated in any one of a number of ways, including, but not limited to, (a) degree of sequence identity; (b) same or similar biological function. Preferably, both (a) and (b) are indicated. The degree of sequence identity may vary, but is preferably at least 50% (when using standard sequence alignment programs known in the art), more preferably at least 60%, more preferably at least about 75%, more preferably at least about 85%. Homology can be determined using software programs readily available in the art, such as those discussed in *Current Protocols in Molecular Biology* (F. M. Ausubel et al., eds., 1987) Supplement 30, section 7.718, Table 7.71. Preferred alignment programs are MacVector (Oxford Molecular Ltd, Oxford, U.K.) and ALIGN Plus (Scientific and Educational Software, Pennsylvania). Another preferred alignment program is Sequencher (Gene Codes, Ann Arbor, Mich.), using default parameters.

The term "nucleotide change" refers to nucleotide substitution, deletion, and/or insertion, as is well understood in the art.

The term "human protein-coding nucleotide sequence" which is "associated with susceptibility to AIDS" as used herein refers to a human nucleotide sequence that encodes a protein that is associated with HIV dissemination (within the organism, i.e., intra-organism infectivity), propagation and/or development of AIDS. Due to the extensive research in the mechanisms underlying progression from HIV infection to the development of AIDS, a number of candidate human genes are believed or known to be associated with one or more of these phenomena. A polynucleotide (including any polypeptide encoded therein) sequence associated with susceptibility to AIDS is one which is either known or implicated to play a role in HIV dissemination, replication, and/or subsequent progression to full-blown AIDS. Examples of such candidate genes are provided below.

"AIDS resistant" means that an organism, such as a chimpanzee, exhibits an ability to avoid, or diminish the extent of, the result of HIV infection (such as propagation and dissemination) and/or development of AIDS, preferably when compared to AIDS-susceptible humans.

"Susceptibility" to AIDS means that an organism, such as a human, fails to avoid, or diminish the extent of, the result of HIV infection (such as propagation and dissemination) and/or development of AIDS, preferably when compared to an organism that is known to be AIDS resistant, such as a non-human primate, such as chimpanzee.

The term "human protein-coding nucleotide sequence" which is "associated with susceptibility to HCV infection" as used herein refers to a human nucleotide sequence that encodes a polypeptide that is associated with HCV dissemination (within the organism, i.e., intra-organism infectivity), propagation and/or development of chronic hepatitis. Candidate human genes are believed or known to be associated with human susceptibility to HCV infection. A polynucleotide (including any polypeptide encoded therein) sequence associated with susceptibility to chronic hepatitis is one which is either known or implicated to play a role in HCV dissemination, replication, and/or subsequent progression to chronic hepatitis or hepatocellular carcinoma. One example of a polynucleotide associated with susceptibility is human p44 exon 2.

"HCV resistant" means that an organism, such as a chimpanzee, exhibits an ability to avoid, or diminish the extent of, the result of HCV infection (such as propagation and dissemination) and/or development of chronic hepatitis, preferably when compared to HCV-susceptible humans.

"Susceptibility" to HCV infection means that an organism, such as a human, fails to avoid, or diminish the extent of, the result of HCV infection (such as propagation and dissemination) and/or development of chronic hepatitis, preferably when compared to an organism that is known to be HCV infection resistant, such as a non-human primate, such as chimpanzee.

The term "brain protein-coding nucleotide sequence" as used herein refers to a nucleotide sequence expressed in the brain that encodes a protein. One example of the "brain protein-coding nucleotide sequence" is a brain cDNA sequence.

As used herein, the term "brain functions unique or enhanced in humans" or "unique functional capabilities of the human brain" or "brain functional capability that is unique or enhanced in humans" refers to any brain function, either in kind or in degree, that is identified and/or observed to be enhanced in humans compared to other non-human primates. Such brain functions include, but are not limited to high capacity information processing, storage and retrieval capabilities, creativity, memory, language abilities, brain-mediated emotional response, locomotion, pain/pleasure sensation, olfaction, and temperament.

"Housekeeping genes" is a term well understood in the art and means those genes associated with general cell function, including but not limited to growth, division, stasis, metabolism, and/or death. "Housekeeping" genes generally perform functions found in more than one cell type. In contrast, cell-specific genes generally perform functions in a particular cell type (such as neurons) and/or class (such as neural cells).

The term "agent", as used herein, means a biological or chemical compound such as a simple or complex organic or inorganic molecule, a peptide, a protein or an oligonucleotide. A vast array of compounds can be synthesized, for example oligomers, such as oligopeptides and oligonucleotides, and synthetic organic and inorganic compounds based on various core structures, and these are also included in the term "agent". In addition, various natural sources can provide compounds for screening, such as plant or animal extracts, and the like. Compounds can be tested singly or in combination with one another.

The term "to modulate function" of a polynucleotide or a polypeptide means that the function of the polynucleotide or polypeptide is altered when compared to not adding an agent. Modulation may occur on any level that affects function. A polynucleotide or polypeptide function may be direct or indirect, and measured directly or indirectly.

A "function of a polynucleotide" includes, but is not limited to, replication; translation; and expression pattern(s). A polynucleotide function also includes functions associated with a polypeptide encoded within the polynucleotide. For example, an agent which acts on a polynucleotide and affects protein expression, conformation, folding (or other physical characteristics), binding to other moieties (such as ligands), activity (or other functional characteristics), regulation and/or other aspects of protein structure or function is considered to have modulated polynucleotide function.

A "function of a polypeptide" includes, but is not limited to, conformation, folding (or other physical characteristics), binding to other moieties (such as ligands), activity (or other functional characteristics), and/or other aspects of protein structure or functions. For example, an agent that acts on a polypeptide and affects its conformation, folding (or other physical characteristics), binding to other moieties (such as ligands), activity (or other functional characteristics), and/or other aspects of protein structure or functions is considered to have modulated polypeptide function. The ways that an effective agent can act to modulate the function of a polypeptide include, but are not limited to 1) changing the conformation, folding or other physical characteristics; 2) changing the binding strength to its natural ligand or changing the specificity of binding to ligands; and 3) altering the activity of the polypeptide.

The terms "modulate susceptibility to development of AIDS" and "modulate resistance to development of AIDS", as used herein, include modulating intra-organism cell-to-cell transmission or infectivity of HIV. The terms further include reducing susceptibility to development of AIDS and/or cell-to-cell transmission or infectivity of HIV. The terms further include increasing resistance to development of AIDS and/or cell-to-cell transmission or infectivity of HIV. One means of assessing whether an agent is one that modulates susceptibility or resistance to development of AIDS is to determine whether at least one index of HIV susceptibility is affected, using a cell-based system as described herein, as compared with an appropriate control. Indicia of HIV susceptibility include, but are not limited to, cell-to-cell transmission of the virus, as measured by total number of cells infected with HIV and syncytia formation.

The terms "modulate susceptibility to HCV infection" and "modulate resistance to HCV infection", as used herein, include modulating intra-organism cell-to-cell transmission or infectivity of HCV. The terms further include reducing susceptibility to development of chronic hepatitis and/or cell-to-cell transmission or infectivity of HCV. The terms further include increasing resistance to infection by HCV and/or cell-to-cell transmission or infectivity of HCV. One means of assessing whether an agent is one that modulates susceptibility or resistance to development of HCV-associated chronic hepatitis is to determine whether at least one index of HCV susceptibility is affected, using a cell-based system as described herein, as compared with an appropriate control. Indicia of HCV susceptibility include, but are not limited to, cell-to-cell transmission of the virus, as measured by total number of cells infected with HCV.

The term "target site" means a location in a polypeptide which can be one or more amino acids and/or is a part of a structural and/or functional motif, e.g., a binding site, a dimerization domain, or a catalytic active site. It also includes a location in a polynucleotide where there is one or more non-synonymous nucleotide changes in a protein coding region, or may also refer to a regulatory region of a positively selected gene. Target sites may be a useful for direct or indirect interaction with an agent, such as a therapeutic agent.

The term "molecular difference" includes any structural and/or functional difference. Methods to detect such differences, as well as examples of such differences, are described herein.

A "functional effect" is a term well known in the art, and means any effect which is exhibited on any level of activity, whether direct or indirect.

An agent that interacts with human p44 polypeptide to form a complex that "mimics the structure" of chimpanzee or other non-human primate p44 polypeptide means that the interaction of the agent with the human p44 polypeptide results in a complex whose three-dimensional structure more closely approximates the three-dimensional structure of the chimpanzee or non-human p44 polypeptide, relative to the human p44 polypeptide alone.

An agent that interacts with human p44 polypeptide to form a complex that "mimics the function" of chimpanzee or other non-human primate p44 polypeptide means that the complex of human p44 polypeptide and agent attain a biological function or enhance a biological function that is characteristic of the chimpanzee or other non-human primate p44 polypeptide, relative to the human p44 polypeptide alone. Such biological function of chimpanzee p44 polypeptide includes, without limitation, microtubule assembly following HCV infection, and resistance to HCV infection of hepatocytes.

General Procedures Known in the Art

For the purposes of this invention, the source of the human and non-human polynucleotide can be any suitable source, e.g., genomic sequences or cDNA sequences. Preferably, cDNA sequences from human and a non-human primate are compared. Human protein-coding sequences can be obtained from public databases such as the Genome Sequence Data Bank and GenBank. These databases serve as repositories of the molecular sequence data generated by ongoing research efforts. Alternatively, human protein-coding sequences may be obtained from, for example, sequencing of cDNA reverse transcribed from mRNA expressed in human cells, or after PCR amplification, according to methods well known in the art. Alternatively, human genomic sequences may be used for sequence comparison. Human genomic sequences can be obtained from public databases or from a sequencing of commercially available human genomic DNA libraries or from genomic DNA, after PCR.

The non-human primate protein-coding sequences can be obtained by, for example, sequencing cDNA clones that are randomly selected from a non-human primate cDNA library. The non-human primate cDNA library can be constructed from total mRNA expressed in a primate cell using standard techniques in the art. In some embodiments, the cDNA is prepared from mRNA obtained from a tissue at a determined developmental stage, or a tissue obtained after the primate has been subjected to certain environmental conditions. cDNA libraries used for the sequence comparison of the present invention can be constructed using conventional cDNA library construction techniques that are explained fully in the literature of the art. Total mRNAs are used as templates to reverse-transcribe cDNAs. Transcribed cDNAs are subcloned into appropriate vectors to establish a cDNA library. The established cDNA library can be maximized for full-length cDNA contents, although less than full-length cDNAs may be used; Furthermore, the sequence frequency can be normalized according to, for example, Bonaldo et al. (1996) *Genome Research* 6:791–806. cDNA clones randomly selected from the constructed cDNA library can be sequenced using standard automated sequencing techniques. Preferably, full-length cDNA clones are used for sequencing. Either the entire or a large portion of cDNA clones from a cDNA library may be sequenced, although it is also possible to practice some embodiments of the invention by sequencing as little as a single cDNA, or several cDNA clones.

In one preferred embodiment of the present invention, non-human primate cDNA clones to be sequenced can be pre-selected according to their expression specificity. In order to select cDNAs corresponding to active genes that are specifically expressed, the cDNAs can be subject to subtraction hybridization using mRNAs obtained from other organs, tissues or cells of the same animal. Under certain hybridization conditions with appropriate stringency and concentration, those cDNAs that hybridize with non-tissue specific mRNAs and thus likely represent "housekeeping" genes will be excluded from the cDNA pool. Accordingly, remaining cDNAs to be sequenced are more likely to be associated with tissue-specific functions. For the purpose of subtraction hybridization, non-tissue-specific mRNAs can be obtained from one organ, or preferably from a combination of different organs and cells. The amount of non-tissue-specific mRNAs are maximized to saturate the tissue-specific cDNAs.

Alternatively, information from online public databases can be used to select or give priority to cDNAs that are more likely to be associated with specific functions. For example, the non-human primate cDNA candidates for sequencing can be selected by PCR using primers designed from candidate human cDNA sequence. Candidate human cDNA sequences are, for example, those that are only found in a specific tissue, such as brain or breast, or that correspond to genes likely to be important in the specific function, such as brain function or breast tissue adipose or glandular development. Such human tissue-specific cDNA sequences can be obtained by searching online human sequence databases such as GenBank, in which information with respect to the expression profile and/or biological activity for cDNA sequences are specified.

Sequences of non-human primate (for example, from an AIDS- or HCV-resistant non-human primate) homologue(s) to a known human gene may be obtained using methods standard in the art, such as from public databases such as GenBank or PCR methods (using, for example, GeneAmp PCR System 9700 thermocyclers (Applied Biosystems, Inc.)). For example non-human primate cDNA candidates for sequencing can be selected by PCR using primers designed from candidate human cDNA sequences. For PCR, primers may be made from the human sequences using standard methods in the art, including publicly available primer design programs such as PRIMER® (Whitehead Institute). The sequence amplified may then be sequenced using standard methods and equipment in the art, such as automated sequencers (Applied Biosystems, Inc.).

General Methods of the Invention

The general method of the invention is as follows. Briefly, nucleotide sequences are obtained from a human source and a non-human source. The human and non-human nucleotide sequences are compared to one another to identify sequences that are homologous. The homologous sequences are analyzed to identify those that have nucleic acid sequence differences between the two species. Then molecular evolution analysis is conducted to evaluate quantitatively and qualitatively the evolutionary significance of the differences. For genes that have been positively selected between two species, e.g., human and chimp, it is useful to determine whether the difference occurs in other non-human primates. Next, the sequence is characterized in terms of molecular/genetic identity and biological function. Finally, the information can be used to identify agents useful in diagnosis and treatment of human medically or commercially relevant conditions.

The general methods of the invention entail comparing human protein-coding nucleotide sequences to protein-coding nucleotide sequences of a non-human, preferably a primate, and most preferably a chimpanzee. Examples of other non-human primates are bonobo, gorilla, orangutan, gibbon, Old World monkeys, and New World monkeys. A phylogenetic tree for primates within the hominoid group is depicted in FIG. 1. Bioinformatics is applied to the comparison and sequences are selected that contain a nucleotide change or changes that is/are evolutionarily significant change(s). The invention enables the identification of genes that have evolved to confer some evolutionary advantage and the identification of the specific evolved changes.

Protein-coding sequences of human and another non-human primate are compared to identify homologous sequences. Protein-coding sequences known to or suspected of having a specific biological function may serve as the starting point for the comparison. Any appropriate mechanism for completing this comparison is contemplated by this invention. Alignment may be performed manually or by software (examples of suitable alignment programs are known in the art). Preferably, protein-coding sequences from a non-human primate are compared to human sequences via database searches, e.g., BLAST searches. The high scoring "hits," i.e., sequences that show a significant similarity after BLAST analysis, will be retrieved and analyzed. Sequences showing a significant similarity can be those having at least about 60%, at least about 75%, at least about 80%, at least about 85%, or at least about 90% sequence identity. Preferably, sequences showing greater than about 80% identity are further analyzed. The homologous sequences identified via database searching can be aligned in their entirety using sequence alignment methods and programs that are known and available in the art, such as the commonly used simple alignment program CLUSTAL V by Higgins et al. (1992) *CABIOS* 8:189–191.

Alternatively, the sequencing and homologous comparison of protein-coding sequences between human and a non-human primate may be performed simultaneously by using the newly developed sequencing chip technology. See, for example, Rava et al. U.S. Pat. No. 5,545,531.

The aligned protein-coding sequences of human and another non-human primate are analyzed to identify nucleotide sequence differences at particular sites. Again, any suitable method for achieving this analysis is contemplated by this invention. If there are no nucleotide sequence differences, the non-human primate protein coding sequence is not usually further analyzed. The detected sequence changes are generally, and preferably, initially checked for accuracy. Preferably, the initial checking comprises performing one or more of the following steps, any and all of which are known in the art: (a) finding the points where there are changes between the non-human primate and human sequences; (b) checking the sequence fluorogram (chromatogram) to determine if the bases that appear unique to non-human primate correspond to strong, clear signals specific for the called base; (c) checking the human hits to see if there is more than one human sequence that corresponds to a sequence change. Multiple human sequence entries for the same gene that have the same nucleotide at a position where there is a different nucleotide in a non-human primate sequence provides independent support that the human sequence is accurate, and that the change is significant. Such changes are examined using public database information and the genetic code to determine whether these nucleotide sequence changes result in a change in the amino acid sequence of the encoded protein. As the definition of "nucleotide change" makes clear, the present invention encompasses at least one nucleotide change, either a substitution, a deletion or an insertion, in a human protein-coding polynucleotide sequence as compared to corresponding sequence from a non-human primate. Preferably, the change is a nucleotide substitution. More preferably, more than one substitution is present in the identified human sequence and is subjected to molecular evolution analysis.

Any of several different molecular evolution analyses or $K_A/K_S$-type methods can be employed to evaluate quantitatively and qualitatively the evolutionary significance of the identified nucleotide changes between human gene sequences and that of a non-human primate. Kreitman and Akashi (1995) *Annu. Rev. Ecol. Syst.* 26:403–422; Li, *Molecular Evolution*, Sinauer Associates, Sunderland, Mass., 1997. For example, positive selection on proteins (i.e., molecular-level adaptive evolution) can be detected in protein-coding genes by pairwise comparisons of the ratios of nonsynonymous nucleotide substitutions per nonsynonymous site ($K_A$) to synonymous substitutions per synonymous site ($K_S$) (Li et al., 1985; Li, 1993). Any comparison of $K_A$ and $K_S$ may be used, although it is particularly convenient and most effective to compare these two variables as a ratio. Sequences are identified by exhibiting a statistically significant difference between $K_A$ and $K_S$ using standard statistical methods.

Preferably, the $K_A/K_S$ analysis by Li et al. is used to carry out the present invention, although other analysis programs that can detect positively selected genes between species can also be used. Li et al. (1985) *Mol. Biol. Evol.* 2:150–174; Li (1993); see also *J. Mol. Evol.* 36:96–99; Messier and Stewart (1997) *Nature* 385:151–154; Nei (1987) *Molecular Evolutionary Genetics* (New York, Columbia University Press). The $K_A/K_S$ method, which comprises a comparison of the rate of non-synonymous substitutions per non-synonymous site with the rate of synonymous substitutions per synonymous site between homologous protein-coding region of genes in terms of a ratio, is used to identify sequence substitutions that may be driven by adaptive selections as opposed to neutral selections during evolution. A synonymous ("silent") substitution is one that, owing to the degeneracy of the genetic code, makes no change to the amino acid sequence encoded; a non-synonymous substitution results in an amino acid replacement. The extent of each type of change can be estimated as $K_A$ and $K_S$, respectively, the numbers of synonymous substitutions per synonymous site and non-synonymous substitutions per non-synonymous site. Calculations of $K_A/K_S$ may be performed manually or by using software. An example of a suitable program is MEGA (Molecular Genetics Institute, Pennsylvania State University).

For the purpose of estimating $K_A$ and $K_S$, either complete or partial human protein-coding sequences are used to calculate total numbers of synonymous and non-synonymous substitutions, as well as non-synonymous and synonymous sites. The length of the polynucleotide sequence analyzed can be any appropriate length. Preferably, the entire coding sequence is compared, in order to determine any and all significant changes. Publicly available computer programs, such as Li93 (Li (1993) *J. Mol. Evol.* 36:96–99) or INA, can be used to calculate the $K_A$ and $K_S$ values for all pairwise comparisons. This analysis can be further adapted to examine sequences in a "sliding window" fashion such that small numbers of important changes are not masked by the whole sequence. "Sliding window" refers to examination of consecutive, overlapping subsections of the gene (the subsections can be of any length).

The comparison of non-synonymous and synonymous substitution rates is represented by the $K_A/K_S$ ratio. $K_A/K_S$ has been shown to be a reflection of the degree to which adaptive evolution has been at work in the sequence under study. Full length or partial segments of a coding sequence can be used for the $K_A/K_S$ analysis. The higher the $K_A/K_S$ ratio, the more likely that a sequence has undergone adaptive evolution and the non-synonymous substitutions are evolutionarily significant. See, for example, Messier and Stewart (1997). Preferably, the $K_A/K_S$ ratio is at least about 0.75, more preferably at least about 1.0, more preferably at least about 1.25, more preferably at least about 1.50, or more preferably at least about 2.00. Preferably, statistical analysis is performed on all elevated $K_A/K_S$ ratios, including, but not limited to, standard methods such as Student's t-test and likelihood ratio tests described by Yang (1998) *Mol. Biol Evol.* 37:441–456.

$K_A/K_S$ ratios significantly greater than unity strongly suggest that positive selection has fixed greater numbers of amino acid replacements than can be expected as a result of chance alone, and is in contrast to the commonly observed pattern in which the ratio is less than or equal to one. Nei (1987); Hughes and Hei (1988) *Nature* 335:167–170; Messier and Stewart (1994) *Current Biol.* 4:911–913; Kreitman and Akashi (1995) *Ann. Rev. Ecol. Syst.* 26:403–422; Messier and Stewart (1997). Ratios less than one generally signify the role of negative, or purifying selection: there is strong pressure on the primary structure of functional, effective proteins to remain unchanged.

All methods for calculating $K_A/K_S$ ratios are based on a pairwise comparison of the number of nonsynonymous substitutions per nonsynonymous site to the number of synonymous substitutions per synonymous site for the protein-coding regions of homologous genes from related species. Each method implements different corrections for estimating "multiple hits" (i.e., more than one nucleotide substitution at the same site). Each method also uses different models for how DNA sequences change over evolutionary time. Thus, preferably, a combination of results from different algorithms is used to increase the level of sensitivity for detection of positively-selected genes and confidence in the result.

Preferably, $K_A/K_S$ ratios should be calculated for orthologous gene pairs, as opposed to paralogous gene pairs. (i.e., a gene which results from speciation, as opposed to a gene that is the result of gene duplication) Messier and Stewart (1997). This distinction may be made by performing additional comparisons with other non-human primates, such as gorilla and orangutan, which allows for phylogenetic tree-building. Orthologous genes when used in tree-building will yield the known "species tree", i.e., will produce a tree that recovers the known biological tree. In contrast, paralogous genes will yield trees which will violate the known biological tree.

It is understood that the methods described herein could lead to the identification of human polynucleotide sequences that are functionally related to human protein-coding sequences. Such sequences may include, but are not limited to, non-coding sequences or coding sequences that do not encode human proteins. These related sequences can be, for example, physically adjacent to the human protein-coding sequences in the human genome, such as introns or 5'- and 3'-flanking sequences (including control elements such as promoters and enhancers). These related sequences may be obtained via searching a public human genome database such as GenBank or, alternatively, by screening and sequencing a human genomic library with a protein-coding sequence as probe. Methods and techniques for obtaining non-coding sequences using related coding sequence are well known to one skilled in the art.

The evolutionarily significant nucleotide changes, which are detected by molecular evolution analysis such as the $K_A/K_S$ analysis, can be further assessed for their unique occurrence in humans (or the non-human primate) or the extent to which these changes are unique in humans (or the non-human primate). For example, the identified changes can be tested for presence/absence in other non-human primate sequences. The sequences with at least one evolutionarily significant change between human and one non-human primate can be used as primers for PCR analysis of other non-human primate protein-coding sequences, and resulting polynucleotides are sequenced to see whether the same change is present in other non-human primates. These comparisons allow further discrimination as to whether the adaptive evolutionary changes are unique to the human lineage as compared to other non-human primates or whether the adaptive change is unique to the non-human primates (i.e., chimpanzee) as compared to humans and other non-human primates. A nucleotide change that is detected in human but not other primates more likely represents a human adaptive evolutionary change. Alternatively, a nucleotide change that is detected in a non-human primate (i.e., chimpanzee) that is not detected in humans or other non-human primates likely represents a chimpanzee adaptive evolutionary change. Other non-human primates used for comparison can be selected based on their phylogenetic relationships with human. Closely related primates can be those within the hominoid sublineage, such as chimpanzee, bonobo, gorilla, and orangutan. Non-human primates can also be those that are outside the hominoid group and thus not so closely related to human, such as the Old World monkeys and New World monkeys. Statistical significance of such comparisons may be determined using established available programs, e.g., t-test as used by Messier and Stewart (1997) *Nature* 385:151–154. Those genes showing statistically high $K_A/K_S$ ratios are very likely to have undergone adaptive evolution.

Sequences with significant changes can be used as probes in genomes from different human populations to see whether the sequence changes are shared by more than one human population. Gene sequences from different human populations can be obtained from databases made available by, for example, the Human Genome Project, the human genome diversity project or, alternatively, from direct sequencing of PCR-amplified DNA from a number of unrelated, diverse human populations. The presence of the identified changes in different human populations would further indicate the evolutionary significance of the changes. Chimpanzee sequences with significant changes can be obtained and evaluated using similar methods to determine whether the sequence changes are shared among many chimpanzees.

Sequences with significant changes between species can be further characterized in terms of their molecular/genetic identities and biological functions, using methods and techniques known to those of ordinary skill in the art. For example, the sequences can be located genetically and physically within the human genome using publicly available bio-informatics programs. The newly identified significant changes within the nucleotide sequence may suggest a potential role of the gene in human evolution and a potential association with human-unique functional capabilities. The putative gene with the identified sequences may be further characterized by, for example, homologue searching. Shared homology of the putative gene with a known gene may indicate a similar biological role or function. Another exemplary method of characterizing a putative gene sequence is on the basis of known sequence motifs. Certain sequence patterns are known to code for regions of proteins having specific biological characteristics such as signal sequences, DNA binding domains, or transmembrane domains.

The identified human sequences with significant changes can also be further evaluated by looking at where the gene is expressed in terms of tissue- or cell type-specificity. For example, the identified coding sequences can be used as probes to perform in situ mRNA hybridization that will reveal the expression patterns of the sequences. Genes that are expressed in certain tissues may be better candidates as being associated with important human functions associated with that tissue, for example brain tissue. The timing of the gene expression during each stage of human development can also be determined.

As another exemplary method of sequence characterization, the functional roles of the identified nucleotide sequences with significant changes can be assessed by conducting functional assays for different alleles of an identified gene in a model system, such as yeast, nematode, *Drosophila*, and mouse. Model systems may be cell-based or in vivo, such as transgenic animals or animals with chimeric organs or tissues. Preferably, the transgenic mouse or chimeric organ mouse system is used. Methods of making cell-based systems and/or transgenic/chimeric animal systems are known in the art and need not be described in detail herein.

As another exemplary method of sequence characterization, the use of computer programs allows modeling and visualizing the three-dimensional structure of the homologous proteins from human and chimpanzee. Specific, exact knowledge of which amino acids have been replaced in a primate's protein(s) allows detection of structural changes that may be associated with functional differences. Thus, use of modeling techniques is closely associated with identification of functional roles discussed in the previous paragraph. The use of individual or combinations of these techniques constitutes part of the present invention. For example, chimpanzee ICAM-3 contains a glutamine residue (Q101) at the site in which human ICAM-3 contains a proline (P101). The human protein is known to bend sharply at this point. Replacement of the proline by glutamine in the chimpanzee protein is likely to result in a much less sharp bend at this point. This has clear implications for packaging of the ICAM-3 chimpanzee protein into HIV virions.

Likewise, chimpanzee p44 has been found to contain an exon (exon2) having several evolutionarily significant nucleotide changes relative to human p44 exon 2. The nonsynonymous changes and corresponding amino acid changes in chimpanzee p44 polypeptide are believed to confer HCV resistance to the chimpanzee. The mechanism may involve enhanced p44 microtubule assembly in hepatocytes.

The sequences identified by the methods described herein have significant uses in diagnosis and treatment of medically or commercially relevant human conditions. Accordingly, the present invention provides methods for identifying agents that are useful in modulating human-unique or human-enhanced functional capabilities and/or correcting defects in these capabilities using these sequences. These methods employ, for example, screening techniques known in the art, such as in vitro systems, cell-based expression systems and transgenic/chimeric animal systems. The approach provided by the present invention not only identifies rapidly evolved genes, but indicates modulations that can be made to the protein that may not be too toxic because they exist in another species.

Screening Methods

The present invention also provides screening methods using the polynucleotides and polypeptides identified and characterized using the above-described methods. These screening methods are useful for identifying agents which may modulate the function(s) of the polynucleotides or polypeptides in a manner that would be useful for a human treatment. Generally, the methods entail contacting at least one agent to be tested with either a cell that has been transfected with a polynucleotide sequence identified by the methods described above, or a preparation of the polypeptide encoded by such polynucleotide sequence, wherein an agent is identified by its ability to modulate function of either the polynucleotide sequence or the polypeptide.

As used herein, the term "agent" means a biological or chemical compound such as a simple or complex organic or inorganic molecule, a peptide, a protein or an oligonucleotide. A vast array of compounds can be synthesized, for example oligomers, such as oligopeptides and oligonucleotides, and synthetic organic and inorganic compounds based on various core structures, and these are also included in the term "agent". In addition, various natural sources can provide compounds for screening, such as plant or animal extracts, and the like. Compounds can be tested singly or in combination with one another.

To "modulate function" of a polynucleotide or a polypeptide means that the function of the polynucleotide or polypeptide is altered when compared to not adding an agent. Modulation may occur on any level that affects function. A polynucleotide or polypeptide function may be direct or indirect, and measured directly or indirectly. A "function" of a polynucleotide includes, but is not limited to, replication, translation, and expression pattern(s). A polynucleotide function also includes functions associated with a polypeptide encoded within the polynucleotide. For example, an agent which acts on a polynucleotide and affects protein expression, conformation, folding (or other physical characteristics), binding to other moieties (such as ligands), activity (or other functional characteristics), regulation and/or other aspects of protein structure or function is considered to have modulated polynucleotide function. The ways that an effective agent can act to modulate the expression of a polynucleotide include, but are not limited to 1) modifying binding of a transcription factor to a transcription factor responsive element in the polynucleotide; 2) modifying the interaction between two transcription factors necessary for expression of the polynucleotide; 3) altering the ability of a transcription factor necessary for expression of the polynucleotide to enter the nucleus; 4) inhibiting the activation of a transcription factor involved in transcription of the polynucleotide; 5) modifying a cell-surface receptor which normally interacts with a ligand and whose binding of the ligand results in expression of the polynucleotide; 6) inhibiting the inactivation of a component of the signal transduction cascade that leads to expression of the polynucleotide; and 7) enhancing the activation of a transcription factor involved in transcription of the polynucleotide.

A "function" of a polypeptide includes, but is not limited to, conformation, folding (or other physical characteristics), binding to other moieties (such as ligands), activity (or other functional characteristics), and/or other aspects of protein structure or functions. For example, an agent that acts on a polypeptide and affects its conformation, folding (or other physical characteristics), binding to other moieties (such as ligands), activity (or other functional characteristics), and/or other aspects of protein structure or functions is considered to have modulated polypeptide function. The ways that an effective agent can act to modulate the function of a polypeptide include, but are not limited to 1) changing the conformation, folding or other physical characteristics; 2) changing the binding strength to its natural ligand or changing the specificity of binding to ligands; and 3) altering the activity of the polypeptide.

A "function" of a polynucleotide includes its expression, i.e., transcription and/or translation. It can also include (without limitation) its conformation, folding and binding to other moieties.

Generally, the choice of agents to be screened is governed by several parameters, such as the particular polynucleotide or polypeptide target, its perceived function, its three-dimensional structure (if known or surmised), and other aspects of rational drug design. Techniques of combinatorial chemistry can also be used to generate numerous permutations of candidates. Those of skill in the art can devise and/or obtain suitable agents for testing.

The in vivo screening assays described herein may have several advantages over conventional drug screening assays: 1) if an agent must enter a cell to achieve a desired therapeutic effect, an in vivo assay can give an indication as to whether the agent can enter a cell; 2) an in vivo screening assay can identify agents that, in the state in which they are added to the assay system are ineffective to elicit at least one characteristic which is associated with modulation of polynucleotide or polypeptide function, but that are modified by cellular components once inside a cell in such a way that they become effective agents; 3) most importantly, an in vivo assay system allows identification of agents affecting any component of a pathway that ultimately results in characteristics that are associated with polynucleotide or polypeptide function.

In general, screening can be performed by adding an agent to a sample of appropriate cells which have been transfected with a polynucleotide identified using the methods of the present invention, and monitoring the effect, i.e., modulation of a function of the polynucleotide or the polypeptide encoded within the polynucleotide. The experiment preferably includes a control sample which does not receive the candidate agent. The treated and untreated cells are then compared by any suitable phenotypic criteria, including but not limited to microscopic analysis, viability testing, ability to replicate, histological examination, the level of a particular RNA or polypeptide associated with the cells, the level of enzymatic activity expressed by the cells or cell lysates, the interactions of the cells when exposed to infectious agents, such as HIV, and the ability of the cells to interact with other cells or compounds. For example, the transfected cells can be exposed to the agent to be tested and, before, during, or after treatment with the agent, the cells can be infected with a virus, such as HCV or HIV, and tested for any indication of susceptibility of the cells to viral infection, including, for example, susceptibility of the cells to cell-to-cell viral infection, replication of the virus, production of a viral protein, and/or syncytia formation following infection with the virus. Differences between treated and untreated cells indicate effects attributable to the candidate agent. Optimally, the agent has a greater effect on experimental cells than on control cells. Appropriate host cells include, but are not limited to, eukaryotic cells, preferably mammalian cells. The choice of cell will at least partially depend on the nature of the assay contemplated.

To test for agents that upregulate the expression of a polynucleotide, a suitable host cell transfected with a polynucleotide of interest, such that the polynucleotide is expressed (as used herein, expression includes transcription and/or translation) is contacted with an agent to be tested. An agent would be tested for its ability to result in increased expression of mRNA and/or polypeptide. Methods of making vectors and transfection are well known in the art. "Transfection" encompasses any method of introducing the exogenous sequence, including, for example, lipofection, transduction, infection or electroporation. The exogenous polynucleotide may be maintained as a non-integrated vector (such as a plasmid) or may be integrated into the host genome.

To identify agents that specifically activate transcription, transcription regulatory regions could be linked to a reporter gene and the construct added to an appropriate host cell. As used herein, the term "reporter gene" means a gene that encodes a gene product that can be identified (i.e., a reporter protein). Reporter genes include, but are not limited to, alkaline phosphatase, chloramphenicol acetyltransferase, β-galactosidase, luciferase and green fluorescence protein (GFP). Identification methods for the products of reporter genes include, but are not limited to, enzymatic assays and fluorimetric assays. Reporter genes and assays to detect their products are well known in the art and are described, for example in Ausubel et al. (1987) and periodic updates. Reporter genes, reporter gene assays, and reagent kits are also readily available from commercial sources. Examples of appropriate cells include, but are not limited to, fungal, yeast, mammalian, and other eukaryotic cells. A practitioner of ordinary skill will be well acquainted with techniques for transfecting eukaryotic cells, including the preparation of a suitable vector, such as a viral vector; conveying the vector into the cell, such as by electroporation; and selecting cells that have been transformed, such as by using a reporter or drug sensitivity element. The effect of an agent on transcription from the regulatory region in these constructs would be assessed through the activity of the reporter gene product.

Besides the increase in expression under conditions in which it is normally repressed mentioned above, expression could be decreased when it would normally be maintained or increased. An agent could accomplish this through a decrease in transcription rate and the reporter gene system described above would be a means to assay for this. The host cells to assess such agents would need to be permissive for expression.

Cells transcribing mRNA (from the polynucleotide of interest) could be used to identify agents that specifically modulate the half-life of mRNA and/or the translation of mRNA. Such cells would also be used to assess the effect of an agent on the processing and/or post-translational modification of the polypeptide. An agent could modulate the amount of polypeptide in a cell by modifying the turnover (i.e., increase or decrease the half-life) of the polypeptide. The specificity of the agent with regard to the mRNA and polypeptide would be determined by examining the products in the absence of the agent and by examining the products of unrelated mRNAs and polypeptides. Methods to examine mRNA half-life, protein processing, and protein turn-over are well know to those skilled in the art.

In vivo screening methods could also be useful in the identification of agents that modulate polypeptide function through the interaction with the polypeptide directly. Such agents could block normal polypeptide-ligand interactions, if any, or could enhance or stabilize such interactions. Such agents could also alter a conformation of the polypeptide. The effect of the agent could be determined using immuno-precipitation reactions. Appropriate antibodies would be used to precipitate the polypeptide and any protein tightly associated with it. By comparing the polypeptides immunoprecipitated from treated cells and from untreated cells, an agent could be identified that would augment or inhibit polypeptide-ligand interactions, if any. Polypeptide-ligand interactions could also be assessed using cross-linking reagents that convert a close, but noncovalent interaction between polypeptides into a covalent interaction. Techniques to examine protein-protein interactions are well known to those skilled in the art. Techniques to assess protein conformation are also well known to those skilled in the art.

It is also understood that screening methods can involve in vitro methods, such as cell-free transcription or translation systems. In those systems, transcription or translation is allowed to occur, and an agent is tested for its ability to modulate function. For an assay that determines whether an agent modulates the translation of mRNA or a polynucleotide, an in vitro transcription/translation system may be used. These systems are available commercially and provide an in vitro means to produce mRNA corresponding to a polynucleotide sequence of interest. After mRNA is made, it can be translated in vitro and the translation products compared. Comparison of translation products between an in vitro expression system that does not contain any agent (negative control) with an in vitro expression system that does contain an agent indicates whether the agent is affecting translation. Comparison of translation products between control and test polynucleotides indicates whether the agent, if acting on this level, is selectively affecting translation (as opposed to affecting translation in a general, non-selective or non-specific fashion). The modulation of polypeptide function can be accomplished in many ways including, but not limited to, the in vivo and in vitro assays listed above as well as in in vitro assays using protein preparations. Polypeptides can be extracted and/or purified from natural or recombinant sources to create protein preparations. An agent can be added to a sample of a protein preparation and the effect monitored; that is whether and how the agent acts on a polypeptide and affects its conformation, folding (or other physical characteristics), binding to other moieties (such as ligands), activity (or other functional characteristics), and/or other aspects of protein structure or functions is considered to have modulated polypeptide function.

In an example for an assay for an agent that binds to a polypeptide encoded by a polynucleotide identified by the methods described herein, a polypeptide is first recombinantly expressed in a prokaryotic or eukaryotic expression system as a native or as a fusion protein in which a polypeptide (encoded by a polynucleotide identified as described above) is conjugated with a well-characterized epitope or protein. Recombinant polypeptide is then purified by, for instance, immunoprecipitation using appropriate antibodies or anti-epitope antibodies or by binding to immobilized ligand of the conjugate. An affinity column made of polypeptide or fusion protein is then used to screen a mixture of compounds which have been appropriately labeled. Suitable labels include, but are not limited to fluorochromes, radioisotopes, enzymes and chemiluminescent compounds. The unbound and bound compounds can be separated by washes using various conditions (e.g. high salt, detergent) that are routinely employed by those skilled in the art. Non-specific binding to the affinity column can be minimized by pre-clearing the compound mixture using an affinity column containing merely the conjugate or the epitope. Similar methods can be used for screening for an agent(s) that competes for binding to polypeptides. In addition to affinity chromatography, there are other techniques such as measuring the change of melting temperature or the fluorescence anisotropy of a protein which will change upon binding another molecule. For example, a BIAcore assay using a sensor chip (supplied by Pharmacia Biosensor, Stitt et al. (1995) *Cell* 80: 661–670) that is covalently coupled to polypeptide may be performed to determine the binding activity of different agents.

It is also understood that the in vitro screening methods of this invention include structural, or rational, drug design, in which the amino acid sequence, three-dimensional atomic structure or other property (or properties) of a polypeptide provides a basis for designing an agent which is expected to bind to a polypeptide. Generally, the design and/or choice of agents in this context is governed by several parameters, such as side-by-side comparison of the structures of a human and homologous non-human primate polypeptides, the perceived function of the polypeptide target, its three-dimensional structure (if known or surmised), and other aspects of rational drug design. Techniques of combinatorial chemistry can also be used to generate numerous permutations of candidate agents.

Also contemplated in screening methods of the invention are transgenic animal systems and animal models containing chimeric organs or tissues, which are known in the art.

The screening methods described above represent primary screens, designed to detect any agent that may exhibit activity that modulates the function of a polynucleotide or polypeptide. The skilled artisan will recognize that secondary tests will likely be necessary in order to evaluate an agent further. For example, a secondary screen may comprise testing the agent(s) in an infectivity assay using mice and other animal models (such as rat), which are known in the art. In addition, a cytotoxicity assay would be performed as a further corroboration that an agent which tested positive in a primary screen would be suitable for use in living organisms. Any assay for cytotoxicity would be suitable for this purpose, including, for example the MTT assay (Promega).

The invention also includes agents identified by the screening methods described herein.

Methods Useful for Identifying Positively Selected Non-Human Traits

In one aspect of the invention, a non-human primate polynucleotide or polypeptide has undergone natural selection that resulted in a positive evolutionarily significant change (i.e., the non-human primate polynucleotide or polypeptide has a positive attribute not present in humans). In this aspect of the invention, the positively selected polynucleotide or polypeptide may be associated with susceptibility or resistance to certain diseases or with other commercially relevant traits. Examples of this embodiment include, but are not limited to, polynucleotides and polypeptides that have been positively selected in non-human primates, preferably chimpanzees, that may be associated with susceptibility or resistance to infectious diseases, cancer, or acne or may be associated with aesthetic conditions of interest to humans, such as hair growth or muscle mass. An example of this embodiment includes polynucleotides and polypeptides associated with the susceptibility or resistance to HIV progression to AIDS. The present invention can thus be useful in gaining insight into the molecular mechanisms that underlie resistance to HIV infection progressing to development of AIDS, providing information that can also be useful in discovering and/or designing agents such as drugs that prevent and/or delay development of AIDS. For example, CD59, which has been identified as a leukocyte and erythrocyte protein whose function is to protect these cells from the complement arm of the body's MAC (membrane attack complex) defense system (Meri et al. (1996) Biochem. J. 616:923–935), has been found to be positively selected in the chimpanzee (see Example 16). It is believed that the CD59 found in chimpanzees confers a resistance to the progression of AIDS that is not found in humans. Thus, the positively selected chimpanzee CD59 can serve in the development of agents or drugs that are useful in arresting the progression of AIDS in humans, as is described in the Examples.

Another example involves the p44 polynucleotides and polypeptides associated with resistance to HCV infection in chimpanzees. This discovery can be useful in discerning the molecular mechanisms that underlie resistance to HCV infection progression to chronic hepatitis and/or hepatocellular carcinoma in chimpanzees, and in providing information useful in the discovery and/or design of agents that prevent and/or delay chronic hepatitis or hepatocellular carcinoma.

Commercially relevant examples include, but are not limited to, polynucleotides and polypeptides that are positively selected in non-human primates that may be associated with aesthetic traits, such as hair growth, acne, or muscle mass. Accordingly, in one aspect, the invention provides methods for identifying a polynucleotide sequence encoding a polypeptide, wherein said polypeptide may be associated with a medically or commercially relevant positive evolutionarily significant change. The method comprises the steps of: (a) comparing human protein-coding nucleotide sequences to protein-coding nucleotide sequences of a non-human primate; and (b) selecting a non-human primate polynucleotide sequence that contains at least one nucleotide change as compared to corresponding sequence of the human, wherein said change is evolutionarily significant. The sequences identified by this method may be further characterized and/or analyzed for their possible association with biologically or medically relevant functions unique or enhanced in non-human primates.

Methods Useful for Identifying Positively Selected Human Traits

This invention specifically provides methods for identifying human polynucleotide and polypeptide sequences that may be associated with unique or enhanced functional capabilities or traits of the human, for example, brain function or longer life span. More particularly, these methods identify those genetic sequences that may be associated with capabilities that are unique or enhanced in humans, including, but not limited to, brain functions such as high capacity information processing, storage and retrieval capabilities, creativity, and language abilities. Moreover, these methods identify those sequences that may be associated to other brain functional features with respect to which the human brain performs at enhanced levels as compared to other non-human primates; these differences may include brain-mediated emotional response, locomotion, pain/pleasure sensation, olfaction, temperament and longer life span.

In this method, the general methods of the invention are applied as described above. Generally, the methods described herein entail (a) comparing human protein-coding polynucleotide sequences to that of a non-human primate; and (b) selecting those human protein-coding polynucleotide sequences having evolutionarily significant changes that may be associated with unique or enhanced functional capabilities of the human as compared to that of the non-human primate.

In this embodiment, the human sequence includes the evolutionarily significant change (i.e., the human sequence differs from more than one non-human primate species sequence in a manner that suggests that such a change is in response to a selective pressure). The identity and function of the protein encoded by the gene that contains the evolutionarily significant change is characterized and a determination is made whether or not the protein can be involved in a unique or enhanced human function. If the protein is involved in a unique or enhanced human function, the information is used in a manner to identify agents that can supplement or otherwise modulate the unique or enhanced human function.

As a non-limiting example of the invention, identifying the genetic (i.e., nucleotide sequence) differences underlying the functional uniqueness of human brain may provide a basis for designing agents that can modulate human brain functions and/or help correct functional defects. These sequences could also be used in developing diagnostic reagents and/or biomedical research tools. The invention also provides methods for a large-scale comparison of human brain protein-coding sequences with those from a non-human primate.

The identified human sequence changes can be used in establishing a database of candidate human genes that may be involved in human brain function. Candidates are ranked as to the likelihood that the gene is responsible for the unique or enhanced functional capabilities found in the human brain compared to chimpanzee or other non-human primates. Moreover, the database not only provides an ordered collection of candidate genes, it also provides the precise molecular sequence differences that exist between human and chimpanzee (and other non-human primates), and thus defines the changes that underlie the functional differences. This information can be useful in the identification of potential sites on the protein that may serve as useful targets for pharmaceutical agents.

Accordingly, the present invention also provides methods for correlating an evolutionarily significant nucleotide change to a brain functional capability that is unique or enhanced in humans, comprising (a) identifying a human nucleotide sequence according to the methods described above; and (b) analyzing the functional effect of the presence or absence of the identified sequence in a model system.

Further studies can be carried out to confirm putative function. For example, the putative function can be assayed in appropriate in vitro assays using transiently or stably transfected mammalian cells in culture, or using mammalian cells transfected with an antisense clone to inhibit expression of the identified polynucleotide to assess the effect of the absence of expression of its encoded polypeptide. Studies such as one-hybrid and two-hybrid studies can be conducted to determine, for example, what other macromolecules the polypeptide interacts with. Transgenic nematodes or *Drosophila* can be used for various functional assays, including behavioral studies. The appropriate studies depend on the nature of the identified polynucleotide and the polypeptide encoded within the polynucleotide, and would be obvious to those skilled in the art.

The present invention also provides polynucleotides and polypeptides identified by the methods of the present invention. In one embodiment, the present invention provides an isolated AATYK nucleotide sequence selected from the group consisting of nucleotides 2180–2329 of SEQ ID NO:14, nucleotides 2978–3478 of SEQ ID NO:14, and nucleotides 3380–3988 of SEQ ID NO:14; and an isolated nucleotide sequence having at least 85% homology to a nucleotide sequence of any of the preceding sequences.

In another embodiment, the invention provides an isolated AATYK polypeptide selected from the group consisting of a polypeptide encoded by a nucleotide sequence selected from the group consisting of SEQ ID NO:17 and SEQ ID NO:18; wherein said encoding is based on the open reading frame (ORF) of SEQ ID NO:14, and a polypeptide encoded by a nucleotide sequence having at least 85% homology to a nucleotide sequence selected from the group consisting of SEQ ID NO:17 and SEQ ID NO:18; wherein said encoding is based on the open reading frame of SEQ ID NO:14.

In a further embodiment, the present invention provides an isolated AATYK polypeptide selected from the group consisting of a polypeptide encoded by a nucleotide sequence selected from the group consisting of nucleotides 1–501 of SEQ ID NO:17, nucleotides 1–150 of SEQ ID NO:17, nucleotides 100–249 of SEQ ID NO:17, nucleotides 202–351 of SEQ ID NO:17, nucleotides 301–450 of SEQ ID NO:17, nucleotides 799–948 of SEQ ID NO:17, nucleotides 901–1050 of SEQ ID NO:17, nucleotides 799–1299 of SEQ ID NO:17, and nucleotides 1201–1809 of SEQ ID NO:17; wherein said encoding is based on the open reading frame of SEQ ID NO:14; and a polypeptide encoded by a nucleotide sequence having at least 85% homology to any of the preceding nucleotide sequences.

In still another embodiment, the invention provides an isolated polypeptide selected from the group consisting of a polypeptide encoded by a nucleotide sequence selected from the group consisting of nucleotides 1–501 of SEQ ID NO:18, nucleotides 799–1299 of SEQ ID NO:18, and nucleotides 1201–1809 of SEQ ID NO:18; wherein said encoding is based on the open reading frame of SEQ ID NO:14; and a polypeptide encoded by a nucleotide sequence having at least 85% homology to nucleotides 1–501 of SEQ ID NO:18, nucleotides 799–1299 of SEQ ID NO:18, and nucleotides 1201–1809 of SEQ ID NO:18.

In another embodiment, the invention provides an isolated polynucleotide comprising SEQ ID NO:17, wherein the coding capacity of the nucleic acid molecule is based on the open reading frame of SEQ ID NO:14. In a preferred embodiment, the polynucleotide is a *Pan troglodytes* polynucleotide.

In another embodiment, the invention provides an isolated polynucleotide comprising SEQ ID NO:18, wherein the coding capacity of the nucleic acid molecule is based on the open reading frame of SEQ ID NO:14. In a preferred embodiment, the polynucleotide is a *Gorilla gorilla* polynucleotide.

In some embodiments, the polynucleotide or polypeptide having 85% homology to an isolated AATYK polynucleotide or polypeptide of the present invention is a homolog, which, when compared to a non-human primate, yields a $K_A/K_S$ ratio of at least 0.75, at least 1.00, at least 1.25, at least 1.50, or at least 2.00.

In other embodiments, the polynucleotide or polypeptide having 85% homology to an isolated AATYK polynucleotide or polypeptide of the present invention is a homolog which is capable of performing the function of the natural AATYK polynucleotide or polypeptide in a functional assay. Suitable assays for assessing the function of an ATTYK polynucleotide or polypeptide include a neuronal differentiation assay such as that described by Raghunath, et al., *Brain Res Mol Brain Res*. (2000) 77:151–62, or a tyrosine phosphorylation assay such as that described in Tomomura, et al., *Oncogene* (2001) 20(9):1022–32. The phrase "capable of performing the function of the natural AATYK polynucleotide or polypeptide in a functional assay" means that the polynucleotide or polypeptide has at least about 10% of the activity of the natural polynucleotide or polypeptide in the functional assay. In other preferred embodiments, has at least about 20% of the activity of the natural polynucleotide or polypeptide in the functional assay. In other preferred embodiments, has at least about 30% of the activity of the natural polynucleotide or polypeptide in the functional assay. In other preferred embodiments, has at least about 40% of the activity of the natural polynucleotide or polypeptide in the functional assay. In other preferred embodiments, has at least about 50% of the activity of the natural polynucleotide or polypeptide in the functional assay. In other preferred embodiments, the polynucleotide or polypeptide has at least about 60% of the activity of the natural polynucleotide or polypeptide in the functional assay. In more preferred embodiments, the polynucleotide or polypeptide has at least about 70% of the activity of the natural polynucleotide or polypeptide in the functional assay. In more preferred embodiments, the polynucleotide or polypeptide has at least about 80% of the activity of the natural polynucleotide or polypeptide in the functional assay. In more preferred embodiments, the polynucleotide or polypeptide has at least about 90% of the activity of the natural polynucleotide or polypeptide in the functional assay.

Description of the AIDS Embodiment (an Example of a Positively Selected Non-Human Trait)

The AIDS (Acquired Immune Deficiency Syndrome) epidemic has been estimated to threaten 30 million people world-wide (UNAIDS/WHO, 1998, "Report on the global HIV/AIDS epidemic"). Well over a million people are infected in developed countries, and in parts of sub-Saharan Africa, 1 in 4 adults now carries the virus (UNAIDS/WHO, 1998). Although efforts to develop vaccines are underway, near term prospects for successful vaccines are grim. Balter and Cohen (1998) *Science* 281:159–160; Baltimore and Heilman (1998) *Scientific Am.* 279:98–103. Further complicating the development of therapeutics is the rapid mutation rate of HIV (the human immunodeficiency virus which is responsible for AIDS), which generates rapid changes in viral proteins. These changes ultimately allow the virus to escape current therapies, which target viral proteins. Dobkin (1998) *Inf Med.* 15(3):159. Even drug cocktails which initially showed great promise are subject to the emergence of drug-resistant mutants. Balter and Cohen (1998); Dobkin (1998). Thus, there is still a serious need for development of therapies which delay or prevent progression of AIDS in HIV-infected individuals. Chun et al. (1997) *Proc. Natl. Acad. Sci. USA* 94:13193–13197; Dobkin (1998).

Human's closest relatives, chimpanzees (*Pan troglodytes*), have unexpectedly proven to be poor models for the study of the disease processes following infection with HIV-1. Novembre et al. (1997); *J. Virol.* 71(5):4086–4091. Once infected with HIV-1, chimpanzees display resistance to progression of the disease. To date, only one chimpanzee individual is known to have developed full-blown AIDS, although more than 1100 captive chimpanzees have been infected. Novembre et al. (1997); Villinger et al. (1997) *J. Med. Primatol.* 26(1–2): 11–18. Clearly, an understanding of the mechanism(s) that confer resistance to progression of the disease in chimpanzees may prove invaluable for efforts to develop therapeutic agents for HIV-infected humans.

It is generally believed that wild chimpanzee populations harbored the HIV-1 virus (perhaps for millennia) prior to its recent cross-species transmission to humans. Dube et al., (1994); *Virology* 202:379–389; Zhu and Ho (1995) *Nature* 374:503–504; Zhu et al. (1998); Quinn (1994) *Proc. Natl. Acad. Sci USA* 91:2407–2414. During this extended period, viral/host co-evolution has apparently resulted in accommodation, explaining chimpanzee resistance to AIDS progression. Bumet and White (1972); *Natural History of Infectious Disease* (Cambridge, Cambridge Univ. Press); Ewald (1991) *Hum. Nat.* 2(i):1–30. All references cited herein are hereby incorporated by reference in their entirety.

One aspect of this invention arises from the observations that (a) because chimpanzees (*Pan troglodytes*) have displayed resistance to development of AIDS although susceptible to HIV infection (Alter et al. (1984) *Science* 226: 549–552; Fultz et al. (1986) *J. Virol.* 58:116–124; Novembre et al. (1997) *J. Virol.* 71(5):4086–4091), while humans are susceptible to developing this devastating disease, certain genes in chimpanzees may contribute to this resistance; and (b) it is possible to evaluate whether changes in human genes when compared to homologous genes from other species (such as chimpanzee) are evolutionarily significant (i.e., indicating positive selective pressure). Thus, protein coding polynucleotides may contain sequence changes that are found in chimpanzees (as well as other AIDS-resistant primates) but not in humans, likely as a result of positive adaptive selection during evolution. Furthermore, such evolutionarily significant changes in polynucleotide and polypeptide sequences may be attributed to an AIDS-resistant non-human primate's (such as chimpanzee) ability to resist development of AIDS. The methods of this invention employ selective comparative analysis to identify candidate genes which may be associated with susceptibility or resistance to AIDS, which may provide new host targets for therapeutic intervention as well as specific information on the changes that evolved to confer resistance. Development of therapeutic approaches that involve host proteins (as opposed to viral proteins and/or mechanisms) may delay or even avoid the emergence of resistant viral mutants. The invention also provides screening methods using the sequences and structural differences identified.

This invention provides methods for identifying human polynucleotide and polypeptide sequences that may be associated with susceptibility to post-infection development of AIDS. Conversely, the invention also provides methods for identifying polynucleotide and polypeptide sequences from an AIDS-resistant non-human primate (such as chimpanzee) that may be associated with resistance to development of AIDS. Identifying the genetic (i.e., nucleotide sequence) and the resulting protein structural and biochemical differences underlying susceptibility or resistance to development of AIDS will likely provide a basis for discovering and/or designing agents that can provide prevention and/or therapy for HIV infection progressing to AIDS. These differences could also be used in developing diagnostic reagents and/or biomedical research tools. For example, identification of proteins which confer resistance may allow development of diagnostic reagents or biomedical research tools based upon the disruption of the disease pathway of which the resistant protein plays a part.

Generally, the methods described herein entail (a) comparing human protein-coding polynucleotide sequences to that of an AIDS resistant non-human primate (such as chimpanzee), wherein the human protein coding polynucleotide sequence is associated with development of AIDS; and (b) selecting those human protein-coding polynucleotide sequences having evolutionarily significant changes that may be associated with susceptibility to development of AIDS. In another embodiment, the methods entail (a) comparing human protein-coding polynucleotide sequences to that of an AIDS-resistant non-human primate (such as chimpanzee), wherein the human protein coding polynucleotide sequence is associated with development of AIDS; and (b) selecting those non-human primate protein-coding polynucleotide sequences having evolutionarily significant changes that may be associated with resistance to development of AIDS.

As is evident, the methods described herein can be applied to other infectious diseases. For example, the methods could be used in a situation in which a non-human primate is known or believed to have harbored the infectious disease for a significant period (i.e., a sufficient time to have allowed positive selection) and is resistant to development of the disease. Thus, in other embodiments, the invention provides methods for identifying a polynucleotide sequence encoding a polypeptide, wherein said polypeptide may be associated with resistance to development of an infectious disease, comprising the steps of: (a) comparing infectious disease-resistant non-human primate protein coding sequences to human protein coding sequences, wherein the human protein coding sequence is associated with development of the infectious disease; and (b) selecting an infectious disease-resistant non-human primate sequence that contains at least one nucleotide change as compared to the corresponding human sequence, wherein the nucleotide change is evolutionarily significant. In another embodiment, the invention provides methods for identifying a human polynucleotide sequence encoding a polypeptide, wherein said polypeptide may be associated with susceptibility to development of an infectious disease, comprising the steps of: (a) comparing human protein coding sequences to protein-coding polynucleotide sequences of an infectious disease-resistant non-human primate, wherein the human protein coding sequence is associated with development of the infectious disease; and (b) selecting a human polynucleotide sequence that contains at least one nucleotide change as compared to the corresponding sequence of an infectious disease-resistant non-human primate, wherein the nucleotide change is evolutionarily significant.

In the present invention, human sequences to be compared with a homologue from an AIDS-resistant non-human primate are selected based on their known or implicated association with HIV propagation (i.e., replication), dissemination and/or subsequent progression to AIDS. Such knowledge is obtained, for example, from published literature and/or public databases (including sequence databases such as GenBank). Because the pathway involved in development of AIDS (including viral replication) involves many genes, a number of suitable candidates may be tested using the methods of this invention. Table 1 contains a exemplary list of genes to be examined. The sequences are generally known in the art.

TABLE 1

Sample List of Human Genes to be/have been Examined

| Gene | Function |
|---|---|
| eIF-5A | initiation factor |
| hPC6A | protease |
| hPC6B | protease |
| $P56^{lck}$ | Signal transduction |
| FK506-binding protein | Immunophilin |
| calnexin | ? |
| Bax | PCD promoter |
| bcl-2 | apoptosis inhibitor |
| lck | tyrosine kinase |
| MAPK (mitogen activated protein kinase) | protein kinase |
| CD43 | sialoglycoprotein |
| CCR2B | chemokine receptor |
| CCR3 | chemokine receptor |
| Bonzo | chemokine receptor |
| BOB | chemokine receptor |
| GPR1 | chemokine receptor |
| stromal-derived factor-1 (SDF-1) | chemokine |
| tumor-necrosis factor-α (TNF-α) | PCD promoter |
| TNF-receptor II (TNFRII) | receptor |
| interferon γ (IFN-γ) | cytokine |
| interleukin 1 α(IL-1 α) | cytokine |
| interleukin 1β(IL-1 β) | cytokine |
| interleukin 2 (IL-2) | cytokine |
| interleukin 4 (IL-4) | cytokine |
| interleukin 6 (IL-6) | cytokine |
| interleukin 10 (IL-10) | cytokine |
| interleukin 13 (IL-13) | cytokine |
| B7 | signaling protein |
| macrophage colony-stimulating factor (M-CSF) | cytokine |
| granulocyte-macrophage colony-stimulating factor | cytokine |
| phosphatidylinositol 3-kinase (PI 3-kinase) | kinase |
| phosphatidylinositol 4-kinase (PI 4-kinase) | kinase |
| HLA class I α chain | histocompatibility antigen |
| $\beta_2$ microglobulin | lymphocyte antigen |
| CD55 | decay-accelerating factor |
| CD63 | glycoprotein antigen |
| CD71 | ? |
| interferon α (IFN-α) | cytokine |
| CD44 | cell adhesion |
| CD8 | glycoprotein |

TABLE 1-continued

Sample List of Human Genes to be/have been Examined

| Gene | Function |
|---|---|
| Genes already examined (13) | |
| ICAM-1 | Immune system |
| ICAM-2 | Immune system |
| ICAM-3 | Immune system |
| leukocyte associated function 1 molecule α (LFA-1) | Immune system |
| leukocyte associated function 1 molecule β (LFA- 1) | Immune system |
| Mac-1 α | Immune system |
| Mac-1 β (equivalent to LFA-1 β) | Immune system |
| DC-SIGN | Immune system |
| CD59 | complement protein |
| CXCR4 | chemokine receptor |
| CCR5 | chemokine receptor |
| MIP-1α | chemokine |
| MIP-1β | chemokine |
| RANTES | chemokine |

Aligned protein-coding sequences of human and an AIDS resistant non-human primate such as chimpanzee are analyzed to identify nucleotide sequence differences at particular sites. The detected sequence changes are generally, and preferably, initially checked for accuracy as described above. The evolutionarily significant nucleotide changes, which are detected by molecular evolution analysis such as the $K_A/K_S$ analysis, can be further assessed to determine whether the non-human primate gene or the human gene has been subjected to positive selection. For example, the identified changes can be tested for presence/absence in other AIDS-resistant non-human primate sequences. The sequences with at least one evolutionarily significant change between human and one AIDS-resistant non-human primate can be used as primers for PCR analysis of other non-human primate protein-coding sequences, and resulting polynucleotides are sequenced to see whether the same change is present in other non-human primates. These comparisons allow further discrimination as to whether the adaptive evolutionary changes are unique to the AIDS-resistant non-human primate (such as chimpanzee) as compared to other non-human primates. For example, a nucleotide change that is detected in chimpanzee but not other primates more likely represents positive selection on the chimpanzee gene. Other non-human primates used for comparison can be selected based on their phylogenetic relationships with human. Closely related primates can be those within the hominoid sublineage, such as chimpanzee, bonobo, gorilla, and orangutan. Non-human primates can also be those that are outside the hominoid group and thus not so closely related to human, such as the Old World monkeys and New World monkeys. Statistical significance of such comparisons may be determined using established available programs, e.g., t-test as used by Messier and Stewart (1997) *Nature* 385: 151–154.

Furthermore, sequences with significant changes can be used as probes in genomes from different humans to see whether the sequence changes are shared by more than one individual. For example, certain individuals are slower to progress to AIDS ("slow progressers") and comparison (a) between a chimpanzee sequence and the homologous sequence from the slow-progresser human individual and/or (b) between an AIDS-susceptible individual and a slow-progresser individual would be of interest. Gene sequences from different human populations can be obtained from databases made available by, for example, the human genome diversity project or, alternatively, from direct sequencing of PCR-amplified DNA from a number of unrelated, diverse human populations. The presence of the identified changes in human slow progressers would further indicate the evolutionary significance of the changes.

As is exemplified herein, the CD59 protein, which has been associated with the chimpanzee's resistance to the progression of AIDS, exhibits an evolutionarily significant nucleotide change relative to human CD59. CD59 (also known as protectin, 1F-5Ag, H 19, HRF20, MACIF, MIRL and P-18) is expressed on peripheral blood leukocytes and erythrocytes, and functions to restrict lysis of human cells by complement (Meri et al. (1996) *Biochem. J.* 316:923). More specifically, CD59 acts as an inhibitor of membrane attack complexes, which are complement proteins that make hole-like lesions in the cell membranes. Thus, CD59 protects the cells of the body from the complement arm of its own defense system (Meri et al., supra). The chimpanzee homolog of this protein was examined because the human homolog has been implicated in the progression of AIDS in infected individuals. It has been shown that CD59 is one of the host cell derived proteins that is selectively taken up by HIV virions (Frank et al. (1996) *AIDS* 10:1611). Additionally, it has been shown that HIV virions that have incorporated host cell CD59 are protected from the action of complement. Thus, in humans, HIV uses CD59 to protect itself from attack by the victim's immune system, and thus to further the course of infection. As is theorized in the examples, positively-selected chimpanzee CD59 may constitute the adaptive change that inhibits disease progression. The virus may be unable to usurp the chimpanzee's CD59 protective role, thereby rendering the virus susceptible to the chimpanzee's immune system.

As is further exemplified herein, the DC-SIGN protein has also been determined to be positively selected in the chimpanzee as compared to humans and gorilla. DC-SIGN is expressed on dendritic cells and has been documented to provide a mechanism for travel of the HIV-1 virus to the lymph nodes where it infects undifferentiated T cells (Geijtenbeek, T. B. H. et al. (2000) *Cell* 100:587–597). Infection of the T cells ultimately leads to compromise of the immune system and subsequently to full-blown AIDS. The HIV-1 virus binds to the extracellular portion of DC-SIGN, and then gains access to the T cells via their CD4 proteins. DC-SIGN has as its ligand ICAM-3, which has a very high $K_A/K_S$ ratio. It may be that the positive selection on chimpanzee ICAM-3 was a result of compensatory changes to permit continued binding to DC-SIGN. As is theorized in the examples, positively-selected chimpanzee DC-SIGN may constitute another adaptive change that inhibits disease progression. Upon resolution of the three-dimensional structure of chimpanzee DC-SIGN and identification of the mechanism by which HIV-1 is prevented from binding to DC-SIGN, it may be possible to design drugs to mimic the effects of chimpanzee DC-SIGN without disrupting the normal functions of human DC-SIGN.

Description of the HCV Embodiment (an Example of a Positively Selected Non-Human Trait)

Some four million Americans are infected with the hepatitis C virus (HCV), and worldwide, the number approaches 40 million (Associated Press, Mar. 11, 1999). Many of these victims are unaware of the infection, which can lead to hepatocellular carcinoma. This disease is nearly always fatal. Roughly 14,500 Americans die each year as a result of the effects of hepatocellular carcinoma (Associated Press, Mar. 11, 1999). Thus identification of therapeutic agents that can ameliorate the effects of chronic infection are valuable both from an ethical and commercial viewpoint.

The chimpanzee is the only organism, other than humans, known to be susceptible to HCV infection (Lanford, R. E. et al. (1991) J. Med. Virol. 34:148–153). While the original host population for HCV has not yet been documented, it is likely that the virus must have originated in either humans or chimpanzees, the only two known susceptible species. It is known that the continent-of-origin for HCV is Africa (personal communication, A. Siddiqui, University of Colorado Health Science Center, Denver). If the chimpanzee population were the original host for HCV, as many HCV researchers believe (personal communication, A. Siddiqui, University of Colorado Health Science Center), then, as is known to be true for the HIV virus, chimpanzees would likely have evolved resistance to the virus. This hypothesis is supported by the well-documented observation that HCV-infected chimpanzees are refractory to the hepatic damage that often occurs in hepatitis C-infected humans (Walker, C. M (1997) Springer Semin. Immunopathol. 19:85–98; McClure, H. M., pp. 121–133 in *The Role of the Chimpanzee in Research*, ed. by Eder, G. et al., 1994, Basel: Karger; Agnello, V. et al. (1998) Hepatology 28:573–584). In fact, although in 2% of HCV-infected humans, the disease course leads to hepatocellular carcinoma, HCV-infected chimpanzees do not develop these tumors (Walker, C. M (1997) Springer Semin. Immunopathol. 19:85–98). Further support for the hypothesis that chimpanzees were the original host population, and that they have, as a result of prolonged experience with the virus, evolved resistance to the ravages of HCV-induced disease, is added by the observation that HCV-infected chimpanzees in general have a milder disease course (i.e., not simply restricted to hepatic effects) than do humans (Lanford, R. E. et al. (1991) J. Med. Virol. 34:148–153; and Walker, C. M (1997) Springer Semin. Immunopathol. 19:85–98).

As is exemplified herein, the p44 gene in chimpanzees has been positively selected relative to its human homolog. The p44 protein was first identified in liver tissues of chimpanzees experimentally infected with HCV (Shimizu, Y. et al. (1985) PNAS USA 82:2138).

The p44 gene, and the protein it codes for, represents a potential therapeutic target, or alternatively a route to a therapeutic, for humans who are chronically infected with hepatitis C. The protein coded for by this gene in chimpanzees is known to be up-regulated in chimpanzee livers after experimental infection of captive chimpanzees (Takahashi, K. et al. (1990) J. Gen. Virol. 71:2005–2011). The p44 gene has been shown to be a member of the family of $\alpha/\beta$ interferon inducible genes (Kitamura, A. et al. (1994) Eur. J. Biochem. 224:877–883). It is suspected that the p44 protein is a mediator in the antiviral activities of interferon.

This is most suggestive, since as noted above, HCV-infected chimpanzees have been documented to be refractory to the hepatic damage that often occurs in HCV-infected humans. The combination of the observations that this protein is only expressed in chimpanzee livers after hepatitis C infection, the fact that chimpanzees are refractory to the hepatic damage that can occur in humans (Agnello, V. et al. (1998) Hepatology 28:573–584), the observation that HCV-infected chimpanzees in general have a milder disease course than do humans, and that the p44 gene has been positively selected in chimpanzees, strongly suggest that the chimpanzee p44 protein confers resistance to hepatic damage in chimpanzees. Whether the protein is responsible for initiating some type of cascade in chimpanzees that fails to occur in infected humans, or whether the selected chimpanzee homolog differs in some critical biochemical functions from its human homolog, is not yet clear. It has been speculated that the milder disease course observed in chimpanzees may be due in part to lower levels of viral replication (Lanford, R. E. et al. (1991) J. Med. Virol. 34:148–153).

This invention includes the medical use of the specific amino acid residues by which chimpanzee p44 differs from human p44. These residues that were positively selected during the period in which chimpanzees evolved an accommodation to the virus, allow the intelligent design of an effective therapeutic approach for chronically HCV-infected humans. Several methods to induce a chimpanzee-like response in infected humans will be apparent to one skilled in the art. Possibilities include the intelligent design of a small molecule therapeutic targeted to the human homolog of the specific amino acid residues selected in chimpanzee evolution. Use of molecular modeling techniques might be valuable here, as one could design a small molecule that causes the human protein to mimic the three-dimensional structure of the chimpanzee protein. Another approach would be the design of a small molecule therapeutic that induces a chimpanzee-like functional response in human p44. Again, this could only be achieved by use of the knowledge obtained by this invention, i.e., which amino acid residues were positively selected to confer resistance to HCV in chimpanzees. Other possibilities will be readily apparent to one skilled in the art.

In addition to screening candidate agents for those that may favorably interact with the human p44 (exon 2) polypeptide so that it may mimic the structure and/or function of chimpanzee p44, the subject invention also concerns the screening of candidate agents that interact with the human p44 polynucleotide promoter, whereby the expression of human p44 may be increased so as to improve the human patient's resistance to HCV infection. Thus, the subject invention includes a method for identifying an agent that modulates expression of a human's p44 polynucleotide, by contacting at least one candidate agent with the human's p44 polynucleotide promoter, and observing whether expression of the human p44 polynucleotide is enhanced. The human p44 promoter has been published in Kitamura et al. (1994) Eur. J. Biochem. 224:877 (FIG. 4).

Description of the Breast Enhancement Embodiment (an Example of a Positively Selected Human Trait)

Relative to non-human primates, female humans exhibit pre-pregnancy, pre-lactation expanded breast tissue. As is discussed in the Examples, this secondary sex characteristic is believed to facilitate evolved behaviors in humans associated with long term pair bonds and long-term rearing of infants. One aspect of this invention concerns identifying those human genes that have been positively selected in the development of enlarged breasts. Specifically, this invention includes a method of determining whether a human polynucleotide sequence which has been associated with enlarged breasts in humans has undergone evolutionarily significant change relative to a non-human primate that does not manifest enlarged breasts, comprising: a) comparing the human polynucleotide sequence with the corresponding non-human primate polynucleotide sequence to identify any nucleotide changes; and b) determining whether the human nucleotide changes are evolutionarily significant.

It has been found that the human BRCA1 gene, which has been associated with normal breast development in humans, has been positively selected relative to the BRCA1 gene of chimpanzees and other non-human primates. The identified evolutionarily significant nucleotide changes could be useful in developing agents that can modulate the function of the BRCA1 gene or protein.

Therapeutic Compositions that Comprise Agents

As described herein, agents can be screened for their capacity to increase or decrease the effectiveness of the positively selected polynucleotide or polypeptide identified according to the subject methods. For example, agents that may be suitable for enhancing breast development may include those which interact directly with the BRCA1 protein or its ligand, or which block inhibitors of BRCA1 protein. Alternatively, an agent may enhance breast development by increasing BRCA1 expression. As the mechanism of BRCA1 is further elucidated, strategies for enhancing its efficacy can be devised.

In another example, agents that may be suitable for reducing the progression of AIDS could include those which directly interact with the human CD59 protein in a manner to make the protein unusable to the HIV virion, possibly by either rendering the human CD59 unsuitable for packing in the virion particle or by changing the orientation of the protein with respect to the cell membrane (or via some other mechanism). The candidate agents can be screened for their capacity to modulate CD59 function using an assay in which the agents are contacted with HIV infected cells which express human CD59, to determine whether syncytia formation or other indicia of the progression of AIDS are reduced. The assay may permit the detection of whether the HIV virion can effectively pack the CD59 and/or utilize the CD59 to inhibit attack by MAC complexes.

One agent that may slow AIDS progression is a human CD59 that has been modified to have multiple GPI links. As described herein, chimp CD59, which contains three GPI links as compared to the single GPI link found in human CD59, slows progression of HIV infections in chimps. Preferably, the modified human CD59 contains three GPI links in tandem.

Another example of an agent that may be suitable for reducing AIDS progression is a compound that directly interacts with human DC-SIGN to reduce its capacity to bind to HIV-1 and transport it to the lymph nodes. Such an agent could bind directly to the HIV-1 binding site on DC-SIGN. The candidate agents can be contacted with dendritic cells expressing DC-SIGN or with a purified extracellular fragment of DC-SIGN and tested for their capacity to inhibit HIV-1 binding.

Various delivery systems are known in the art that can be used to administer agents identified according to the subject methods. Such delivery systems include aqueous solutions, encapsulation in liposomes, microparticles or microcapsules or conjugation to a moiety that facilitates intracellular admission.

Therapeutic compositions comprising agents may be administered parenterally by injection, although other effective administration forms, such as intra-articular injection, inhalant mists, orally-active formulations, transdermal iontophoresis or suppositories are also envisioned. The carrier may contain other pharmacologically-acceptable excipients for modifying or maintaining the pH, osmolarity, viscosity, clarify, color, sterility, stability, rate of dissolution, or odor of the formulation. The carrier may also contain other pharmacologically-acceptable excipients for modifying or maintaining the stability, rate of dissolution, release or absorption of the agent. Such excipients are those substances usually and customarily employed to formulate dosages for parenteral administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or requiring reconstitution immediately prior to administration. The manner of administering formulations containing agents for systemic delivery may be via subcutaneous, intramuscular, intravenous, intranasal or vaginal or rectal suppository. Alternatively, the formulations may be administered directly to the target organ (e.g., breast).

The amount of agent which will be effective in the treatment of a particular disorder or condition will depend on the nature of the disorder or condition, which can be determined by standard clinical techniques. In addition, in vitro or in vivo assays may optionally be employed to help identify optimal dosage ranges. The precise dose to be employed in the formulation will also depend on the route of administration, and the seriousness or advancement of the disease or condition, and should be decided according to the practitioner and each patient's circumstances. Effective doses may be extrapolated from dose-response curves derived from in vitro or animal model test systems. For example, an effective amount of an agent identified according to the subject methods is readily determined by administering graded doses of a bivalent compound of the invention and observing the desired effect.

Description of a Method for Obtaining Candidate Polynucleotides that May be Associated with Human Diseases, and Diagnostic Methods Derived Therefrom According to the subject invention, BRCA1 exon 11 is an evolutionarily significant polynucleotide that has undergone positive selection in humans relative to chimpanzees, and is associated with the enhanced breast development observed in humans relative to chimpanzees (see Example 14). Exon 11 has also been found to have mutations that are associated with the development of breast cancer. BRCA1 exon 11 mutations are known to be associated with both familial and spontaneous breast cancers (Kachhap, S. K. et al. (2001) Indian J. Exp. Biol. 39(5):391–400; Hadjisavvas, A. et al. (2002) Oncol. Rep. 9(2):383–6; Khoo, U. S. et al. (1999) Oncogene 18(32):4643–6).

Encompassed within the subject invention are methods that are based on the principle that human polynucleotides that are evolutionarily significant relative to a non-human primate, and which are associated with a improved physiological condition in the human, may also be associated with decreased resistance or increased susceptibility to one or more diseases. In one embodiment, mutations in positively selected human BRCA1 polynucleotide exon 11 may be linked to elevated risk of breast, ovarian and/or prostate cancer. This phenomenon may represent a trade-off between enhanced development of one trait and loss or reduction in another trait in polynucleotides encoding polypeptides of multiple functions. In this way, identification of positively selected human polynucleotides can serve to identify a pool of genes that are candidates for susceptibility to human diseases.

Thus, in one embodiment, the subject invention provides a method for obtaining a pool of candidate polynucleotides that are useful in screening for identification of polynucleotides associated with increased susceptibility or decreased resistance to one or more human diseases. The method of identifying the candidate polynucleotides comprises comparing the human polynucleotide sequences with non-human primate polynucleotide sequences to identify any nucleotide changes, and determining whether those nucleotide changes are evolutionarily significant. Evolutionary significance can be determined by any of the methods described herein including the $K_A/K_S$ method. Because evolutionary significance involves the number of non-silent nucleotide changes over a defined length of polynucleotide, it is the polynucleotide containing the group of nucleotide changes that is referred to herein as "evolutionarily significant." That is, a single nucleotide change in a human polynucleotide relative to a non-human primate cannot be analyzed for evolutionary significance without considering the length of the polynucleotide and the existence or (non-existence) of other non-silent nucleotide changes in the defined polynucleotide. Thus, in referring to an "evolutionarily significant polynucleotide" and the nucleotide changes therein, the size of the polynucleotide is generally considered to be between about 30 and the total number of nucleotides encompassed in the polynucleotide or gene sequence (e.g., up to 3,000–5,000 nucleotides or longer). Further, while individual nucleotide changes cannot be analyzed in isolation as to their evolutionary significance, nucleotide changes that contribute to the evolutionary significance of a polynucleotide are referred to herein as "evolutionarily significant nucleotide changes."

The subject method further comprises a method of correlating an evolutionarily significant nucleotide change in a candidate polynucleotide to decreased resistance to development of a disease in humans, comprising identifying evolutionarily significant candidate polynucleotides as described herein, and further analyzing the functional effect of the evolutionarily significant nucleotide change(s) in one or more of the candidate polynucleotides in a suitable model system, wherein the presence of a functional effect indicates a correlation between the evolutionarily significant nucleotide change in the candidate polynucleotide and the decreased resistance to development of the disease in humans. As discussed herein, model systems may be cell-based or in vivo. For example, the evolutionarily significant human BRCA1 exon 11 (or variations thereof having fewer evolutionarily significant nucleotide changes) could be transfected or knock-out genomically inserted into mice or non-human primates (e.g., chimpanzees) to determine if it induces the functional effect of breast, ovarian or prostate cancer in the test animals. Such test results would indicate whether specific evolutionarily significant changes in exon 11 are associated with increased incidence of breast, ovarian or prostate cancer.

In addition to evaluating the evolutionarily significant nucleotide changes in candidate polynucleotides for their relevance to development of disease, the subject invention also includes the evaluation of other nucleotide changes of candidate human polynucleotides, such as alleles or mutant polynucleotides, that may be responsible for the development of the disease. For example, the evolutionarily significant BRCA1 exon 11 has a number of allelic or mutant exon 11s in human populations that have been found to be associated with breast, ovarian or prostate cancer (Rosen, E. M. et al. (2001) Cancer Invest. 19(4):396–412; Elit, L. et al. (2001) Int. J. Gynecol. Cancer 11(3):241–3; Shen, D. et al. (2000) J. Natl. Med. Assoc. 92(1):29–35; Khoo, U. S. et al. (1999) Oncogene 18(32):4643–6; Presneau, N. et al. (1998) Hum. Genet. 103(3):334–9; Dong, J. et al. (1998) Hum. Genet. 103(2):154–61; and Xu, C. F. et al. (1997) Genes Chromosomes 18(2):102–10). For example, Grade, K. et al. (1996) J. Cancer Res. Clin. Oncol. 122(11):702–6, report that of 127 human BRCA1 mutations published by 1996, 55% of them are localized in exon 11. Many of the cancer-causing mutations in BRCA1 exon 11 are not considered to be predominantly present in humans, and are therefore not considered to contribute to the evolutionarily significance of BRCA1 exon 11. Polynucleotides that are strongly positively selected for the development of one trait in humans may be hotspots for nucleotide changes (evolutionarily significant or otherwise) that are associated with the development of a disease. Thus, according to the subject invention, identification of candidate polynucleotides that have been positively selected, is a very efficient start to identifying corresponding mutant or allelic polynucleotides associated with a disease.

To identify whether mutants or alleles of evolutionarily significant polynucleotides in humans can be correlated to decreased resistance or increased susceptibility to the disease, the variant polynucleotide can be tested in a suitable model, such as the MCF10a normal human epithelial cell line (Favy, DA et al. (2001) Biochem. Biophys. Res. Commun. 274(1):73–8). This model system for breast cancer can involve transfection of or knock-out genomic insertion into the MCF10a normal human breast epithelial cell line with mutant or allelic BRCA1 exon 11 polynucleotides to determine whether the nucleotide changes in the mutant or allelic polynucleotides result in conversion of the cell line to a neoplastic phenotype, i.e., a phenotype similar to cancer cell lines MCF-7, MDA-MB231 or HBL100 (Favy et al., supra). Additionally, mutants of candidate polynucleotides can be compared to patient genetic data to determine whether, for example, BRCA1 exon 11 mutant nucleotide changes are present in familial and/or sporadic breast, ovarian and/or prostate tumors. In this way, mutations in candidate evolutionarily significant human polynucleotides can be evaluated for their functional effect and their correlation to development of breast, ovarian and/or prostate cancer in humans.

The following examples are provided to further assist those of ordinary skill in the art. Such examples are intended to be illustrative and therefore should not be regarded as limiting the invention. A number of exemplary modifications and variations are described in this application and others will become apparent to those of skill in this art. Such variations are considered to fall within the scope of the invention as described and claimed herein.

EXAMPLES

Example 1 cDNA Library Construction

A chimpanzee cDNA library is constructed using chimpanzee tissue. Total RNA is extracted from the tissue (RNeasy kit, Quiagen; RNAse-free Rapid Total RNA kit, 5 Prime-3 Prime, Inc.) and the integrity and purity of the RNA are determined according to conventional molecular cloning methods. Poly A+ RNA is isolated (Mini-Oligo(dT) Cellulose Spin Columns, 5 Prime-3 Prime, Inc.) and used as template for the reverse-transcription of cDNA with oligo (dT) as a primer. The synthesized cDNA is treated and modified for cloning using commercially available kits. Recombinants are then packaged and propagated in a host cell line. Portions of the packaging mixes are amplified and the remainder retained prior to amplification. The library can be normalized and the numbers of independent recombinants in the library is determined.

Example 2

Sequence Comparison

Suitable primers based on a candidate human gene are prepared and used for PCR amplification of chimpanzee cDNA either from a cDNA library or from cDNA prepared from mRNA. Selected chimpanzee cDNA clones from the cDNA library are sequenced using an automated sequencer, such as an ABI 377. Commonly used primers on the cloning vector such as the M13 Universal and Reverse primers are used to carry out the sequencing. For inserts that are not completely sequenced by end sequencing, dye-labeled terminators are used to fill in remaining gaps.

The detected sequence differences are initially checked for accuracy, for example by finding the points where there are differences between the chimpanzee and human sequences; checking the sequence fluorogram (chromatogram) to determine if the bases that appear unique to human correspond to strong, clear signals specific for the called base; checking the human hits to see if there is more than one human sequence that corresponds to a sequence change; and other methods known in the art, as needed. Multiple human sequence entries for the same gene that have the same nucleotide at a position where there is a different chimpanzee nucleotide provides independent support that the human sequence is accurate, and that the chimpanzee/human difference is real. Such changes are examined using public database information and the genetic code to determine whether these DNA sequence changes result in a change in the amino acid sequence of the encoded protein. The sequences can also be examined by direct sequencing of the encoded protein.

Example 3

Molecular Evolution Analysis

The chimpanzee and human sequences under comparison are subjected to $K_A/K_S$ analysis. In this analysis, publicly available computer programs, such as Li 93 and INA, are used to determine the number of non-synonymous changes per site ($K_A$) divided by the number of synonymous changes per site ($K_S$) for each sequence under study as described above. Full-length coding regions or partial segments of a coding region can be used. The higher the $K_A/K_S$ ratio, the more likely that a sequence has undergone adaptive evolution. Statistical significance of $K_A/K_S$ values is determined using established statistic methods and available programs such as the t-test.

To further lend support to the significance of a high $K_A/K_S$ ratio, the sequence under study can be compared in multiple chimpanzee individuals and in other non-human primates, e.g., gorilla, orangutan, bonobo. These comparisons allow further discrimination as to whether the adaptive evolutionary changes are unique to the human lineage compared to other non-human primates. The sequences can also be examined by direct sequencing of the gene of interest from representatives of several diverse human populations to assess to what degree the sequence is conserved in the human species.

Example 4

Identification of Positively Selected ICAM-1, ICAM-2 and ICAM-3

Using the methods of the invention described herein, the intercellular adhesion molecules ICAM-1, ICAM-2 and ICAM-3 have been shown to have been strongly positively selected. The ICAM molecules are involved in several immune response interactions and are known to play a role in progression to AIDS in HIV infected humans. The ICAM proteins, members of the Ig superfamily, are ligands for the integrin leukocyte associated function 1 molecule (LFA-1). Makgoba et al. (1988) *Nature* 331:86–88. LFA-1 is expressed on the surface of most leukocytes, while ICAMs are expressed on the surface of both leukocytes and other cell types. Larson et al (1989) *J. Cell Biol.* 108:703–712. ICAM and LFA-1 proteins are involved in several immune response interactions, including T-cell function, and targeting of leukocytes to areas of inflammation. Larson et al. (1989).

Total RNA was prepared using either the RNeasy® kit (Qiagen), or the RNAse-free Rapid Total RNA kit (5 Prime-3 Prime, Inc.) from primate tissues (chimpanzee brain and blood, gorilla blood and spleen, orangutan blood) or from cells harvested from the following B lymphocyte cell lines: CARL (chimpanzee), ROK (gorilla), and PUTI (orangutan). mRNA was isolated from total RNA using the Mini-Oligo(dT) Cellulose Spin Columns (5 Prime-3 Prime, Inc.). cDNA was synthesized from mRNA with oligo dT and/or random priming using the cDNA Synthesis Kit (Stratagene®). The protein-coding region of the primate ICAM-1 gene was amplified from cDNA using primers (concentration=100 nmole/μl) designed by hand from the published human sequence. PCR conditions for ICAM-1 amplification were 94° C. initial pre-melt (4 min), followed by 35 cycles of 94° C. (15 sec), 58° C. (1 min 15 sec), 72° C. (1 min 15 sec), and a final 72° C. extension for 10 minutes. PCR was accomplished using Ready-to-Go™ PCR beads (Amersham Pharmacia Biotech) in a 50 microliter total reaction volume. Appropriately-sized products were purified from agarose gels using the QiaQuick® Gel Extraction kit (Qiagen). Both strands of the amplification products were sequenced directly using the Big Dye Cycle Sequencing Kit and analyzed on a 373A DNA sequencer (ABI BioSystems).

Comparison of the protein-coding portions of the human, gorilla (*Gorilla gorilla*), and orangutan (*Pongo pygmaeus*) ICAM-1 genes to that of the chimpanzee yielded statistically significant $K_A/K_S$ ratios (Table 2). The protein-coding portions of the human and chimpanzee ICAM-1 genes were previously published and the protein-coding portions of gorilla (*Gorilla gorilla*), and orangutan (*Pongopy gmaeus*) ICAM-1 genes are shown in FIGS. 3 and 4, respectively.

For this experiment, pairwise $K_A/K_S$ ratios were calculated for the mature protein using the algorithm of Li (1985; 1993). Statistically significant comparisons (determined by t-tests) are shown in bold. Although the comparison to gorilla and human was sufficient to demonstrate that chimpanzee ICAM-1 has been positively-selected, the orangutan ICAM-1 was compared as well, since the postulated historical range of gorillas in Africa suggests that gorillas could have been exposed to the HIV-1 virus. Nowak and Paradiso (1983) *Walker's Mammals of the World* (Baltimore, Md., The Johns Hopkins University Press). The orangutan, however, has always been confined to Southeast Asia and is thus unlikely to have been exposed to HIV over an evolutionary time frame. (Nowak and Paradiso, 1983) (Gorillas are most closely-related to humans and chimpanzees, while orangutans are more distantly-related.)

TABLE 2

$K_A/K_S$ Ratios: ICAM-1 Whole Protein Comparisons

| Species Compared | $K_A/K_S$ Ratio |
| --- | --- |
| Chimpanzee to Human | 2.1 (P < 0.01) |
| Chimpanzee to Gorilla | 1.9 (P < 0.05) |
| Chimpanzee to Orangutan | 1.4 (P < 0.05) |
| Human to Gorilla | 1.0 |
| Human to Orangutan | 0.87 |
| Gorilla to Orangutan | 0.95 |

Even among those proteins for which positive selection has been demonstrated, few show $K_A/K_S$ ratios as high as these ICAM-1 comparisons. Lee and Vacquier (1992) *Biol. Bull.* 182:97–104; Swanson and Vacquier (1995) *Proc. Natl. Acad. Sci. USA* 92:4957–4961; Messier and Stewart (1997); Sharp (1997) *Nature* 385:111–112. The results are consistent with strong selective pressure resulting in adaptive changes in the chimpanzee ICAM-1 molecule.

The domains (D1 and D2) of the ICAM-1 molecule which bind to LFA-1 have been documented. Staunton et al. (1990). *Cell* 61:243–254. Pairwise $K_A/K_S$ comparisons between primate ICAM-1 genes. $K_A/K_S$ ratios were calculated for domains D1 and D2 only, using the algorithm of Li (1985; 1993) (Table 3). Statistically significant comparisons (determined by t-tests) are shown in bold. The very high, statistically significant $K_A/K_S$ ratios for domains D1 and D2 suggest that these regions of the protein were very strongly positively-selected. These regions of chimpanzee ICAM-1 display even more striking $K_A/K_S$ ratios (Table 3) than are seen for the whole protein comparisons, thus suggesting that the ICAM-1/LFA-1 interaction has been subjected to unusually strong selective pressures.

TABLE 3

$K_A/K_S$ Ratios: Domains D1 + D2 of ICAM-1

| Species Compared | $K_A/K_S$ Ratio |
| --- | --- |
| Chimpanzee to Human | 3.1 (P < 0.01) |
| Chimpanzee to Gorilla | 2.5 (P < 0.05) |
| Chimpanzee to Orangutan | 1.5 (P < 0.05) |
| Human to Gorilla | 1.0 |
| Human to Orangutan | 0.90 |
| Gorilla to Orangutan | 1.0 |

Example 5

Characterization of ICAM-1, ICAM-2 and ICAM-3 Positively Selected Sequences

A sequence identified by the methods of this invention may be further tested and characterized by cell transfection experiments. For example, human cells in culture, when transfected with a chimpanzee polynucleotide identified by the methods described herein (such as ICAM-1 (or ICAM-2 or ICAM-3); see below), could be tested for reduced viral dissemination and/or propagation using standard assays in the art, and compared to control cells. Other indicia may also be measured, depending on the perceived or apparent functional nature of the polynucleotide/polypeptide to be tested. For example, in the case of ICAM-1 (or ICAM-2 or ICAM-3), syncytia formation may be measured and compared to control (untransfected) cells. This would test whether the resistance arises from prevention of syncytia formation in infected cells.

Cells which are useful in characterizing sequences identified by the methods of this invention and their effects on cell-to-cell infection by HIV-1 are human T-cell lines which are permissive for infection with HIV-1, including, e.g., H9 and HUT78 cell lines, which are available from the ATCC.

For cell transfection assays, ICAM-1 (or ICAM-2 or ICAM-3) cDNA (or any cDNA identified by the methods described herein) can be cloned into an appropriate expression vector. To obtain maximal expression, the cloned ICAM-1 (or ICAM-2 or ICAM-3) coding region is operably linked to a promoter which is active in human T cells, such as, for example, an IL-2 promoter. Alternatively, an ICAM-1 (or ICAM-2 or ICAM-3) cDNA can be placed under transcriptional control of a strong constitutive promoter, or an inducible promoter. Expression systems are well known in the art, as are methods for introducing an expression vector into cells. For example, an expression vector comprising an ICAM-1 (or ICAM-2 or ICAM-3) cDNA can be introduced into cells by DEAE-dextran or by electroporation, or any other known method. The cloned ICAM-1 (or ICAM-2 or ICAM-3) molecule is then expressed on the surface of the cell. Determination of whether an ICAM-1 (or ICAM-2 or ICAM-3) cDNA is expressed on the cell surface can be accomplished using antibody(ies) specific for ICAM-1 (or ICAM-2 or ICAM-3). In the case of chimpanzee ICAM-1 (or ICAM-2 or ICAM-3) expressed on the surface of human T cells, an antibody which distinguishes between chimpanzee and human ICAM-1 (or ICAM-2 or ICAM-3) can be used. This antibody can be labeled with a detectable label, such as a fluorescent dye. Cells expressing chimpanzee ICAM-1 (or ICAM-2 or ICAM-3) on their surfaces can be detected using fluorescence-activated cell sorting and the anti-ICAM-1 (or ICAM-2 or ICAM-3) antibody appropriately labeled, using well-established techniques.

Transfected human cells expressing chimpanzee ICAM-1 (or ICAM-2 or ICAM-3) on their cell surface can then be tested for syncytia formation, and/or for HIV replication, and/or for number of cells infected as an index of cell-to-cell infectivity. The chimpanzee ICAM-1 (or ICAM-2 or ICAM-3)-expressing cells can be infected with HIV-1 at an appropriate dose, for example tissue culture infectious dose 50, i.e., a dose which can infect 50% of the cells. Cells can be plated at a density of about $5 \times 10^5$ cells/ml in appropriate tissue culture medium, and, after infection, monitored for syncytia formation, and/or viral replication, and/or number of infected cells in comparison to control, uninfected cells. Cells which have not been transfected with chimpanzee ICAM-1 (or ICAM-2 or ICAM-3) also serve as controls. Syncytia formation is generally observed in HIV-1-infected cells (which are not expressing chimpanzee ICAM-1 (or ICAM-2 or ICAM-3)) approximately 10 days post-infection.

To monitor HIV replication, cell supernatants can be assayed for the presence and amount of p24 antigen. Any assay method to detect p24 can be used, including, for example, an ELISA assay in which rabbit anti-p24 antibodies are used as capture antibody, biotinylated rabbit anti-p24 antibodies serve as detection antibody, and the assay is developed with avidin-horse radish peroxidase. To determine the number of infected cells, any known method, including indirect immunofluorescence methods, can be used. In indirect immunofluorescence methods, human HIV-positive serum can be used as a source of anti-HIV antibodies to bind to infected cells. The bound antibodies can be detected using FITC-conjugated anti-human IgG, the cells visualized by fluorescence microscopy and counted.

Another method for assessing the role of a molecule such as ICAM-1 (or ICAM-2 or ICAM-3) involves successive infection of cells with HIV. Human cell lines, preferably those that do not express endogenous ICAM (although cell lines that do express endogenous ICAM may also be used), are transfected with either human or chimpanzee ICAM-1 or -2 or -3. In one set of experiments, HIV is collected from the supernatant of HIV-infected human ICAM-1 (or ICAM-2 or ICAM-3)-expressing cells and used to infect chimpanzee ICAM-1 (or ICAM-2 or ICAM-3)-expressing cells or human ICAM-1 (or ICAM-2 or ICAM-3)-expressing cells. Initial infectivity, measured as described above, of both the chimpanzee ICAM-1 (or ICAM-2 or ICAM-3)- and the human ICAM-1 (or ICAM-2 or ICAM-3)-expressing cells would be expected to be high. After several rounds of replication, cell to cell infectivity would be expected to decrease in the chimpanzee ICAM-1 (or ICAM-2 or ICAM-3) expressing cells, if chimpanzee ICAM-1 (or ICAM-2 or ICAM-3) confers resistance. In a second set of experiments, HIV is collected from the supernatant of HIV-infected chimpanzee ICAM-1 (or ICAM-2 or ICAM-3)-expressing cells, and used to infect human ICAM-1 (or ICAM-2 or ICAM-3)-expressing cells. In this case, the initial infectivity would be expected to be much lower than in the first set of experiments, if ICAM-1 (or ICAM-2 or ICAM-3) is involved in susceptibility to HIV progression. After several rounds of replication, the cell to cell infectivity would be expected to increase.

The identified human sequences can be used in establishing a database of candidate human genes that may be involved in conferring, or contributing to, AIDS susceptibility or resistance. Moreover, the database not only provides an ordered collection of candidate genes, it also provides the precise molecular sequence differences that exist between human and an AIDS-resistant non-human primate (such as chimpanzee) and thus defines the changes that underlie the functional differences.

Example 6

Molecular Modeling of ICAM-1 and ICAM-3

Modeling of the three-dimensional structure of ICAM-1 and ICAM-3 has provided additional evidence for the role of these proteins in explaining chimpanzee resistance to AIDS progression.

In the case of ICAM-1, 5 of the 6 amino acid replacements that are unique to the chimpanzee lineage are immediately adjacent (i.e., physically touching) to those amino acids identified by mutagenic studies as critical to LFA-1 binding. These five amino acid replacements are human L18 to chimp Q18, human K29 to chimp D29, human P45 to chimp G45, human R49 to chimp W49, and human E171 to chimp Q171. This positioning cannot be predicted from the primary structure (i.e., the actual sequence of amino acids). None of the amino acid residues critical for binding has changed in the chimpanzee ICAM-1 protein.

Such positioning argues strongly that the chimpanzee ICAM-1 protein's basic function is unchanged between humans and chimpanzees; however, evolution has wrought fine-tuned changes that may help confer upon chimpanzees their resistance to progression of AIDS. The nature of the amino acid replacements is being examined to allow exploitation of the three-dimensional structural information for developing agents for therapeutic intervention. Strikingly, 4 of the 5 chimpanzee residues are adjacent to critical binding residues that have been identified as N-linked glycosylation sites. This suggests that differences exist in binding constants (to LFA-1) for human and chimpanzee ICAM-1. These binding constants are being determined. Should the binding constants prove lower in chimpanzee ICAM-1, it is possible to devise small molecule agents to mimic (by way of steric hindrance) the change in binding constants as a potential therapeutic strategy for HIV-infected humans. Similarly, stronger binding constants, if observed for chimpanzee ICAM-1, will suggest alternative strategies for developing therapeutic interventions for HIV-1 infected humans.

In the case of ICAM-3, a critical amino acid residue replacement from proline (observed in seven humans) to glutamine (observed in three chimpanzees) is predicted from our modeling studies to significantly change the positional angle between domains 2 and 3 of human and chimpanzee ICAM-3. The human protein displays an acute angle at this juncture. Klickstein, et al., 1996 J. Biol. Chem. 27:239 20-27. Loss of this sharp angle (bend) is predicted to render chimpanzee ICAM-3 less easily packaged into HIV-1 virions (In infected humans, after ICAMs are packaged into HIV virions, cell-to-cell infectivity dramatically increases. Barbeau, B. et al., 1998 J. Virol. 72:7125–7136). This failure to easily package chimp ICAM-3 into HIV virions could then prevent the increase in cell-to-cell infectivity seen in infected humans. This would then account for chimpanzee resistance to AIDS progression.

A small molecule therapeutic intervention whereby binding of a suitably-designed small molecule to the human proline residue causes (as a result of steric hindrance) the human ICAM-1 protein to mimic the larger (i.e., less-acute) angle of chimpanzee ICAM-3 is possible. Conservation between the 2 proteins of the critical binding residues (and the general resemblance of immune responses between humans and chimpanzees) argues that alteration of this angle will not compromise the basic function of human ICAM-3. However, the human ICAM-3 protein would be rendered resistant to packaging into HIV virions, thus mimicking (in HIV-1 infected humans) the postulated pathway by which infected chimpanzees resist progression to AIDS.

Essentially the same procedures were used to identify positively selected chimpanzee ICAM-2 and ICAM-3 (see Table 4). The ligand binding domain of ICAM-1 has been localized as exhibiting especially striking positive selection in contrast to ICAMs-2 and -3, for which positive selection resulted in amino acid replacements throughout the protein. Thus, this comparative genomic analysis reveals that positive selection on ICAMs in chimpanzees has altered the proteins' primary structure, for example, in important binding domains. These alterations may have conferred resistance to AIDS progression in chimpanzees.

TABLE 4

$K_A/K_S$ Ratios: ICAM-2 and 3 Whole Protein Comparisons

| Species Compared | $K_A/K_S$ Ratio |
|---|---|
| Chimpanzee to Human ICAM-2 | 2.1 (P < 0.01) |
| Chimpanzee to Human ICAM-3 | 3.7 (P < 0.01) |

Figure 5B:
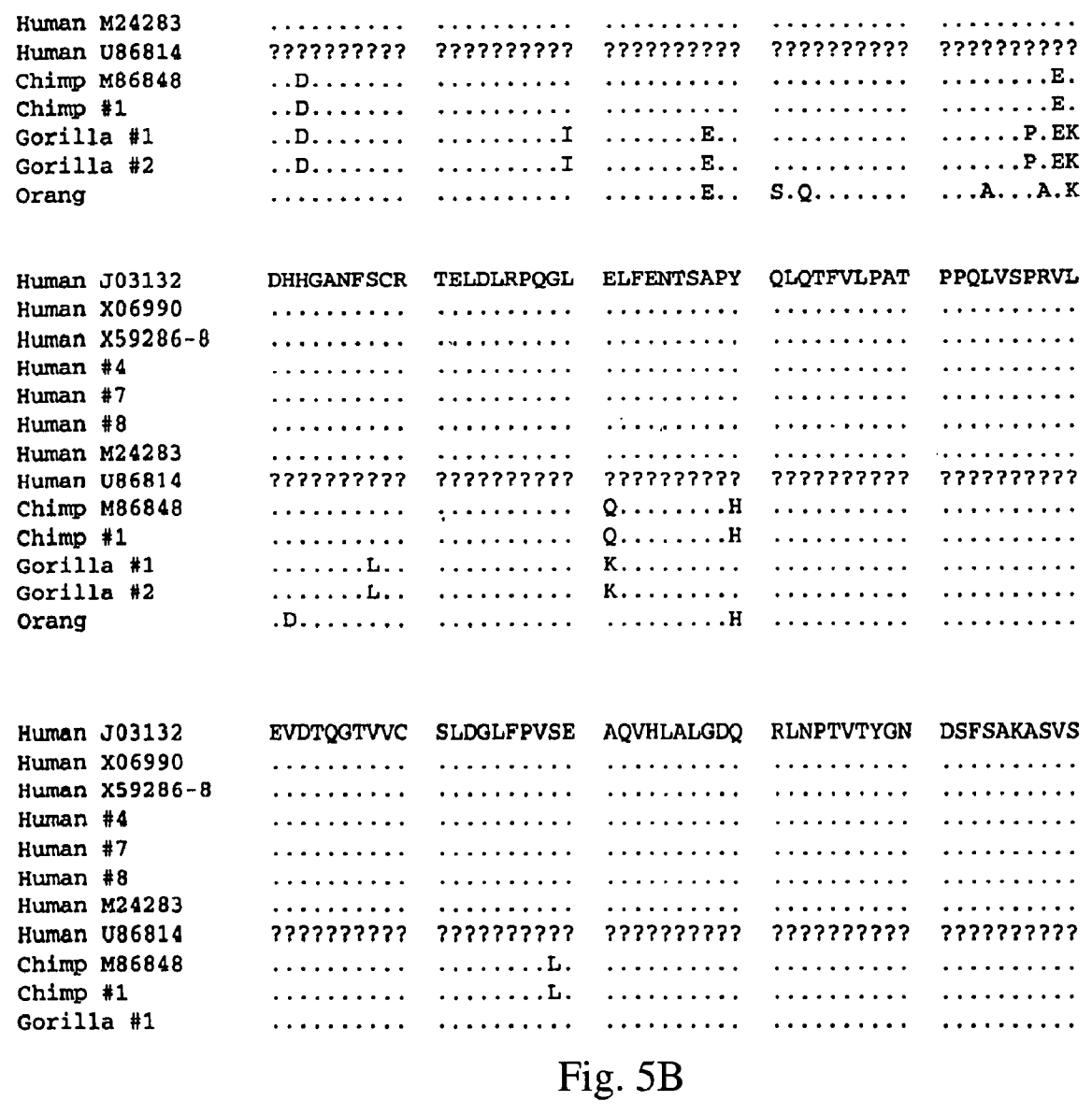

Binding of ICAM-1, -2, and -3 has been demonstrated to play an essential role in the formation of syncytia (i.e., giant, multi-nucleated cells) in HIV-infected cells in vitro. Pantaleo et al. (1991) *J. Ex. Med.* 173:511–514. Syncytia formation is followed by the depletion of $CD^+$ cells in vitro. Pantaleo et al. (1991); Levy (1993) *Microbiol. Rev.* 57:183–189; Butini et al. (1994) *Eur. J. Immunol.* 24:2191–2195; Finkel and Banda (1994) *Curr. Opin. Immunol.* 6:605–615. Although syncytia formation is difficult to detect in vivo, clusters of infected cells are seen in lymph nodes of infected individuals. Pantaleo et al., (1993) *N. Eng. J. Med.* 328:327–335; Finkel and Banda (1994); Embretson et al. (1993) *Nature* 362:359–362; Pantaleo et al. (1993) *Nature* 362:355–358. Syncytia may simply be scavenged from the body too quickly to be detected. Fouchier et al. (1996) *Virology* 219:87–95. Syncytia-mediated loss of $CD4^+$ cells in vivo has been speculated to occur; this could contribute directly to compromise of the immune system, leading to opportunistic infection and full-blown AIDS. Sodrosky et al. (1986) *Nature* 322:470–474; Hildreth and Orentas (1989) *Science* 244:1075–1078; Finkel and Banda (1994). Thus critical changes in chimpanzee ICAM-1, ICAM-2 or ICAM-3 may deter syncytia formation in chimpanzee and help explain chimpanzee resistance to AIDS progression. Because of the polyfunctional nature of ICAMs, these positively selected changes in the ICAM genes may additionally confer resistance to other infectious diseases or may play a role in other inflammatory processes that may also be of value in the development of human therapeutics. The polypeptide sequence alignments of ICAM-1, -2, and -3 are shown in FIGS. 5, 6, and 7, respectively.

Example 7

Identifying Positive Selection of MIP-1α

MIP-1α is a chemokine that has been shown to suppress HIV-1 replication in human cells in vitro (Cocchi, F. et al., 1995 Science 270:1811–1815). The chimpanzee homologue of the human MIP-1α gene was PCR-amplified and sequenced. Calculation of the $K_A/K_S$ ratio (2.1, P<0.05) and comparison to the gorilla homologue reveals that the chimpanzee gene has been positively-selected. As for the other genes discussed herein, the nature of the chimpanzee amino acid replacements is being examined to determine how to exploit the chimpanzee protein for therapeutic intervention.

Example 8

Identifying Positive Selection of 17-β-Hydroxysteroid Dehydrogenase

Using the methods of the present invention, a chimpanzee gene expressed in brain has been positively-selected ($K_A/K_S=1.6$) as compared to its human homologue (GenBank Acc. # X87176) has been identified. The human gene, 17-β hydroxysteroid dehydrogenase type IV, codes for a protein known to degrade the two most potent estrogens, β-estradiol, and 5-diol (Adamski, J. et al. 1995 *Biochem J.* 311: 437–443). Estrogen-related cancers (including, for example, breast and prostate cancers) account for some 40% of human cancers. Interestingly, reports in the literature suggest that chimpanzees are resistant to tumorigenesis, especially those that are estrogen-related. This protein may have been positively-selected in chimpanzees to allow more efficient degradation of estrogens, thus conferring upon chimpanzees resistance to such cancers. If so, the specific amino acid replacements observed in the chimpanzee protein may supply important information for therapeutic intervention in human cancers.

Example 9 cDNA Library Construction for Chimpanzee Brain Tissue

A chimpanzee brain cDNA library is constructed using chimpanzee brain tissue. The chimpanzee brain tissue can be obtained after natural death so that no killing of an animal is necessary for this study. In order to increase the chance of obtaining intact mRNAs expressed in brain, however, the brain is obtained as soon as possible after the animal's death. Preferably, the weight and age of the animal are determined prior to death. The brain tissue used for constructing a cDNA library is preferably the whole brain in order to maximize the inclusion of mRNA expressed in the entire brain. Brain tissue is dissected from the animal following standard surgical procedures.

Total RNA is extracted from the brain tissue and the integrity and purity of the RNA are determined according to conventional molecular cloning methods. Poly A+ RNA is selected and used as template for the reverse-transcription of cDNA with oligo (dT) as a primer. The synthesized cDNA is treated and modified for cloning using commercially available kits. Recombinants are then packaged and propagated in a host cell line. Portions of the packaging mixes are amplified and the remainder retained prior to amplification. The library can be normalized and the numbers of independent recombinants in the library is determined.

Example 10

Sequence Comparison of Chimpanzee and Human Brain cDNA

Randomly selected chimpanzee brain cDNA clones from the cDNA library are sequenced using an automated sequencer, such as the ABI 377. Commonly used primers on the cloning vector such as the M13 Universal and Reverse primers are used to carry out the sequencing. For inserts that are not completely sequenced by end sequencing, dye-labeled terminators are used to fill in remaining gaps.

The resulting chimpanzee sequences are compared to human sequences via database searches, e.g., BLAST searches. The high scoring "hits," i.e., sequences that show a significant (e.g., >80%) similarity after BLAST analysis, are retrieved and analyzed. The two homologous sequences are then aligned using the alignment program CLUSTAL V developed by Higgins et al. Any sequence divergence, including nucleotide substitution, insertion and deletion, can be detected and recorded by the alignment.

The detected sequence differences are initially checked for accuracy by finding the points where there are differences between the chimpanzee and human sequences; checking the sequence fluorogram (chromatogram) to determine if the bases that appear unique to human correspond to strong, clear signals specific for the called base; checking the human hits to see if there is more than one human sequence that corresponds to a sequence change; and other methods known in the art as needed. Multiple human sequence entries for the same gene that have the same nucleotide at a position where there is a different chimpanzee nucleotide provides independent support that the human sequence is accurate, and that the chimpanzee/human difference is real. Such changes are examined using public database information and the genetic code to determine whether these DNA sequence changes result in a change in the amino acid sequence of the encoded protein. The sequences can also be examined by direct sequencing of the encoded protein.

Example 11

Molecular Evolution Analysis of Human Brain Sequences Relative to Other Primates The chimpanzee and human sequences under comparison are subjected to $K_A/K_S$ analysis. In this analysis, publicly available computer programs, such as Li 93 and INA, are used to determine the number of non-synonymous changes per site ($K_A$) divided by the number of synonymous changes per site ($K_S$) for each sequence under study as described above. This ratio, $K_A/K_S$, has been shown to be a reflection of the degree to which adaptive evolution, i.e., positive selection, has been at work in the sequence under study. Typically, full-length coding regions have been used in these comparative analyses. However, partial segments of a coding region can also be used effectively. The higher the $K_A/K_S$ ratio, the more likely that a sequence has undergone adaptive evolution. Statistical significance of $K_A/K_S$ values is determined using established statistic methods and available programs such as the t-test. Those genes showing statistically high $K_A/K_S$ ratios between chimpanzee and human genes are very likely to have undergone adaptive evolution.

To further lend support to the significance of a high $K_A/K_S$ ratio, the sequence under study can be compared in other non-human primates, e.g., gorilla, orangutan, bonobo. These comparisons allow further discrimination as to whether the adaptive evolutionary changes are unique to the human lineage compared to other non-human primates. The sequences can also be examined by direct sequencing of the gene of interest from representatives of several diverse human populations to assess to what degree the sequence is conserved in the human species.

Example 12

Further Sequence Characterization of Selected Human Brain Sequences

Human brain nucleotide sequences containing evolutionarily significant changes are further characterized in terms of their molecular and genetic properties, as well as their biological functions. The identified coding sequences are used as probes to perform in situ mRNA hybridization that reveals the expression pattern of the gene, either or both in terms of what tissues and cell types in which the sequences are expressed, and when they are expressed during the course of development or during the cell cycle. Sequences that are expressed in brain may be better candidates as being associated with important human brain functions. Moreover, the putative gene with the identified sequences are subjected to homologue searching in order to determine what functional classes the sequences belong to.

Furthermore, for some proteins, the identified human sequence changes may be useful in estimating the functional consequence of the change. By using such criteria a database of candidate genes can be generated. Candidates are ranked as to the likelihood that the gene is responsible for the unique or enhanced abilities found in the human brain compared to chimpanzee or other non-human primates, such as high capacity information processing, storage and retrieval capabilities, language abilities, as well as others. In this way, this approach provides a new strategy by which such genes can be identified. Lastly, the database not only provides an ordered collection of candidate genes, it also provides the precise molecular sequence differences that exist between human and chimpanzee (and other non-human primates), and thus defines the changes that underlie the functional differences.

In some cases functional differences are evaluated in suitable model systems, including, but not limited to, in vitro analysis such as indicia of long term potentiation (LTP), and use of transgenic animals or other suitable model systems. These will be immediately apparent to those skilled in the art.

Example 13

Identification of Positive Selection in a Human Tyrosine Kinase Gene

Using the methods of the present invention, a human gene (GenBank Acc.# AB014541), expressed in brain has been identified, that has been positively-selected as compared to its gorilla homologue. This gene, which codes for a tyrosine kinase, is homologous to a well-characterized mouse gene (GenBank Acc.# AF011908) whose gene product, called AATYK, is known to trigger apoptosis (Gaozza, E. et al. 1997 Oncogene 15:3127–313.5). The literature suggests that this protein controls apoptosis in the developing mouse brain (thus, in effect, "sculpting" the developing brain). The AATYK-induced apoptosis that occurs during brain development has been demonstrated to be necessary for normal brain development.

There is increasing evidence that inappropriate apoptosis contributes to the pathology of human neurodegenerative diseases, including retinal degeneration, Huntington's disease, Alzheimer's disease, Parkinson's disease and spinal muscular atrophy, an inherited childhood motoneuron disease. On the other hand in neural tumour cells, such as neuroblastoma and medulloblastoma cells, apoptotic pathways may be disabled and the cells become resistant to chemotherapeutic drugs that kill cancer cells by inducing apoptosis. A further understanding of apoptosis pathways and the function of apoptosis genes should lead to a better understanding of these conditions and permit the use of AATYKI in diagnosis of such conditions.

Positively-selected human and chimpanzee AATYK may constitute another adaptive change that has implications for disease progression. Upon resolution of the three-dimensional structure of human and chimpanzee AATYK, it may be possible to design drugs to modulate the function of AATYK in a desired manner without disrupting any of the normal functions of human AATTK.

It has been demonstrated that mouse AATYK is an active, non-receptor, cytosolic kinase which induces neuronal differentiation in human adrenergic neuroblastoma (NB):SH-SY5Y cells. AATYK also promotes differentiation induced by other agents, including all-trans retinoic acid (RA), 12-O-Tetradecanoyl phorbol 13-acetate (TPA) and IGF-I. Raghunath, et al., Brain Res Mol Brain Res. (2000) 77:151–62. In experiments with rats, it was found that the AATYK protein was expressed in virtually all regions of the adult rat brain in which neurons are present, including olfactory bulb, forebrain, cortex, midbrain, cerebellum and pons. Immunohistochemical labeling of adult brain sections showed the highest levels of AATYK expression in the cerebellum and olfactory bulb. Expression of AATYK was also up-regulated as a function of retinoic acid-induced neuronal differentiation of p19 embryonal carcinoma cells, supporting a role for this protein in mature neurons and neuronal differentiation. Baker, et al., Oncogene (2001) 20:1015–21.

Nicolini, et al., Anticancer Res (1998) 18:2477–81 showed that retinoic acid (RA) differentiated SH-SY5Y cells were a suitable and reliable model to test the neurotoxicity of chemotherapeutic drugs without the confusing effects of the neurotrophic factors commonly used to induce neuronal differentiation. The neurotoxic effect and the course of the changes is similar to that observed in clinical practice and in in vivo experimental models. Thus, the model is proposed as a screening method to test the neurotoxicity of chemotherapy drugs and the possible effect of neuroprotectant molecules and drugs. Similarly, AATYK differentiated SYSY-5Y cells could be used as a model for screening chemotherapeutic drugs and possible side effects of neuroprotectant molecules and drugs.

It has also been shown that AATYK mRNA is expressed in neurons throughout the adult mouse brain. AATYK possessed tyrosine kinase activity and was autophosphorylated when expressed in 293 cells. AATYK mRNA expression was rapidly induced in cultured mouse cerebellar granule cells during apoptosis induced by KCl. The number of apoptotic granule cells overexpressing wild-type AATYK protein was significantly greater than the number of apoptotic granule cells overexpressing a mutant AATYK that lacked tyrosine kinase activity. These findings suggest that through its tyrosine kinase activity, AATYK is also involved in the apoptosis of mature neurons. Tomomura, et al., Oncogene (2001) 20(9):1022–32.

The tyrosine kinase domain of AATYK protein is highly conserved between mouse, chimpanzee, and human (as are most tyrosine kinases). Interestingly, however, the region of the protein to which signaling proteins bind has been positively-selected in humans, but strongly conserved in both chimpanzees and mice. The region of the human protein to which signaling proteins bind has not only been positively-selected as a result of point nucleotide mutations, but additionally displays duplication of several src homology 2 (SH2) binding domains that exist only as single copies in mouse and chimpanzee. This suggests that a different set of signaling proteins may bind to the human protein, which could then trigger different pathways for apoptosis in the developing human brain compared to those in mice and chimpanzees. Such a gene thus may contribute to unique or enhanced human cognitive abilities. Human AATYK has been mapped on 25.3 region of chromosome 17. Seki, et al., J Hum Genet (1999) 44:141–2.

Chimpanzee DNA was sequenced as part of a high-throughput sequencing project on a MegaBACE 1000 sequencer (AP Biotech). DNA sequences were used as query sequences in a BLAST search of the GenBank database. Two random chimpanzee sequences, termed stch856 and stch610, returned results for two genes in the non-redundant database of GenBank: NM_004920 (human apoptosis-associated tyrosine kinase, AATYK) and AB014541 (human KIAA641, identical nucleotide sequence to NM_004920), shown in FIG. 14A, and also showed a high $K_A/K_S$ ratio compared to these human sequences. Primers were designed for PCR and sequencing of AATYK. Sequence was obtained for the 3 prime end of this gene in chimp and gorilla. The 5 prime end of the gene was difficult to amplify, and no sequence was confirmed in human and gorilla. The human AATYK gene (SEQ ID NO:14) has a coding region of 3624 bp (nucleotides 413–4036 of SEQ ID NO:14), and codes for a protein of 1207 amino acids (SEQ ID NO:16). 1809 bp were sequenced in both chimp and gorilla. See FIGS. 15A and 15B. The partial sequences (SEQ ID NO:17 and SEQ ID NO:18) did not include the start or stop codons, although they were very close to the stop codon on the 3 prime end (21 codons away). These sequences correspond to nucleotides 2170–3976 or 2179–3988 of the corresponding human sequences taking into account the gaps described below.

There were also several pairs of amino acid insertions/deletions among chimp, human and gorilla in the coding region. The following sequences are in reading frame:

```
Chimp              GGTGAGGGCCCCGGCCCCGGGCCC
(SEQ ID NO: 19)

Human         2819 GGTGAGGGC::::::CCCGGGCCC 2836
(SEQ ID NO: 20)

Gorilla            GGCGAGGGC::::::CCCGGGCCC
(SEQ ID NO: 21)

Chimp              CTGGAGGCTGAGGCCGAGGCCGAG
(SEQ ID NO: 22)

Human         2912 CTCGAGGCT::::::GAGGCCGAG 2929
(SEQ ID NO: 23)

Gorilla            CTGGAGGCT::::::GAGGCCGAG
(SEQ ID NO: 24)

Chimp              CCCACGCCC::::::GCTCCCTTC
(SEQ ID NO: 25)

Human         3890 CCCACGCCCACGCCCGCTCCCTTC 3913
(SEQ ID NO: 26)

Gorilla            CCCACGCCC::::::GCTCCCTTC
(SEQ ID NO: 27)

Chimp              CCCACGTCCACGTCCCGCTTCTCC
(SEQ ID NO: 28)

Human         3938 CCCACGTCC::::::CGCTTCTCC 3955
(SEQ ID NO: 29)

Gorilla            CCCACGTCC::::::CGCTTCTCC
(SEQ ID NO: 30)
```

Each of these insertions/deletions affected two amino acids and did not change the reading frame of the sequence. Sliding window $K_A/K_S$ for chimp to human, chimp to gorilla, and human to gorilla, excluding the insertion/deletion regions noted above, showed a high Ka/Ks ratio for some areas. See Table 9.

The highest Ka/Ks ratios are human to gorilla and chimp to gorilla, suggesting that both the human and chimp gene have undergone selection, and is consistent with the idea that the two species share some enhanced cognitive abilities relative to the other great apes (gorillas, for example). Such data bolsters the view that this gene may play a role with regard to enhanced cognitive functions. It should also be noted that in general, the human-containing pairwise comparisons are higher than the analogous chimp-containing comparisons.

TABLE 9

$K_A/K_S$ ratios for various windows of AATYK on chimp, human, and gorilla

| AATYK | | $K_A$ | $K_S$ | $K_A/K_S$ | $K_A$ SE | $K_S$ SE | size bp | bp of partial CDS | t | bp of NM 004920 (pub human AATYK) |
|---|---|---|---|---|---|---|---|---|---|---|
| chimp | gorilla | 0.02287 | 0.03243 | 0.705211 | 0.00433 | 0.00832 | 1809 | 1–1809 | 1.019266 | 2180–3988 |
| chimp | human | 0.01538 | 0.01989 | 0.773253 | 0.00366 | 0.0062 | 1809 | 1–1809 | 0.626415 | 2180–3988 |
| human | gorilla | 0.02223 | 0.03204 | 0.69382 | 0.00429 | 0.00848 | 1809 | 1–1809 | 1.032263 | 2180–3988 |
| ch1 | hu1 | 0.03126 | 0.02009 | 1.555998 | 0.01834 | 0.02034 | 150 | 1–150 | 0.407851 | 2180–2329 |
| ch2 | hu2 | 0.03142 | 0.04043 | 0.777146 | 0.01844 | 0.02919 | 150 | 100–249 | 0.260958 | 2279–2428 |
| ch3 | hu3 | 0.02073 | 0.02036 | 1.018173 | 0.01481 | 0.02087 | 150 | 202–351 | 0.014458 | 2381–2530 |
| ch4 | hu4 | 0.02733 | 0.02833 | 0.964702 | 0.01753 | 0.02383 | 150 | 301–450 | 0.033803 | 2480–2629 |
| ch5 | hu5 | 0 | 0.05152 | 0 | 0 | 0.03802 | 150 | 400–549 | 1.355076 | 2579–2728 |
| ch6 | hu6 | 0.00836 | 0.03904 | 0.214139 | 0.00838 | 0.03964 | 150 | 502–651 | 0.75723 | 2681–2830 |
| ch7 | hu7 | 0.00888 | 0.05893 | 0.150687 | 0.0089 | 0.0439 | 150 | 601–750 | 1.11736 | 2780–2929 |
| ch8 | hu8 | 0.02223 | 0.03829 | 0.580569 | 0.01589 | 0.03886 | 150 | 700–849 | 0.382534 | 2879–3028 |
| ch9 | hu9 | 0.04264 | 0.03644 | 1.170143 | 0.02173 | 0.02628 | 150 | 799–948 | 0.181817 | 2978–3127 |
| ch10 | hu10 | 0.02186 | 0.01823 | 1.199122 | 0.01563 | 0.01851 | 150 | 901–1050 | 0.149837 | 3080–3229 |
| ch11 | hu11 | 0.01087 | 0 | #DIV/0! | 0.01093 | 0 | 150 | 1000–1149 | 0.994511 | 3179–3328 |
| ch12 | hu12 | 0.01093 | 0 | #DIV/0! | 0.01099 | 0 | 150 | 1099–1248 | 0.99454 | 3278–3427 |
| ch13 | hu13 | 0.01031 | 0 | #DIV/0! | 0.01036 | 0 | 150 | 1201–1350 | 0.995174 | 3380–3529 |
| ch14 | hu14 | 0.01053 | 0 | #DIV/0! | 0.01058 | 0 | 150 | 1300–1449 | 0.995274 | 3479–3628 |
| ch15 | hu15 | 0.01835 | 0.02006 | 0.914756 | 0.01315 | 0.02057 | 150 | 1399–1548 | 0.070042 | 3578–3727 |
| ch16 | hu16 | 0 | 0.02027 | 0 | 0 | 0.02062 | 150 | 1501–1650 | 0.983026 | 3680–3829 |
| ch17 | hu17 | 0.00666 | 0 | #DIV/0! | 0.00667 | 0 | 210 | 1600–1809 | 0.998501 | 3779–3988 |
| chA | huA | 0.02366 | 0.02618 | 0.903743 | 0.00875 | 0.01251 | 501 | 1–501 | 0.165069 | 2180–2680 |
| chB | huB | 0.01159 | 0.03863 | 0.300026 | 0.00585 | 0.01811 | 501 | 400–900 | 1.420809 | 2579–3079 |
| chC | huC | 0.02212 | 0.0108 | 2.048148 | 0.00846 | 0.00768 | 501 | 799–1299 | 0.990721 | 2978–3478 |
| chD | huD | 0.00851 | 0.00734 | 1.159401 | 0.00458 | 0.00602 | 609 | 1201–1809 | 0.154676 | 3380–3988 |
| chA | gorA | 0.02082 | 0.04868 | 0.427691 | 0.00795 | 0.0191 | 501 | 1–501 | 1.346644 | 2180–2680 |
| chB | gorB | 0.01416 | 0.04039 | 0.350582 | 0.00639 | 0.0172 | 501 | 400–900 | 1.429535 | 2579–3079 |
| chC | gorC | 0.01737 | 0.00538 | 3.228625 | 0.00717 | 0.00542 | 501 | 799–1299 | 1.333991 | 2978–3478 |
| chD | gorD | 0.00644 | 0.00244 | 2.639344 | 0.00408 | 0.00346 | 609 | 1201–1809 | 0.747722 | 3380–3988 |
| huA | gorA | 0.02246 | 0.02759 | 0.814063 | 0.00829 | 0.01523 | 501 | 1–501 | 0.295847 | 2180–2680 |
| huB | gorB | 0.01418 | 0.06809 | 0.208254 | 0.0064 | 0.02388 | 501 | 400–900 | 2.180583 | 2579–3079 |
| huC | gorC | 0.01993 | 0.00541 | 3.683919 | 0.00762 | 0.00544 | 501 | 799–1299 | 1.550854 | 2978–3478 |
| huD | gorD | 0.00723 | 0.00488 | 1.481557 | 0.0042 | 0.0049 | 609 | 1201–1809 | 0.364133 | 3380–3988 |

Example 14

Positively Selected Human BRCA1 Gene

Comparative evolutionary analysis of the BRCA1 genes of several primate species has revealed that the human BRCA1 gene has been subjected to positive selection. Initially, 1141 codons of exon 11 of the human and chimpanzee BRCA1 genes (Hacia et al. (1998) Nature Genetics 18:155–158) were compared and a strikingly high $K_A/K_S$ ratio, 3.6, was found when calculated by the method of Li (Li (1993) J. Mol. Evol. 36:96–99; Li et al. (1985) Mol. Biol. Evol. 2:150–174). In fact, statistically significant elevated ratios were obtained for this comparison regardless of the particular algorithm used (see Table 5A). Few genes (or portions of genes) have been documented to display ratios of this magnitude (Messier et al. (1997) Nature 385:151–154; Endo et al. (1996) Mol. Biol. Evol. 13:685–690; and Sharp (1997) Nature 385:111–112). We thus chose to sequence the complete protein-coding region (5589 bp) of the chimpanzee BRCA1 gene, in order to compare it to the full-length protein-coding sequence of the human gene. In many cases, even when positive selection can be shown to have operated on limited regions of a particular gene, $K_A/K_S$ analysis of the full-length protein-coding sequence fails to reveal evidence of positive selection (Messier et al. (1997), supra). This is presumably because the signal of positive selection can be masked by noise when only small regions of a gene have been positively selected, unless selective pressures are especially strong. However, comparison of the full-length human and chimpanzee BRCA1 sequences still yielded $K_A/K_S$ ratios in excess of one, by all algorithms we employed (Table 5A). This suggests that the selective pressure on BRCA1 was intense. A sliding-window $K_A/K_S$ analysis was also performed, in which intervals of varying lengths (from 150 to 600 bp) were examined, in order to determine the pattern of selection within the human BRCA1 gene. This analysis suggests that positive selection seems to have been concentrated in exon 11.

TABLE 5A

Human-Chimpanzee $K_A/K_S$ Comparisons

| Method | $K_A/K_S$ (exon 11) | $K_A/K_S$ (full-length) |
|---|---|---|
| Li (1993) J. Mol. Evol. 36: 96; Li et al. (1985) Mol. Biol. Evol. 2: 150 | 3.6*** | 2.3* |
| Ina Y. (1995) J. Mol. Evol. 40: 190 | 3.3** | 2.1* |
| Kumar et al., MEGA: Mol. Evol. Gen. Anal. (PA St. Univ, 1993) | 2.2* | 1.2 |

TABLE 5B $K_A/K_S$ for Exon 11 of BRCA1 from Additional Primates

| Comparison | | $K_A$ | $K_S$ | $K_A/K_S$ |
|---|---|---|---|---|
| Human | Chimpanzee | 0.010 | 0.003 | 3.6* |
| | Gorilla | 0.009 | 0.009 | 1.1 |
| | Orangutan | 0.018 | 0.020 | 0.9 |
| Chimpanzee | Gorilla | 0.006 | 0.007 | 0.8 |
| | Orangutan | 0.014 | 0.019 | 0.7 |
| Gorilla | Orangutan | 0.014 | 0.025 | 0.6 |

The Table 5B ratios were calculated according to Li (1993) J. Mol. Evol. 36:96; Li et al. (1985) Mol. Biol. Evol. 2:150. For all comparisons, statistical significance was calculated by t-tests, as suggested in Zhang et al. (1998) Proc. Natl. Acad. Sci. USA 95:3708. Statistically significant comparisons are indicated by one or more asterisks, with P values as follows: *, P<0.05, , P<0.01, *, P<0.005. Exon sequences are from Hacia et al. (1998) Nature Genetics 18:155. GenBank accession numbers: human, NM_000058.1, chimpanzee, AF019075, gorilla, AF019076, orangutan, AF019077, rhesus, AF019078.

Figure 9:
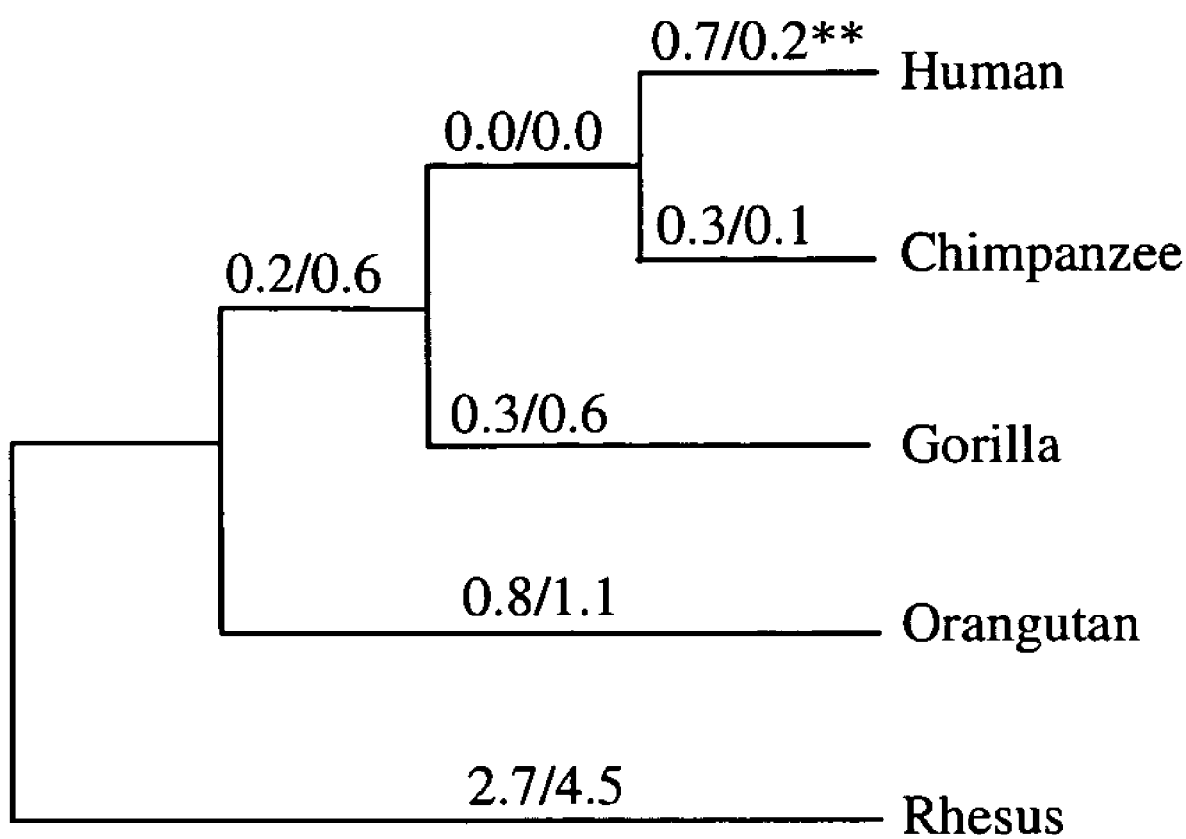
FIG. 9 illustrates the known phylogenetic tree for the species compared in Example 14, with values of $b_N$ and $b_S$ mapped upon appropriate branches. Values of $b_N$ and $b_S$ were calculated by the method described in Zhang et al. (1998) *Proc. Natl. Acad. Sci. USA* 95:3708–3713. Values are shown above the branches; all values are shown 100×, for reasons of clarity. Statistical significance was calculated as for comparisons in Table 5 (Example 14), and levels of statistical significance are as shown as in Table 5. Note that only the branch leading from the human/chimpanzee common ancestor to modern humans shows a statistically significant value for $b_N$-$b_S$.

The elevated $K_A/K_S$ ratios revealed by pairwise comparisons of the human and chimpanzee BRCA1 sequences demonstrate the action of positive selection, but such comparisons alone do not reveal which of the two genes compared, the human or the chimpanzee, has been positively selected. However, if the primate BRCA1 sequences are considered in a proper phylogenetic framework, only those pairwise comparisons which include the human gene show ratios greater than one, indicating that only the human gene has been positively selected (Table 5B). To confirm that positive selection operated on exon 11 of BRCA1 exclusively within the human lineage, the statistical test of positive selection proposed by Zhang et al. (1998) Proc. Natl. Acad. Sci. USA 95:3708–3713, was used. This test is especially appropriate when the number of nucleotides is large, as in the present case (3423 bp). This procedure first determines nonsynonymous nucleotide substitutions per nonsynonymous site ($b_N$) and synonymous substitutions per synonymous site ($b_S$) for each individual branch of a phylogenetic tree (Zhang et al. (1998), supra). Positive selection is supported only on those branches for which $b_N–b_S$ can be shown to be statistically significant (Zhang et al. (1998), supra). For BRCA1, this is true for only one branch of the primate tree shown in FIG. 9: the branch which leads from the human/chimpanzee common ancestor to modern humans, where $b_N/b_S=3.6$. Thus, we believe that in the case of the BRCA1 gene, positive selection operated directly and exclusively on the human lineage.

While it is formally possible that elevated $K_A/K_S$ ratios might reflect some locus or chromosomal-specific anomaly (such as suppression of $K_S$ due, for example, to isochoric differences in GC content), rather than the effects of positive selection, this is unlikely in the present case, for several reasons. First, the estimated $K_S$ values for the hominoid BRCA1 genes, including human, were compared to those previously estimated for other well-studied hominoid loci, including lysozyme (Messier et al. (1997), supra) and ECP (Zhang et al. (1998), supra). There is no evidence for a statistically significant difference in these values. This argues against some unusual suppression of $K_S$ in human BRCA1. Second, examination of GC content (Sueoka, N. in Evolving Genes and Proteins (eds. Bryson, V. & Vogel, H. J.) 479–496 (Academic Press, NY, 1964)) and codon usage patterns (Sharp et al. (1988) Nucl. Acids Res. 16:8207–8211) of the primate BRCA1 genes shows no significant differences from average mammalian values.

This demonstration of strong positive selection on the human BRCA1 gene constitutes the first molecular support for a theory long advanced by anthropologists. Human infants require, and receive, prolonged periods of post-birth care—longer than in any of our close primate relatives. Short, R. V. (1976) Proc. R. Soc. Lond. B 195:3–24, first postulated that human females can only furnish such extended care to human infants in the context of a long term pair bond with a male partner who provides assistance. The maintenance of long term pair bonds was strengthened by development of exaggerated (as compared to our close primate relatives) human secondary sex characteristics including enlarged female breasts (Short (1976), supra). Thus, strong selective pressures resulted in development of enlarged human breasts which develop prior to first pregnancy and lactation, contrary to the pattern seen in our hominoid relatives (Dixson, A. F. in *Primate Sexuality: Comparative Studies of the Prosimians, Monkeys, Apes and Human Beings.* 214 (Oxford Univ. Press, Oxford, 1998)).

Evidence suggests that in addition to its function as a tumor suppressor (Xu et al. (1999) *Mol. Cell* 3(3):389–395; Shen et al. (1998) *Oncogene* 17(24):3115–3124; C. (1999) *Nature Genetics* 22:10; and Xu et al. (1999) *Nature Genetics* 22:37–43), the BRCA1 protein plays an important role in normal development of breast tissue (Dennis, C. (1999), supra; Xu et al. (1999) *Nature Genetics* 22:37–43; and Thompson et al. (1999) *Nature Genetics* 9:444–450), particularly attainment of typical mammary gland and duct size (Dennis, C. (1999), supra; and Xu et al. (1999) *Nature Genetics* 22:37–43). These facts suggest that positive selection on this gene in humans promoted expansion of the female human breast, and ultimately, helped promote long term care of dependent human infants. This long term dependency of human infants was essential for the development and transmission of complex human culture. Because positive selection seems to have been concentrated upon exon 11 of BRCA1, the prediction follows that the region of the BRCA1 protein encoded by exon 11 specifically plays a role in normal breast development. The data provided here suggests that strong selective pressures during human evolution led to amino acid replacements in BRCA1 that promoted a unique pattern of breast development in human females, which facilitated the evolution of some human behaviors.

Example 15

Characterization of BRCA1 Polynucleotide and Polypeptide

Having identified evolutionarily significant nucleotide changes in the BRCA1 gene and corresponding amino acid changes in the BRCA1 protein, the next step is to test these molecules in a suitable model system to analyze the functional effect of the nucleotide and amino acid changes on the model. For example, the human BRCA1 polynucleotide can be transfected into a cultured host cell such as adipocytes to determine its effect on cell growth or replication.

Example 16

Identification of Positively-Selected CD59

Comparative evolutionary analysis of the CD59 genes of several primate species has revealed that the chimpanzee CD59 gene has been subjected to positive selection. CD59 protein is also known as protectin, 1F-5Ag, H19, HRF20, MACIF, MIRL, and P-18. CD59 is expressed on all peripheral blood leukocytes and erythrocytes (Meri et al. (1996) *Biochem. J.* 316:923–935). Its function is to restrict lysis of human cells by complement (Meri et al. (1996), supra). More specifically, CD59 acts as one of the inhibitors of membrane attack complexes (MACs). MACs are complexes of 20 some complement proteins that make hole-like lesions in cell membranes (Meri et al. (1996), supra). These MACs, in the absence of proper restrictive elements (i.e., CD59 and a few other proteins) would destroy host cells as well as invading pathogens. Essentially then, CD59 protects the cells of the body from the complement arm of its own defense systems (Meri et al. (1996), supra). The chimpanzee homolog of this protein was examined because the human homolog has been implicated in progression to AIDS in infected individuals. It has been shown that CD59 is one of the host cell derived proteins that is selectively taken up by HIV virions (Frank et al. (1996) *AIDS* 10:1611–1620). Additionally, it has been shown (Saifuddin et al. (1995) *J. Exp. Med.* 182:501–509) that HIV virions which have incorporated host cell CD59 are protected from the action of complement. Thus it appears that in humans, HIV uses CD59 to protect itself from attack by the victim's immune system, and thus to further the course of infection.

To obtain primate CD59 cDNA sequences, total RNA was prepared (using either the RNeasy® kit (Qiagen), or the RNAse-free Rapid Total RNA kit (5 Prime-3 Prime, Inc.)) from primate tissues (whole fresh blood from chimpanzees, gorillas, and orangutans). mRNA was isolated from total RNA using the Mini-Oligo(dT) Cellulose Spin Columns (5 Prime-3 Prime, Inc.). cDNA was synthesized from mRNA with oligo dT and/or random priming using the SuperScript Preamplification System for First Strand. cDNA Synthesis (Gibco BRL). The protein-coding region of the primate CD59 gene was amplified from cDNA using primers (concentration=100 nmole/µl) designed from the published human sequence. PCR conditions for CD59 amplification were 94° C. initial pre-melt (4 min), followed by 35 cycles of 94° C. (15 sec), 58° C. (1 min 15 sec), 72° C. (1 min 15 sec), and a final 72° C. extension for 10 minutes. PCR was accomplished on a Perkin-Elmer GeneAmp® PCR System 9700 thermocycler, using Ready-to-Go PCR beads (Amersham Pharmacia Biotech) in a 50 µl total reaction volume. Appropriately-sized products were purified from agarose gels using the QiaQuick Gel Extraction kit (Qiagen). Both strands of the amplification products were sequenced directly using the Big Dye Cycle Sequencing Kit and analyzed on a 373A DNA sequencer (ABI BioSystems).

As shown in Table 6, all comparisons to the chimpanzee CD59 sequence display $K_A/K_S$ ratios greater than one, demonstrating that it is the chimpanzee CD59 gene that has been positively-selected.

TABLE 6

$K_A/K_S$ Ratios for Selected Primate CD59 cDNA Sequences

| Genes Compared | $K_A/K_S$ Ratios |
| --- | --- |
| Chimpanzee to Human | 1.8 |
| Chimpanzee to Gorilla | 1.5 |
| Chimpanzee to Orangutan | 2.3 |
| Chimpanzee to Green Monkey | 3.0 |

Example 17

Characterization of CD59 Positively-Selected Sequences

Proceeding on the hypothesis that strong selection pressure has resulted in adaptive changes in the chimpanzee CD59 molecule such that disease progression is retarded because the virus is unable to usurp CD59's protective role for itself, it then follows that comparisons of the CD59 gene of other closely-related non-human primates to the human gene should display $K_A/K_S$ ratios less than one for those species that have not been confronted by the HIV-1 virus over evolutionary periods. Conversely, all comparisons to the chimpanzee gene should display $K_A/K_S$ ratios greater than one. These two tests, taken together, will definitively establish whether the chimpanzee or human gene was positively selected. Although the gorilla (*Gorilla gorilla*) is the closest relative to humans and chimpanzees, its postulated historical range in Africa suggests that gorillas could have been at some time exposed to the HIV-1 virus. We thus examined the CD59 gene from both the gorilla and the orangutan (*Pongo pygmaeus*). The latter species, confined to Southeast Asia, is unlikely to have been exposed to HIV over an evolutionary time frame. The nucleotide sequences of the human and orangutan genes were determined by direct sequencing of cDNAs prepared from RNA previously isolated from whole fresh blood taken from these two species. The next step is to determine how chimpanzee CD59 contributes to chimpanzee resistance to progression to full-blown AIDS using assays of HIV replication in cell culture. Human white blood cell lines, transfected with, and expressing, the chimpanzee CD59 protein, should display reduced rates of viral replication (using standard assays familiar to practitioners of the art) as compared to control lines of untransfected human cells. In contrast, chimpanzee white blood cell lines expressing human CD59 should display increased viral loads as compared to control, untransfected chimpanzee cell lines.

Example 18

Molecular Modeling of CD59

Figure 10:
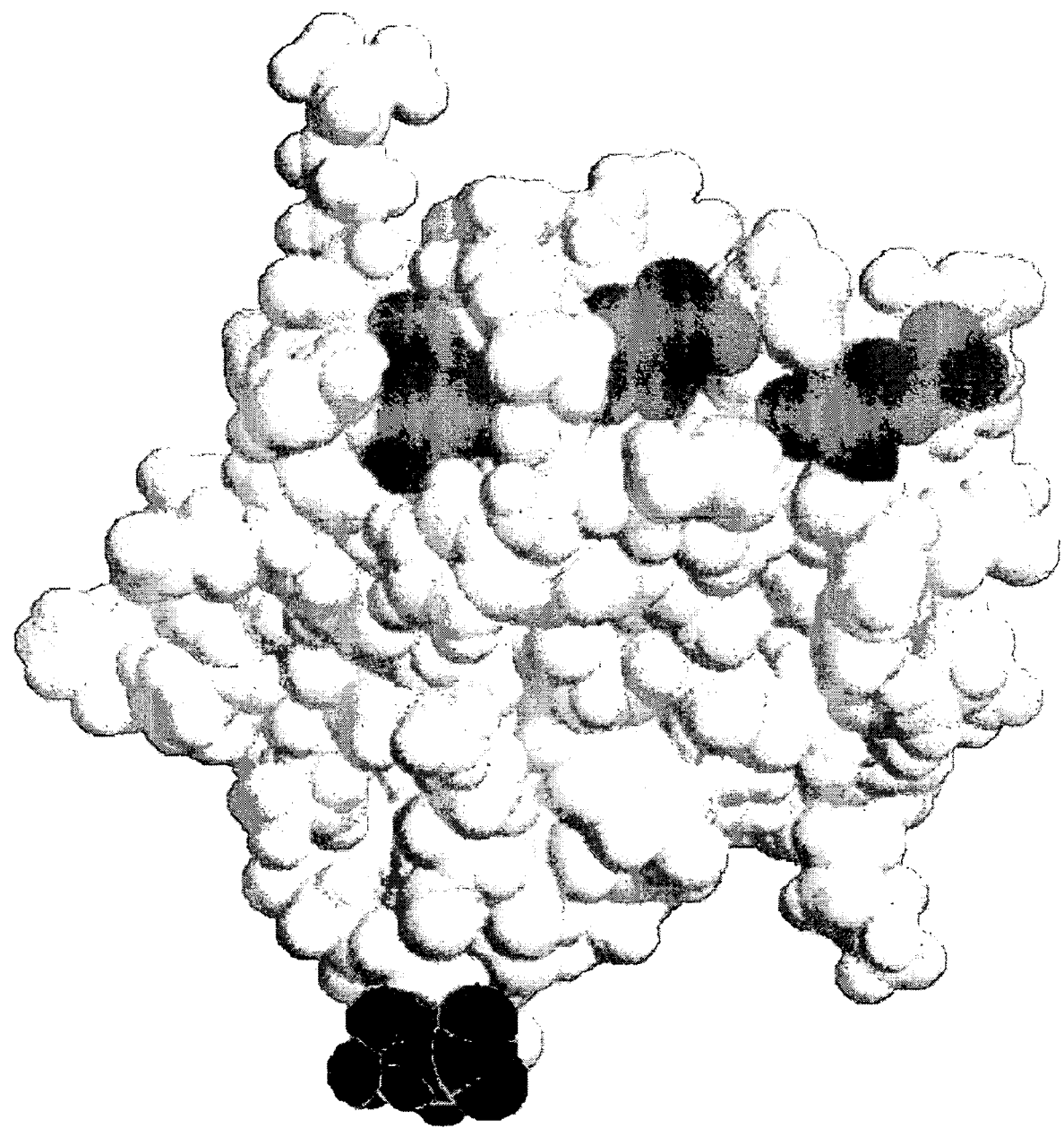
FIG. 10 illustrates a space-filling model of human CD59 with the duplicated GPI link (Asn) indicated by the darkest shading. This GPI link is duplicated in chimpanzees so that chimp CD59 contains 3 GPI links. The three areas of intermediate shading in FIG. 10 are other residues which differ between chimp and human.

Modeling of the inferred chimpanzee protein sequence of CD59 upon the known three-dimensional structure of human (Meri et al. 1996 *Biochem J.* 316:923–935) has provided additional evidence for the role of this protein in explaining chimpanzee resistance to AIDS progression. It has been shown that in human CD59, residue Asn 77 is the link for the GPI anchor (Meri et al. (1996) *Biochem J.* 316:923–935), which is essential for function of the protein. The GPI anchor is responsible for anchoring the protein to the cell membrane (Meri et al. (1996), supra). Our sequencing of the chimpanzee CD59 gene reveals that the inferred protein structure of chimpanzee CD59 contains a duplication of the section of the protein that contains the GPI link, i.e., NEQLENGG (see Table 7 and FIG. 10).

TABLE 7

Comparison of Human and Chimpanzee CD59 Amino Acid Sequence

Human  SLQCYNCPNP TADCKTAVNC SSDFDACLIT KAGLQVYNKC

Chimp- SLQCYNCPNP TADCKTAVNC SSDFDACLIT KAGLQVYNKC
anzee

Human  WK*F*EHCNF*ND* *V*TTRLRENEL TYYCCKKDLC NFNEQLENGG

Chimp- WK*L*EHCNF*KD* *L*TTRLRENEL TYYCCKKDLC NFNEQLENGG
anzee

Human  -----------------TSLS EKTVLL*L*VTP FLAAAAWSLHP

Chimp- *NEQLENGGNE QLENGG*TSLS EKTVLL*R*VTP FLAAAAWSLHP
anzee

Human (SEQ ID NO: 12)
Chimpanzee (SEQ ID NO: 13)
Italics/underline indicates variation in amino acids.

This suggests that while the basic function of CD59 is most likely conserved between chimpanzee and human, some changes have probably occurred in the orientation of the protein with respect to the cell membrane. This may render the chimpanzee protein unusable to the HIV virion when it is incorporated by the virion. Alternatively, the chimpanzee protein may not be subject to incorporation by the HIV virion, in contrast to the human CD59. Either of these (testable) alternatives would likely mean that in the chimpanzee, HIV virions are subject to attack by MAC complexes. This would thus reduce amounts of virus available to replicate, and thus contribute to chimpanzee resistance to progression to full-blown AIDS. Once these alternatives have been tested to determine which is correct, then the information can be used to design a therapeutic intervention for infected humans that mimics the chimpanzee resistance to progression to full-blown AIDS.

Example 19

Identification of Positively-Selected DC-SIGN

Comparative evolutionary analyses of DC-SIGN genes of human, chimpanzee and gorilla have revealed that the chimpanzee DC-SIGN gene has been subjected to positive selection. FIGS. 11–13 (SEQ. ID. NOS. 6–8) show the nucleotide sequences of human, chimpanzee and gorilla DC-SIGN genes, respectively. Table 8 provides the $K_A/K_S$ values calculated by pairwise comparison of the human, chimpanzee and gorilla DC-SIGN genes. Note that only those comparisons with chimpanzee show $K_A/K_S$ values-greater than one, indicating that the chimpanzee gene has been positively selected.

TABLE 8

$K_A/K_S$ Ratios for Selected Primate DC-SIGN cDNA Sequences

| Genes Compared | $K_A/K_S$ Ratios |
| --- | --- |
| Chimpanzee to Human | 1.3 |
| Human to Gorilla | 0.87 |
| Chimpanzee to Gorilla | 1.3 |

As discussed herein, DC-SIGN is expressed on dendritic cells and is known to provide a mechanism for transport of HIV-1 virus to the lymph nodes. HIV-1 binds to the extracellular portion of DC-SIGN and infects the undifferentiated T cells in the lymph nodes via their CD4 proteins. This expansion in infection ultimately leads to compromise of the immune system and subsequently to full-blown AIDS. Interestingly, DC-SIGNS's major ligand appears to be ICAM-3. As described herein, chimpanzee ICAM-3 shows the highest $K_A/K_S$ ratio of any known AIDS-related protein. It is not yet clear whether positive selection on chimpanzee ICAM-3 was a result of compensatory changes that allow ICAM-3 to retain its ability to bind to DC-SIGN.

Example 20

Detection of Positive Selection Upon Chimpanzee p44

As is often true, whole protein comparisons for human and chimpanzee p44 display $K_A/K_S$ ratios less than one. This is because the accumulated "noise" of silent substitutions in the full-length CDS can obscure the signal of positive selection if it has occurred in a small section of the protein. However, examination of exon 2 of the chimpanzee and human homologs reveals that this portion of the gene (and the polypeptide it codes for) has been positively selected. The $K_A/K_S$ ratio for exon 2 is 1.5 (P<0.05). Use of this invention allowed identification of the specific region of the protein that has been positively selected.

Two alleles of p44 were detected in chimpanzees that differ by a single synonymous substitution (see FIG. 16). For human to chimpanzee, the whole protein $K_A/K_S$ ratio for allele A is 0.42, while the ratio for allele B is 0.45.

In FIG. 16, the CDS of human (Acc. NM_006417) and chimpanzee (Acc. D90034) p44 gene are aligned, with the positively selected exon 2 underlined (note that exon 2 begins at the start of the CDS, as exon 1 is non-coding.). Human is labeled Hs (Homo sapiens), chimpanzee is labeled Pt (Pan troglodytes). Nonsynonymous differences between the two sequences are in bold, synonymous differences are in italics. Chimpanzee has a single heterozygous base (position 212), shown as "M", using the IUPAC code to signify either adenine ("A") or cytosine ("C"). Note that one of these ("C") represents a nonsynonymous difference from human, while "A" is identical to the same position in the human homolog. Thus these two chimpanzee alleles differ slightly in their $K_A/K_S$ ratios relative to human p44.

Example 21

Methods for Screening Agents that May be Useful in Treatment of HCV in Humans

Candidate agents can be screened in vitro for interaction with purified p44, especially exon 2. Candidate agents can be designed to interact with human p44 exon 2 so that human p44 can mimic the structure and/or function of chimpanzee p44. Human and chimpanzee p44 are known and can be synthesized using methods known in the art.

Molecular modeling of small molecules to dock with their targets, computer assisted new lead design, and computer assisted drug discovery are well known in the art and are described, e.g., in Cohen, N.C. (ed.) Guidebook on Molecular Modeling in Drug Design, Academic Press (1996). Additionally, there are numerous commercially available molecular modeling software packages.

Affinity chromatography can be used to partition candidate agents that bind in vitro to human p44 (especially exon 2) from those that do not. It may also be useful to partition candidate agents that no only bind to human p44 exon 2, but also do not bind to chimpanzee p44 exon 2, so as to eliminate those agents that are not specific to the human p44 exon 2.

Optionally, x-ray crystallography structures of p44-agent complexes can be compared to x-ray structures of human p44 and chimpanzee p44 to determine if the human p44-agent complexes more closely resemble x-ray structures of chimpanzee p44 structures.

Further, candidate agents can be screened for favorable interactions with p44 during HCV infection of hepatocytes in vitro. Fournier et al. (1998) J. Gen. Virol. 79:2367 report that adult normal human hepatocytes in primary culture can be successfully infected with HCV and used as an in vitro HCV model (see also Rumin et al. (1999) J. Gen. Virology 80:3007). Favre et al. (2001) CR Acad. Sci. III 324(12): 1141–8, report that a robust in vitro infection of hepatocytes with HCV is facilitated by removal of cell-bound lipoproteins prior to addition of viral inocula from human sera. Further, Kitamura et al. (1994) Eur. J. Biochem. 224:877–83, report that IFNα/β induces human p44 gene in hepatocytes in vitro. The p44 protein is produced in vivo in infected human livers (Patzwahl, R. et al. (2000) J. Virology 75(3):1332). While it is presently not clear if p44 is produced by human hepatocytes in vitro during HCV infection, if it is not, IFNα/β could be added to induce p44. This in vitro system could serve as a suitable model for screening candidate agents for their capacity to favorably interact with human p44 in HCV infected hepatocytes.

An assay for favorable interaction of candidate agents with p44 in in vitro cultured cells could be the enhancement of p44 assembly into microtubules in the cultured hepatocytes. Assembled chimpanzee p44 microtubular aggregates associated with NANB hepatitis infection in chimpanzees have been detected by antibodies described in Takahashi, K. et al. (1990) J. Gen. Virology 71(Pt9):2005–11. These antibodies may be useful in detecting human p44 microtubular aggregates. Alternatively, antibodies to human p44 can be made using methods known in the art.

A direct link between enhanced p44 microtubular assembly and increased resistance to HCV infection in chimpanzees or humans is not known at this time. However, the literature does indicate that increased p44 microtubular assembly is associated with HCV infection in chimpanzees, and chimpanzees are able to resist HCV infection. Specifically, Patzwahl, R. et al. (2000) J. Virology 75:1332–38, reports that p44 is a "component of the double-walled membranous tubules which appear as a distinctive alteration in the cytoplasm of hepatocytes after intravenous administration of human non-A, non-B (NANB) hepatitis inocula in chimpanzees." Likewise, Takahashi, K. et al. (1990) J. Gen. Virology 71(Pt9):2005–11, report that p44 is expressed in NANB hepatitis infected chimpanzees and is a host (and not a viral) protein. Additionally, Patzwahl, R. et al. (2000), supra, report that p44 expression is increased in HCV infected human livers; it is not clear whether the human p44 assembles into microtubules. Finally, Kitamura, A. et al. (1994) Eur. J. Biochem. 224:877 suggest at page 882 that "p44 may function as a mediator of anti-viral activity of interferons against hepatitis C . . . infection, through association with the microtubule aggregates."

A suitable control could be in vitro cultured chimpanzee hepatocytes that are infected with HCV, and which presumably would express p44 that assembles into microtubules and resist the HCV infection.

The foregoing in vitro model could serve to identify those candidate agents that interact with human p44 to produce a function (microtubule assembly or HCV resistance) that is characteristic of chimpanzee p44 during HCV infection. Candidate agents can also be screened in in vivo animal models for inhibition of HCV. Several in vivo human HCV models have been described in the literature. Mercer, D. et al. (2001) Nat. Med. 7(8):927–33, report that a suitable small animal model for human HCV is a SCID mouse carrying a plasminogen activator transgene (Alb-uPA) with transplanted normal human hepatocytes. The mice have chimeric human livers, and when HCV is administered via inoculation with infected human serum, serum viral titres increase. HCV viral proteins were localized to the human hepatocyte nodules.

Galun, E. et al. (1995) describe a chimeric mouse model developed from BNX (beige/nude/X-linked immunodeficient) mice preconditioned by total body irradiation and reconstituted with SCID mouse bone marrow cells, into which were implanted HCV-infected liver fragments from human patients, or normal liver incubated with HCV serum.

LaBonte, P. et al. (2002) J. Med. Virol. 66(3):312–9, describe a mouse model developed by orthotopic implantation of human hepatocellular carcinoma cells (HCC) into athymic nude mice. The human tumors produce HCV RNA.

Any of the foregoing mouse models could be treated with IFN-α/β to induce p44 production (if necessary), and candidate agents could be added to detect any inhibition in HCV infection by, e.g., reduction in serum viral titer.

As a control, chimpanzee liver hepatocytes can be implanted into SCID or another suitable mouse to create a chimeric liver, and infected with HCV. Presumably, the chimp livers in the control mouse model would express p44 and be more resistant to HCV infection.

The experimental mice with the human hepatocytes are administered candidate agents and the course of the HCV infection (e.g., viral titres) is then monitored in the control and experimental models. Those agents that improve resistance in the experimental mice to the point where the human p44 function approaches (or perhaps exceeds) the chimpanzee p44 function in the control mouse model, are agents that may be suitable for human clinical trials.

Example 22

Structure/Function Implications of Changes in Chimpanzee ICAMs

Using published crystal structures, we examined the locations of the unique chimpanzee amino acid replacements in ICAM 1, with respect to amino acids that are critical for binding and dimerization (Casasnovas et al. (1998) Proc. Natl. Acad. Sci, USA 95:4134–4139; Bella et al. (1998) Proc. Natl. Acad. Sci. USA 95:4140–4145).

One of the amino acid replacements we found to be unique to the chimpanzee lineage is Leu-18 (replaced by the more hydrophilic Glu-18), one of the leucines in a leucine cluster that creates a hydrophobic dimerization surface critical for human ICAM 1 dimerization (Jun et al. (2001) J. Biol. Chem. 276:29019–29027) (hydrophobicity score of 3.8 Leu replace by −3.5 Glu). The distortion of the hydrophobic surface in chimpanzee ICAM 1 suggests that selective pressure may have been directed towards mediating ICAM 1 dimerization in the chimpanzee.

In contrast, we found that all ICAM 1 residues thought to be involved in human LFA-1 binding (Diamond et al. (1991) Cell 65:961–971; Fisher et al. (1997) Mol. Biol. Cell 8:501–515; Edwards et al. (1998) J. Biol. Chem. 273:28937–28944; Shimaoka et al. (2003) Cell 112:99–111) are identical in chimpanzee and human ICAM 1. Indeed, these critical residues are highly conserved in all of the primate ICAMs we examined. Moreover, we found that the residues in the LFA-1 protein critical for binding to ICAM 1 (Shimaoka et al., 2003; Huth et al. (2000) Proc. Natl. Aad. Sci. USA 97:5231–5236), as well as for binding to ICAM 2 and ICAM 3 are also identical between chimpanzee and human. Our pairwise Ka/Ks comparisons of the chimpanzee and human LFA-1 genes also suggest conservation. (The LFA-1 protein contains two subunits, designated alpha and beta: Human LFA-1 alpha subunit to the chimpanzee LFA-1 alpha subunit: Ka/Ks=0.30; Human LFA-1 beta subunit to the chimpanzee LFA-1 beta subunit: Ka/Ks=0.053.). Thus, it is likely that the ICAM 1/LFA-1 binding interaction is fundamentally the same between humans and chimpanzees, except for the influence of the state of ICAM 1 dimerization, which, as described above, does appear to have been modulated in the chimpanzee as a result of adaptive evolution.

One of the unique chimpanzee ICAM 1 replacements we identified, Lys-29 to Asp-29, is immediately adjacent to a cluster of ICAM 1/LFA-1 binding residues, particularly Asn-66, which forms part of the contact surface for ICAM 1/LFA-1 binding. The amide side chain of Asn-66 is known to interact with Glu-241 of LFA-1, an interaction that has been shown to be absolutely critical for ICAM 1/LFA-1 binding. The interaction of Asn-66 with Glu-241 may be influenced by the replacement of the basic Lys-29 (humans) with the acidic Asp-29 (chimpanzee).

Lys-29 is reported to be a binding amino acid for the major group of human rhinoviruses, which use human ICAM 1 as a receptor (Register et al. (1991) J. Virol. 65:6589–6596). We considered the possibility that the selective force acting upon chimpanzee ICAM 1 was exposure to the rhinoviruses. Residue 49 is the only other rhinovirus-binding site that differs between chimpanzee and human; in this case, the chimpanzee sequence retains the ancestral Trp, while human shows a derived Arg, i.e., the human ICAM 1 sequence has changed, while the chimpanzee sequence has been conserved. Thus, this site provides evidence that exposure to rhinoviruses was not a selective force on chimpanzee ICAM 1.

As noted above, ICAM 1 also binds Mac-1. As for LFA-1, it appears unlikely that the binding interaction of ICAM 1 and Mac-1 has been the target of positive selection between chimpanzees and humans, for three reasons. First, our pairwise comparisons of the chimpanzee and human Mac-1 genes suggest conservation. (Like LFA-1, Mac-1 contains an alpha and a beta subunit. Human Mac-1 alpha subunit to the chimpanzee alpha subunit: Ka/Ks=0.30. Human Mac-1 beta subunit to the chimpanzee Mac-1 beta subunit, Ka/Ks=0.42). Second, domain 3 of ICAM 1 has long been known to be critical for Mac-1 binding (Diamond et al., 1991). As noted above, unlike domains 1 and 2, this domain is well conserved between humans and chimpanzee ICAM 1. Third, we found that ICAM 1 residues shown to be critical (Diamond et al., 1991) for Mac-1 binding (Asp-229, Asn-240, Glu-254, Asn-269) are identical between human and chimpanzee ICAM 1; indeed these are almost completely identical in all primate ICAM 1 sequences examined.

While de Groot et al. (2002 *Proc. Natl. Acad. Sci. U.S.A.* 99:11748–11753) suggest that chimpanzee resistance to progression to AIDS may result from the limited set of MHC orthologs that modern chimpanzees retain, we postulate that this explanation is questionable. First, human populations retain homologues of these same chimpanzee MHC proteins in relatively high frequencies, yet humans, with only very limited exceptions, do not appear naturally resistant to HIV-1 induced immunodeficiency. Second, the analysis presented by de Groot et al. (based upon use of Tajima's "D", a statistical test for the action of positive selection) suggests that these genes have evolved neutrally. There is no support for positive selection on these chimpanzee loci, although MHC genes in other species have been documented to show molecular level selection (Hughes and Nei, (1988) *Nature* 335:167–170; Hughes and Nei, (1989) *Proc. Natl. Acad. Sci. U.S.A.* 86:958–962). Chimpanzee resistance to HIV-1 progression is unlikely to be conferred by the MHC alleles that remain in present day chimpanzee populations.

As detailed above, the changes we identified in chimpanzee ICAM 1, in particular, appear likely to modulate dimerization of chimpanzee ICAM 1. As ICAM 1-mediated cell adhesion functions (such as those exploited by HIV-1) are dependent upon binding to ligand, and as such binding has been shown to be influenced by the state of ICAM 1 dimerization, we propose that binding of chimpanzee ICAM 1 to its ligands is not blocked, but rather modulated, thus altering the cell adhesion functions needed by HIV-1, perhaps reducing viral infectivity.

Example 23

Two-step Screening Process

We used a two-step screening process as a rigorous filter to narrow in on other genes responsible for chimpanzee disease resistance. Firstly, we restricted our search to those genes whose expression pattern changes after experimental HIV infection of human cells. Secondly, we screened this subset for genes that had undergone positive selection.

Several groups have reported in the literature investigations of the altered pattern of gene expression that results from infection of human cells in vitro. Each group has used different cell lines and experimental protocols, thus, although some overlap exists in results for all these studies, each investigation has also yielded a unique set of genes. Because of the large number of affected genes in such studies (in one study 3% of genes of T cells were affected), many investigators select small subsets of genes to characterize more completely; for example, Scheuring et al. (1998 AIDS 12: 563–570). selected 12 differentially expressed bands and described 4 host genes. Ryo et al. (1999, FEBS Letters 462(1–2): 182–186) found 142 differentially expressed genes by SAGE analysis (minimum 5-fold difference in expression), of which they selected 53 that matched known genes and concluded that the genes whose expression was up-regulated by infection played a role in accelerated HIV replication and those down-regulated played a role in host cell defense. They subsequently sequenced and identified 13 cDNA fragments and observed coordinated expression of certain genes. (Ryo et al. 2000 AIDS Res. Hum. Retroviruses 16: 995–1005). Corbeil et al. (2001 Genome Res 11: 1198–204) examined 6800 specific genes over 8 time points in a T-cell line to follow expression of genes involved in mitochondrial function and integrity, DNA repair, and apoptosis, but these authors as well as others caution that levels of key genes vary at different time points after infection. Vahey et al. (2003 AIDS Res. & Hum. Retroviruses 19: 369–387) used high density arrays of 5600 cellular genes from cells infected in vitro and also saw temporal patterns of coordinated expression of many genes. Su et al. (2002 Oncogene 21: 3592–602) examined differential gene expression in astrocytes infected with HIV-1. Two groups have been examining potential resistance mechanisms. Simm et al. (2001 Gene 269: 93–101) report eleven genes expressed differentially after HIV-1 inoculation of HIV-1 resistant vs. susceptible T cell lines, of which 5 are novel genes. Krasnoselskaya et al. (2002 AIDS Res. Hum. Retroviruses 18: 591–604) looked at gene expression differences between NF90-expressing cells (which are able to inhibit viral replication) vs. control cells and found 90 genes that had 4-fold or greater changes in expression, many having to do with interferon response.

We developed a method to select a subset of genes differentially expressed upon infection by HIV. We randomly chose genes reported by these others to be up or down regulated after HIV infection of human cells and designed primers to them. We obtained chimpanzee blood (Buckshire Labs, PA) and isolated mRNA. RT-PCR amplified chimpanzee homologs of the human genes. We determined the DNA sequence of each amplicon. We then performed pairwise Ka/Ks comparison of chimpanzee amplicon sequence vs. the homologous human sequence by means of EG's ATP software. Analysis was performed both upon complete coding regions, as well as on sliding windows (composed of smaller sections of the protein-coding region), in order to facilitate identification of small regions of these genes that have been positively selected. Candidate genes with elevated Ka/Ks ratios were amplified and sequenced from multiple chimpanzee and human individuals, in order to ascertain the degree of genetic heterogeneity that exists in the two species for these loci.

The efficacy of this two step process was demonstrated: of 100 chimpanzee genes we examined, only four showed the signature of positive selection. Thus, although the collection of genes whose expression patterns were altered as a result of immunodeficiency virus infection was extensive, we were able to narrow our search to four genes/proteins.

Example 24

CD98 Heavy Chain (GenBank J03569)

CD98 is a heterodimeric transmembrane glycoprotein (Rintoul et al. 2002). CD98 is a highly conserved protein, expressed nearly ubiquitously among cell types. The high level of evolutionary conservation observed among mammalian CD98 homologs makes even more striking the observation that CD98 has been positively selected between humans and chimpanzees. The positively selected portion of the coding sequence (approx. 730 bp in the heavy chain) shows a Ka/Ks ratio=1.7. (As is often the case, the full-length comparisons of CD98 between human and chimpanzee display a Ka/Ks ratio <1. Full-length comparisons frequently mask the signature of positive selection because the 'noise' of synonymous substitutions throughout the full coding sequence overwhelms the signal of positive selection in those cases when only a short portion of the sequence has been adaptively altered.)

CD98 has been linked (Rintoul et al. 2002) to cellular activation; evidence suggests that CD98 activates a tyrosine kinase-controlled signal transduction pathway (Warren et al. 1996) There is also evidence that CD98 regulates intracellular calcium concentrations through a $Na^+/Ca2^+$ exchanger (Michalak et al. 1986).

Strong evidence links CD98 to control of the inflammatory process (Rintoul et al. 2002). Intriguingly, Rintoul et al. (2002) state that "compelling evidence exists for a connection between CD98 and virus-induced cell fusion". Ito et al. (1996) and Ohgimoto et al. (1995) have shown that antibodies to CD98 promote cell fusion that is induced by the gp160 envelope glycoprotein of HIV. The link to inflammatory processes and to virus-induced (and HIV-induced cell fusion, in particular) is significant. ICAMs are well known agents of the inflammatory response, and their part in HIV-induced cell fusion is well documented (Castilletti et al. 1995; Ott et al. 1997; Fortin et al. 1999). Thus the positively selected chimpanzee ICAMs participate with positively selected chimpanzee CD98 to effect HIV resistance.

Example 25 p44 (GenBank NM_006417)

Two alleles were detected in chimpanzees (alleles A & B). Human to chimpanzee full-length comparisons gave Ka/Ks ratios of 0.42 for allele A and 0.45 for allele B. However, examination of exon 2 of the chimpanzee and human homologs revealed that this portion of the gene had been positively selected.

The protein p44 was discovered by Shimizu et al. (1985). These authors infected chimpanzees with non-A, non-B hepatitis (hepatitis C) and identified p44 as a protein that was expressed upon infection. For several years, p44 was a marker of hepatitis C infection, until the virus was cloned in 1989 and direct virus diagnostic techniques became available. Although chimpanzees have been used as a model for human hepatitis C, it has been well-documented that HCV-infected chimpanzees are refractory to the hepatic damage that often occurs in HCV-infected humans, perhaps due to lower levels of viral replication (Lanford et al. 1991). p44 is a member of the family of alpha/beta interferon inducible genes and thought to be a mediator of the antiviral activities of interferon induced by double-stranded RNA replicative intermediates (Kitamura et al. 1994). As HIV infection is characterized by a double-stranded RNA replicative intermediate, it was not surprising to find in Vahey et al's study (2003) on genes differentially expressed upon HIV infection, that p44 is listed among the hundreds of genes reported. However, while infection with hepatitis B virus does induce p44 expression, infection by the hepatitis G virus, which also is expected to replicate via a double-stranded RNA intermediate, does not induce expression of p44 (Shimizu et al. 0.2001). This positively selected protein, which is up-regulated after infection by both hepatitis C and HIV-1, is clearly of interest.

Example 26

IFN-p56K (GenBank M24594)

The positively selected portion of the coding sequence (approx. 1245 bp) shows a Ka/Ks ratio=2.5. Strikingly, for this protein, even the full-length comparison of between the human and chimpanzee homologs displays a Ka/Ks ratio greater than one (1.3)

IFN-p56k is a 56-kilodalton protein that plays a role in the control of protein synthesis. Generally, protein synthesis is initiated when eIF4F, eIF4G, and eIF4E and eIF3 work in concert to bring together ribosomes with messenger RNA. Many viruses usurp the host protein synthesis "machinery" to stop production of host proteins and instead produce virus-encoded proteins. Two HIV-1 encoded proteins appear to play a role in redirecting protein synthesis to HIV-encoded proteins. HIV protease has been shown to cleave eIF4GI (but not 11), resulting in inhibition of cap-dependent mRNA translation while protein synthesis using non-capped mRNAs with internal ribosome entry sites (such as HIV mRNAs) continues or is even stimulated (Alvarez et al. 2003). HIV Vpr has been shown to act on a number of host cell functions, including enhancing expression of viral mRNAs. Vpr interacts directly with eIF3f, one of the twelve subunits of eIF3. When IFN-p56K is present, it binds to another of the subunits of eIF3 (eIF3e) and stops protein translation. IFN-p56K likely represents a host protein that is expressed during virus infection as part of a general antiviral interferon-mediated response.

In vitro, no mRNA encoding IFN-p56k is detectable in cells in the absence of treatment with interferon or dsRNA. After the addition of interferon or dsRNA, the amount of IFN-p56K mRNA increases; it has been reported to be the most abundant interferon-induced mRNA among the over one hundred INF-induced mRNAs measured (Der et al. 1998). IFN-p56K is inducible by interferons alpha, beta, and gamma, by virus infection (HIV, hepatitis C, Sendai virus, vesicular stomatitis virus, encephalomyocarditis virus, and cytomegalovirus) or by the presence of dsRNA.

Guo and Sen (2000) have characterized IFN-p56K extensively. The IFN-p56K protein has eight tetratricopeptide motifs; such motifs are generally associated with mediation of protein-protein interactions. Upon induction of expression of the IFN-p56K gene by the presence of interferon, IFI-56pK is present in the cytoplasm and eIF3e is located in the nucleus.

Upon the interaction of HIV Vpr with eIF3f, the latter translocates into the nucleus. Upon the interaction of IFN-p56K with eIF3e, the latter translocates into the cytoplasm.

Example 27

Staf50 (GenBank X82200)

This protein has been shown to be induced by both type I and type II human interferons (Tissot and Mechti 1995), and importantly, Staf50 has been shown to down-regulate transcription of the long terminal repeat of HIV-1 (Tissot and Mechti 1995). Thus, in addition to the fact that this protein is upregulated after HIV-1 infection, and the fact that it has been positively selected in HIV-resistant chimpanzees, this protein also plays a role on regulation of HIV-1 infection.

As is reported to be the case for IFN-p56K (and perhaps for p44), Staf50 appears to be part of a general antiviral response, mediated by the interferons. Chang and Laimins (2000) demonstrated by microarray analysis that the regulation of StafSO is altered as a result of infection by the human papillomavirus type 31. Like p44 and IFN-p56K (Patzwahl et al. 2001), Staf50 has been shown to be upregulated in the chimpanzee liver after hepatitis C infection (Bigger et al. 2001).

Staf50 is the human homolog of mouse Rpt-1, which is known to negatively regulate the gene that codes for the IL-2 receptor (Bigger et al. 2001).

Although the foregoing invention has been described in some detail by way of illustration and example for purposes of clarity and understanding, it will be apparent to those of ordinary skill in the art that certain changes and modifications can be practiced. Therefore, the description and examples should not be construed as limiting the scope of the invention, which is delineated by the appended claims.

What is claimed is:

1. A method of determining whether a polynucleotide sequence of a non-human primate which has been or may be associated with a physiological trait in the non-human primate has undergone evolutionarily significant change relative to humans that exhibit the physiological trait to a lesser degree, comprising:

(a) comparing the non-human polynucleotide sequence with the corresponding human primate polynucleotide sequence to identify any nucleotide changes, wherein the polynucleotide sequence is selected from the group consisting of ICAM-1 polynucleotide sequence, ICAM-2 polynucleotide sequence, ICAM-3 polynucleotide sequence, CD98 polynucleotide sequence, p44 polynucleotide sequence, IFN-p56k polynucleotide sequence, and Staf50 polynucleotide sequence; and (b) determining whether said non-human nucleotide changes are evolutionarily significant, whereby a polynucleotide sequence of a non-human primate which has been or may be associated with a physiological trait in the non-human primate has undergone evolutionarily significant change relative to humans that exhibits the physiological trait to a lesser degree is identified.

2. The method of claim 1, wherein the polynucleotide sequence of a non-human primate is selected from the group consisting of SEQ ID NO:2, SEQ ID NO:4, SEQ ID NO:5, SEQ ID NO:58, SEQ ID NO:61, SEQ ID NO:64, SEQ ID NO:67, SEQ ID NO:70, SEQ ID NO:73, SEQ ID NO:79, SEQ ID NO:82, SEQ ID NO:37, SEQ ID NO:43, SEQ ID NO:31, and SEQ ID NO:49.

3. A method of identifying an agent which may modulate a physiological trait, said method comprising contacting at least one agent to be tested with a cell that has been transfected with the corresponding human polynucleotide sequence of claim 1, wherein an agent is identified by its ability to modulate the function of the polynucleotide sequence.

4. The method of claim 3, wherein the physiological trait is resistance to the progression of a viral disease, the corresponding human polynucleotide is selected from the group consisting of ICAM-1 polynucleotide, ICAM-2 polynucleotide, and ICAM-3 polynucleotide, CD98 polynucleotide, p44 polynucleotide, IFN-p56k polynucleotide, and Staf50 polynucleotide, and the modulated function is increased resistance to the progression of a viral disease.

5. The method of claim 3, wherein the physiological trait is selected from the group consisting of binding of a polypeptide to its ligand, virus-mediated cellular pathogenesis, cell to cell infectivity, virus-mediated cell fusion, virus-mediated syncytia formation, and virus budding rate.

6. The method of claim 5, wherein said polypeptide is selected from the group consisting of ICAM-1, ICAM-2, ICAM-3, CD98, p44, IFN-p56k, and Staf50.

7. The method of claim 4, wherein the polynucleotide is a polynucleotide comprising a polynucleotide selected from the group consisting of SEQ ID NO.:1, SEQ ID NO.:55, SEQ ID NO.:76, SEQ ID NO.:34, SEQ ID NO.:40, SEQ ID NO.:46, and SEQ ID NO.:52, or fragments thereofof about 18–225 nucleotides and having at least one human nucleotide that corresponds to a non-human primate evolutionarily significant nucleotide change.

8. The method of claim 3, wherein the physiological trait is resistance to the progression of a viral disease, the polynucleotide is selected from the group consisting of CD98, p44, IFN-p56k, and Staf50, and the modulated function is increased resistance to the progression of hepatitis C—caused hepatitis.

9. The method of claim 3, wherein the physiological trait is resistance to the progression of a viral disease, the polynucleotide is selected from the group consisting of CD98, p44, IFN-p56k, and Staf50, and the modulated function is increased resistance to the progression of AIDS.

10. The method of claim 9, wherein the polynucleotide is a polynucleotide selected from the group consisting of SEQ ID NO.:34, SEQ ID NO.:40, SEQ ID NO.:46, and SEQ ID NO.:52.

11. The method of claim 3, wherein the physiological trait is resistance to the progression of AIDS, the polynucleotide is selected from the group consisting of human ICAM-1 polynucleotide, human ICAM-2 polynucleotide, and human ICAM-3 polynucleotide, and the modulated function is increased resistance to the progression of AIDS.

12. The method of claim 11, wherein the polynucleotide is selected from the group consisting of SEQ ID NO.1, SEQ ID NO.:55, SEQ ID NO.:76, a polynucleotide encoding the polypeptide SEQ ID NO:6, a polynucleotide encoding the polypeptide SEQ ID NO:7, a polynucleotide encoding the polypeptide SEQ ID NO:8, a polynucleotide encoding the polypeptide SEQ ID NO:57, and a polynucleotide encoding the polypeptide SEQ ID NO:78.

13. The method of claim 3, wherein the physiological trait is resistance to the progression of AIDS, the polynucleotide is a human ICAM-1 polynucleotide, and the modulated function is dimerization of two ICAM-1 polypeptides.

14. The method of claim 13, wherein the polynucleotide is a polynucleotide selected from the group consisting of SEQ ID NO.1, and a polynucleotide encoding the polypeptide SEQ ID NO:6.

15. A method of identifying an agent which may modulate a physiological trait, said method comprising contacting at least one agent to be tested with a polypeptide encoded by a corresponding human polynucleotide sequence of claim 1, or a composition comprising said polypeptide, wherein an agent is identified by its ability to modulate function of the human polypeptide.

16. The method of claim 15, wherein the physiological trait is resistance to the progression of AIDS, the polynucleotide is selected from the group consisting of a human ICAM-1 polynucleotide, human ICAM-2 polynucleotide, and human ICAM-3 polynucleotide, and the modulated function is increased resistance to the progression of AIDS.

17. The method of claim 15, wherein the physiological trait is resistance to the progression of AIDS, the polynucleotide is a human ICAM-1 polynucleotide, and the modulated function is dimerization of two ICAM-1 polypeptides.

18. A method of correlating a polynucleotide sequence of a non-human primate with greater resistance to progression of an infectious disease relative to humans, comprising:

(a) identifying a human polynucleotide sequence, wherein the expression is modulated upon infection of a human cell with an infectious agent that causes the infectious disease;

(b) comparing the human polynucleotide sequences of (a) with a corresponding polynucleotide sequence of a non-human primate that exhibits greater resistance to progression of disease caused by the infectious agent to identify any nucleotide changes; and (c) determining whether said non-human primate nucleotide changes are evolutionarily significant, whereby the polynucleotide sequence of the non-human primate is correlated with greater resistance to progression of an infectious disease relative to humans.

19. A method for identifying a target site on a human polypeptide which may be suitable for therapeutic intervention, comprising identifying amino acid changes in the human polypeptide corresponding to evolutionarily significant nucleotide changes identified according to the method of claim 1, as target sites.

20. A method for identifying a target site on a human polynucleotide which may be suitable for therapeutic intervention, comprising identifying nucleotide changes in the human polynucleotide that are evolutionarily significant according to the method of claim 1 as target sites.

21. A method of identifying an agent which may modulate a physiological trait, said method comprising contacting at least one agent to be tested with a cell that has been transfected with the human polynucleotide sequence of claim 1, wherein an agent is identified by its ability to modulate function of the polynucleotide.

22. A method of identifying an agent which may modulate a physiological trait, said method comprising contacting at least one agent to be tested with a polypeptide encoded by the polynucleotide sequence of claim 1, or a composition comprising said polypeptide, wherein an agent is identified by its ability to modulate function of the polypeptide.

* * * * *